US011999772B2

(12) United States Patent
Adams et al.

(10) Patent No.: US 11,999,772 B2
(45) Date of Patent: Jun. 4, 2024

(54) ANTIBODIES COMPRISING A POLYPEPTIDE INSERTED IN FRAMEWORK 3 REGION

(71) Applicant: UCB BIOPHARMA SRL, Brussels (BE)

(72) Inventors: Ralph Adams, Slough (GB); Terence Seward Baker, Slough (GB); Xiaofeng Liu, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 817 days.

(21) Appl. No.: 17/259,090

(22) PCT Filed: Jul. 10, 2019

(86) PCT No.: PCT/EP2019/068570

§ 371 (c)(1),
(2) Date: Jan. 8, 2021

(87) PCT Pub. No.: WO2020/011868

PCT Pub. Date: Jan. 16, 2020

(65) Prior Publication Data

US 2022/0073581 A1 Mar. 10, 2022

(30) Foreign Application Priority Data

Jul. 11, 2018 (GB) ...................................... 1811368

(51) Int. Cl.

| | |
|---|---|
| ***C07K 16/00*** | (2006.01) |
| ***C07K 14/505*** | (2006.01) |
| ***C07K 14/535*** | (2006.01) |
| ***C07K 14/54*** | (2006.01) |
| ***C07K 14/55*** | (2006.01) |
| ***C07K 16/18*** | (2006.01) |
| ***C07K 16/24*** | (2006.01) |
| ***C07K 16/28*** | (2006.01) |

(52) U.S. Cl.

CPC ........ *C07K 14/5443* (2013.01); *C07K 14/505* (2013.01); *C07K 14/535* (2013.01); *C07K 14/5428* (2013.01); *C07K 14/55* (2013.01); *C07K 16/18* (2013.01); *C07K 16/244* (2013.01); *C07K 16/248* (2013.01); *C07K 16/2809* (2013.01); *C07K 16/2818* (2013.01); *C07K 2317/24* (2013.01); *C07K 2317/31* (2013.01); *C07K 2317/55* (2013.01); *C07K 2317/56* (2013.01); *C07K 2317/567* (2013.01); *C07K 2317/569* (2013.01); *C07K 2317/622* (2013.01); *C07K 2317/76* (2013.01)

(58) Field of Classification Search

None

See application file for complete search history.

(56) References Cited

U.S. PATENT DOCUMENTS

| | | | |
|---|---|---|---|
| 5,219,996 | A | 6/1993 | Bodmer et al. |
| 5,545,806 | A | 8/1996 | Lonberg et al. |
| 5,569,825 | A | 10/1996 | Lonberg et al. |
| 5,585,089 | A | 12/1996 | Queen et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,667,425 | A | 9/1997 | Pineau et al. |
| 5,770,429 | A | 6/1998 | Lonberg et al. |
| 7,282,199 | B2 | 10/2007 | Gao et al. |
| 7,588,772 | B2 | 9/2009 | Kay et al. |
| 7,790,449 | B2 | 9/2010 | Gao et al. |
| 7,906,111 | B2 | 3/2011 | Wilson et al. |
| 2005/0266000 | A1 | 12/2005 | Bond et al. |
| 2011/0236353 | A1 | 9/2011 | Wilson et al. |
| 2017/0210818 | A1* | 7/2017 | Wang .................... C07K 14/47 |

FOREIGN PATENT DOCUMENTS

| | | | |
|---|---|---|---|
| EP | 0438474 | A1 | 7/1991 |
| EP | 0463151 | A1 | 1/1992 |
| EP | 0546073 | B1 | 9/1997 |
| WO | 1990/04036 | A1 | 4/1990 |
| WO | 1991/10741 | A1 | 7/1991 |
| WO | 1992/22583 | A2 | 12/1992 |
| WO | 1998/25971 | A1 | 6/1998 |
| WO | 2003/42397 | A2 | 5/2003 |
| WO | 2005/003169 | A2 | 1/2005 |
| WO | 2005/003170 | A2 | 1/2005 |
| WO | 2005/003171 | A2 | 1/2005 |
| WO | 2005/033321 | A2 | 4/2005 |
| WO | 2005/113605 | A1 | 12/2005 |
| WO | 2006/110689 | A2 | 10/2006 |
| WO | 2007/106120 | A2 | 9/2007 |
| WO | 2007/109254 | A2 | 9/2007 |
| WO | 2008/038024 | A1 | 4/2008 |
| WO | 2009/040562 | A1 | 4/2009 |

(Continued)

OTHER PUBLICATIONS

Du et al., J. Am. Chem. Soc. 2017, 139, 18607-18615. (Year: 2017).*
Luo et al., Angew. Chem. Int. Ed. 2015, 54, 14531-14534. (Year: 2015).*
Zhang et al., J. Am. Chem. Soc. 2015, 137, 38-41. (Year: 2015).*
Liu et al., Proc Natl Acad Sci U S A. 2015;112(5): 1356-1361. (Year: 2015).*
Li et al. (PLoS Comput Biol 11(7): e1004327, 2015). (Year: 2015).*
Li et al. (PLoS ONE 9(3): e92870, 2014). (Year: 2014).*
Briney et al. (Genes Immun. 2012;13(7):523-529). (Year: 2012).*
Adair et al., Therapeutic Antibodies, Drug Design Reviews—Online, 2(3):209-217 (2005).
Alfthan et al., Properties of a single-chain antibody containing different linker peptides, Prot. Eng., 8(7):725-731 (1995).

(Continued)

*Primary Examiner* — Zachary S Skelding
(74) *Attorney, Agent, or Firm* — MARSHALL, GERSTEIN & BORUN LLP

(57) ABSTRACT

The present invention provides antibodies comprising a variable (V) domain and an insert polypeptide, wherein the insert polypeptide is within the framework 3 region of the V domain.

32 Claims, 25 Drawing Sheets

Specification includes a Sequence Listing.

(56) References Cited

FOREIGN PATENT DOCUMENTS

| WO | 2010/035012 A1 | 4/2010 |
|---|---|---|
| WO | 2015/197772 A1 | 12/2015 |

OTHER PUBLICATIONS

Altschul et al., Basic local alignment search tool, J. Mol. Biol., 215(3):403-410 (1990).
Altschul et al., Gapped BLAST and PSI-BLAST: a new generation of protein database search programs, Nucleic Acids Res., 25:3389-3402 (1997).
Angal et al., A single amino acid substitution abolishes the heterogeneity of chimeric mouse/human (IgG4) antibody, Molecular Immunology, 30(1):105-108 (1993).
Cain et al., A CHO cell line engineered to express XBP1 and ERO1-La has increased levels of transient protein expression, Biotechnology Progress, 29(3):697-706 (2013).
Crameri et al., DNA shuffling of a family of genes from diverse species accelerates directed evolution, Nature, 391:288-291 (1998).
Fang et al., An antibody delivery system for regulated expression of therapeutic levels of monoclonal antibodies in vivo, Mol Ther., 15(6):1153-9 (2007).
Fang et al., Stable antibody expression at therapeutic levels using the 2A peptide, Nature Biotechnology, 23:584-590 (2005).
Fischer et al., Bispecific antibodies: molecules that enable novel therapeutic strategies, Pathobiology, 74(1):3-14 (2007).
Gish et al., Identification of protein coding regions by database similarity search, Nature Genet., 3(3):266-272 (1993).
Harris, Processing of C-terminal lysine and arginine residues of proteins isolated from mammalian cell culture, Journal of Chromatography, 705(1):129-134 (1995).
Holliger et al., Engineered antibody fragments and the rise of single domains, Nature Biotechnology, 23(9):1126-1136 (2005).
Holt et al., Domain antibodies: proteins for therapy, Trends in Biotechnology, 21(11):484-490 (2003).
Huston et al., Protein engineering of antibody binding sites: recovery of specific activity in an anti-digoxin single-chain Fv analogue produced in *Escherichia coli*, PNAS, 85(16):5879-5883 (1988).
International Application No. PCT/EP2019/068570, International Preliminary Report on Patentability, dated Jan. 21, 2021.
International Application No. PCT/EP2019/068570, International Search Report and Written Opinion, dated Nov. 13, 2019.
Kashmiri et al., SDR grafting—a new approach to antibody humanization, Methods, 36(1):25-34 (2005).
Low et al., Mimicking somatic hypermutation: affinity maturation of antibodies displayed on bacteriophage using a bacterial mutator strain, J. Mol. Biol., 260(3):359-368 (1996).
Luo et al., Vl-linker-Vh orientation-dependent expression of single chain Fv-containing an engineered disulfide-stabilized bond in the framework regions, J. Biochem., 118(4):825-831 (1995).
Madden et al., Applications of network BLAST server, Meth. Enzymol., 266:131-141 (1996).
Marks et al., By-passing immunization: building high affinity human antibodies by chain shuffling, Bio/Technology, 10(7):779-783 (1992).
Medesan et al., Delineation of the amino acid residues involved in transcytosis and catabolism of mouse IgG1, J. Immunol., 158(5):2211-2217 (1997).
Nguyen et al., The pharmacokinetics of an albumin-binding Fab (AB.Fab) can be modulated as a function of affinity for albumin, Protein Engineering, Design & Selection, 19(7):291-297 (2006).
Nikoloudis et al., A complete, multi-level conformational clustering of antibody complementarity-determining regions, Peerj, 2:e456 (2014).
Patten et al., Applications of DNA shuffling to pharmaceuticals and vaccines, Curr. Opin. Biotechnol., 8(6):724-733 (1997).
Pluckthun et al., New protein engineering approaches to multivalent and bispecific antibody fragments, Immunotechnology, 3(2):83-105 (1997).
Ridgway et al., 'Knobs-into-holes' engineering of antibody CH3 domains for heavy chain heterodimerization, Protein Eng., 9(7):617-621 (1996).
Segal et al., Bispecific antibodies in cancer therapy, Curr. Opin. Immunol., 11(5):558-562 (1999).
Simon et al., A functional antibody mutant with an insertion in the framework region 3 loop of the VH domain: implications for antibody engineering, Protein Eng., 5(3):229-34 (1992).
Tang et al., Selection of linkers for a catalytic single-chain antibody using phage display technology, J. Biol. Chem., 271(26):15682-15686 (1996).
Thompson et al., Affinity maturation of a high-affinity human monoclonal antibody against the third hypervariable loop of human immunodeficiency virus: use of phage display to improve affinity and broaden strain reactivity, J. Mol. Biol., 256(1):77-88 (1996).
Turner et al., Importance of the linker in expression of single-chain Fv antibody fragments: optimisation of peptide sequence using phage display technology, Jimm., 205:42-54 (1997).
Verma et al., Antibody engineering: comparison of bacterial, yeast, insect and mammalian expression systems, Journal of Immunological Methods, 216(1-2):165-181 (1998).
Wang et al., Reshaping Antibody Diversity, Cell, 153(6):1379-1393 (2013).
Ward et al., Binding activities of a repertoire of single immunoglobulin variable domains secreted from *Escherichia coli*, Nature, 341:544-546 (1989).
Weatherill et al., Towards a universal disulphide stabilised single chain Fv format: importance of interchain disulphide bond location and vL-vH orientation, Protein Engineering, Design & Selection, 25(7):321-329 (2012).
Wright et al., Phage display of chelating recombinant antibody libraries, Mol. Immunol., 44(11):2860-2869 (2007).
Yang et al., CDR walking mutagenesis for the affinity maturation of a potent human anti-HIV-1 antibody into the picomolar range, J. Mol. Biol., 254(3):392-403 (1995).
Zhang et al., PowerBLAST: a new network BLAST application for interactive or automated sequence analysis and annotation, Genome Res., 7(6):649-656 (1997).
Kepler et al., "Immunoglobulin gene insertions and deletions in the affinity maturation of HIV-1 broadly reactive neutralizing antibodies," Cell Host Microbe, 16(3): 304-313 (2014).
Barbas III et al., "Recombinant human Fab fragments neutralize human type 1 immunodeficiency virus in vitro", Proc. Natl. Acad. Sci, vol. 89(19):9339-9343 (1992).
Hlavacek et al., "Steric Effects on Multivalent Ligand-Receptor Binding: Exclusion of Ligand Sites by Bound Cell Surface Receptors", Biophysical Journal, 76(6):3031-3043 (1999).
Roitt et al., Immunology, Mir, pp. 110-111 (2000).
Tobi et al., "Structural changes involved in protein binding correlate with intrinsic motives of proteins in the unbound state", PNAS, 102(52):18908-18913 (2005).
Skamaki, In Vitro Evolution of Antibody Affinity using Libraries with Insertions and Deletions, A dissertation submitted for the degree of Doctor of Philosophy, University of Cambridge, 1-52 (2017).

* cited by examiner

A

B

A

B

A

B

A

B

A

B

A

B

A

B

A

B

A

B

A

B

C

A

B

A

B

C

D

SEQUENCE LISTING

<160> NUMBER OF SEQ ID NOS: 144

<210> SEQ ID NO 1
<211> LENGTH: 217
<212> TYPE: PRT
<213> ORGANISM: Artificial Sequence
<220> FEATURE:
<223> OTHER INFORMATION: CA645 Light Chain gL5

<400> SEQUENCE: 1

```
Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 2
<211> LENGTH: 110
<212> TYPE: PRT
<213> ORGANISM: Artificial Sequence
<220> FEATURE:
<223> OTHER INFORMATION: CA645 VL domain (gL5)

<400> SEQUENCE: 2

```
Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80
```

```
Pro Glu Asp Phe Ala Thr Tyr Tyr Cys Gly Gly Gly Tyr Ser Ser Ile
                85                  90                  95

Ser Asp Thr Thr Phe Gly Gly Gly Thr Lys Val Glu Ile Lys
            100                 105                 110


<210> SEQ ID NO 3
<211> LENGTH: 12
<212> TYPE: PRT
<213> ORGANISM: Artificial Sequence
<220> FEATURE:
<223> OTHER INFORMATION: CA645 CDR L1

<400> SEQUENCE: 3

Gln Ser Ser Pro Ser Val Trp Ser Asn Phe Leu Ser
1               5                   10


<210> SEQ ID NO 4
<211> LENGTH: 7
<212> TYPE: PRT
<213> ORGANISM: Artificial Sequence
<220> FEATURE:
<223> OTHER INFORMATION: CA645 CDR L2

<400> SEQUENCE: 4

Glu Ala Ser Lys Leu Thr Ser
1               5


<210> SEQ ID NO 5
<211> LENGTH: 11
<212> TYPE: PRT
<213> ORGANISM: Artificial Sequence
<220> FEATURE:
<223> OTHER INFORMATION: CA645 CDR L3

<400> SEQUENCE: 5

Gly Gly Gly Tyr Ser Ser Ile Ser Asp Thr Thr
1               5                   10


<210> SEQ ID NO 6
<211> LENGTH: 224
<212> TYPE: PRT
<213> ORGANISM: Artificial Sequence
<220> FEATURE:
<223> OTHER INFORMATION: CA645 Heavy Chain gH5

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Ala Ser Thr Lys Gly Pro Ser
        115                 120                 125
```

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220


<210> SEQ ID NO 7
<211> LENGTH: 121
<212> TYPE: PRT
<213> ORGANISM: Artificial Sequence
<220> FEATURE:
<223> OTHER INFORMATION: CA645 VH domain (gH5)

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120


<210> SEQ ID NO 8
<211> LENGTH: 10
<212> TYPE: PRT
<213> ORGANISM: Artificial Sequence
<220> FEATURE:
<223> OTHER INFORMATION: CA645 CDR H1

<400> SEQUENCE: 8

Gly Ile Asp Leu Ser Asn Tyr Ala Ile Asn
1               5                   10


<210> SEQ ID NO 9
<211> LENGTH: 16
<212> TYPE: PRT
<213> ORGANISM: Artificial Sequence
<220> FEATURE:
<223> OTHER INFORMATION: CA645 CDR H2

<400> SEQUENCE: 9

Ile Ile Trp Ala Ser Gly Thr Thr Phe Tyr Ala Thr Trp Ala Lys Gly
1               5                   10                  15
```

<210> SEQ ID NO 10
<211> LENGTH: 13
<212> TYPE: PRT
<213> ORGANISM: Artificial Sequence
<220> FEATURE:
<223> OTHER INFORMATION: CA645 CDR H3

<400> SEQUENCE: 10

Thr Val Pro Gly Tyr Ser Thr Ala Pro Tyr Phe Asp Leu
1 5 10

<210> SEQ ID NO 11
<211> LENGTH: 7
<212> TYPE: PRT
<213> ORGANISM: Artificial Sequence
<220> FEATURE:
<223> OTHER INFORMATION: Flexible linker

<400> SEQUENCE: 11

Ser Gly Gly Gly Gly Ser Glu
1 5

<210> SEQ ID NO 12
<211> LENGTH: 6
<212> TYPE: PRT
<213> ORGANISM: Artificial Sequence
<220> FEATURE:
<223> OTHER INFORMATION: Flexible linker

<400> SEQUENCE: 12

Asp Lys Thr His Thr Ser
1 5

<210> SEQ ID NO 13
<211> LENGTH: 6
<212> TYPE: PRT
<213> ORGANISM: Artificial Sequence
<220> FEATURE:
<223> OTHER INFORMATION: Flexible linker

<400> SEQUENCE: 13

Ser Gly Gly Gly Gly Ser
1 5

<210> SEQ ID NO 14
<211> LENGTH: 11
<212> TYPE: PRT
<213> ORGANISM: Artificial Sequence
<220> FEATURE:
<223> OTHER INFORMATION: Flexible linker

<400> SEQUENCE: 14

Ser Gly Gly Gly Gly Ser Gly Gly Gly Gly Ser
1 5 10

<210> SEQ ID NO 15
<211> LENGTH: 16
<212> TYPE: PRT
<213> ORGANISM: Artificial Sequence
<220> FEATURE:
<223> OTHER INFORMATION: Flexible linker

<400> SEQUENCE: 15

Ser Gly Gly Gly Gly Ser Gly Gly Gly Gly Ser Gly Gly Gly Gly Ser
1 5 10 15

<210> SEQ ID NO 16

<211> LENGTH: 21
<212> TYPE: PRT
<213> ORGANISM: Artificial Sequence
<220> FEATURE:
<223> OTHER INFORMATION: Flexible linker

<400> SEQUENCE: 16

Ser Gly Gly Gly Gly Ser Gly Gly Gly Gly Ser Gly Gly Gly Gly Ser
1 5 10 15

Gly Gly Gly Gly Ser
20

<210> SEQ ID NO 17
<211> LENGTH: 26
<212> TYPE: PRT
<213> ORGANISM: Artificial Sequence
<220> FEATURE:
<223> OTHER INFORMATION: Flexible linker

<400> SEQUENCE: 17

Ser Gly Gly Gly Gly Ser Gly Gly Gly Gly Ser Gly Gly Gly Gly Ser
1 5 10 15

Gly Gly Gly Gly Ser Gly Gly Gly Gly Ser
20 25

<210> SEQ ID NO 18
<211> LENGTH: 11
<212> TYPE: PRT
<213> ORGANISM: Artificial Sequence
<220> FEATURE:
<223> OTHER INFORMATION: Flexible linker

<400> SEQUENCE: 18

Ala Ala Ala Gly Ser Gly Gly Ala Ser Ala Ser
1 5 10

<210> SEQ ID NO 19
<211> LENGTH: 16
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 19

Ala Ala Ala Gly Ser Gly Xaa Gly Gly Gly Ser Gly Ala Ser Ala Ser
1 5 10 15

<210> SEQ ID NO 20
<211> LENGTH: 21
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 20

Ala Ala Ala Gly Ser Gly Xaa Gly Gly Gly Ser Xaa Gly Gly Gly Ser 1 5 10 15

Gly Ala Ser Ala Ser
20

<210> SEQ ID NO 21
<211> LENGTH: 26
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 21

Ala Ala Ala Gly Ser Gly Xaa Gly Gly Gly Ser Xaa Gly Gly Gly Ser
1 5 10 15

Xaa Gly Gly Gly Ser Gly Ala Ser Ala Ser
20 25

<210> SEQ ID NO 22
<211> LENGTH: 31
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 22

Ala Ala Ala Gly Ser Gly Xaa Gly Gly Gly Ser Xaa Gly Gly Gly Ser
1 5 10 15

Xaa Gly Gly Gly Ser Xaa Gly Gly Gly Ser Gly Ala Ser Ala Ser
20 25 30

<210> SEQ ID NO 23
<211> LENGTH: 13
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 23

```
Ala Ala Ala Gly Ser Gly Xaa Ser Gly Ala Ser Ala Ser
1               5                   10


<210> SEQ ID NO 24
<211> LENGTH: 28
<212> TYPE: PRT
<213> ORGANISM: Artificial Sequence
<220> FEATURE:
<223> OTHER INFORMATION: Flexible linker

<400> SEQUENCE: 24

Pro Gly Gly Asn Arg Gly Thr Thr Thr Thr Arg Arg Pro Ala Thr Thr
1               5                   10                  15

Thr Gly Ser Ser Pro Gly Pro Thr Gln Ser His Tyr
            20                  25


<210> SEQ ID NO 25
<211> LENGTH: 11
<212> TYPE: PRT
<213> ORGANISM: Artificial Sequence
<220> FEATURE:
<223> OTHER INFORMATION: Flexible linker

<400> SEQUENCE: 25

Ala Thr Thr Thr Gly Ser Ser Pro Gly Pro Thr
1               5                   10


<210> SEQ ID NO 26
<211> LENGTH: 6
<212> TYPE: PRT
<213> ORGANISM: Artificial Sequence
<220> FEATURE:
<223> OTHER INFORMATION: Flexible linker

<400> SEQUENCE: 26

Ala Thr Thr Thr Gly Ser
1               5


<210> SEQ ID NO 27
<211> LENGTH: 21
<212> TYPE: PRT
<213> ORGANISM: Artificial Sequence
<220> FEATURE:
<223> OTHER INFORMATION: Flexible linker

<400> SEQUENCE: 27

Glu Pro Ser Gly Pro Ile Ser Thr Ile Asn Ser Pro Pro Ser Lys Glu
1               5                   10                  15

Ser His Lys Ser Pro
            20


<210> SEQ ID NO 28
<211> LENGTH: 15
<212> TYPE: PRT
<213> ORGANISM: Artificial Sequence
<220> FEATURE:
<223> OTHER INFORMATION: Flexible linker

<400> SEQUENCE: 28

Gly Thr Val Ala Ala Pro Ser Val Phe Ile Phe Pro Pro Ser Asp
1               5                   10                  15


<210> SEQ ID NO 29
<211> LENGTH: 15
<212> TYPE: PRT
<213> ORGANISM: Artificial Sequence
```

<220> FEATURE:
<223> OTHER INFORMATION: Flexible linker

<400> SEQUENCE: 29

Gly Gly Gly Gly Ile Ala Pro Ser Met Val Gly Gly Gly Gly Ser
1 5 10 15

<210> SEQ ID NO 30
<211> LENGTH: 15
<212> TYPE: PRT
<213> ORGANISM: Artificial Sequence
<220> FEATURE:
<223> OTHER INFORMATION: Flexible linker

<400> SEQUENCE: 30

Gly Gly Gly Gly Lys Val Glu Gly Ala Gly Gly Gly Gly Gly Ser
1 5 10 15

<210> SEQ ID NO 31
<211> LENGTH: 15
<212> TYPE: PRT
<213> ORGANISM: Artificial Sequence
<220> FEATURE:
<223> OTHER INFORMATION: Flexible linker

<400> SEQUENCE: 31

Gly Gly Gly Gly Ser Met Lys Ser His Asp Gly Gly Gly Gly Ser
1 5 10 15

<210> SEQ ID NO 32
<211> LENGTH: 15
<212> TYPE: PRT
<213> ORGANISM: Artificial Sequence
<220> FEATURE:
<223> OTHER INFORMATION: Flexible linker

<400> SEQUENCE: 32

Gly Gly Gly Gly Asn Leu Ile Thr Ile Val Gly Gly Gly Gly Ser
1 5 10 15

<210> SEQ ID NO 33
<211> LENGTH: 15
<212> TYPE: PRT
<213> ORGANISM: Artificial Sequence
<220> FEATURE:
<223> OTHER INFORMATION: Flexible linker

<400> SEQUENCE: 33

Gly Gly Gly Gly Val Val Pro Ser Leu Pro Gly Gly Gly Gly Ser
1 5 10 15

<210> SEQ ID NO 34
<211> LENGTH: 12
<212> TYPE: PRT
<213> ORGANISM: Artificial Sequence
<220> FEATURE:
<223> OTHER INFORMATION: Flexible linker

<400> SEQUENCE: 34

Gly Gly Glu Lys Ser Ile Pro Gly Gly Gly Gly Ser
1 5 10

<210> SEQ ID NO 35
<211> LENGTH: 18
<212> TYPE: PRT
<213> ORGANISM: Artificial Sequence
<220> FEATURE:

<223> OTHER INFORMATION: Flexible linker

<400> SEQUENCE: 35

Arg Pro Leu Ser Tyr Arg Pro Pro Phe Pro Phe Gly Phe Pro Ser Val
1 5 10 15

Arg Pro

<210> SEQ ID NO 36
<211> LENGTH: 18
<212> TYPE: PRT
<213> ORGANISM: Artificial Sequence
<220> FEATURE:
<223> OTHER INFORMATION: Flexible linker

<400> SEQUENCE: 36

Tyr Pro Arg Ser Ile Tyr Ile Arg Arg Arg His Pro Ser Pro Ser Leu
1 5 10 15

Thr Thr

<210> SEQ ID NO 37
<211> LENGTH: 18
<212> TYPE: PRT
<213> ORGANISM: Artificial Sequence
<220> FEATURE:
<223> OTHER INFORMATION: Flexible linker

<400> SEQUENCE: 37

Thr Pro Ser His Leu Ser His Ile Leu Pro Ser Phe Gly Leu Pro Thr
1 5 10 15

Glu Asn

<210> SEQ ID NO 38
<211> LENGTH: 18
<212> TYPE: PRT
<213> ORGANISM: Artificial Sequence
<220> FEATURE:
<223> OTHER INFORMATION: Flexible linker

<400> SEQUENCE: 38

Arg Pro Val Ser Pro Phe Thr Phe Pro Arg Leu Ser Asn Ser Trp Leu
1 5 10 15

Pro Ala

<210> SEQ ID NO 39
<211> LENGTH: 18
<212> TYPE: PRT
<213> ORGANISM: Artificial Sequence
<220> FEATURE:
<223> OTHER INFORMATION: Flexible linker

<400> SEQUENCE: 39

Ser Pro Ala Ala His Phe Pro Arg Ser Ile Pro Arg Pro Gly Pro Ile
1 5 10 15

Arg Thr

<210> SEQ ID NO 40
<211> LENGTH: 18
<212> TYPE: PRT
<213> ORGANISM: Artificial Sequence
<220> FEATURE:
<223> OTHER INFORMATION: Flexible linker

<400> SEQUENCE: 40

```
Ala Pro Gly Pro Ser Ala Pro Ser His Arg Ser Leu Pro Ser Arg Ala
1               5                   10                  15

Phe Gly


<210> SEQ ID NO 41
<211> LENGTH: 18
<212> TYPE: PRT
<213> ORGANISM: Artificial Sequence
<220> FEATURE:
<223> OTHER INFORMATION: Flexible linker

<400> SEQUENCE: 41

Pro Arg Asn Ser Ile His Phe Leu His Pro Leu Leu Val Ala Pro Leu
1               5                   10                  15

Gly Ala


<210> SEQ ID NO 42
<211> LENGTH: 18
<212> TYPE: PRT
<213> ORGANISM: Artificial Sequence
<220> FEATURE:
<223> OTHER INFORMATION: Flexible linker

<400> SEQUENCE: 42

Met Pro Ser Leu Ser Gly Val Leu Gln Val Arg Tyr Leu Ser Pro Pro
1               5                   10                  15

Asp Leu


<210> SEQ ID NO 43
<211> LENGTH: 18
<212> TYPE: PRT
<213> ORGANISM: Artificial Sequence
<220> FEATURE:
<223> OTHER INFORMATION: Flexible linker

<400> SEQUENCE: 43

Ser Pro Gln Tyr Pro Ser Pro Leu Thr Leu Thr Leu Pro Pro His Pro
1               5                   10                  15

Ser Leu


<210> SEQ ID NO 44
<211> LENGTH: 18
<212> TYPE: PRT
<213> ORGANISM: Artificial Sequence
<220> FEATURE:
<223> OTHER INFORMATION: Flexiible linker

<400> SEQUENCE: 44

Asn Pro Ser Leu Asn Pro Pro Ser Tyr Leu His Arg Ala Pro Ser Arg
1               5                   10                  15

Ile Ser


<210> SEQ ID NO 45
<211> LENGTH: 17
<212> TYPE: PRT
<213> ORGANISM: Artificial Sequence
<220> FEATURE:
<223> OTHER INFORMATION: Flexible linker

<400> SEQUENCE: 45

Leu Pro Trp Arg Thr Ser Leu Leu Pro Ser Leu Pro Leu Arg Arg Arg
1               5                   10                  15

Pro
```

<210> SEQ ID NO 46
<211> LENGTH: 18
<212> TYPE: PRT
<213> ORGANISM: Artificial Sequence
<220> FEATURE:
<223> OTHER INFORMATION: Flexible linker

<400> SEQUENCE: 46

```
Pro Pro Leu Phe Ala Lys Gly Pro Val Gly Leu Leu Ser Arg Ser Phe
1               5                   10                  15

Pro Pro
```

<210> SEQ ID NO 47
<211> LENGTH: 18
<212> TYPE: PRT
<213> ORGANISM: Artificial Sequence
<220> FEATURE:
<223> OTHER INFORMATION: Flexible linker

<400> SEQUENCE: 47

```
Val Pro Pro Ala Pro Val Val Ser Leu Arg Ser Ala His Ala Arg Pro
1               5                   10                  15

Pro Tyr
```

<210> SEQ ID NO 48
<211> LENGTH: 17
<212> TYPE: PRT
<213> ORGANISM: Artificial Sequence
<220> FEATURE:
<223> OTHER INFORMATION: Flexible linker

<400> SEQUENCE: 48

```
Leu Arg Pro Thr Pro Pro Arg Val Arg Ser Tyr Thr Cys Cys Pro Thr
1               5                   10                  15

Pro
```

<210> SEQ ID NO 49
<211> LENGTH: 18
<212> TYPE: PRT
<213> ORGANISM: Artificial Sequence
<220> FEATURE:
<223> OTHER INFORMATION: Flexible linker

<400> SEQUENCE: 49

```
Pro Asn Val Ala His Val Leu Pro Leu Leu Thr Val Pro Trp Asp Asn
1               5                   10                  15

Leu Arg
```

<210> SEQ ID NO 50
<211> LENGTH: 18
<212> TYPE: PRT
<213> ORGANISM: Artificial Sequence
<220> FEATURE:
<223> OTHER INFORMATION: Flexible linker

<400> SEQUENCE: 50

```
Cys Asn Pro Leu Leu Pro Leu Cys Ala Arg Ser Pro Ala Val Arg Thr
1               5                   10                  15

Phe Pro
```

<210> SEQ ID NO 51
<211> LENGTH: 11

<212> TYPE: PRT
<213> ORGANISM: Artificial Sequence
<220> FEATURE:
<223> OTHER INFORMATION: Rigid linker

<400> SEQUENCE: 51

Gly Ala Pro Ala Pro Ala Ala Pro Ala Pro Ala
1 5 10

<210> SEQ ID NO 52
<211> LENGTH: 4
<212> TYPE: PRT
<213> ORGANISM: Artificial Sequence
<220> FEATURE:
<223> OTHER INFORMATION: Rigid linker

<400> SEQUENCE: 52

Pro Pro Pro Pro
1

<210> SEQ ID NO 53
<211> LENGTH: 112
<212> TYPE: PRT
<213> ORGANISM: Homo sapiens

<400> SEQUENCE: 53

Asn Trp Val Asn Val Ile Ser Asp Leu Lys Lys Ile Glu Asp Leu Ile
1 5 10 15

Gln Ser Met His Ile Asp Ala Thr Leu Tyr Thr Glu Ser Asp Val His
20 25 30

Pro Ser Cys Lys Val Thr Ala Met Lys Cys Phe Leu Leu Glu Leu Gln
35 40 45

Val Ile Ser Leu Glu Ser Gly Asp Ala Ser Ile His Asp Thr Val Glu
50 55 60

Asn Leu Ile Ile Leu Ala Asn Asn Ser Leu Ser Ser Asn Gly Asn Val
65 70 75 80

Thr Glu Ser Gly Cys Lys Glu Cys Glu Glu Leu Glu Glu Lys Asn Ile
85 90 95

Lys Glu Phe Leu Gln Ser Phe Val His Ile Val Gln Met Phe Ile Asn
100 105 110

<210> SEQ ID NO 54
<211> LENGTH: 352
<212> TYPE: PRT
<213> ORGANISM: Artificial Sequence
<220> FEATURE:
<223> OTHER INFORMATION: CA645 Fab HC Fwk3 IL-15

<400> SEQUENCE: 54

Glu Val Gln Leu Leu Glu Ser Gly Gly Gly Leu Val Gln Pro Gly Gly
1 5 10 15

Ser Leu Arg Leu Ser Cys Ala Val Ser Gly Ile Asp Leu Ser Asn Tyr
20 25 30

Ala Ile Asn Trp Val Arg Gln Ala Pro Gly Lys Gly Leu Glu Trp Ile
35 40 45

Gly Ile Ile Trp Ala Ser Gly Thr Thr Phe Tyr Ala Thr Trp Ala Lys
50 55 60

Gly Arg Phe Thr Ile Ser Arg Asp Asn Lys Tyr Gln Ser Gly Gly Ser
65 70 75 80

Gly Met Gly Asn Trp Val Asn Val Ile Ser Asp Leu Lys Lys Ile Glu
85 90 95

```
Asp Leu Ile Gln Ser Met His Ile Asp Ala Thr Leu Tyr Thr Glu Ser
            100                 105                 110

Asp Val His Pro Ser Cys Lys Val Thr Ala Met Lys Cys Phe Leu Leu
        115                 120                 125

Glu Leu Gln Val Ile Ser Leu Glu Ser Gly Asp Ala Ser Ile His Asp
    130                 135                 140

Thr Val Glu Asn Leu Ile Ile Leu Ala Asn Asn Ser Leu Ser Ser Asn
145                 150                 155                 160

Gly Asn Val Thr Glu Ser Gly Cys Lys Glu Cys Glu Glu Leu Glu Glu
                165                 170                 175

Lys Asn Ile Lys Glu Phe Leu Gln Ser Phe Val His Ile Val Gln Met
            180                 185                 190

Phe Ile Asn Ser Gly Gly Ser Tyr Thr Tyr Lys Asn Thr Val Tyr Leu
        195                 200                 205

Gln Met Asn Ser Leu Arg Ala Glu Asp Thr Ala Val Tyr Tyr Cys Ala
    210                 215                 220

Arg Thr Val Pro Gly Tyr Ser Thr Ala Pro Tyr Phe Asp Leu Trp Gly
225                 230                 235                 240

Gln Gly Thr Leu Val Thr Val Ser Ser Ala Ser Thr Lys Gly Pro Ser
                245                 250                 255

Val Phe Pro Leu Ala Pro Ser Ser Lys Ser Thr Ser Gly Gly Thr Ala
            260                 265                 270

Ala Leu Gly Cys Leu Val Lys Asp Tyr Phe Pro Glu Pro Val Thr Val
        275                 280                 285

Ser Trp Asn Ser Gly Ala Leu Thr Ser Gly Val His Thr Phe Pro Ala
    290                 295                 300

Val Leu Gln Ser Ser Gly Leu Tyr Ser Leu Ser Ser Val Val Thr Val
305                 310                 315                 320

Pro Ser Ser Ser Leu Gly Thr Gln Thr Tyr Ile Cys Asn Val Asn His
                325                 330                 335

Lys Pro Ser Asn Thr Lys Val Asp Lys Lys Val Glu Pro Lys Ser Cys
            340                 345                 350


<210> SEQ ID NO 55
<211> LENGTH: 133
<212> TYPE: PRT
<213> ORGANISM: Homo sapiens

<400> SEQUENCE: 55

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
```

```
        115                 120                 125

Ile Ser Thr Leu Thr
    130


<210> SEQ ID NO 56
<211> LENGTH: 368
<212> TYPE: PRT
<213> ORGANISM: Artificial Sequence
<220> FEATURE:
<223> OTHER INFORMATION: CA645 Fab HC Fwk3 IL-2

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Gly Gly Gly Ser Gly Gly
65                  70                  75                  80

Gly Gly Ala Pro Thr Ser Ser Ser Thr Lys Lys Thr Gln Leu Gln Leu
                85                  90                  95

Glu His Leu Leu Leu Asp Leu Gln Met Ile Leu Asn Gly Ile Asn Asn
            100                 105                 110

Tyr Lys Asn Pro Lys Leu Thr Arg Met Leu Thr Phe Lys Phe Tyr Met
        115                 120                 125

Pro Lys Lys Ala Thr Glu Leu Lys His Leu Gln Cys Leu Glu Glu Glu
    130                 135                 140

Leu Lys Pro Leu Glu Glu Val Leu Asn Leu Ala Gln Ser Lys Asn Phe
145                 150                 155                 160

His Leu Arg Pro Arg Asp Leu Ile Ser Asn Ile Asn Val Ile Val Leu
                165                 170                 175

Glu Leu Lys Gly Ser Glu Thr Thr Phe Met Cys Glu Tyr Ala Asp Glu
            180                 185                 190

Thr Ala Thr Ile Val Glu Phe Leu Asn Arg Trp Ile Thr Phe Cys Gln
        195                 200                 205

Ser Ile Ile Ser Thr Leu Thr Gly Gly Gly Lys Asn Thr Val Tyr Leu
    210                 215                 220

Gln Met Asn Ser Leu Arg Ala Glu Asp Thr Ala Val Tyr Tyr Cys Ala
225                 230                 235                 240

Arg Thr Val Pro Gly Tyr Ser Thr Ala Pro Tyr Phe Asp Leu Trp Gly
                245                 250                 255

Gln Gly Thr Leu Val Thr Val Ser Ser Ala Ser Thr Lys Gly Pro Ser
            260                 265                 270

Val Phe Pro Leu Ala Pro Ser Ser Lys Ser Thr Ser Gly Gly Thr Ala
        275                 280                 285

Ala Leu Gly Cys Leu Val Lys Asp Tyr Phe Pro Glu Pro Val Thr Val
    290                 295                 300

Ser Trp Asn Ser Gly Ala Leu Thr Ser Gly Val His Thr Phe Pro Ala
305                 310                 315                 320

Val Leu Gln Ser Ser Gly Leu Tyr Ser Leu Ser Ser Val Val Thr Val
                325                 330                 335

Pro Ser Ser Ser Leu Gly Thr Gln Thr Tyr Ile Cys Asn Val Asn His
```

```
            340                 345                 350

Lys Pro Ser Asn Thr Lys Val Asp Lys Lys Val Glu Pro Lys Ser Cys
        355                 360                 365


<210> SEQ ID NO 57
<211> LENGTH: 178
<212> TYPE: PRT
<213> ORGANISM: Homo sapiens

<400> SEQUENCE: 57

Ala Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Val Ser Glu Cys Ala Thr Tyr Lys Leu Cys His Pro
        35                  40                  45

Glu Glu Leu Val Leu Leu Gly His Ser Leu Gly Ile Pro Trp Ala Pro
    50                  55                  60

Leu Ser Ser Cys Pro Ser Gln Ala Leu Gln Leu Ala Gly Cys Leu Ser
65                  70                  75                  80

Gln Leu His Ser Gly Leu Phe Leu Tyr Gln Gly Leu Leu Gln Ala Leu
                85                  90                  95

Glu Gly Ile Ser Pro Glu Leu Gly Pro Thr Leu Asp Thr Leu Gln Leu
            100                 105                 110

Asp Val Ala Asp Phe Ala Thr Thr Ile Trp Gln Gln Met Glu Glu Leu
        115                 120                 125

Gly Met Ala Pro Ala Leu Gln Pro Thr Gln Gly Ala Met Pro Ala Phe
    130                 135                 140

Ala Ser Ala Phe Gln Arg Arg Ala Gly Gly Val Leu Val Ala Ser His
145                 150                 155                 160

Leu Gln Ser Phe Leu Glu Val Ser Tyr Arg Val Leu Arg His Leu Ala
                165                 170                 175

Gln Pro


<210> SEQ ID NO 58
<211> LENGTH: 412
<212> TYPE: PRT
<213> ORGANISM: Artificial Sequence
<220> FEATURE:
<223> OTHER INFORMATION: CA645 Fab HC Fwk3 G-CSF

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Gly Gly Gly Gly Ser Ala
65                  70                  75                  80

Thr Pro Leu Gly Pro Ala Ser Ser Leu Pro Gln Ser Phe Leu Leu Lys
                85                  90                  95

Cys Leu Glu Gln Val Arg Lys Ile Gln Gly Asp Gly Ala Ala Leu Gln
            100                 105                 110
```

```
Glu Lys Leu Val Ser Glu Cys Ala Thr Tyr Lys Leu Cys His Pro Glu
        115                 120                 125

Glu Leu Val Leu Leu Gly His Ser Leu Gly Ile Pro Trp Ala Pro Leu
    130                 135                 140

Ser Ser Cys Pro Ser Gln Ala Leu Gln Leu Ala Gly Cys Leu Ser Gln
145                 150                 155                 160

Leu His Ser Gly Leu Phe Leu Tyr Gln Gly Leu Leu Gln Ala Leu Glu
                165                 170                 175

Gly Ile Ser Pro Glu Leu Gly Pro Thr Leu Asp Thr Leu Gln Leu Asp
            180                 185                 190

Val Ala Asp Phe Ala Thr Thr Ile Trp Gln Gln Met Glu Glu Leu Gly
        195                 200                 205

Met Ala Pro Ala Leu Gln Pro Thr Gln Gly Ala Met Pro Ala Phe Ala
    210                 215                 220

Ser Ala Phe Gln Arg Arg Ala Gly Gly Val Leu Val Ala Ser His Leu
225                 230                 235                 240

Gln Ser Phe Leu Glu Val Ser Tyr Arg Val Leu Arg His Leu Ala Gln
                245                 250                 255

Pro Ser Gly Gly Gly Gly Lys Asn Thr Val Tyr Leu Gln Met Asn Ser
            260                 265                 270

Leu Arg Ala Glu Asp Thr Ala Val Tyr Tyr Cys Ala Arg Thr Val Pro
        275                 280                 285

Gly Tyr Ser Thr Ala Pro Tyr Phe Asp Leu Trp Gly Gln Gly Thr Leu
    290                 295                 300

Val Thr Val Ser Ser Ala Ser Thr Lys Gly Pro Ser Val Phe Pro Leu
305                 310                 315                 320

Ala Pro Ser Ser Lys Ser Thr Ser Gly Gly Thr Ala Ala Leu Gly Cys
                325                 330                 335

Leu Val Lys Asp Tyr Phe Pro Glu Pro Val Thr Val Ser Trp Asn Ser
            340                 345                 350

Gly Ala Leu Thr Ser Gly Val His Thr Phe Pro Ala Val Leu Gln Ser
        355                 360                 365

Ser Gly Leu Tyr Ser Leu Ser Ser Val Val Thr Val Pro Ser Ser Ser
    370                 375                 380

Leu Gly Thr Gln Thr Tyr Ile Cys Asn Val Asn His Lys Pro Ser Asn
385                 390                 395                 400

Thr Lys Val Asp Lys Lys Val Glu Pro Lys Ser Cys
                405                 410
```

<210> SEQ ID NO 59
<211> LENGTH: 127
<212> TYPE: PRT
<213> ORGANISM: Homo sapiens

<400> SEQUENCE: 59

```
Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80
```

```
Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125


<210> SEQ ID NO 60
<211> LENGTH: 362
<212> TYPE: PRT
<213> ORGANISM: Artificial Sequence
<220> FEATURE:
<223> OTHER INFORMATION: CA645 Fab HC Fwk3 GM-CSF

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Gly Gly Gly Ser Gly Gly
65                  70                  75                  80

Gly Gly Ala Pro Ala Arg Ser Pro Ser Pro Ser Thr Gln Pro Trp Glu
                85                  90                  95

His Val Asn Ala Ile Gln Glu Ala Arg Arg Leu Leu Asn Leu Ser Arg
            100                 105                 110

Asp Thr Ala Ala Glu Met Asn Glu Thr Val Glu Val Ile Ser Glu Met
        115                 120                 125

Phe Asp Leu Gln Glu Pro Thr Cys Leu Gln Thr Arg Leu Glu Leu Tyr
    130                 135                 140

Lys Gln Gly Leu Arg Gly Ser Leu Thr Lys Leu Lys Gly Pro Leu Thr
145                 150                 155                 160

Met Met Ala Ser His Tyr Lys Gln His Cys Pro Pro Thr Pro Glu Thr
                165                 170                 175

Ser Cys Ala Thr Gln Ile Ile Thr Phe Glu Ser Phe Lys Glu Asn Leu
            180                 185                 190

Lys Asp Phe Leu Leu Val Ile Pro Phe Asp Cys Trp Glu Pro Val Gln
        195                 200                 205

Glu Gly Gly Gly Lys Asn Thr Val Tyr Leu Gln Met Asn Ser Leu Arg
    210                 215                 220

Ala Glu Asp Thr Ala Val Tyr Tyr Cys Ala Arg Thr Val Pro Gly Tyr
225                 230                 235                 240

Ser Thr Ala Pro Tyr Phe Asp Leu Trp Gly Gln Gly Thr Leu Val Thr
                245                 250                 255

Val Ser Ser Ala Ser Thr Lys Gly Pro Ser Val Phe Pro Leu Ala Pro
            260                 265                 270

Ser Ser Lys Ser Thr Ser Gly Gly Thr Ala Ala Leu Gly Cys Leu Val
        275                 280                 285

Lys Asp Tyr Phe Pro Glu Pro Val Thr Val Ser Trp Asn Ser Gly Ala
    290                 295                 300

Leu Thr Ser Gly Val His Thr Phe Pro Ala Val Leu Gln Ser Ser Gly
305                 310                 315                 320
```

```
Leu Tyr Ser Leu Ser Ser Val Val Thr Val Pro Ser Ser Ser Leu Gly
                325                 330                 335

Thr Gln Thr Tyr Ile Cys Asn Val Asn His Lys Pro Ser Asn Thr Lys
            340                 345                 350

Val Asp Lys Lys Val Glu Pro Lys Ser Cys
        355                 360


<210> SEQ ID NO 61
<211> LENGTH: 359
<212> TYPE: PRT
<213> ORGANISM: Artificial Sequence
<220> FEATURE:
<223> OTHER INFORMATION: CA645 Fab HC with GM-CSF at C-terminus of CH1

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Gly Gly Gly Ser Gly Gly Gly Ala Pro Ala Arg Ser Pro Ser Pro
225                 230                 235                 240

Ser Thr Gln Pro Trp Glu His Val Asn Ala Ile Gln Glu Ala Arg Arg
                245                 250                 255

Leu Leu Asn Leu Ser Arg Asp Thr Ala Ala Glu Met Asn Glu Thr Val
            260                 265                 270

Glu Val Ile Ser Glu Met Phe Asp Leu Gln Glu Pro Thr Cys Leu Gln
        275                 280                 285

Thr Arg Leu Glu Leu Tyr Lys Gln Gly Leu Arg Gly Ser Leu Thr Lys
    290                 295                 300

Leu Lys Gly Pro Leu Thr Met Met Ala Ser His Tyr Lys Gln His Cys
305                 310                 315                 320
```

```
Pro Pro Thr Pro Glu Thr Ser Cys Ala Thr Gln Ile Ile Thr Phe Glu
                325                 330                 335

Ser Phe Lys Glu Asn Leu Lys Asp Phe Leu Leu Val Ile Pro Phe Asp
            340                 345                 350

Cys Trp Glu Pro Val Gln Glu
        355


<210> SEQ ID NO 62
<211> LENGTH: 124
<212> TYPE: PRT
<213> ORGANISM: Murine

<400> SEQUENCE: 62

Ala Pro Thr Arg Ser Pro Ile Thr Val Thr Arg Pro Trp Lys His Val
1               5                   10                  15

Glu Ala Ile Lys Glu Ala Leu Asn Leu Leu Asp Asp Met Pro Val Thr
            20                  25                  30

Leu Asn Glu Glu Val Glu Val Val Ser Asn Glu Phe Ser Phe Lys Lys
        35                  40                  45

Leu Thr Cys Val Gln Thr Arg Leu Lys Ile Phe Glu Gln Gly Leu Arg
    50                  55                  60

Gly Asn Phe Thr Lys Leu Lys Gly Ala Leu Asn Met Thr Ala Ser Tyr
65                  70                  75                  80

Tyr Gln Thr Tyr Cys Pro Pro Thr Pro Glu Thr Asp Cys Glu Thr Gln
                85                  90                  95

Val Thr Thr Tyr Ala Asp Phe Ile Asp Ser Leu Lys Thr Phe Leu Thr
            100                 105                 110

Asp Ile Pro Phe Glu Cys Lys Lys Pro Gly Gln Lys
        115                 120


<210> SEQ ID NO 63
<211> LENGTH: 359
<212> TYPE: PRT
<213> ORGANISM: Artificial Sequence
<220> FEATURE:
<223> OTHER INFORMATION: CA645 Fab HC Fwk3 mGM-CSF

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Gly Gly Gly Ser Gly Gly
65                  70                  75                  80

Gly Gly Ala Pro Thr Arg Ser Pro Ile Thr Val Thr Arg Pro Trp Lys
                85                  90                  95

His Val Glu Ala Ile Lys Glu Ala Leu Asn Leu Leu Asp Asp Met Pro
            100                 105                 110

Val Thr Leu Asn Glu Glu Val Glu Val Val Ser Asn Glu Phe Ser Phe
        115                 120                 125

Lys Lys Leu Thr Cys Val Gln Thr Arg Leu Lys Ile Phe Glu Gln Gly
    130                 135                 140
```

```
Leu Arg Gly Asn Phe Thr Lys Leu Lys Gly Ala Leu Asn Met Thr Ala
145                 150                 155                 160

Ser Tyr Tyr Gln Thr Tyr Cys Pro Pro Thr Pro Glu Thr Asp Cys Glu
                165                 170                 175

Thr Gln Val Thr Thr Tyr Ala Asp Phe Ile Asp Ser Leu Lys Thr Phe
            180                 185                 190

Leu Thr Asp Ile Pro Phe Glu Cys Lys Lys Pro Gly Gln Lys Gly Gly
        195                 200                 205

Gly Lys Asn Thr Val Tyr Leu Gln Met Asn Ser Leu Arg Ala Glu Asp
    210                 215                 220

Thr Ala Val Tyr Tyr Cys Ala Arg Thr Val Pro Gly Tyr Ser Thr Ala
225                 230                 235                 240

Pro Tyr Phe Asp Leu Trp Gly Gln Gly Thr Leu Val Thr Val Ser Ser
                245                 250                 255

Ala Ser Thr Lys Gly Pro Ser Val Phe Pro Leu Ala Pro Ser Ser Lys
            260                 265                 270

Ser Thr Ser Gly Gly Thr Ala Ala Leu Gly Cys Leu Val Lys Asp Tyr
        275                 280                 285

Phe Pro Glu Pro Val Thr Val Ser Trp Asn Ser Gly Ala Leu Thr Ser
    290                 295                 300

Gly Val His Thr Phe Pro Ala Val Leu Gln Ser Ser Gly Leu Tyr Ser
305                 310                 315                 320

Leu Ser Ser Val Val Thr Val Pro Ser Ser Ser Leu Gly Thr Gln Thr
                325                 330                 335

Tyr Ile Cys Asn Val Asn His Lys Pro Ser Asn Thr Lys Val Asp Lys
            340                 345                 350

Lys Val Glu Pro Lys Ser Cys
        355


<210> SEQ ID NO 64
<211> LENGTH: 356
<212> TYPE: PRT
<213> ORGANISM: Artificial Sequence
<220> FEATURE:
<223> OTHER INFORMATION: CA645 Fab HC with mGM-CSF at C-terminus of CH1

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Gly Gly Gly Ser Gly Gly Gly Gly Ala Pro Thr Arg Ser Pro Ile Thr
225                 230                 235                 240

Val Thr Arg Pro Trp Lys His Val Glu Ala Ile Lys Glu Ala Leu Asn
                245                 250                 255

Leu Leu Asp Asp Met Pro Val Thr Leu Asn Glu Glu Val Glu Val Val
            260                 265                 270

Ser Asn Glu Phe Ser Phe Lys Lys Leu Thr Cys Val Gln Thr Arg Leu
        275                 280                 285

Lys Ile Phe Glu Gln Gly Leu Arg Gly Asn Phe Thr Lys Leu Lys Gly
    290                 295                 300

Ala Leu Asn Met Thr Ala Ser Tyr Tyr Gln Thr Tyr Cys Pro Pro Thr
305                 310                 315                 320

Pro Glu Thr Asp Cys Glu Thr Gln Val Thr Thr Tyr Ala Asp Phe Ile
                325                 330                 335

Asp Ser Leu Lys Thr Phe Leu Thr Asp Ile Pro Phe Glu Cys Lys Lys
            340                 345                 350

Pro Gly Gln Lys
        355
```

<210> SEQ ID NO 65
<211> LENGTH: 166
<212> TYPE: PRT
<213> ORGANISM: Homo sapiens

<400> SEQUENCE: 65

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160
```

```
Cys Arg Thr Gly Asp Arg
                165


<210> SEQ ID NO 66
<211> LENGTH: 401
<212> TYPE: PRT
<213> ORGANISM: Artificial Sequence
<220> FEATURE:
<223> OTHER INFORMATION: CA645 Fab HC Fwk3 EPO

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Gly Gly Gly Ser Gly Gly
65                  70                  75                  80

Gly Gly Ala Pro Pro Arg Leu Ile Cys Asp Ser Arg Val Leu Glu Arg
                85                  90                  95

Tyr Leu Leu Glu Ala Lys Glu Ala Glu Asn Ile Thr Thr Gly Cys Ala
            100                 105                 110

Glu His Cys Ser Leu Asn Glu Asn Ile Thr Val Pro Asp Thr Lys Val
        115                 120                 125

Asn Phe Tyr Ala Trp Lys Arg Met Glu Val Gly Gln Gln Ala Val Glu
    130                 135                 140

Val Trp Gln Gly Leu Ala Leu Leu Ser Glu Ala Val Leu Arg Gly Gln
145                 150                 155                 160

Ala Leu Leu Val Asn Ser Ser Gln Pro Trp Glu Pro Leu Gln Leu His
                165                 170                 175

Val Asp Lys Ala Val Ser Gly Leu Arg Ser Leu Thr Thr Leu Leu Arg
            180                 185                 190

Ala Leu Gly Ala Gln Lys Glu Ala Ile Ser Pro Pro Asp Ala Ala Ser
        195                 200                 205

Ala Ala Pro Leu Arg Thr Ile Thr Ala Asp Thr Phe Arg Lys Leu Phe
    210                 215                 220

Arg Val Tyr Ser Asn Phe Leu Arg Gly Lys Leu Lys Leu Tyr Thr Gly
225                 230                 235                 240

Glu Ala Cys Arg Thr Gly Asp Arg Gly Gly Gly Lys Asn Thr Val Tyr
                245                 250                 255

Leu Gln Met Asn Ser Leu Arg Ala Glu Asp Thr Ala Val Tyr Tyr Cys
            260                 265                 270

Ala Arg Thr Val Pro Gly Tyr Ser Thr Ala Pro Tyr Phe Asp Leu Trp
        275                 280                 285

Gly Gln Gly Thr Leu Val Thr Val Ser Ser Ala Ser Thr Lys Gly Pro
    290                 295                 300

Ser Val Phe Pro Leu Ala Pro Ser Ser Lys Ser Thr Ser Gly Gly Thr
305                 310                 315                 320

Ala Ala Leu Gly Cys Leu Val Lys Asp Tyr Phe Pro Glu Pro Val Thr
                325                 330                 335

Val Ser Trp Asn Ser Gly Ala Leu Thr Ser Gly Val His Thr Phe Pro
            340                 345                 350
```

Ala Val Leu Gln Ser Ser Gly Leu Tyr Ser Leu Ser Ser Val Val Thr
355 360 365

Val Pro Ser Ser Ser Leu Gly Thr Gln Thr Tyr Ile Cys Asn Val Asn
370 375 380

His Lys Pro Ser Asn Thr Lys Val Asp Lys Lys Val Glu Pro Lys Ser
385 390 395 400

Cys

<210> SEQ ID NO 67
<211> LENGTH: 125
<212> TYPE: PRT
<213> ORGANISM: Artificial Sequence
<220> FEATURE:
<223> OTHER INFORMATION: VHH6

<400> SEQUENCE: 67

Asp Val Gln Phe Val Glu Ser Gly Gly Gly Ser Val His Ala Gly Gly
1 5 10 15

Ser Leu Arg Leu Asn Cys Ala Thr Ser Gly Tyr Ile Tyr Ser Thr Tyr
20 25 30

Cys Met Gly Trp Phe Arg Gln Ala Pro Gly Lys Glu Arg Glu Gly Val
35 40 45

Ala His Ile Tyr Thr Asn Ser Gly Arg Thr Tyr Tyr Ala Asp Ser Val
50 55 60

Lys Gly Arg Phe Thr Ile Ser Gln Asp Asn Ala Lys Asn Thr Val Tyr
65 70 75 80

Leu Gln Met Asn Ser Leu Lys Pro Glu Asp Thr Ala Ile Tyr Tyr Cys
85 90 95

Ala Ala Arg Pro Ser Ile Arg Cys Ala Ser Phe Ser Ala Thr Glu Tyr
100 105 110

Lys Asp Trp Gly Gln Gly Thr Gln Val Thr Val Ser Ser
115 120 125

<210> SEQ ID NO 68
<211> LENGTH: 369
<212> TYPE: PRT
<213> ORGANISM: Artificial Sequence
<220> FEATURE:
<223> OTHER INFORMATION: CA645 Fab HC Fwk3 VHH6

<400> SEQUENCE: 68

Glu Val Gln Leu Leu Glu Ser Gly Gly Gly Leu Val Gln Pro Gly Gly
1 5 10 15

Ser Leu Arg Leu Ser Cys Ala Val Ser Gly Ile Asp Leu Ser Asn Tyr
20 25 30

Ala Ile Asn Trp Val Arg Gln Ala Pro Gly Lys Gly Leu Glu Trp Ile
35 40 45

Gly Ile Ile Trp Ala Ser Gly Thr Thr Phe Tyr Ala Thr Trp Ala Lys
50 55 60

Gly Arg Phe Thr Ile Ser Arg Asp Asn Ser Gly Gly Gly Gly Ser Gly
65 70 75 80

Gly Gly Gly Ser Asp Val Gln Phe Val Glu Ser Gly Gly Gly Ser Val
85 90 95

His Ala Gly Gly Ser Leu Arg Leu Asn Cys Ala Thr Ser Gly Tyr Ile
100 105 110

Tyr Ser Thr Tyr Cys Met Gly Trp Phe Arg Gln Ala Pro Gly Lys Glu
115 120 125

```
Arg Glu Gly Val Ala His Ile Tyr Thr Asn Ser Gly Arg Thr Tyr Tyr
    130                 135                 140

Ala Asp Ser Val Lys Gly Arg Phe Thr Ile Ser Gln Asp Asn Ala Lys
145                 150                 155                 160

Asn Thr Val Tyr Leu Gln Met Asn Ser Leu Lys Pro Glu Asp Thr Ala
                165                 170                 175

Ile Tyr Tyr Cys Ala Ala Arg Pro Ser Ile Arg Cys Ala Ser Phe Ser
            180                 185                 190

Ala Thr Glu Tyr Lys Asp Trp Gly Gln Gly Thr Gln Val Thr Val Ser
        195                 200                 205

Ser Gly Gly Gly Gly Ser Gly Gly Gly Gly Ser Lys Asn Thr Val Tyr
    210                 215                 220

Leu Gln Met Asn Ser Leu Arg Ala Glu Asp Thr Ala Val Tyr Tyr Cys
225                 230                 235                 240

Ala Arg Thr Val Pro Gly Tyr Ser Thr Ala Pro Tyr Phe Asp Leu Trp
                245                 250                 255

Gly Gln Gly Thr Leu Val Thr Val Ser Ser Ala Ser Thr Lys Gly Pro
            260                 265                 270

Ser Val Phe Pro Leu Ala Pro Ser Ser Lys Ser Thr Ser Gly Gly Thr
        275                 280                 285

Ala Ala Leu Gly Cys Leu Val Lys Asp Tyr Phe Pro Glu Pro Val Thr
    290                 295                 300

Val Ser Trp Asn Ser Gly Ala Leu Thr Ser Gly Val His Thr Phe Pro
305                 310                 315                 320

Ala Val Leu Gln Ser Ser Gly Leu Tyr Ser Leu Ser Ser Val Val Thr
                325                 330                 335

Val Pro Ser Ser Ser Leu Gly Thr Gln Thr Tyr Ile Cys Asn Val Asn
            340                 345                 350

His Lys Pro Ser Asn Thr Lys Val Asp Lys Lys Val Glu Pro Lys Ser
        355                 360                 365

Cys
```

<210> SEQ ID NO 69
<211> LENGTH: 119
<212> TYPE: PRT
<213> ORGANISM: Artificial Sequence
<220> FEATURE:
<223> OTHER INFORMATION: VHH15

<400> SEQUENCE: 69

```
Gln Val Gln Leu Val Glu Ser Gly Gly Gly Ser Val Gln Ala Gly Gly
1               5                   10                  15

Ser Leu Arg Leu Ser Cys Val Ala Ala Ser Gly Tyr Thr Gly Cys Thr
            20                  25                  30

Tyr Asp Met Arg Trp Tyr Arg Gln Ala Pro Gly Lys Glu Arg Glu Phe
        35                  40                  45

Val Ser Gly Ile Asp Ser Asp Gly Arg Ala Thr Tyr Ala Asp Ser Val
    50                  55                  60

Lys Gly Arg Phe Thr Ile Ser Gln Ser Asn Ala Lys Ile Ala Val Tyr
65                  70                  75                  80

Leu Gln Met Asp Ser Leu Lys Leu Glu Asp Thr Ala Met Tyr Tyr Cys
                85                  90                  95

Asn Leu Gln Cys Leu Arg Tyr Pro Gly Glu Tyr Tyr Trp Gly Gln Gly
            100                 105                 110
```

```
Thr Gln Val Thr Val Ser Ser
        115


<210> SEQ ID NO 70
<211> LENGTH: 363
<212> TYPE: PRT
<213> ORGANISM: Artificial Sequence
<220> FEATURE:
<223> OTHER INFORMATION: CA645 Fab HC Fwk3 VHH15

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Gly Gly Gly Gly Ser Gly
65                  70                  75                  80

Gly Gly Gly Ser Gln Val Gln Leu Val Glu Ser Gly Gly Gly Ser Val
                85                  90                  95

Gln Ala Gly Gly Ser Leu Arg Leu Ser Cys Val Ala Ala Ser Gly Tyr
            100                 105                 110

Thr Gly Cys Thr Tyr Asp Met Arg Trp Tyr Arg Gln Ala Pro Gly Lys
        115                 120                 125

Glu Arg Glu Phe Val Ser Gly Ile Asp Ser Asp Gly Arg Ala Thr Tyr
    130                 135                 140

Ala Asp Ser Val Lys Gly Arg Phe Thr Ile Ser Gln Ser Asn Ala Lys
145                 150                 155                 160

Ile Ala Val Tyr Leu Gln Met Asp Ser Leu Lys Leu Glu Asp Thr Ala
                165                 170                 175

Met Tyr Tyr Cys Asn Leu Gln Cys Leu Arg Tyr Pro Gly Glu Tyr Tyr
            180                 185                 190

Trp Gly Gln Gly Thr Gln Val Thr Val Ser Ser Gly Gly Gly Gly Ser
        195                 200                 205

Gly Gly Gly Gly Ser Lys Asn Thr Val Tyr Leu Gln Met Asn Ser Leu
    210                 215                 220

Arg Ala Glu Asp Thr Ala Val Tyr Tyr Cys Ala Arg Thr Val Pro Gly
225                 230                 235                 240

Tyr Ser Thr Ala Pro Tyr Phe Asp Leu Trp Gly Gln Gly Thr Leu Val
                245                 250                 255

Thr Val Ser Ser Ala Ser Thr Lys Gly Pro Ser Val Phe Pro Leu Ala
            260                 265                 270

Pro Ser Ser Lys Ser Thr Ser Gly Gly Thr Ala Ala Leu Gly Cys Leu
        275                 280                 285

Val Lys Asp Tyr Phe Pro Glu Pro Val Thr Val Ser Trp Asn Ser Gly
    290                 295                 300

Ala Leu Thr Ser Gly Val His Thr Phe Pro Ala Val Leu Gln Ser Ser
305                 310                 315                 320

Gly Leu Tyr Ser Leu Ser Ser Val Val Thr Val Pro Ser Ser Ser Leu
                325                 330                 335

Gly Thr Gln Thr Tyr Ile Cys Asn Val Asn His Lys Pro Ser Asn Thr
            340                 345                 350
```

```
Lys Val Asp Lys Lys Val Glu Pro Lys Ser Cys
        355                 360


<210> SEQ ID NO 71
<211> LENGTH: 190
<212> TYPE: PRT
<213> ORGANISM: Homo sapiens

<400> SEQUENCE: 71

Gln Gly Trp Gln Ala Phe Lys Asn Asp Ala Thr Glu Ile Ile Pro Glu
1               5                   10                  15

Leu Gly Glu Tyr Pro Glu Pro Pro Pro Glu Leu Glu Asn Asn Lys Thr
            20                  25                  30

Met Asn Arg Ala Glu Asn Gly Gly Arg Pro Pro His His Pro Phe Glu
        35                  40                  45

Thr Lys Asp Val Ser Glu Tyr Ser Cys Arg Glu Leu His Phe Thr Arg
    50                  55                  60

Tyr Val Thr Asp Gly Pro Cys Arg Ser Ala Lys Pro Val Thr Glu Leu
65                  70                  75                  80

Val Cys Ser Gly Gln Cys Gly Pro Ala Arg Leu Leu Pro Asn Ala Ile
                85                  90                  95

Gly Arg Gly Lys Trp Trp Arg Pro Ser Gly Pro Asp Phe Arg Cys Ile
            100                 105                 110

Pro Asp Arg Tyr Arg Ala Gln Arg Val Gln Leu Leu Cys Pro Gly Gly
        115                 120                 125

Glu Ala Pro Arg Ala Arg Lys Val Arg Leu Val Ala Ser Cys Lys Cys
    130                 135                 140

Lys Arg Leu Thr Arg Phe His Asn Gln Ser Glu Leu Lys Asp Phe Gly
145                 150                 155                 160

Thr Glu Ala Ala Arg Pro Gln Lys Gly Arg Lys Pro Arg Pro Arg Ala
                165                 170                 175

Arg Ser Ala Lys Ala Asn Gln Ala Glu Leu Glu Asn Ala Tyr
            180                 185                 190


<210> SEQ ID NO 72
<211> LENGTH: 88
<212> TYPE: PRT
<213> ORGANISM: Artificial Sequence
<220> FEATURE:
<223> OTHER INFORMATION: Core domain of human sclerostin

<400> SEQUENCE: 72

Cys Arg Glu Leu His Phe Thr Arg Tyr Val Thr Asp Gly Pro Cys Arg
1               5                   10                  15

Ser Ala Lys Pro Val Thr Glu Leu Val Cys Ser Gly Gln Cys Gly Pro
            20                  25                  30

Ala Arg Leu Leu Pro Asn Ala Ile Gly Arg Gly Lys Trp Trp Arg Pro
        35                  40                  45

Ser Gly Pro Asp Phe Arg Cys Ile Pro Asp Arg Tyr Arg Ala Gln Arg
    50                  55                  60

Val Gln Leu Leu Cys Pro Gly Gly Glu Ala Pro Arg Ala Arg Lys Val
65                  70                  75                  80

Arg Leu Val Ala Ser Cys Lys Cys
                85


<210> SEQ ID NO 73
<211> LENGTH: 314
<212> TYPE: PRT
```

<213> ORGANISM: Artificial Sequence
<220> FEATURE:
<223> OTHER INFORMATION: CA645 Fab heavy chain with human sclerostin core domain inserted into framework 3, single S linkers

<400> SEQUENCE: 73

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Ser Cys Arg Glu Leu His
65                  70                  75                  80

Phe Thr Arg Tyr Val Thr Asp Gly Pro Cys Arg Ser Ala Lys Pro Val
                85                  90                  95

Thr Glu Leu Val Cys Ser Gly Gln Cys Gly Pro Ala Arg Leu Leu Pro
            100                 105                 110

Asn Ala Ile Gly Arg Gly Lys Trp Trp Arg Pro Ser Gly Pro Asp Phe
        115                 120                 125

Arg Cys Ile Pro Asp Arg Tyr Arg Ala Gln Arg Val Gln Leu Leu Cys
    130                 135                 140

Pro Gly Gly Glu Ala Pro Arg Ala Arg Lys Val Arg Leu Val Ala Ser
145                 150                 155                 160

Cys Lys Cys Ser Lys Asn Thr Val Tyr Leu Gln Met Asn Ser Leu Arg
                165                 170                 175

Ala Glu Asp Thr Ala Val Tyr Tyr Cys Ala Arg Thr Val Pro Gly Tyr
            180                 185                 190

Ser Thr Ala Pro Tyr Phe Asp Leu Trp Gly Gln Gly Thr Leu Val Thr
        195                 200                 205

Val Ser Ser Ala Ser Thr Lys Gly Pro Ser Val Phe Pro Leu Ala Pro
    210                 215                 220

Ser Ser Lys Ser Thr Ser Gly Gly Thr Ala Ala Leu Gly Cys Leu Val
225                 230                 235                 240

Lys Asp Tyr Phe Pro Glu Pro Val Thr Val Ser Trp Asn Ser Gly Ala
                245                 250                 255

Leu Thr Ser Gly Val His Thr Phe Pro Ala Val Leu Gln Ser Ser Gly
            260                 265                 270

Leu Tyr Ser Leu Ser Ser Val Val Thr Val Pro Ser Ser Ser Leu Gly
        275                 280                 285

Thr Gln Thr Tyr Ile Cys Asn Val Asn His Lys Pro Ser Asn Thr Lys
    290                 295                 300

Val Asp Lys Lys Val Glu Pro Lys Ser Cys
305                 310
```

<210> SEQ ID NO 74
<211> LENGTH: 333
<212> TYPE: PRT
<213> ORGANISM: Artificial Sequence
<220> FEATURE:
<223> OTHER INFORMATION: CA645 Fab heavy chain with human sclerostin core domain inserted into framework 3, Gly-Ser (2X G4S) linkers

<400> SEQUENCE: 74

```
Glu Val Gln Leu Leu Glu Ser Gly Gly Gly Leu Val Gln Pro Gly Gly
```

```
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Gly Gly Gly Gly Ser Gly
65                  70                  75                  80

Gly Gly Gly Ser Cys Arg Glu Leu His Phe Thr Arg Tyr Val Thr Asp
                85                  90                  95

Gly Pro Cys Arg Ser Ala Lys Pro Val Thr Glu Leu Val Cys Ser Gly
            100                 105                 110

Gln Cys Gly Pro Ala Arg Leu Leu Pro Asn Ala Ile Gly Arg Gly Lys
        115                 120                 125

Trp Trp Arg Pro Ser Gly Pro Asp Phe Arg Cys Ile Pro Asp Arg Tyr
    130                 135                 140

Arg Ala Gln Arg Val Gln Leu Leu Cys Pro Gly Gly Glu Ala Pro Arg
145                 150                 155                 160

Ala Arg Lys Val Arg Leu Val Ala Ser Cys Lys Cys Ser Gly Gly Gly
                165                 170                 175

Gly Ser Gly Gly Gly Gly Ser Lys Asn Thr Val Tyr Leu Gln Met Asn
            180                 185                 190

Ser Leu Arg Ala Glu Asp Thr Ala Val Tyr Tyr Cys Ala Arg Thr Val
        195                 200                 205

Pro Gly Tyr Ser Thr Ala Pro Tyr Phe Asp Leu Trp Gly Gln Gly Thr
    210                 215                 220

Leu Val Thr Val Ser Ser Ala Ser Thr Lys Gly Pro Ser Val Phe Pro
225                 230                 235                 240

Leu Ala Pro Ser Ser Lys Ser Thr Ser Gly Gly Thr Ala Ala Leu Gly
                245                 250                 255

Cys Leu Val Lys Asp Tyr Phe Pro Glu Pro Val Thr Val Ser Trp Asn
            260                 265                 270

Ser Gly Ala Leu Thr Ser Gly Val His Thr Phe Pro Ala Val Leu Gln
        275                 280                 285

Ser Ser Gly Leu Tyr Ser Leu Ser Ser Val Val Thr Val Pro Ser Ser
    290                 295                 300

Ser Leu Gly Thr Gln Thr Tyr Ile Cys Asn Val Asn His Lys Pro Ser
305                 310                 315                 320

Asn Thr Lys Val Asp Lys Lys Val Glu Pro Lys Ser Cys
                325                 330


<210> SEQ ID NO 75
<211> LENGTH: 323
<212> TYPE: PRT
<213> ORGANISM: Artificial Sequence
<220> FEATURE:
<223> OTHER INFORMATION: CA645 Fab heavy chain with human sclerostin
      core domain inserted into framework 3, rigid linkers

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30
```

```
Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Ile Pro Phe Thr Val Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Glu Ala Pro Arg Ala Arg Lys Val Arg
145                 150                 155                 160

Leu Val Ala Ser Cys Lys Cys Glu Tyr His Gly Leu Gln Lys Asn Thr
                165                 170                 175

Val Tyr Leu Gln Met Asn Ser Leu Arg Ala Glu Asp Thr Ala Val Tyr
            180                 185                 190

Tyr Cys Ala Arg Thr Val Pro Gly Tyr Ser Thr Ala Pro Tyr Phe Asp
        195                 200                 205

Leu Trp Gly Gln Gly Thr Leu Val Thr Val Ser Ser Ala Ser Thr Lys
    210                 215                 220

Gly Pro Ser Val Phe Pro Leu Ala Pro Ser Ser Lys Ser Thr Ser Gly
225                 230                 235                 240

Gly Thr Ala Ala Leu Gly Cys Leu Val Lys Asp Tyr Phe Pro Glu Pro
                245                 250                 255

Val Thr Val Ser Trp Asn Ser Gly Ala Leu Thr Ser Gly Val His Thr
            260                 265                 270

Phe Pro Ala Val Leu Gln Ser Ser Gly Leu Tyr Ser Leu Ser Ser Val
        275                 280                 285

Val Thr Val Pro Ser Ser Ser Leu Gly Thr Gln Thr Tyr Ile Cys Asn
    290                 295                 300

Val Asn His Lys Pro Ser Asn Thr Lys Val Asp Lys Lys Val Glu Pro
305                 310                 315                 320

Lys Ser Cys


<210> SEQ ID NO 76
<211> LENGTH: 425
<212> TYPE: PRT
<213> ORGANISM: Artificial Sequence
<220> FEATURE:
<223> OTHER INFORMATION: CA645 Fab heavy chain with human mature
      full-length sclerostin inserted into framework 3, Gly-Ser (1X G4S)
      linkers

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60
```

```
Gly Arg Phe Thr Ile Ser Arg Asp Asn Ser Gly Gly Gly Gly Ser Gln
65                  70                  75                  80

Gly Trp Gln Ala Phe Lys Asn Asp Ala Thr Glu Ile Ile Pro Glu Leu
                85                  90                  95

Gly Glu Tyr Pro Glu Pro Pro Pro Glu Leu Glu Asn Asn Lys Thr Met
            100                 105                 110

Asn Arg Ala Glu Asn Gly Gly Arg Pro Pro His His Pro Phe Glu Thr
        115                 120                 125

Lys Asp Val Ser Glu Tyr Ser Cys Arg Glu Leu His Phe Thr Arg Tyr
    130                 135                 140

Val Thr Asp Gly Pro Cys Arg Ser Ala Lys Pro Val Thr Glu Leu Val
145                 150                 155                 160

Cys Ser Gly Gln Cys Gly Pro Ala Arg Leu Leu Pro Asn Ala Ile Gly
                165                 170                 175

Arg Gly Lys Trp Trp Arg Pro Ser Gly Pro Asp Phe Arg Cys Ile Pro
            180                 185                 190

Asp Arg Tyr Arg Ala Gln Arg Val Gln Leu Leu Cys Pro Gly Gly Glu
        195                 200                 205

Ala Pro Arg Ala Arg Lys Val Arg Leu Val Ala Ser Cys Lys Cys Lys
    210                 215                 220

Arg Leu Thr Arg Phe His Asn Gln Ser Glu Leu Lys Asp Phe Gly Thr
225                 230                 235                 240

Glu Ala Ala Arg Pro Gln Lys Gly Arg Lys Pro Arg Pro Arg Ala Arg
                245                 250                 255

Ser Ala Lys Ala Asn Gln Ala Glu Leu Glu Asn Ala Tyr Ser Gly Gly
            260                 265                 270

Gly Gly Ser Lys Asn Thr Val Tyr Leu Gln Met Asn Ser Leu Arg Ala
        275                 280                 285

Glu Asp Thr Ala Val Tyr Tyr Cys Ala Arg Thr Val Pro Gly Tyr Ser
    290                 295                 300

Thr Ala Pro Tyr Phe Asp Leu Trp Gly Gln Gly Thr Leu Val Thr Val
305                 310                 315                 320

Ser Ser Ala Ser Thr Lys Gly Pro Ser Val Phe Pro Leu Ala Pro Ser
                325                 330                 335

Ser Lys Ser Thr Ser Gly Gly Thr Ala Ala Leu Gly Cys Leu Val Lys
            340                 345                 350

Asp Tyr Phe Pro Glu Pro Val Thr Val Ser Trp Asn Ser Gly Ala Leu
        355                 360                 365

Thr Ser Gly Val His Thr Phe Pro Ala Val Leu Gln Ser Ser Gly Leu
    370                 375                 380

Tyr Ser Leu Ser Ser Val Val Thr Val Pro Ser Ser Ser Leu Gly Thr
385                 390                 395                 400

Gln Thr Tyr Ile Cys Asn Val Asn His Lys Pro Ser Asn Thr Lys Val
                405                 410                 415

Asp Lys Lys Val Glu Pro Lys Ser Cys
            420                 425
```

<210> SEQ ID NO 77
<211> LENGTH: 10
<212> TYPE: PRT
<213> ORGANISM: Artificial Sequence
<220> FEATURE:
<223> OTHER INFORMATION: Flexible linker

<400> SEQUENCE: 77

```
Lys Tyr Gln Ser Gly Gly Ser Gly Met Gly
1               5                   10


<210> SEQ ID NO 78
<211> LENGTH: 7
<212> TYPE: PRT
<213> ORGANISM: Artificial Sequence
<220> FEATURE:
<223> OTHER INFORMATION: Flexible linker

<400> SEQUENCE: 78

Ser Gly Gly Ser Tyr Thr Tyr
1               5


<210> SEQ ID NO 79
<211> LENGTH: 8
<212> TYPE: PRT
<213> ORGANISM: Artificial Sequence
<220> FEATURE:
<223> OTHER INFORMATION: Flexible linker

<400> SEQUENCE: 79

Gly Gly Gly Ser Gly Gly Gly Gly
1               5


<210> SEQ ID NO 80
<211> LENGTH: 7
<212> TYPE: PRT
<213> ORGANISM: Artificial Sequence
<220> FEATURE:
<223> OTHER INFORMATION: Flexible linker

<400> SEQUENCE: 80

Gly Ser Ser Ser Ser Gly Ser
1               5


<210> SEQ ID NO 81
<211> LENGTH: 5
<212> TYPE: PRT
<213> ORGANISM: Artificial Sequence
<220> FEATURE:
<223> OTHER INFORMATION: Flexible linker

<400> SEQUENCE: 81

Ser Gly Gly Gly Gly
1               5


<210> SEQ ID NO 82
<211> LENGTH: 5
<212> TYPE: PRT
<213> ORGANISM: Artificial Sequence
<220> FEATURE:
<223> OTHER INFORMATION: Rigid linker

<400> SEQUENCE: 82

Ile Pro Phe Thr Val
1               5


<210> SEQ ID NO 83
<211> LENGTH: 347
<212> TYPE: PRT
<213> ORGANISM: Artificial Sequence
<220> FEATURE:
<223> OTHER INFORMATION: CA497 Fab heavy chain with human IL-15 inserted
      into framework 3, Gly-Ser linkers

<400> SEQUENCE: 83
```

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Val Ile Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Phe Asn Ala Asp Ile Ser Tyr Tyr Arg Glu Ser Val
    50                  55                  60

Lys Gly Arg Phe Thr Ile Ser Arg Asp Asp Ser Gly Gly Gly Ser Gly
65                  70                  75                  80

Gly Gly Gly Asn Trp Val Asn Val Ile Ser Asp Leu Lys Lys Ile Glu
                85                  90                  95

Asp Leu Ile Gln Ser Met His Ile Asp Ala Thr Leu Tyr Thr Glu Ser
            100                 105                 110

Asp Val His Pro Ser Cys Lys Val Thr Ala Met Lys Cys Phe Leu Leu
        115                 120                 125

Glu Leu Gln Val Ile Ser Leu Glu Ser Gly Asp Ala Ser Ile His Asp
    130                 135                 140

Thr Val Glu Asn Leu Ile Ile Leu Ala Asn Asn Ser Leu Ser Ser Asn
145                 150                 155                 160

Gly Asn Val Thr Glu Ser Gly Cys Lys Glu Cys Glu Glu Leu Glu Glu
                165                 170                 175

Lys Asn Ile Lys Glu Phe Leu Gln Ser Phe Val His Ile Val Gln Met
            180                 185                 190

Phe Ile Asn Gly Gly Gly Lys Asn Thr Leu Tyr Leu Gln Met Asn Ser
        195                 200                 205

Leu Lys Thr Glu Asp Thr Ala Val Tyr Tyr Cys Thr Thr Asp Ala Asn
    210                 215                 220

Arg Gln Asn Tyr Asp Trp Phe Ala Tyr Trp Gly Gln Gly Thr Leu Val
225                 230                 235                 240

Thr Val Ser Ser Ala Ser Thr Lys Gly Pro Ser Val Phe Pro Leu Ala
                245                 250                 255

Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
                325                 330                 335

Lys Val Asp Lys Lys Val Glu Pro Lys Ser Cys
            340                 345
```

<210> SEQ ID NO 84
<211> LENGTH: 218
<212> TYPE: PRT
<213> ORGANISM: Artificial Sequence
<220> FEATURE:
<223> OTHER INFORMATION: CA497 Fab light chain

<400> SEQUENCE: 84

```
Ala Ile Gln Leu Thr Gln Ser Pro Ser Ser Leu Ser Ala Ser Val Gly
1               5                   10                  15
```

```
Asp Arg Val Thr Ile Thr Cys Lys Ala Ser Glu Ser Val Ser Ser Ser
            20                  25                  30

Met Tyr Ser Tyr Met His Trp Tyr Gln Gln Lys Pro Gly Lys Ala Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Trp
                85                  90                  95

Thr Ala Pro Arg Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 85
<211> LENGTH: 346
<212> TYPE: PRT
<213> ORGANISM: Artificial Sequence
<220> FEATURE:
<223> OTHER INFORMATION: CA240 Fab heavy chain with human IL-15 inserted into framework 3, Gly-Ser linkers

<400> SEQUENCE: 85

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Asn Asp Tyr
            20                  25                  30

Phe Met Asn Trp Val Arg Gln Ala Pro Gly Lys Gly Leu Glu Trp Val
        35                  40                  45

Ala Gln Met Arg Asn Lys Asn Tyr Gln Tyr Gly Thr Tyr Tyr Ala Glu
    50                  55                  60

Ser Leu Glu Gly Arg Phe Thr Ile Ser Arg Asp Asp Ser Gly Gly Gly
65                  70                  75                  80

Ser Gly Gly Gly Gly Asn Trp Val Asn Val Ile Ser Asp Leu Lys Lys
                85                  90                  95

Ile Glu Asp Leu Ile Gln Ser Met His Ile Asp Ala Thr Leu Tyr Thr
            100                 105                 110

Glu Ser Asp Val His Pro Ser Cys Lys Val Thr Ala Met Lys Cys Phe
        115                 120                 125

Leu Leu Glu Leu Gln Val Ile Ser Leu Glu Ser Gly Asp Ala Ser Ile
    130                 135                 140

His Asp Thr Val Glu Asn Leu Ile Ile Leu Ala Asn Asn Ser Leu Ser
```

```
145                 150                 155                 160

Ser Asn Gly Asn Val Thr Glu Ser Gly Cys Lys Glu Cys Glu Glu Leu
                165                 170                 175

Glu Glu Lys Asn Ile Lys Glu Phe Leu Gln Ser Phe Val His Ile Val
            180                 185                 190

Gln Met Phe Ile Asn Gly Gly Gly Lys Asn Ser Leu Tyr Leu Gln Met
        195                 200                 205

Asn Ser Leu Lys Thr Glu Asp Thr Ala Val Tyr Tyr Cys Ala Arg Glu
    210                 215                 220

Ser Tyr Tyr Gly Phe Thr Ser Tyr Trp Gly Gln Gly Thr Leu Val Thr
225                 230                 235                 240

Val Ser Ser Ala Ser Thr Lys Gly Pro Ser Val Phe Pro Leu Ala Pro
                245                 250                 255

Ser Ser Lys Ser Thr Ser Gly Gly Thr Ala Ala Leu Gly Cys Leu Val
            260                 265                 270

Lys Asp Tyr Phe Pro Glu Pro Val Thr Val Ser Trp Asn Ser Gly Ala
        275                 280                 285

Leu Thr Ser Gly Val His Thr Phe Pro Ala Val Leu Gln Ser Ser Gly
    290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
                325                 330                 335

Val Asp Lys Lys Val Glu Pro Lys Ser Cys
            340                 345


<210> SEQ ID NO 86
<211> LENGTH: 214
<212> TYPE: PRT
<213> ORGANISM: Artificial Sequence
<220> FEATURE:
<223> OTHER INFORMATION: CA240 Fab light chain

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Gly Ile Ser
            20                  25                  30

Leu Ser Trp Tyr Gln Gln Lys Pro Gly Lys Ala Pro Lys Leu Leu Ile
        35                  40                  45

Tyr Asn Ala Asn Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Ala Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 87
<211> LENGTH: 219
<212> TYPE: PRT
<213> ORGANISM: Artificial Sequence
<220> FEATURE:
<223> OTHER INFORMATION: HyHEL5 heavy chain

<400> SEQUENCE: 87

Glu Val Gln Leu Gln Gln Ser Gly Ala Glu Leu Met Lys Pro Gly Ala
1               5                   10                  15

Ser Val Lys Ile Ser Cys Lys Ala Ser Gly Tyr Thr Phe Ser Asp Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr His Glu Arg Phe
    50                  55                  60

Lys Gly Lys Ala Thr Phe Thr Ala Asp Thr Ser Ser Ser Thr Ala Tyr
65                  70                  75                  80

Met Gln Leu Asn Ser Leu Thr Ser Glu Asp Ser Gly Val Tyr Tyr Cys
                85                  90                  95

Leu His Gly Asn Tyr Asp Phe Asp Gly Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys
    210                 215


<210> SEQ ID NO 88
<211> LENGTH: 212
<212> TYPE: PRT
<213> ORGANISM: Artificial Sequence
<220> FEATURE:
<223> OTHER INFORMATION: HyHEL5 light chain

<400> SEQUENCE: 88

Asp Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Asn Tyr Met
            20                  25                  30
```

```
Tyr Trp Tyr Gln Gln Lys Ser Gly Thr Ser Pro Lys Arg Trp Ile Tyr
        35                  40                  45

Asp Thr Ser Lys Leu Ala Ser Gly Val Pro Val Arg Phe Ser Gly Ser
    50                  55                  60

Gly Ser Gly Thr Ser Tyr Ser Leu Thr Ile Ser Ser Met Glu Thr Glu
65                  70                  75                  80

Asp Ala Ala Thr Tyr Tyr Cys Gln Gln Trp Gly Arg Asn Pro Thr Phe
                85                  90                  95

Gly Gly Gly Thr Lys Leu Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210
```

<210> SEQ ID NO 89
<211> LENGTH: 127
<212> TYPE: PRT
<213> ORGANISM: Artificial Sequence
<220> FEATURE:
<223> OTHER INFORMATION: D3L11

<400> SEQUENCE: 89

```
Asp Val Gln Leu Val Glu Ser Gly Gly Gly Ser Val Gln Ala Gly Gly
1               5                   10                  15

Ser Leu Arg Leu Ser Cys Ala Ala Ser Gly Ser Thr Asp Ser Ile Glu
            20                  25                  30

Tyr Met Thr Trp Phe Arg Gln Ala Pro Gly Lys Ala Arg Glu Gly Val
        35                  40                  45

Ala Ala Leu Tyr Thr His Thr Gly Asn Thr Tyr Tyr Thr Asp Ser Val
    50                  55                  60

Lys Gly Arg Phe Thr Ile Ser Gln Asp Lys Ala Lys Asn Met Ala Tyr
65                  70                  75                  80

Leu Arg Met Asp Ser Val Lys Ser Glu Asp Thr Ala Ile Tyr Thr Cys
                85                  90                  95

Gly Ala Thr Arg Lys Tyr Val Pro Val Arg Phe Ala Leu Asp Gln Ser
            100                 105                 110

Ser Tyr Asp Tyr Trp Gly Gln Gly Thr Gln Val Thr Val Ser Ser
        115                 120                 125
```

<210> SEQ ID NO 90
<211> LENGTH: 360
<212> TYPE: PRT
<213> ORGANISM: Artificial Sequence
<220> FEATURE:
<223> OTHER INFORMATION: Anti-lysozyme HyHEL5 light chain with anti-lysozyme VHH D3L11 inserted into framework 3, Gly-Ser linkers

<400> SEQUENCE: 90

```
Asp Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Asn Tyr Met
            20                  25                  30

Tyr Trp Tyr Gln Gln Lys Ser Gly Thr Ser Pro Lys Arg Trp Ile Tyr
        35                  40                  45

Asp Thr Ser Lys Leu Ala Ser Gly Val Pro Val Arg Phe Ser Gly Ser
    50                  55                  60

Gly Ser Gly Ser Gly Gly Gly Gly Ser Asp Val Gln Leu Val Glu Ser
65                  70                  75                  80

Gly Gly Gly Ser Val Gln Ala Gly Gly Ser Leu Arg Leu Ser Cys Ala
                85                  90                  95

Ala Ser Gly Ser Thr Asp Ser Ile Glu Tyr Met Thr Trp Phe Arg Gln
            100                 105                 110

Ala Pro Gly Lys Ala Arg Glu Gly Val Ala Ala Leu Tyr Thr His Thr
        115                 120                 125

Gly Asn Thr Tyr Tyr Thr Asp Ser Val Lys Gly Arg Phe Thr Ile Ser
    130                 135                 140

Gln Asp Lys Ala Lys Asn Met Ala Tyr Leu Arg Met Asp Ser Val Lys
145                 150                 155                 160

Ser Glu Asp Thr Ala Ile Tyr Thr Cys Gly Ala Thr Arg Lys Tyr Val
                165                 170                 175

Pro Val Arg Phe Ala Leu Asp Gln Ser Ser Tyr Asp Tyr Trp Gly Gln
            180                 185                 190

Gly Thr Gln Val Thr Val Ser Ser Gly Gly Gly Gly Ser Gly Gly Gly
        195                 200                 205

Gly Ser Gly Gly Gly Gly Ser Thr Ser Tyr Ser Leu Thr Ile Ser Ser
    210                 215                 220

Met Glu Thr Glu Asp Ala Ala Thr Tyr Tyr Cys Gln Gln Trp Gly Arg
225                 230                 235                 240

Asn Pro Thr Phe Gly Gly Gly Thr Lys Leu Glu Ile Lys Arg Thr Val
                245                 250                 255

Ala Ala Pro Ser Val Phe Ile Phe Pro Pro Ser Asp Glu Gln Leu Lys
            260                 265                 270

Ser Gly Thr Ala Ser Val Val Cys Leu Leu Asn Asn Phe Tyr Pro Arg
        275                 280                 285

Glu Ala Lys Val Gln Trp Lys Val Asp Asn Ala Leu Gln Ser Gly Asn
    290                 295                 300

Ser Gln Glu Ser Val Thr Glu Gln Asp Ser Lys Asp Ser Thr Tyr Ser
305                 310                 315                 320

Leu Ser Ser Thr Leu Thr Leu Ser Lys Ala Asp Tyr Glu Lys His Lys
                325                 330                 335

Val Tyr Ala Cys Glu Val Thr His Gln Gly Leu Ser Ser Pro Val Thr
            340                 345                 350

Lys Ser Phe Asn Arg Gly Glu Cys
        355                 360
```

<210> SEQ ID NO 91
<211> LENGTH: 352
<212> TYPE: PRT
<213> ORGANISM: Artificial Sequence
<220> FEATURE:
<223> OTHER INFORMATION: Anti-lysozyme HyHEL5 light chain with anti-IL-6
VHH15 inserted into framework 3, Gly-Ser linkers

<400> SEQUENCE: 91

```
Asp Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Asn Tyr Met
            20                  25                  30

Tyr Trp Tyr Gln Gln Lys Ser Gly Thr Ser Pro Lys Arg Trp Ile Tyr
        35                  40                  45

Asp Thr Ser Lys Leu Ala Ser Gly Val Pro Val Arg Phe Ser Gly Ser
    50                  55                  60

Gly Ser Gly Ser Gly Gly Gly Gly Ser Gln Val Gln Leu Val Glu Ser
65                  70                  75                  80

Gly Gly Gly Ser Val Gln Ala Gly Gly Ser Leu Arg Leu Ser Cys Val
                85                  90                  95

Ala Ala Ser Gly Tyr Thr Gly Cys Thr Tyr Asp Met Arg Trp Tyr Arg
            100                 105                 110

Gln Ala Pro Gly Lys Glu Arg Glu Phe Val Ser Gly Ile Asp Ser Asp
        115                 120                 125

Gly Arg Ala Thr Tyr Ala Asp Ser Val Lys Gly Arg Phe Thr Ile Ser
    130                 135                 140

Gln Ser Asn Ala Lys Ile Ala Val Tyr Leu Gln Met Asp Ser Leu Lys
145                 150                 155                 160

Leu Glu Asp Thr Ala Met Tyr Tyr Cys Asn Leu Gln Cys Leu Arg Tyr
                165                 170                 175

Pro Gly Glu Tyr Tyr Trp Gly Gln Gly Thr Gln Val Thr Val Ser Ser
            180                 185                 190

Gly Gly Gly Gly Ser Gly Gly Gly Gly Ser Gly Gly Gly Gly Ser Thr
        195                 200                 205

Ser Tyr Ser Leu Thr Ile Ser Ser Met Glu Thr Glu Asp Ala Ala Thr
    210                 215                 220

Tyr Tyr Cys Gln Gln Trp Gly Arg Asn Pro Thr Phe Gly Gly Gly Thr
225                 230                 235                 240

Lys Leu Glu Ile Lys Arg Thr Val Ala Ala Pro Ser Val Phe Ile Phe
                245                 250                 255

Pro Pro Ser Asp Glu Gln Leu Lys Ser Gly Thr Ala Ser Val Val Cys
            260                 265                 270

Leu Leu Asn Asn Phe Tyr Pro Arg Glu Ala Lys Val Gln Trp Lys Val
        275                 280                 285

Asp Asn Ala Leu Gln Ser Gly Asn Ser Gln Glu Ser Val Thr Glu Gln
    290                 295                 300

Asp Ser Lys Asp Ser Thr Tyr Ser Leu Ser Ser Thr Leu Thr Leu Ser
305                 310                 315                 320

Lys Ala Asp Tyr Glu Lys His Lys Val Tyr Ala Cys Glu Val Thr His
                325                 330                 335

Gln Gly Leu Ser Ser Pro Val Thr Lys Ser Phe Asn Arg Gly Glu Cys
            340                 345                 350
```

<210> SEQ ID NO 92
<211> LENGTH: 365
<212> TYPE: PRT
<213> ORGANISM: Artificial Sequence
<220> FEATURE:
<223> OTHER INFORMATION: CA645 light chain with anti-lysozyme VHH D3L11 inserted into framework 3, Gly-Ser linkers

<400> SEQUENCE: 92

```
Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Ser Gly Gly Gly Gly Ser Asp Val Gln Leu Val
65                  70                  75                  80

Glu Ser Gly Gly Gly Ser Val Gln Ala Gly Gly Ser Leu Arg Leu Ser
                85                  90                  95

Cys Ala Ala Ser Gly Ser Thr Asp Ser Ile Glu Tyr Met Thr Trp Phe
            100                 105                 110

Arg Gln Ala Pro Gly Lys Ala Arg Glu Gly Val Ala Ala Leu Tyr Thr
        115                 120                 125

His Thr Gly Asn Thr Tyr Tyr Thr Asp Ser Val Lys Gly Arg Phe Thr
    130                 135                 140

Ile Ser Gln Asp Lys Ala Lys Asn Met Ala Tyr Leu Arg Met Asp Ser
145                 150                 155                 160

Val Lys Ser Glu Asp Thr Ala Ile Tyr Thr Cys Gly Ala Thr Arg Lys
                165                 170                 175

Tyr Val Pro Val Arg Phe Ala Leu Asp Gln Ser Ser Tyr Asp Tyr Trp
            180                 185                 190

Gly Gln Gly Thr Gln Val Thr Val Ser Ser Gly Gly Gly Gly Ser Gly
        195                 200                 205

Gly Gly Gly Ser Gly Gly Gly Gly Ser Thr Asp Phe Thr Leu Thr Ile
    210                 215                 220

Ser Ser Leu Gln Pro Glu Asp Phe Ala Thr Tyr Tyr Cys Gly Gly Gly
225                 230                 235                 240

Tyr Ser Ser Ile Ser Asp Thr Thr Phe Gly Gly Gly Thr Lys Val Glu
                245                 250                 255

Ile Lys Arg Thr Val Ala Ala Pro Ser Val Phe Ile Phe Pro Pro Ser
            260                 265                 270

Asp Glu Gln Leu Lys Ser Gly Thr Ala Ser Val Val Cys Leu Leu Asn
        275                 280                 285

Asn Phe Tyr Pro Arg Glu Ala Lys Val Gln Trp Lys Val Asp Asn Ala
    290                 295                 300

Leu Gln Ser Gly Asn Ser Gln Glu Ser Val Thr Glu Gln Asp Ser Lys
305                 310                 315                 320

Asp Ser Thr Tyr Ser Leu Ser Ser Thr Leu Thr Leu Ser Lys Ala Asp
                325                 330                 335

Tyr Glu Lys His Lys Val Tyr Ala Cys Glu Val Thr His Gln Gly Leu
            340                 345                 350

Ser Ser Pro Val Thr Lys Ser Phe Asn Arg Gly Glu Cys
        355                 360                 365
```

```
<210> SEQ ID NO 93
<211> LENGTH: 360
<212> TYPE: PRT
<213> ORGANISM: Artificial Sequence
<220> FEATURE:
<223> OTHER INFORMATION: CA645 Fab heavy chain with human IL-15 inserted
      into framework 3 with bovine long linker
```

<400> SEQUENCE: 93

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Thr Ser Val His Gln Glu
65                  70                  75                  80

Thr Lys Lys Tyr Gln Ser Asn Trp Val Asn Val Ile Ser Asp Leu Lys
                85                  90                  95

Lys Ile Glu Asp Leu Ile Gln Ser Met His Ile Asp Ala Thr Leu Tyr
            100                 105                 110

Thr Glu Ser Asp Val His Pro Ser Cys Lys Val Thr Ala Met Lys Cys
        115                 120                 125

Phe Leu Leu Glu Leu Gln Val Ile Ser Leu Glu Ser Gly Asp Ala Ser
    130                 135                 140

Ile His Asp Thr Val Glu Asn Leu Ile Ile Leu Ala Asn Asn Ser Leu
145                 150                 155                 160

Ser Ser Asn Gly Asn Val Thr Glu Ser Gly Cys Lys Glu Cys Glu Glu
                165                 170                 175

Leu Glu Glu Lys Asn Ile Lys Glu Phe Leu Gln Ser Phe Val His Ile
            180                 185                 190

Val Gln Met Phe Ile Asn Ser Tyr Thr Tyr Asn Tyr Glu Trp His Val
        195                 200                 205

Asp Val Lys Asn Thr Val Tyr Leu Gln Met Asn Ser Leu Arg Ala Glu
    210                 215                 220

Asp Thr Ala Val Tyr Tyr Cys Ala Arg Thr Val Pro Gly Tyr Ser Thr
225                 230                 235                 240

Ala Pro Tyr Phe Asp Leu Trp Gly Gln Gly Thr Leu Val Thr Val Ser
                245                 250                 255

Ser Ala Ser Thr Lys Gly Pro Ser Val Phe Pro Leu Ala Pro Ser Ser
            260                 265                 270

Lys Ser Thr Ser Gly Gly Thr Ala Ala Leu Gly Cys Leu Val Lys Asp
        275                 280                 285

Tyr Phe Pro Glu Pro Val Thr Val Ser Trp Asn Ser Gly Ala Leu Thr
    290                 295                 300

Ser Gly Val His Thr Phe Pro Ala Val Leu Gln Ser Ser Gly Leu Tyr
305                 310                 315                 320

Ser Leu Ser Ser Val Val Thr Val Pro Ser Ser Ser Leu Gly Thr Gln
                325                 330                 335

Thr Tyr Ile Cys Asn Val Asn His Lys Pro Ser Asn Thr Lys Val Asp
            340                 345                 350

Lys Lys Val Glu Pro Lys Ser Cys
        355                 360
```

<210> SEQ ID NO 94
<211> LENGTH: 350
<212> TYPE: PRT
<213> ORGANISM: Artificial Sequence
<220> FEATURE:
<223> OTHER INFORMATION: CA645 Fab heavy chain with human IL-15 inserted into framework 3 with bovine short linker

<400> SEQUENCE: 94

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Glu Thr Lys Lys Tyr Gln
65                  70                  75                  80

Ser Asn Trp Val Asn Val Ile Ser Asp Leu Lys Lys Ile Glu Asp Leu
                85                  90                  95

Ile Gln Ser Met His Ile Asp Ala Thr Leu Tyr Thr Glu Ser Asp Val
            100                 105                 110

His Pro Ser Cys Lys Val Thr Ala Met Lys Cys Phe Leu Leu Glu Leu
        115                 120                 125

Gln Val Ile Ser Leu Glu Ser Gly Asp Ala Ser Ile His Asp Thr Val
    130                 135                 140

Glu Asn Leu Ile Ile Leu Ala Asn Asn Ser Leu Ser Ser Asn Gly Asn
145                 150                 155                 160

Val Thr Glu Ser Gly Cys Lys Glu Cys Glu Glu Leu Glu Glu Lys Asn
                165                 170                 175

Ile Lys Glu Phe Leu Gln Ser Phe Val His Ile Val Gln Met Phe Ile
            180                 185                 190

Asn Ser Tyr Thr Tyr Asn Tyr Glu Lys Asn Thr Val Tyr Leu Gln Met
        195                 200                 205

Asn Ser Leu Arg Ala Glu Asp Thr Ala Val Tyr Tyr Cys Ala Arg Thr
    210                 215                 220

Val Pro Gly Tyr Ser Thr Ala Pro Tyr Phe Asp Leu Trp Gly Gln Gly
225                 230                 235                 240

Thr Leu Val Thr Val Ser Ser Ala Ser Thr Lys Gly Pro Ser Val Phe
                245                 250                 255

Pro Leu Ala Pro Ser Ser Lys Ser Thr Ser Gly Gly Thr Ala Ala Leu
            260                 265                 270

Gly Cys Leu Val Lys Asp Tyr Phe Pro Glu Pro Val Thr Val Ser Trp
        275                 280                 285

Asn Ser Gly Ala Leu Thr Ser Gly Val His Thr Phe Pro Ala Val Leu
    290                 295                 300

Gln Ser Ser Gly Leu Tyr Ser Leu Ser Ser Val Val Thr Val Pro Ser
305                 310                 315                 320

Ser Ser Leu Gly Thr Gln Thr Tyr Ile Cys Asn Val Asn His Lys Pro
                325                 330                 335

Ser Asn Thr Lys Val Asp Lys Lys Val Glu Pro Lys Ser Cys
            340                 345                 350
```

<210> SEQ ID NO 95
<211> LENGTH: 356
<212> TYPE: PRT
<213> ORGANISM: Artificial Sequence
<220> FEATURE:
<223> OTHER INFORMATION: CA645 Fab heavy chain with human IL-15 inserted into framework 3 with 2xG4S linker

<400> SEQUENCE: 95

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Gly Gly Gly Gly Ser Gly
65                  70                  75                  80

Gly Gly Gly Ser Asn Trp Val Asn Val Ile Ser Asp Leu Lys Lys Ile
                85                  90                  95

Glu Asp Leu Ile Gln Ser Met His Ile Asp Ala Thr Leu Tyr Thr Glu
            100                 105                 110

Ser Asp Val His Pro Ser Cys Lys Val Thr Ala Met Lys Cys Phe Leu
        115                 120                 125

Leu Glu Leu Gln Val Ile Ser Leu Glu Ser Gly Asp Ala Ser Ile His
    130                 135                 140

Asp Thr Val Glu Asn Leu Ile Ile Leu Ala Asn Asn Ser Leu Ser Ser
145                 150                 155                 160

Asn Gly Asn Val Thr Glu Ser Gly Cys Lys Glu Cys Glu Glu Leu Glu
                165                 170                 175

Glu Lys Asn Ile Lys Glu Phe Leu Gln Ser Phe Val His Ile Val Gln
            180                 185                 190

Met Phe Ile Asn Gly Gly Gly Gly Ser Gly Gly Gly Gly Ser Lys Asn
        195                 200                 205

Thr Val Tyr Leu Gln Met Asn Ser Leu Arg Ala Glu Asp Thr Ala Val
    210                 215                 220

Tyr Tyr Cys Ala Arg Thr Val Pro Gly Tyr Ser Thr Ala Pro Tyr Phe
225                 230                 235                 240

Asp Leu Trp Gly Gln Gly Thr Leu Val Thr Val Ser Ser Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
                325                 330                 335

Asn Val Asn His Lys Pro Ser Asn Thr Lys Val Asp Lys Lys Val Glu
            340                 345                 350

Pro Lys Ser Cys
        355
```

<210> SEQ ID NO 96
<211> LENGTH: 12
<212> TYPE: PRT
<213> ORGANISM: Artificial Sequence
<220> FEATURE:
<223> OTHER INFORMATION: Linker

<400> SEQUENCE: 96

```
Thr Ser Val His Gln Glu Thr Lys Lys Tyr Gln Ser
1               5                   10


<210> SEQ ID NO 97
<211> LENGTH: 12
<212> TYPE: PRT
<213> ORGANISM: Artificial Sequence
<220> FEATURE:
<223> OTHER INFORMATION: Linker

<400> SEQUENCE: 97

Ser Tyr Thr Tyr Asn Tyr Glu Trp His Val Asp Val
1               5                   10


<210> SEQ ID NO 98
<211> LENGTH: 7
<212> TYPE: PRT
<213> ORGANISM: Artificial Sequence
<220> FEATURE:
<223> OTHER INFORMATION: Linker

<400> SEQUENCE: 98

Glu Thr Lys Lys Tyr Gln Ser
1               5


<210> SEQ ID NO 99
<211> LENGTH: 7
<212> TYPE: PRT
<213> ORGANISM: Artificial Sequence
<220> FEATURE:
<223> OTHER INFORMATION: Linker

<400> SEQUENCE: 99

Ser Tyr Thr Tyr Asn Tyr Glu
1               5


<210> SEQ ID NO 100
<211> LENGTH: 188
<212> TYPE: PRT
<213> ORGANISM: Homo sapiens

<400> SEQUENCE: 100

Asn Cys Trp Leu Arg Gln Ala Lys Asn Gly Arg Cys Gln Val Leu Tyr
1               5                   10                  15

Lys Thr Glu Leu Ser Lys Glu Glu Cys Cys Ser Thr Gly Arg Leu Ser
            20                  25                  30

Thr Ser Trp Thr Glu Glu Asp Val Asn Asp Asn Thr Leu Phe Lys Trp
        35                  40                  45

Met Ile Phe Asn Gly Gly Ala Pro Asn Cys Ile Pro Cys Lys Glu Pro
    50                  55                  60

Arg Cys Val Cys Ala Pro Asp Cys Ser Asn Ile Thr Trp Lys Gly Pro
65                  70                  75                  80

Val Cys Gly Leu Asp Gly Lys Thr Tyr Arg Asn Glu Cys Ala Leu Leu
                85                  90                  95

Lys Ala Arg Cys Lys Glu Gln Pro Glu Leu Glu Val Gln Tyr Gln Gly
            100                 105                 110

Arg Cys Lys Lys Thr Cys Arg Asp Val Phe Cys Pro Gly Ser Ser Thr
        115                 120                 125

Cys Val Val Asp Gln Thr Asn Asn Ala Tyr Cys Val Thr Cys Asn Arg
    130                 135                 140

Ile Cys Pro Glu Pro Ala Ser Ser Glu Gln Tyr Leu Cys Gly Asn Asp
```

```
145                 150                 155                 160

Gly Val Thr Tyr Ser Ser Ala Cys His Leu Arg Lys Ala Thr Cys Leu
                165                 170                 175

Leu Gly Arg Ser Ile Gly Leu Ala Gly Glu Tyr Lys
            180                 185


<210> SEQ ID NO 101
<211> LENGTH: 627
<212> TYPE: PRT
<213> ORGANISM: Artificial Sequence
<220> FEATURE:
<223> OTHER INFORMATION: CA645 Fab heavy chain with two human IL-10
      monomers inserted into framework 3

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Gly Gly Gly Gly Ser Gly
65                  70                  75                  80

Ser Asn Cys Trp Leu Arg Gln Ala Lys Asn Gly Arg Cys Gln Val Leu
                85                  90                  95

Tyr Lys Thr Glu Leu Ser Lys Glu Glu Cys Cys Ser Thr Gly Arg Leu
            100                 105                 110

Ser Thr Ser Trp Thr Glu Glu Asp Val Asn Asp Asn Thr Leu Phe Lys
        115                 120                 125

Trp Met Ile Phe Asn Gly Gly Ala Pro Asn Cys Ile Pro Cys Lys Glu
    130                 135                 140

Pro Arg Cys Val Cys Ala Pro Asp Cys Ser Asn Ile Thr Trp Lys Gly
145                 150                 155                 160

Pro Val Cys Gly Leu Asp Gly Lys Thr Tyr Arg Asn Glu Cys Ala Leu
                165                 170                 175

Leu Lys Ala Arg Cys Lys Glu Gln Pro Glu Leu Glu Val Gln Tyr Gln
            180                 185                 190

Gly Arg Cys Lys Lys Thr Cys Arg Asp Val Phe Cys Pro Gly Ser Ser
        195                 200                 205

Thr Cys Val Val Asp Gln Thr Asn Asn Ala Tyr Cys Val Thr Cys Asn
    210                 215                 220

Arg Ile Cys Pro Glu Pro Ala Ser Ser Glu Gln Tyr Leu Cys Gly Asn
225                 230                 235                 240

Asp Gly Val Thr Tyr Ser Ser Ala Cys His Leu Arg Lys Ala Thr Cys
                245                 250                 255

Leu Leu Gly Arg Ser Ile Gly Leu Ala Gly Glu Tyr Lys Gly Gly Gly
            260                 265                 270

Gly Ser Gly Gly Gly Gly Ser Gly Gly Gly Gly Ser Asn Cys Trp Leu
        275                 280                 285

Arg Gln Ala Lys Asn Gly Arg Cys Gln Val Leu Tyr Lys Thr Glu Leu
    290                 295                 300

Ser Lys Glu Glu Cys Cys Ser Thr Gly Arg Leu Ser Thr Ser Trp Thr
305                 310                 315                 320
```

```
Glu Glu Asp Val Asn Asp Asn Thr Leu Phe Lys Trp Met Ile Phe Asn
                325                 330                 335

Gly Gly Ala Pro Asn Cys Ile Pro Cys Lys Glu Pro Arg Cys Val Cys
            340                 345                 350

Ala Pro Asp Cys Ser Asn Ile Thr Trp Lys Gly Pro Val Cys Gly Leu
        355                 360                 365

Asp Gly Lys Thr Tyr Arg Asn Glu Cys Ala Leu Leu Lys Ala Arg Cys
    370                 375                 380

Lys Glu Gln Pro Glu Leu Glu Val Gln Tyr Gln Gly Arg Cys Lys Lys
385                 390                 395                 400

Thr Cys Arg Asp Val Phe Cys Pro Gly Ser Ser Thr Cys Val Val Asp
                405                 410                 415

Gln Thr Asn Asn Ala Tyr Cys Val Thr Cys Asn Arg Ile Cys Pro Glu
            420                 425                 430

Pro Ala Ser Ser Glu Gln Tyr Leu Cys Gly Asn Asp Gly Val Thr Tyr
        435                 440                 445

Ser Ser Ala Cys His Leu Arg Lys Ala Thr Cys Leu Leu Gly Arg Ser
    450                 455                 460

Ile Gly Leu Ala Tyr Glu Gly Gly Gly Gly Ser Gly Ser Lys Asn Thr
465                 470                 475                 480

Val Tyr Leu Gln Met Asn Ser Leu Arg Ala Glu Asp Thr Ala Val Tyr
                485                 490                 495

Tyr Cys Ala Arg Thr Val Pro Gly Tyr Ser Thr Ala Pro Tyr Phe Asp
            500                 505                 510

Leu Trp Gly Gln Gly Thr Leu Val Thr Val Ser Ser Ala Ser Thr Lys
        515                 520                 525

Gly Pro Ser Val Phe Pro Leu Ala Pro Ser Ser Lys Ser Thr Ser Gly
    530                 535                 540

Gly Thr Ala Ala Leu Gly Cys Leu Val Lys Asp Tyr Phe Pro Glu Pro
545                 550                 555                 560

Val Thr Val Ser Trp Asn Ser Gly Ala Leu Thr Ser Gly Val His Thr
                565                 570                 575

Phe Pro Ala Val Leu Gln Ser Ser Gly Leu Tyr Ser Leu Ser Ser Val
            580                 585                 590

Val Thr Val Pro Ser Ser Ser Leu Gly Thr Gln Thr Tyr Ile Cys Asn
        595                 600                 605

Val Asn His Lys Pro Ser Asn Thr Lys Val Asp Lys Lys Val Glu Pro
    610                 615                 620

Lys Ser Cys
625
```

<210> SEQ ID NO 102
<211> LENGTH: 110
<212> TYPE: PRT
<213> ORGANISM: Artificial Sequence
<220> FEATURE:
<223> OTHER INFORMATION: CA645-Cys VL domain (gL5)

<400> SEQUENCE: 102

```
Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45
```

```
Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Cys Gly Thr Lys Val Glu Ile Lys
            100                 105                 110


<210> SEQ ID NO 103
<211> LENGTH: 121
<212> TYPE: PRT
<213> ORGANISM: Artificial Sequence
<220> FEATURE:
<223> OTHER INFORMATION: CA645-Cys VH domain (gH5)

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120


<210> SEQ ID NO 104
<211> LENGTH: 6
<212> TYPE: PRT
<213> ORGANISM: Artificial Sequence
<220> FEATURE:
<223> OTHER INFORMATION: Rigid linker

<400> SEQUENCE: 104

Glu Tyr His Gly Leu Gln
1               5


<210> SEQ ID NO 105
<211> LENGTH: 119
<212> TYPE: PRT
<213> ORGANISM: Artificial Sequence
<220> FEATURE:
<223> OTHER INFORMATION: CA645 VH domain (gH1)

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
```

```
    50                  55                  60

Gly Arg Phe Thr Ile Ser Arg Asp Ser Thr Thr Val Tyr Leu Gln Met
65                  70                  75                  80

Asn Ser Leu Arg Ala Glu Asp Thr Ala Val Tyr Tyr Cys Ala Arg Thr
                85                  90                  95

Val Pro Gly Tyr Ser Thr Ala Pro Tyr Phe Asp Leu Trp Gly Gln Gly
            100                 105                 110

Thr Leu Val Thr Val Ser Ser
        115


<210> SEQ ID NO 106
<211> LENGTH: 121
<212> TYPE: PRT
<213> ORGANISM: Artificial Sequence
<220> FEATURE:
<223> OTHER INFORMATION: CA645 VH domain (gH37)

<400> SEQUENCE: 106

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Ala Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120


<210> SEQ ID NO 107
<211> LENGTH: 120
<212> TYPE: PRT
<213> ORGANISM: Artificial Sequence
<220> FEATURE:
<223> OTHER INFORMATION: CA645 VH domain (gH47)

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Ala Val Tyr Tyr Cys Ala Arg
                85                  90                  95

Thr Val Pro Gly Tyr Ser Ala Ala Pro Tyr Phe Asp Leu Trp Gly Gln
            100                 105                 110
```

```
Gly Thr Leu Val Thr Val Ser Ser
        115                 120


<210> SEQ ID NO 108
<211> LENGTH: 110
<212> TYPE: PRT
<213> ORGANISM: Artificial Sequence
<220> FEATURE:
<223> OTHER INFORMATION: CA645 VL domain (gL1)

<400> SEQUENCE: 108

Asp Ile Val Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Lys
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Gly Gly Thr Lys Val Glu Ile Lys
            100                 105                 110


<210> SEQ ID NO 109
<211> LENGTH: 110
<212> TYPE: PRT
<213> ORGANISM: Artificial Sequence
<220> FEATURE:
<223> OTHER INFORMATION: CA645 VL domain (gL4)

<400> SEQUENCE: 109

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Gly Gly Thr Lys Val Glu Ile Lys
            100                 105                 110


<210> SEQ ID NO 110
<211> LENGTH: 112
<212> TYPE: PRT
<213> ORGANISM: Artificial Sequence
<220> FEATURE:
<223> OTHER INFORMATION: CA645-Cys VL domain (gL4)

<400> SEQUENCE: 110

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
```

```
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Cys Gly Thr Lys Val Glu Ile Lys Arg Thr
            100                 105                 110


<210> SEQ ID NO 111
<211> LENGTH: 11
<212> TYPE: PRT
<213> ORGANISM: Artificial Sequence
<220> FEATURE:
<223> OTHER INFORMATION: Albumin binding peptide

<400> SEQUENCE: 111

Asp Leu Cys Leu Arg Asp Trp Gly Cys Leu Trp
1               5                   10


<210> SEQ ID NO 112
<211> LENGTH: 11
<212> TYPE: PRT
<213> ORGANISM: Artificial Sequence
<220> FEATURE:
<223> OTHER INFORMATION: Albumin binding peptide

<400> SEQUENCE: 112

Asp Ile Cys Leu Pro Arg Trp Gly Cys Leu Trp
1               5                   10


<210> SEQ ID NO 113
<211> LENGTH: 15
<212> TYPE: PRT
<213> ORGANISM: Artificial Sequence
<220> FEATURE:
<223> OTHER INFORMATION: Albumin binding peptide

<400> SEQUENCE: 113

Met Glu Asp Ile Cys Leu Pro Arg Trp Gly Cys Leu Trp Gly Asp
1               5                   10                  15


<210> SEQ ID NO 114
<211> LENGTH: 20
<212> TYPE: PRT
<213> ORGANISM: Artificial Sequence
<220> FEATURE:
<223> OTHER INFORMATION: Albumin binding peptide

<400> SEQUENCE: 114

Gln Arg Leu Met Glu Asp Ile Cys Leu Pro Arg Trp Gly Cys Leu Trp
1               5                   10                  15

Glu Asp Asp Glu
            20


<210> SEQ ID NO 115
<211> LENGTH: 20
<212> TYPE: PRT
<213> ORGANISM: Artificial Sequence
<220> FEATURE:
<223> OTHER INFORMATION: Albumin binding peptide
```

<400> SEQUENCE: 115

Gln Gly Leu Ile Gly Asp Ile Cys Leu Pro Arg Trp Gly Cys Leu Trp
1 5 10 15

Gly Arg Ser Val
20

<210> SEQ ID NO 116
<211> LENGTH: 21
<212> TYPE: PRT
<213> ORGANISM: Artificial Sequence
<220> FEATURE:
<223> OTHER INFORMATION: Albumin binding peptide

<400> SEQUENCE: 116

Gln Gly Leu Ile Gly Asp Ile Cys Leu Pro Arg Trp Gly Cys Leu Trp
1 5 10 15

Gly Arg Ser Val Lys
20

<210> SEQ ID NO 117
<211> LENGTH: 15
<212> TYPE: PRT
<213> ORGANISM: Artificial Sequence
<220> FEATURE:
<223> OTHER INFORMATION: Albumin binding peptide

<400> SEQUENCE: 117

Glu Asp Ile Cys Leu Pro Arg Trp Gly Cys Leu Trp Glu Asp Asp
1 5 10 15

<210> SEQ ID NO 118
<211> LENGTH: 18
<212> TYPE: PRT
<213> ORGANISM: Artificial Sequence
<220> FEATURE:
<223> OTHER INFORMATION: Albumin binding peptide

<400> SEQUENCE: 118

Arg Leu Met Glu Asp Ile Cys Leu Pro Arg Trp Gly Cys Leu Trp Glu
1 5 10 15

Asp Asp

<210> SEQ ID NO 119
<211> LENGTH: 16
<212> TYPE: PRT
<213> ORGANISM: Artificial Sequence
<220> FEATURE:
<223> OTHER INFORMATION: Albumin binding peptide

<400> SEQUENCE: 119

Met Glu Asp Ile Cys Leu Pro Arg Trp Gly Cys Leu Trp Glu Asp Asp
1 5 10 15

<210> SEQ ID NO 120
<211> LENGTH: 15
<212> TYPE: PRT
<213> ORGANISM: Artificial Sequence
<220> FEATURE:
<223> OTHER INFORMATION: Albumin binding peptide

<400> SEQUENCE: 120

Met Glu Asp Ile Cys Leu Pro Arg Trp Gly Cys Leu Trp Glu Asp
1 5 10 15

<210> SEQ ID NO 121
<211> LENGTH: 18
<212> TYPE: PRT
<213> ORGANISM: Artificial Sequence
<220> FEATURE:
<223> OTHER INFORMATION: Albumin binding peptide

<400> SEQUENCE: 121

Arg Leu Met Glu Asp Ile Cys Leu Ala Arg Trp Gly Cys Leu Trp Glu
1               5                   10                  15

Asp Asp

<210> SEQ ID NO 122
<211> LENGTH: 20
<212> TYPE: PRT
<213> ORGANISM: Artificial Sequence
<220> FEATURE:
<223> OTHER INFORMATION: Albumin binding peptide

<400> SEQUENCE: 122

Glu Val Arg Ser Phe Cys Thr Arg Trp Pro Ala Glu Lys Ser Cys Lys
1               5                   10                  15

Pro Leu Arg Gly
            20

<210> SEQ ID NO 123
<211> LENGTH: 20
<212> TYPE: PRT
<213> ORGANISM: Artificial Sequence
<220> FEATURE:
<223> OTHER INFORMATION: Albumin binding peptide

<400> SEQUENCE: 123

Arg Ala Pro Glu Ser Phe Val Cys Tyr Trp Glu Thr Ile Cys Phe Glu
1               5                   10                  15

Arg Ser Glu Gln
            20

<210> SEQ ID NO 124
<211> LENGTH: 11
<212> TYPE: PRT
<213> ORGANISM: Artificial Sequence
<220> FEATURE:
<223> OTHER INFORMATION: Albumin binding peptide

<400> SEQUENCE: 124

Glu Met Cys Tyr Phe Pro Gly Ile Cys Trp Met
1               5                   10

<210> SEQ ID NO 125
<211> LENGTH: 224
<212> TYPE: PRT
<213> ORGANISM: Artificial Sequence
<220> FEATURE:
<223> OTHER INFORMATION: CA497 Fab Heavy Chain

<400> SEQUENCE: 125

Glu Val Gln Leu Val Glu Ser Gly Gly Gly Leu Val Lys Pro Gly Gly
1               5                   10                  15

Ser Leu Arg Leu Ser Cys Ala Ala Ser Gly Val Ile Phe Ser Asp Tyr
            20                  25                  30

Tyr Met Ala Trp Val Arg Gln Ala Pro Gly Lys Gly Leu Glu Trp Val
        35                  40                  45

```
Ala Ser Ile Asn Phe Asn Ala Asp Ile Ser Tyr Tyr Arg Glu Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Asp Ala Asn Arg Gln Asn Tyr Asp Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220


<210> SEQ ID NO 126
<211> LENGTH: 223
<212> TYPE: PRT
<213> ORGANISM: Artificial Sequence
<220> FEATURE:
<223> OTHER INFORMATION: CA240 Fab Heavy chain

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Asn Asp Tyr
            20                  25                  30

Phe Met Asn Trp Val Arg Gln Ala Pro Gly Lys Gly Leu Glu Trp Val
        35                  40                  45

Ala Gln Met Arg Asn Lys Asn Tyr Gln Tyr Gly Thr Tyr Tyr Ala Glu
    50                  55                  60

Ser Leu Glu Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Ser Tyr Tyr Gly Phe Thr Ser Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220


<210> SEQ ID NO 127
<211> LENGTH: 247
<212> TYPE: PRT
<213> ORGANISM: Artificial Sequence
<220> FEATURE:
<223> OTHER INFORMATION: CA497 dsscFv (vHvL)

<400> SEQUENCE: 127

Glu Val Gln Leu Val Glu Ser Gly Gly Gly Leu Val Lys Pro Gly Gly
1               5                   10                  15

Ser Leu Arg Leu Ser Cys Ala Ala Ser Gly Val Ile Phe Ser Asp Tyr
            20                  25                  30

Tyr Met Ala Trp Val Arg Gln Ala Pro Gly Lys Cys Leu Glu Trp Val
        35                  40                  45

Ala Ser Ile Asn Phe Asn Ala Asp Ile Ser Tyr Tyr Arg Glu Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Asp Ala Asn Arg Gln Asn Tyr Asp Trp Phe Ala Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Ala Ile Gln Leu Thr Gln Ser Pro
    130                 135                 140

Ser Ser Leu Ser Ala Ser Val Gly Asp Arg Val Thr Ile Thr Cys Lys
145                 150                 155                 160

Ala Ser Glu Ser Val Ser Ser Ser Met Tyr Ser Tyr Met His Trp Tyr
                165                 170                 175

Gln Gln Lys Pro Gly Lys Ala Pro Lys Leu Leu Ile Tyr Arg Ala Ser
            180                 185                 190

Asn Leu Glu Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Ser Trp Thr Ala Pro Arg Thr Phe Gly Cys
225                 230                 235                 240

Gly Thr Lys Val Glu Ile Lys
                245


<210> SEQ ID NO 128
<211> LENGTH: 247
<212> TYPE: PRT
<213> ORGANISM: Artificial Sequence
<220> FEATURE:
<223> OTHER INFORMATION: CA497 dsscFv (vLvH)

<400> SEQUENCE: 128

Ala Ile Gln Leu Thr Gln Ser Pro Ser Ser Leu Ser Ala Ser Val Gly
1               5                   10                  15

Asp Arg Val Thr Ile Thr Cys Lys Ala Ser Glu Ser Val Ser Ser Ser
            20                  25                  30
```

```
Met Tyr Ser Tyr Met His Trp Tyr Gln Gln Lys Pro Gly Lys Ala Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Trp
                85                  90                  95

Thr Ala Pro Arg Thr Phe Gly Cys Gly Thr Lys Val Glu Ile Lys Gly
            100                 105                 110

Gly Gly Gly Ser Gly Gly Gly Gly Ser Gly Gly Gly Gly Ser Glu Val
        115                 120                 125

Gln Leu Val Glu Ser Gly Gly Gly Leu Val Lys Pro Gly Gly Ser Leu
    130                 135                 140

Arg Leu Ser Cys Ala Ala Ser Gly Val Ile Phe Ser Asp Tyr Tyr Met
145                 150                 155                 160

Ala Trp Val Arg Gln Ala Pro Gly Lys Cys Leu Glu Trp Val Ala Ser
                165                 170                 175

Ile Asn Phe Asn Ala Asp Ile Ser Tyr Tyr Arg Glu Ser Val Lys Gly
            180                 185                 190

Arg Phe Thr Ile Ser Arg Asp Asp Ser Lys Asn Thr Leu Tyr Leu Gln
        195                 200                 205

Met Asn Ser Leu Lys Thr Glu Asp Thr Ala Val Tyr Tyr Cys Thr Thr
    210                 215                 220

Asp Ala Asn Arg Gln Asn Tyr Asp Trp Phe Ala Tyr Trp Gly Gln Gly
225                 230                 235                 240

Thr Leu Val Thr Val Ser Ser
                245


<210> SEQ ID NO 129
<211> LENGTH: 491
<212> TYPE: PRT
<213> ORGANISM: Artificial Sequence
<220> FEATURE:
<223> OTHER INFORMATION: CA645 Fab HC Fwk3 CA497 dsscFv (vHvL)

<400> SEQUENCE: 129

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Gly Gly Gly Gly Ser Gly
65                  70                  75                  80

Gly Gly Gly Ser Glu Val Gln Leu Val Glu Ser Gly Gly Gly Leu Val
                85                  90                  95

Lys Pro Gly Gly Ser Leu Arg Leu Ser Cys Ala Ala Ser Gly Val Ile
            100                 105                 110

Phe Ser Asp Tyr Tyr Met Ala Trp Val Arg Gln Ala Pro Gly Lys Cys
        115                 120                 125

Leu Glu Trp Val Ala Ser Ile Asn Phe Asn Ala Asp Ile Ser Tyr Tyr
    130                 135                 140
```

```
Arg Glu Ser Val Lys Gly Arg Phe Thr Ile Ser Arg Asp Asp Ser Lys
145                 150                 155                 160

Asn Thr Leu Tyr Leu Gln Met Asn Ser Leu Lys Thr Glu Asp Thr Ala
                165                 170                 175

Val Tyr Tyr Cys Thr Thr Asp Ala Asn Arg Gln Asn Tyr Asp Trp Phe
            180                 185                 190

Ala Tyr Trp Gly Gln Gly Thr Leu Val Thr Val Ser Ser Gly Gly Gly
        195                 200                 205

Gly Ser Gly Gly Gly Gly Ser Gly Gly Gly Gly Ser Ala Ile Gln Leu
    210                 215                 220

Thr Gln Ser Pro Ser Ser Leu Ser Ala Ser Val Gly Asp Arg Val Thr
225                 230                 235                 240

Ile Thr Cys Lys Ala Ser Glu Ser Val Ser Ser Ser Met Tyr Ser Tyr
                245                 250                 255

Met His Trp Tyr Gln Gln Lys Pro Gly Lys Ala Pro Lys Leu Leu Ile
            260                 265                 270

Tyr Arg Ala Ser Asn Leu Glu Ser Gly Val Pro Ser Arg Phe Ser Gly
        275                 280                 285

Ser Gly Ser Gly Thr Asp Phe Thr Leu Thr Ile Ser Ser Leu Gln Pro
    290                 295                 300

Glu Asp Phe Ala Thr Tyr Tyr Cys Gln Gln Ser Trp Thr Ala Pro Arg
305                 310                 315                 320

Thr Phe Gly Cys Gly Thr Lys Val Glu Ile Lys Gly Gly Gly Gly Ser
                325                 330                 335

Gly Gly Gly Gly Ser Lys Asn Thr Val Tyr Leu Gln Met Asn Ser Leu
            340                 345                 350

Arg Ala Glu Asp Thr Ala Val Tyr Tyr Cys Ala Arg Thr Val Pro Gly
        355                 360                 365

Tyr Ser Thr Ala Pro Tyr Phe Asp Leu Trp Gly Gln Gly Thr Leu Val
    370                 375                 380

Thr Val Ser Ser Ala Ser Thr Lys Gly Pro Ser Val Phe Pro Leu Ala
385                 390                 395                 400

Pro Ser Ser Lys Ser Thr Ser Gly Gly Thr Ala Ala Leu Gly Cys Leu
                405                 410                 415

Val Lys Asp Tyr Phe Pro Glu Pro Val Thr Val Ser Trp Asn Ser Gly
            420                 425                 430

Ala Leu Thr Ser Gly Val His Thr Phe Pro Ala Val Leu Gln Ser Ser
        435                 440                 445

Gly Leu Tyr Ser Leu Ser Ser Val Val Thr Val Pro Ser Ser Ser Leu
    450                 455                 460

Gly Thr Gln Thr Tyr Ile Cys Asn Val Asn His Lys Pro Ser Asn Thr
465                 470                 475                 480

Lys Val Asp Lys Lys Val Glu Pro Lys Ser Cys
                485                 490
```

<210> SEQ ID NO 130
<211> LENGTH: 491
<212> TYPE: PRT
<213> ORGANISM: Artificial Sequence
<220> FEATURE:
<223> OTHER INFORMATION: CA645 Fab HC Fwk3 CA497 dsscFv (vLvH)

<400> SEQUENCE: 130

```
Glu Val Gln Leu Leu Glu Ser Gly Gly Gly Leu Val Gln Pro Gly Gly
1               5                   10                  15
```

```
Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Gly Gly Gly Gly Ser Gly
65                  70                  75                  80

Gly Gly Gly Ser Ala Ile Gln Leu Thr Gln Ser Pro Ser Ser Leu Ser
                85                  90                  95

Ala Ser Val Gly Asp Arg Val Thr Ile Thr Cys Lys Ala Ser Glu Ser
            100                 105                 110

Val Ser Ser Ser Met Tyr Ser Tyr Met His Trp Tyr Gln Gln Lys Pro
        115                 120                 125

Gly Lys Ala Pro Lys Leu Leu Ile Tyr Arg Ala Ser Asn Leu Glu Ser
    130                 135                 140

Gly Val Pro Ser Arg Phe Ser Gly Ser Gly Ser Gly Thr Asp Phe Thr
145                 150                 155                 160

Leu Thr Ile Ser Ser Leu Gln Pro Glu Asp Phe Ala Thr Tyr Tyr Cys
                165                 170                 175

Gln Gln Ser Trp Thr Ala Pro Arg Thr Phe Gly Cys Gly Thr Lys Val
            180                 185                 190

Glu Ile Lys Gly Gly Gly Gly Ser Gly Gly Gly Gly Ser Gly Gly Gly
        195                 200                 205

Gly Ser Glu Val Gln Leu Val Glu Ser Gly Gly Gly Leu Val Lys Pro
    210                 215                 220

Gly Gly Ser Leu Arg Leu Ser Cys Ala Ala Ser Gly Val Ile Phe Ser
225                 230                 235                 240

Asp Tyr Tyr Met Ala Trp Val Arg Gln Ala Pro Gly Lys Cys Leu Glu
                245                 250                 255

Trp Val Ala Ser Ile Asn Phe Asn Ala Asp Ile Ser Tyr Tyr Arg Glu
            260                 265                 270

Ser Val Lys Gly Arg Phe Thr Ile Ser Arg Asp Asp Ser Lys Asn Thr
        275                 280                 285

Leu Tyr Leu Gln Met Asn Ser Leu Lys Thr Glu Asp Thr Ala Val Tyr
    290                 295                 300

Tyr Cys Thr Thr Asp Ala Asn Arg Gln Asn Tyr Asp Trp Phe Ala Tyr
305                 310                 315                 320

Trp Gly Gln Gly Thr Leu Val Thr Val Ser Ser Gly Gly Gly Gly Ser
                325                 330                 335

Gly Gly Gly Gly Ser Lys Asn Thr Val Tyr Leu Gln Met Asn Ser Leu
            340                 345                 350

Arg Ala Glu Asp Thr Ala Val Tyr Tyr Cys Ala Arg Thr Val Pro Gly
        355                 360                 365

Tyr Ser Thr Ala Pro Tyr Phe Asp Leu Trp Gly Gln Gly Thr Leu Val
    370                 375                 380

Thr Val Ser Ser Ala Ser Thr Lys Gly Pro Ser Val Phe Pro Leu Ala
385                 390                 395                 400

Pro Ser Ser Lys Ser Thr Ser Gly Gly Thr Ala Ala Leu Gly Cys Leu
                405                 410                 415

Val Lys Asp Tyr Phe Pro Glu Pro Val Thr Val Ser Trp Asn Ser Gly
            420                 425                 430
```

```
Ala Leu Thr Ser Gly Val His Thr Phe Pro Ala Val Leu Gln Ser Ser
        435                 440                 445

Gly Leu Tyr Ser Leu Ser Ser Val Val Thr Val Pro Ser Ser Ser Leu
    450                 455                 460

Gly Thr Gln Thr Tyr Ile Cys Asn Val Asn His Lys Pro Ser Asn Thr
465                 470                 475                 480

Lys Val Asp Lys Lys Val Glu Pro Lys Ser Cys
                485                 490


<210> SEQ ID NO 131
<211> LENGTH: 718
<212> TYPE: PRT
<213> ORGANISM: Artificial Sequence
<220> FEATURE:
<223> OTHER INFORMATION: CA645 IgG4P HC Fwk3 CA497 dsscFv (vHvL)

<400> SEQUENCE: 131

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Gly Gly Gly Gly Ser Gly
65                  70                  75                  80

Gly Gly Gly Ser Glu Val Gln Leu Val Glu Ser Gly Gly Gly Leu Val
                85                  90                  95

Lys Pro Gly Gly Ser Leu Arg Leu Ser Cys Ala Ala Ser Gly Val Ile
            100                 105                 110

Phe Ser Asp Tyr Tyr Met Ala Trp Val Arg Gln Ala Pro Gly Lys Cys
        115                 120                 125

Leu Glu Trp Val Ala Ser Ile Asn Phe Asn Ala Asp Ile Ser Tyr Tyr
    130                 135                 140

Arg Glu Ser Val Lys Gly Arg Phe Thr Ile Ser Arg Asp Asp Ser Lys
145                 150                 155                 160

Asn Thr Leu Tyr Leu Gln Met Asn Ser Leu Lys Thr Glu Asp Thr Ala
                165                 170                 175

Val Tyr Tyr Cys Thr Thr Asp Ala Asn Arg Gln Asn Tyr Asp Trp Phe
            180                 185                 190

Ala Tyr Trp Gly Gln Gly Thr Leu Val Thr Val Ser Ser Gly Gly Gly
        195                 200                 205

Gly Ser Gly Gly Gly Gly Ser Gly Gly Gly Gly Ser Ala Ile Gln Leu
    210                 215                 220

Thr Gln Ser Pro Ser Ser Leu Ser Ala Ser Val Gly Asp Arg Val Thr
225                 230                 235                 240

Ile Thr Cys Lys Ala Ser Glu Ser Val Ser Ser Ser Met Tyr Ser Tyr
                245                 250                 255

Met His Trp Tyr Gln Gln Lys Pro Gly Lys Ala Pro Lys Leu Leu Ile
            260                 265                 270

Tyr Arg Ala Ser Asn Leu Glu Ser Gly Val Pro Ser Arg Phe Ser Gly
        275                 280                 285

Ser Gly Ser Gly Thr Asp Phe Thr Leu Thr Ile Ser Ser Leu Gln Pro
    290                 295                 300
```

-continued

```
Glu Asp Phe Ala Thr Tyr Tyr Cys Gln Gln Ser Trp Thr Ala Pro Arg
305                 310                 315                 320

Thr Phe Gly Cys Gly Thr Lys Val Glu Ile Lys Gly Gly Gly Gly Ser
                325                 330                 335

Gly Gly Gly Gly Ser Lys Asn Thr Val Tyr Leu Gln Met Asn Ser Leu
            340                 345                 350

Arg Ala Glu Asp Thr Ala Val Tyr Tyr Cys Ala Arg Thr Val Pro Gly
        355                 360                 365

Tyr Ser Thr Ala Pro Tyr Phe Asp Leu Trp Gly Gln Gly Thr Leu Val
    370                 375                 380

Thr Val Ser Ser Ala Ser Thr Lys Gly Pro Ser Val Phe Pro Leu Ala
385                 390                 395                 400

Pro Ser Ser Lys Ser Thr Ser Gly Gly Thr Ala Ala Leu Gly Cys Leu
                405                 410                 415

Val Lys Asp Tyr Phe Pro Glu Pro Val Thr Val Ser Trp Asn Ser Gly
            420                 425                 430

Ala Leu Thr Ser Gly Val His Thr Phe Pro Ala Val Leu Gln Ser Ser
        435                 440                 445

Gly Leu Tyr Ser Leu Ser Ser Val Val Thr Val Pro Ser Ser Ser Leu
    450                 455                 460

Gly Thr Gln Thr Tyr Ile Cys Asn Val Asn His Lys Pro Ser Asn Thr
465                 470                 475                 480

Lys Val Asp Lys Lys Val Glu Pro Lys Ser Cys Asp Lys Thr His Thr
                485                 490                 495

Cys Pro Pro Cys Pro Ala Pro Glu Leu Leu Gly Gly Pro Ser Val Phe
            500                 505                 510

Leu Phe Pro Pro Lys Pro Lys Asp Thr Leu Met Ile Ser Arg Thr Pro
        515                 520                 525

Glu Val Thr Cys Val Val Val Asp Val Ser His Glu Asp Pro Glu Val
    530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
                565                 570                 575

Leu Thr Val Leu His Gln Asp Trp Leu Asn Gly Lys Glu Tyr Lys Cys
            580                 585                 590

Lys Val Ser Asn Lys Ala Leu Pro Ala Pro Ile Glu Lys Thr Ile Ser
        595                 600                 605

Lys Ala Lys Gly Gln Pro Arg Glu Pro Gln Val Tyr Thr Leu Pro Pro
    610                 615                 620

Ser Arg Asp Glu Leu Thr Lys Asn Gln Val Ser Leu Thr Cys Leu Val
625                 630                 635                 640

Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
            660                 665                 670

Gly Ser Phe Phe Leu Tyr Ser Lys Leu Thr Val Asp Lys Ser Arg Trp
        675                 680                 685

Gln Gln Gly Asn Val Phe Ser Cys Ser Val Met His Glu Ala Leu His
    690                 695                 700

Asn His Tyr Thr Gln Lys Ser Leu Ser Leu Ser Pro Gly Lys
705                 710                 715
```

```
<210> SEQ ID NO 132
<211> LENGTH: 718
<212> TYPE: PRT
<213> ORGANISM: Artificial Sequence
<220> FEATURE:
<223> OTHER INFORMATION: CA645 IgG4P HC Fwk3 CA497 dsscFv (vLvH)

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Gly Gly Gly Gly Ser Gly
65                  70                  75                  80

Gly Gly Gly Ser Ala Ile Gln Leu Thr Gln Ser Pro Ser Ser Leu Ser
                85                  90                  95

Ala Ser Val Gly Asp Arg Val Thr Ile Thr Cys Lys Ala Ser Glu Ser
            100                 105                 110

Val Ser Ser Ser Met Tyr Ser Tyr Met His Trp Tyr Gln Gln Lys Pro
        115                 120                 125

Gly Lys Ala Pro Lys Leu Leu Ile Tyr Arg Ala Ser Asn Leu Glu Ser
    130                 135                 140

Gly Val Pro Ser Arg Phe Ser Gly Ser Gly Ser Gly Thr Asp Phe Thr
145                 150                 155                 160

Leu Thr Ile Ser Ser Leu Gln Pro Glu Asp Phe Ala Thr Tyr Tyr Cys
                165                 170                 175

Gln Gln Ser Trp Thr Ala Pro Arg Thr Phe Gly Cys Gly Thr Lys Val
            180                 185                 190

Glu Ile Lys Gly Gly Gly Gly Ser Gly Gly Gly Gly Ser Gly Gly Gly
        195                 200                 205

Gly Ser Glu Val Gln Leu Val Glu Ser Gly Gly Gly Leu Val Lys Pro
    210                 215                 220

Gly Gly Ser Leu Arg Leu Ser Cys Ala Ala Ser Gly Val Ile Phe Ser
225                 230                 235                 240

Asp Tyr Tyr Met Ala Trp Val Arg Gln Ala Pro Gly Lys Cys Leu Glu
                245                 250                 255

Trp Val Ala Ser Ile Asn Phe Asn Ala Asp Ile Ser Tyr Tyr Arg Glu
            260                 265                 270

Ser Val Lys Gly Arg Phe Thr Ile Ser Arg Asp Asp Ser Lys Asn Thr
        275                 280                 285

Leu Tyr Leu Gln Met Asn Ser Leu Lys Thr Glu Asp Thr Ala Val Tyr
    290                 295                 300

Tyr Cys Thr Thr Asp Ala Asn Arg Gln Asn Tyr Asp Trp Phe Ala Tyr
305                 310                 315                 320

Trp Gly Gln Gly Thr Leu Val Thr Val Ser Ser Gly Gly Gly Gly Ser
                325                 330                 335

Gly Gly Gly Gly Ser Lys Asn Thr Val Tyr Leu Gln Met Asn Ser Leu
            340                 345                 350

Arg Ala Glu Asp Thr Ala Val Tyr Tyr Cys Ala Arg Thr Val Pro Gly
        355                 360                 365

Tyr Ser Thr Ala Pro Tyr Phe Asp Leu Trp Gly Gln Gly Thr Leu Val
```

```
    370                 375                 380

Thr Val Ser Ser Ala Ser Thr Lys Gly Pro Ser Val Phe Pro Leu Ala
385                 390                 395                 400

Pro Ser Ser Lys Ser Thr Ser Gly Gly Thr Ala Ala Leu Gly Cys Leu
                405                 410                 415

Val Lys Asp Tyr Phe Pro Glu Pro Val Thr Val Ser Trp Asn Ser Gly
            420                 425                 430

Ala Leu Thr Ser Gly Val His Thr Phe Pro Ala Val Leu Gln Ser Ser
        435                 440                 445

Gly Leu Tyr Ser Leu Ser Ser Val Val Thr Val Pro Ser Ser Ser Leu
    450                 455                 460

Gly Thr Gln Thr Tyr Ile Cys Asn Val Asn His Lys Pro Ser Asn Thr
465                 470                 475                 480

Lys Val Asp Lys Lys Val Glu Pro Lys Ser Cys Asp Lys Thr His Thr
                485                 490                 495

Cys Pro Pro Cys Pro Ala Pro Glu Leu Leu Gly Gly Pro Ser Val Phe
            500                 505                 510

Leu Phe Pro Pro Lys Pro Lys Asp Thr Leu Met Ile Ser Arg Thr Pro
        515                 520                 525

Glu Val Thr Cys Val Val Val Asp Val Ser His Glu Asp Pro Glu Val
    530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
                565                 570                 575

Leu Thr Val Leu His Gln Asp Trp Leu Asn Gly Lys Glu Tyr Lys Cys
            580                 585                 590

Lys Val Ser Asn Lys Ala Leu Pro Ala Pro Ile Glu Lys Thr Ile Ser
        595                 600                 605

Lys Ala Lys Gly Gln Pro Arg Glu Pro Gln Val Tyr Thr Leu Pro Pro
    610                 615                 620

Ser Arg Asp Glu Leu Thr Lys Asn Gln Val Ser Leu Thr Cys Leu Val
625                 630                 635                 640

Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
            660                 665                 670

Gly Ser Phe Phe Leu Tyr Ser Lys Leu Thr Val Asp Lys Ser Arg Trp
        675                 680                 685

Gln Gln Gly Asn Val Phe Ser Cys Ser Val Met His Glu Ala Leu His
    690                 695                 700

Asn His Tyr Thr Gln Lys Ser Leu Ser Leu Ser Pro Gly Lys
705                 710                 715
```

<210> SEQ ID NO 133
<211> LENGTH: 213
<212> TYPE: PRT
<213> ORGANISM: Artificial Sequence
<220> FEATURE:
<223> OTHER INFORMATION: Anti-CD3 Light chain

<400> SEQUENCE: 133

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
```

```
            20                  25                  30

Asn Trp Tyr Gln Gln Thr Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 134
<211> LENGTH: 222
<212> TYPE: PRT
<213> ORGANISM: Artificial Sequence
<220> FEATURE:
<223> OTHER INFORMATION: Anti-CD3 Fab HC

<400> SEQUENCE: 134

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220


<210> SEQ ID NO 135
<211> LENGTH: 446
<212> TYPE: PRT
<213> ORGANISM: Artificial Sequence
<220> FEATURE:
<223> OTHER INFORMATION: Anti-CD3 IgG4P HC

<400> SEQUENCE: 135

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
```

```
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445


<210> SEQ ID NO 136
<211> LENGTH: 214
<212> TYPE: PRT
<213> ORGANISM: Artificial Sequence
<220> FEATURE:
<223> OTHER INFORMATION: Anti-CD28 Light Chain

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 137
<211> LENGTH: 223
<212> TYPE: PRT
<213> ORGANISM: Artificial Sequence
<220> FEATURE:
<223> OTHER INFORMATION: Anti-CD28 Fab HC

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220


<210> SEQ ID NO 138
<211> LENGTH: 447
<212> TYPE: PRT
<213> ORGANISM: Artificial Sequence
<220> FEATURE:
<223> OTHER INFORMATION: Anti-CD28  IgG4P HC

<400> SEQUENCE: 138

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95
```

```
Thr Arg Ser His Tyr Gly Leu Asp Trp Asn Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 139
<211> LENGTH: 488
<212> TYPE: PRT
<213> ORGANISM: Artificial Sequence
<220> FEATURE:
<223> OTHER INFORMATION: Anti-CD28 Fab HC Fwk3 anti-CD3 dsscFv (vHvL)

<400> SEQUENCE: 139

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Gly Gly Gly Gly Ser
65                  70                  75                  80

Gly Gly Gly Gly Ser Gln Val Gln Leu Val Gln Ser Gly Gly Gly Val
                85                  90                  95

Val Gln Pro Gly Arg Ser Leu Arg Leu Ser Cys Lys Ala Ser Gly Tyr
            100                 105                 110

Thr Phe Thr Arg Tyr Thr Met His Trp Val Arg Gln Ala Pro Gly Lys
        115                 120                 125

Cys Leu Glu Trp Ile Gly Tyr Ile Asn Pro Ser Arg Gly Tyr Thr Asn
    130                 135                 140

Tyr Asn Gln Lys Phe Lys Asp Arg Phe Thr Ile Ser Arg Asp Asn Ser
145                 150                 155                 160

Lys Asn Thr Ala Phe Leu Gln Met Asp Ser Leu Arg Pro Glu Asp Thr
                165                 170                 175

Gly Val Tyr Phe Cys Ala Arg Tyr Tyr Asp Asp His Tyr Cys Leu Asp
            180                 185                 190

Tyr Trp Gly Gln Gly Thr Pro Val Thr Val Ser Ser Gly Gly Gly Gly
        195                 200                 205

Ser Gly Gly Gly Gly Ser Gly Gly Gly Gly Ser Gly Gly Gly Gly Ser
    210                 215                 220

Asp Ile Gln Met Thr Gln Ser Pro Ser Ser Leu Ser Ala Ser Val Gly
225                 230                 235                 240

Asp Arg Val Thr Ile Thr Cys Ser Ala Ser Ser Ser Val Ser Tyr Met
                245                 250                 255

Asn Trp Tyr Gln Gln Thr Pro Gly Lys Ala Pro Lys Leu Leu Ile Tyr
            260                 265                 270

Asp Thr Ser Lys Leu Ala Ser Gly Val Pro Ser Arg Phe Ser Gly Ser
        275                 280                 285

Gly Ser Gly Thr Asp Tyr Thr Phe Thr Ile Ser Ser Leu Gln Pro Glu
    290                 295                 300

Asp Ile Ala Thr Tyr Tyr Cys Gln Gln Trp Ser Ser Asn Pro Phe Thr
305                 310                 315                 320

Phe Gly Cys Gly Thr Lys Leu Glu Ile Lys Gly Gly Gly Gly Ser Gly
                325                 330                 335

Gly Gly Gly Ser Ile Ser Thr Ala Tyr Met Glu Leu Ser Arg Leu Arg
            340                 345                 350

Ser Asp Asp Thr Ala Val Tyr Phe Cys Thr Arg Ser His Tyr Gly Leu
        355                 360                 365

Asp Trp Asn Phe Asp Val Trp Gly Gln Gly Thr Thr Val Thr Val Ser
    370                 375                 380

Ser Ala Ser Thr Lys Gly Pro Ser Val Phe Pro Leu Ala Pro Ser Ser
385                 390                 395                 400

Lys Ser Thr Ser Gly Gly Thr Ala Ala Leu Gly Cys Leu Val Lys Asp
                405                 410                 415

Tyr Phe Pro Glu Pro Val Thr Val Ser Trp Asn Ser Gly Ala Leu Thr
            420                 425                 430

Ser Gly Val His Thr Phe Pro Ala Val Leu Gln Ser Ser Gly Leu Tyr
```

```
        435                 440                 445

Ser Leu Ser Ser Val Val Thr Val Pro Ser Ser Ser Leu Gly Thr Gln
    450                 455                 460

Thr Tyr Ile Cys Asn Val Asn His Lys Pro Ser Asn Thr Lys Val Asp
465                 470                 475                 480

Lys Lys Val Glu Pro Lys Ser Cys
                485


<210> SEQ ID NO 140
<211> LENGTH: 487
<212> TYPE: PRT
<213> ORGANISM: Artificial Sequence
<220> FEATURE:
<223> OTHER INFORMATION: Anti-CD3 Fab HC Fwk3 anti-CD3 dsscFv (vHvL)

<400> SEQUENCE: 140

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Gly Gly Gly Gly Ser
65                  70                  75                  80

Gly Gly Gly Gly Ser Gln Val Gln Leu Val Gln Ser Gly Gly Gly Val
                85                  90                  95

Val Gln Pro Gly Arg Ser Leu Arg Leu Ser Cys Lys Ala Ser Gly Tyr
            100                 105                 110

Thr Phe Thr Arg Tyr Thr Met His Trp Val Arg Gln Ala Pro Gly Lys
        115                 120                 125

Cys Leu Glu Trp Ile Gly Tyr Ile Asn Pro Ser Arg Gly Tyr Thr Asn
    130                 135                 140

Tyr Asn Gln Lys Phe Lys Asp Arg Phe Thr Ile Ser Arg Asp Asn Ser
145                 150                 155                 160

Lys Asn Thr Ala Phe Leu Gln Met Asp Ser Leu Arg Pro Glu Asp Thr
                165                 170                 175

Gly Val Tyr Phe Cys Ala Arg Tyr Tyr Asp Asp His Tyr Cys Leu Asp
            180                 185                 190

Tyr Trp Gly Gln Gly Thr Pro Val Thr Val Ser Ser Gly Gly Gly Gly
        195                 200                 205

Ser Gly Gly Gly Gly Ser Gly Gly Gly Gly Ser Gly Gly Gly Gly Ser
    210                 215                 220

Asp Ile Gln Met Thr Gln Ser Pro Ser Ser Leu Ser Ala Ser Val Gly
225                 230                 235                 240

Asp Arg Val Thr Ile Thr Cys Ser Ala Ser Ser Ser Val Ser Tyr Met
                245                 250                 255

Asn Trp Tyr Gln Gln Thr Pro Gly Lys Ala Pro Lys Leu Leu Ile Tyr
            260                 265                 270

Asp Thr Ser Lys Leu Ala Ser Gly Val Pro Ser Arg Phe Ser Gly Ser
        275                 280                 285

Gly Ser Gly Thr Asp Tyr Thr Phe Thr Ile Ser Ser Leu Gln Pro Glu
    290                 295                 300

Asp Ile Ala Thr Tyr Tyr Cys Gln Gln Trp Ser Ser Asn Pro Phe Thr
```

```
305                 310                 315                 320

Phe Gly Cys Gly Thr Lys Leu Glu Ile Lys Gly Gly Gly Gly Ser Gly
                325                 330                 335

Gly Gly Gly Ser Lys Asn Thr Ala Phe Leu Gln Met Asp Ser Leu Arg
            340                 345                 350

Pro Glu Asp Thr Gly Val Tyr Phe Cys Ala Arg Tyr Tyr Asp Asp His
        355                 360                 365

Tyr Cys Leu Asp Tyr Trp Gly Gln Gly Thr Pro Val Thr Val Ser Ser
    370                 375                 380

Ala Ser Thr Lys Gly Pro Ser Val Phe Pro Leu Ala Pro Ser Ser Lys
385                 390                 395                 400

Ser Thr Ser Gly Gly Thr Ala Ala Leu Gly Cys Leu Val Lys Asp Tyr
                405                 410                 415

Phe Pro Glu Pro Val Thr Val Ser Trp Asn Ser Gly Ala Leu Thr Ser
            420                 425                 430

Gly Val His Thr Phe Pro Ala Val Leu Gln Ser Ser Gly Leu Tyr Ser
        435                 440                 445

Leu Ser Ser Val Val Thr Val Pro Ser Ser Ser Leu Gly Thr Gln Thr
    450                 455                 460

Tyr Ile Cys Asn Val Asn His Lys Pro Ser Asn Thr Lys Val Asp Lys
465                 470                 475                 480

Lys Val Glu Pro Lys Ser Cys
                485


<210> SEQ ID NO 141
<211> LENGTH: 712
<212> TYPE: PRT
<213> ORGANISM: Artificial Sequence
<220> FEATURE:
<223> OTHER INFORMATION: Anti-CD28 IgG4P HC Fwk3 anti-CD3 dsscFv (vHvL)

<400> SEQUENCE: 141

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Gly Gly Gly Gly Ser
65                  70                  75                  80

Gly Gly Gly Gly Ser Gln Val Gln Leu Val Gln Ser Gly Gly Gly Val
                85                  90                  95

Val Gln Pro Gly Arg Ser Leu Arg Leu Ser Cys Lys Ala Ser Gly Tyr
            100                 105                 110

Thr Phe Thr Arg Tyr Thr Met His Trp Val Arg Gln Ala Pro Gly Lys
        115                 120                 125

Cys Leu Glu Trp Ile Gly Tyr Ile Asn Pro Ser Arg Gly Tyr Thr Asn
    130                 135                 140

Tyr Asn Gln Lys Phe Lys Asp Arg Phe Thr Ile Ser Arg Asp Asn Ser
145                 150                 155                 160

Lys Asn Thr Ala Phe Leu Gln Met Asp Ser Leu Arg Pro Glu Asp Thr
                165                 170                 175

Gly Val Tyr Phe Cys Ala Arg Tyr Tyr Asp Asp His Tyr Cys Leu Asp
```

```
            180                 185                 190

Tyr Trp Gly Gln Gly Thr Pro Val Thr Val Ser Ser Gly Gly Gly Gly
        195                 200                 205

Ser Gly Gly Gly Gly Ser Gly Gly Gly Gly Ser Gly Gly Gly Gly Ser
    210                 215                 220

Asp Ile Gln Met Thr Gln Ser Pro Ser Ser Leu Ser Ala Ser Val Gly
225                 230                 235                 240

Asp Arg Val Thr Ile Thr Cys Ser Ala Ser Ser Ser Val Ser Tyr Met
                245                 250                 255

Asn Trp Tyr Gln Gln Thr Pro Gly Lys Ala Pro Lys Leu Leu Ile Tyr
            260                 265                 270

Asp Thr Ser Lys Leu Ala Ser Gly Val Pro Ser Arg Phe Ser Gly Ser
        275                 280                 285

Gly Ser Gly Thr Asp Tyr Thr Phe Thr Ile Ser Ser Leu Gln Pro Glu
    290                 295                 300

Asp Ile Ala Thr Tyr Tyr Cys Gln Gln Trp Ser Ser Asn Pro Phe Thr
305                 310                 315                 320

Phe Gly Cys Gly Thr Lys Leu Glu Ile Lys Gly Gly Gly Gly Ser Gly
                325                 330                 335

Gly Gly Gly Ser Ile Ser Thr Ala Tyr Met Glu Leu Ser Arg Leu Arg
            340                 345                 350

Ser Asp Asp Thr Ala Val Tyr Phe Cys Thr Arg Ser His Tyr Gly Leu
        355                 360                 365

Asp Trp Asn Phe Asp Val Trp Gly Gln Gly Thr Thr Val Thr Val Ser
    370                 375                 380

Ser Ala Ser Thr Lys Gly Pro Ser Val Phe Pro Leu Ala Pro Cys Ser
385                 390                 395                 400

Arg Ser Thr Ser Glu Ser Thr Ala Ala Leu Gly Cys Leu Val Lys Asp
                405                 410                 415

Tyr Phe Pro Glu Pro Val Thr Val Ser Trp Asn Ser Gly Ala Leu Thr
            420                 425                 430

Ser Gly Val His Thr Phe Pro Ala Val Leu Gln Ser Ser Gly Leu Tyr
        435                 440                 445

Ser Leu Ser Ser Val Val Thr Val Pro Ser Ser Ser Leu Gly Thr Lys
    450                 455                 460

Thr Tyr Thr Cys Asn Val Asp His Lys Pro Ser Asn Thr Lys Val Asp
465                 470                 475                 480

Lys Arg Val Glu Ser Lys Tyr Gly Pro Pro Cys Pro Pro Cys Pro Ala
                485                 490                 495

Pro Glu Phe Leu Gly Gly Pro Ser Val Phe Leu Phe Pro Pro Lys Pro
            500                 505                 510

Lys Asp Thr Leu Met Ile Ser Arg Thr Pro Glu Val Thr Cys Val Val
        515                 520                 525

Val Asp Val Ser Gln Glu Asp Pro Glu Val Gln Phe Asn Trp Tyr Val
    530                 535                 540

Asp Gly Val Glu Val His Asn Ala Lys Thr Lys Pro Arg Glu Glu Gln
545                 550                 555                 560

Phe Asn Ser Thr Tyr Arg Val Val Ser Val Leu Thr Val Leu His Gln
                565                 570                 575

Asp Trp Leu Asn Gly Lys Glu Tyr Lys Cys Lys Val Ser Asn Lys Gly
            580                 585                 590

Leu Pro Ser Ser Ile Glu Lys Thr Ile Ser Lys Ala Lys Gly Gln Pro
        595                 600                 605
```

```
Arg Glu Pro Gln Val Tyr Thr Leu Pro Pro Ser Gln Glu Glu Met Thr
    610                 615                 620

Lys Asn Gln Val Ser Leu Thr Cys Leu Val Lys Gly Phe Tyr Pro Ser
625                 630                 635                 640

Asp Ile Ala Val Glu Trp Glu Ser Asn Gly Gln Pro Glu Asn Asn Tyr
                645                 650                 655

Lys Thr Thr Pro Pro Val Leu Asp Ser Asp Gly Ser Phe Phe Leu Tyr
            660                 665                 670

Ser Arg Leu Thr Val Asp Lys Ser Arg Trp Gln Glu Gly Asn Val Phe
        675                 680                 685

Ser Cys Ser Val Met His Glu Ala Leu His Asn His Tyr Thr Gln Lys
    690                 695                 700

Ser Leu Ser Leu Ser Leu Gly Lys
705                 710


<210> SEQ ID NO 142
<211> LENGTH: 711
<212> TYPE: PRT
<213> ORGANISM: Artificial Sequence
<220> FEATURE:
<223> OTHER INFORMATION: Anti-CD3 IgG4P HC Fwk3 anti-CD3 dsscFv (vHvL)

<400> SEQUENCE: 142

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Gly Gly Gly Gly Ser
65                  70                  75                  80

Gly Gly Gly Gly Ser Gln Val Gln Leu Val Gln Ser Gly Gly Gly Val
                85                  90                  95

Val Gln Pro Gly Arg Ser Leu Arg Leu Ser Cys Lys Ala Ser Gly Tyr
            100                 105                 110

Thr Phe Thr Arg Tyr Thr Met His Trp Val Arg Gln Ala Pro Gly Lys
        115                 120                 125

Cys Leu Glu Trp Ile Gly Tyr Ile Asn Pro Ser Arg Gly Tyr Thr Asn
    130                 135                 140

Tyr Asn Gln Lys Phe Lys Asp Arg Phe Thr Ile Ser Arg Asp Asn Ser
145                 150                 155                 160

Lys Asn Thr Ala Phe Leu Gln Met Asp Ser Leu Arg Pro Glu Asp Thr
                165                 170                 175

Gly Val Tyr Phe Cys Ala Arg Tyr Tyr Asp Asp His Tyr Cys Leu Asp
            180                 185                 190

Tyr Trp Gly Gln Gly Thr Pro Val Thr Val Ser Ser Gly Gly Gly Gly
        195                 200                 205

Ser Gly Gly Gly Gly Ser Gly Gly Gly Gly Ser Gly Gly Gly Gly Ser
    210                 215                 220

Asp Ile Gln Met Thr Gln Ser Pro Ser Ser Leu Ser Ala Ser Val Gly
225                 230                 235                 240

Asp Arg Val Thr Ile Thr Cys Ser Ala Ser Ser Ser Val Ser Tyr Met
                245                 250                 255
```

```
Asn Trp Tyr Gln Gln Thr Pro Gly Lys Ala Pro Lys Leu Leu Ile Tyr
            260                 265                 270

Asp Thr Ser Lys Leu Ala Ser Gly Val Pro Ser Arg Phe Ser Gly Ser
        275                 280                 285

Gly Ser Gly Thr Asp Tyr Thr Phe Thr Ile Ser Ser Leu Gln Pro Glu
    290                 295                 300

Asp Ile Ala Thr Tyr Tyr Cys Gln Gln Trp Ser Ser Asn Pro Phe Thr
305                 310                 315                 320

Phe Gly Cys Gly Thr Lys Leu Glu Ile Lys Gly Gly Gly Gly Ser Gly
                325                 330                 335

Gly Gly Gly Ser Lys Asn Thr Ala Phe Leu Gln Met Asp Ser Leu Arg
            340                 345                 350

Pro Glu Asp Thr Gly Val Tyr Phe Cys Ala Arg Tyr Tyr Asp Asp His
        355                 360                 365

Tyr Cys Leu Asp Tyr Trp Gly Gln Gly Thr Pro Val Thr Val Ser Ser
    370                 375                 380

Ala Ser Thr Lys Gly Pro Ser Val Phe Pro Leu Ala Pro Cys Ser Arg
385                 390                 395                 400

Ser Thr Ser Glu Ser Thr Ala Ala Leu Gly Cys Leu Val Lys Asp Tyr
                405                 410                 415

Phe Pro Glu Pro Val Thr Val Ser Trp Asn Ser Gly Ala Leu Thr Ser
            420                 425                 430

Gly Val His Thr Phe Pro Ala Val Leu Gln Ser Ser Gly Leu Tyr Ser
        435                 440                 445

Leu Ser Ser Val Val Thr Val Pro Ser Ser Ser Leu Gly Thr Lys Thr
    450                 455                 460

Tyr Thr Cys Asn Val Asp His Lys Pro Ser Asn Thr Lys Val Asp Lys
465                 470                 475                 480

Arg Val Glu Ser Lys Tyr Gly Pro Pro Cys Pro Pro Cys Pro Ala Pro
                485                 490                 495

Glu Phe Leu Gly Gly Pro Ser Val Phe Leu Phe Pro Pro Lys Pro Lys
            500                 505                 510

Asp Thr Leu Met Ile Ser Arg Thr Pro Glu Val Thr Cys Val Val Val
        515                 520                 525

Asp Val Ser Gln Glu Asp Pro Glu Val Gln Phe Asn Trp Tyr Val Asp
    530                 535                 540

Gly Val Glu Val His Asn Ala Lys Thr Lys Pro Arg Glu Glu Gln Phe
545                 550                 555                 560

Asn Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Gly Leu
            580                 585                 590

Pro Ser Ser Ile Glu Lys Thr Ile Ser Lys Ala Lys Gly Gln Pro Arg
        595                 600                 605

Glu Pro Gln Val Tyr Thr Leu Pro Pro Ser Gln Glu Glu Met Thr Lys
    610                 615                 620

Asn Gln Val Ser Leu Thr Cys Leu Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Tyr Ser
            660                 665                 670
```

```
Arg Leu Thr Val Asp Lys Ser Arg Trp Gln Glu Gly Asn Val Phe Ser
        675                 680                 685

Cys Ser Val Met His Glu Ala Leu His Asn His Tyr Thr Gln Lys Ser
    690                 695                 700

Leu Ser Leu Ser Leu Gly Lys
705                 710


<210> SEQ ID NO 143
<211> LENGTH: 251
<212> TYPE: PRT
<213> ORGANISM: Artificial Sequence
<220> FEATURE:
<223> OTHER INFORMATION: CA645 scFv (VH-VL)

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Val Ser Ala Ser Val Gly Asp Arg Val
145                 150                 155                 160

Thr Ile Thr Cys Gln Ser Ser Pro Ser Val Trp Ser Asn Phe Leu Ser
                165                 170                 175

Trp Tyr Gln Gln Lys Pro Gly Lys Ala Pro Lys Leu Leu Ile Tyr Glu
            180                 185                 190

Ala Ser Lys Leu Thr Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gly Gly Gly Tyr Ser Ser Ile Ser Asp Thr
225                 230                 235                 240

Thr Phe Gly Gln Gly Thr Lys Val Glu Ile Lys
                245                 250


<210> SEQ ID NO 144
<211> LENGTH: 251
<212> TYPE: PRT
<213> ORGANISM: Artificial Sequence
<220> FEATURE:
<223> OTHER INFORMATION: CA645 dsscFv (VH-VL)

<400> SEQUENCE: 144

Glu Val Gln Leu Leu Glu Ser Gly Gly Gly Leu Val Gln Pro Gly Gly
1               5                   10                  15
```

-continued

```
Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Val Ser Ala Ser Val Gly Asp Arg Val
145                 150                 155                 160

Thr Ile Thr Cys Gln Ser Ser Pro Ser Val Trp Ser Asn Phe Leu Ser
                165                 170                 175

Trp Tyr Gln Gln Lys Pro Gly Lys Ala Pro Lys Leu Leu Ile Tyr Glu
            180                 185                 190

Ala Ser Lys Leu Thr Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gly Gly Gly Tyr Ser Ser Ile Ser Asp Thr
225                 230                 235                 240

Thr Phe Gly Cys Gly Thr Lys Val Glu Ile Lys
                245                 250
```

ANTIBODIES COMPRISING A POLYPEPTIDE INSERTED IN FRAMEWORK 3 REGION

CROSS-REFERENCE TO RELATED APPLICATION

This application is a U.S. national stage under 35 U.S.C. § 371 of International Patent Application No. PCT/EP2019/068570, filed Jul. 10, 2019, which claims the benefit of and priority to Great Britain Application No. 1811368.8, filed on Jul. 11, 2018, the content of each of which is incorporated by reference herein in its entirety and for all purposes.

FIELD OF THE INVENTION

The present invention relates to antibodies comprising a variable (V) domain and an insert polypeptide within the framework 3 region of the V domain. Such antibodies may provide improved functionality and/or pharmacokinetics for the insert polypeptide.

BACKGROUND OF THE INVENTION

The high specificity and affinity of antibodies makes them ideal diagnostic and therapeutic agents. Advances in the field of recombinant antibody technology have resulted in the production of antibody fragments, such as Fv, Fab, Fab' and F(ab')2 fragments. These smaller molecules retain the antigen binding activity of whole antibodies and can also exhibit improved tissue penetration and pharmacokinetic properties in comparison to whole immunoglobulin molecules. Indeed, antibody fragments are proving to be versatile therapeutic agents. Whilst such fragments appear to exhibit a number of advantages over whole immunoglobulins, they also suffer from an increased rate of clearance from serum since they lack the Fc domain that imparts a long lifetime in vivo (Medasan et al., 1997, J. Immunol. 158: 2211-2217). Previous approaches to improving the serum half-life of antibody molecules include conjugation to agents or domains which interact with the FcRn receptor, such as human serum albumin (HSA). PEG has also been shown to improve serum half-life.

Antibodies with dual specificity, i.e. which bind to two different antigens have been previously described (for reviews, see Segal et al., 1999, Curr. Opin. Immunol. 11:558-562; Pluckthun & Pack, 1997, Immunotechnology, 3:83-105; Fischer and Leger, 2007, Pathobiology, 74: 3-14). Previous approaches to making hetero-bispecific antibody-based molecules have generally employed chemical cross-linking or protein engineering techniques. Chemical cross-linking suffers from poor yields of hetero- and homo-dimer formation, and the requirement for their subsequent chromatographic separation. Protein engineering approaches have either been highly elaborate (e.g. knobs-into-holes engineering; Ridgway et al., 1996, Protein Eng. 9(7):617-621) or have used molecules with inappropriate stability characteristics (e.g. diabodies, scFv). In some cases, bispecific antibodies can also suffer from steric hindrance problems such that both antigens cannot bind simultaneously to each antibody arm. Single variable domain antibodies also known as single domain antibodies or sdAbs, correspond to the variable regions of either the heavy (VH) or light (VL) chain of an antibody. Murine single-domain antibodies were described by Ward et al., 1989, Nature, 341, 544-546. Human and 'camelised' human single domain antibodies have also been described (Holt et al., 2003, Trends in Biotechnology, 21, 484-490). Single domain antibodies have also been obtained from the camelids (camels and llamas) and cartilaginous fish (wobbegong and nurse sharks). These organisms have evolved high affinity single V-like domains (called VHH in camelids and V-NAR in sharks), mounted on an Fc-equivalent constant domain framework as an integral and crucial component of their immune system (see Holliger & Hudson, for a review; 2005, Nature Biotechnology, 23 (9): 1126-1136).

As such, there remains a need to provide further engineered antibodies such as fusion proteins comprising an antibody portion which exhibits one or more desired properties, such as increased functionality (e.g. multi-valent binding) or improved pharmacokinetics (e.g. increased half-life in serum). It is the object of the present invention to provide a novel engineered antibody format which exhibit increased functionality (e.g. increased binding to its antigen, bi-specific binding, or multi-valent binding) or improved pharmacokinetics (e.g. increased half-life in serum). In particular, the present invention provides a novel bispecific antibody format, in particular stable and capable of simultaneously binding two antigens.

SUMMARY OF THE INVENTION

In one aspect, the present invention provides an antibody comprising a variable (V) domain and an insert polypeptide, wherein the insert polypeptide is within the framework 3 region of the V domain.

In some embodiments, the V domain is a VH domain, and the antibody may further comprise a VL domain.

In some embodiments, the V domain is a VL domain, and the antibody may further comprise a VH domain.

In some embodiments, the insert polypeptide is between amino acid residues 73 and 76 of the VH domain. For example, the insert polypeptide may be in the VH domain: (i) between amino acid residues 73 and 74; (ii) between amino acid residues 74 and 75; or (iii) between amino acid residues 75 and 76.

In some embodiments, one or more amino acid residues between 73 and 76 of the VH domain are replaced by the insert polypeptide.

In some embodiments, the insert polypeptide is between amino acid residues 67 and 70 of the VL domain. For example, the insert polypeptide may be in the VL domain: (i) between amino acid residues 67 and 68; (ii) between amino acid residues 68 and 69; or (iii) between amino acid residues 69 and 70.

In some embodiments, one or more amino acid residues between 67 and 70 of the VL domain are replaced by the insert polypeptide.

In some embodiments, the antibody of the invention further comprises a linker sequence, preferably of at least one, two, three, four, five, six, seven, eight, nine or ten amino acids joining the N- and/or C-terminal end of the insert polypeptide to the framework 3 region.

In some embodiments, the antibody of the invention is a full-length antibody or a binding fragment thereof. In some embodiments, the antibody is a full-length IgG or a binding fragment thereof. In some embodiments, the antibody is a Fab, Fab', $F(ab')_2$, VHH, or scFv, in particular dsscFv.

In some embodiments, the antibody of the invention is humanised.

In some embodiments, the antibody of the invention comprises a V domain which binds to human serum albumin (HSA). In one embodiment, the antibody comprises a VL domain comprising CDR-L1 having the sequence SEQ ID NO: 3; CDR-L2 having the sequence SEQ ID NO: 4; CDR-L3 having the sequence SEQ ID NO: 5. In one embodiment, the antibody comprises a VL domain comprising SEQ ID NO: 2. In one embodiment, the antibody comprises a light (L) chain comprising SEQ ID NO: 1. In one embodiment, the antibody comprises a VH domain comprising CDR-H1 having the sequence SEQ ID NO: 8; CDR-H2 having the sequence SEQ ID NO: 9; CDR-H3 having the sequence SEQ ID NO: 10. In one embodiment, the antibody comprises a VH domain comprising SEQ ID NO: 7. In one embodiment, the antibody comprises a heavy (H) chain comprising SEQ ID NO: 6.

In some embodiments, the insert polypeptide is a cytokine, preferably wherein the cytokine is selected from IL-10, IL-15, IL-2, G-CSF, GM-CSF and EPO. In other embodiments, the insert polypeptide is sclerostin. In other embodiments, the insert polypeptide is a second antibody, preferably wherein the second antibody is an scFv, in particular a dsscFv, or a domain antibody such as a VH or VL or VHH. The VHH may comprise a sequence selected from SEQ ID NOs: 67, 69 and 89. In such embodiments, the antibody may bind its cognate antigen by said V domain with a binding affinity which is at least 50%, 60%, 70%, 80% or 90% when compared to the antibody without the insert polypeptide present.

In some embodiments, the second antibody binds to the same antigen as the V domain. Preferably, the second antibody binds to a different epitope as the V domain. In such embodiments, the antibody may bind its cognate antigen with a binding affinity which is greater than when compared to the antibody without the second antibody present. In some embodiments, the second antibody binds to a different antigen to the first antibody, i-e the antibody comprising a V domain. In some embodiments, the second antibody binds to IL-17 and the first antibody, i-e the antibody comprising a V domain, binds to HSA. In some embodiments, the second antibody binds to CD3 and the first antibody, i-e the antibody comprising a V domain, binds to CD28. In some embodiments, the second antibody binds to CD28 and the first antibody, i-e the antibody comprising a V domain binds to CD3.

The present invention also provides isolated polynucleotide(s), such as a DNA molecule(s), and cloning or expression vector(s) which encodes an antibody disclosed herein. Also provided is a host cell comprising said polynucleotide (s) or vector(s). The present invention further provides a process for the production of an antibody as disclosed herein, comprising culturing said host cell and isolating the antibody.

In another aspect, the present invention also provides a pharmaceutical composition comprising an antibody comprising a V domain and an insert polypeptide as disclosed herein in combination with one or more of a pharmaceutically acceptable excipient, diluent or carrier. Also provided is said antibody or said pharmaceutical composition for use in therapy. Also provided is a method of therapy comprising administering said antibody or said pharmaceutical composition to a subject in need of the therapy. Also provided is the use of said antibody for the manufacture of a medicament.

IgG4; (B) CA645 Fab-Fwk3 CA497 dsscFv (vHvL); (C) CA645 Fab-Fwk3 CA497 dsscFv (vLvH).

Figure 22:
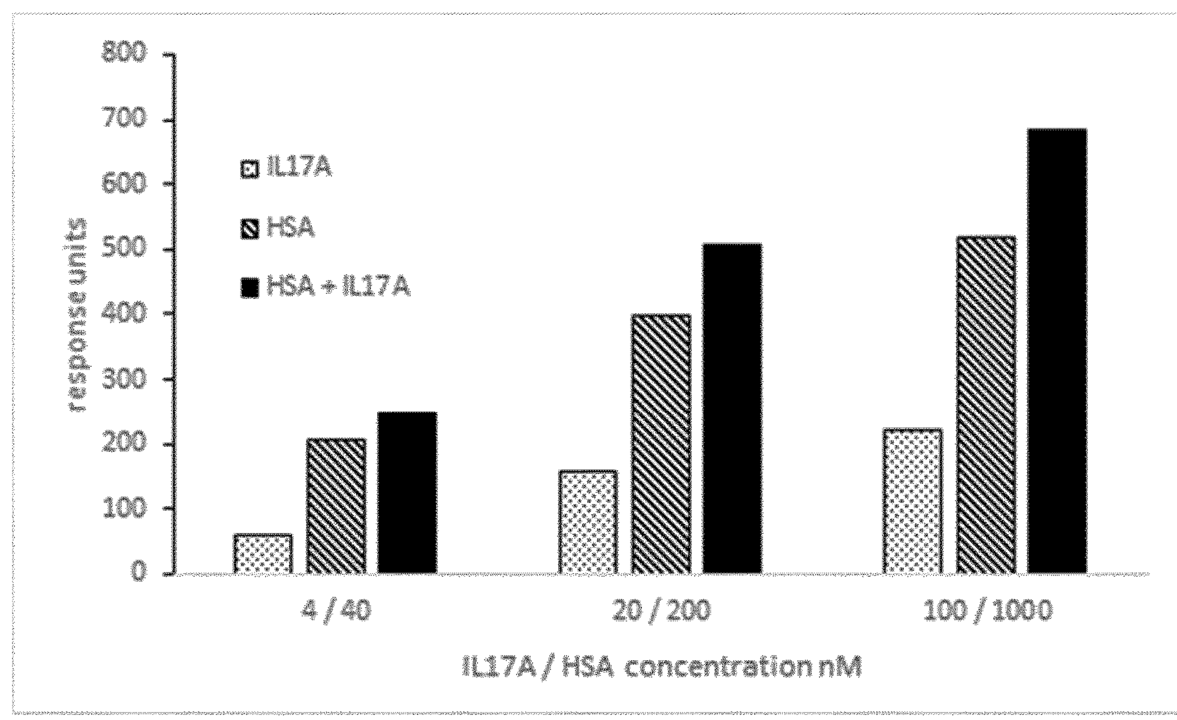

FIG. 22: SPR analysis showing the binding of IL-17A and HSA to immobilized CA645 IgG4P comprising an anti-IL-17 CA497 dsscFv (vHvL) inserted into Fwk3 region.

Figure 23:
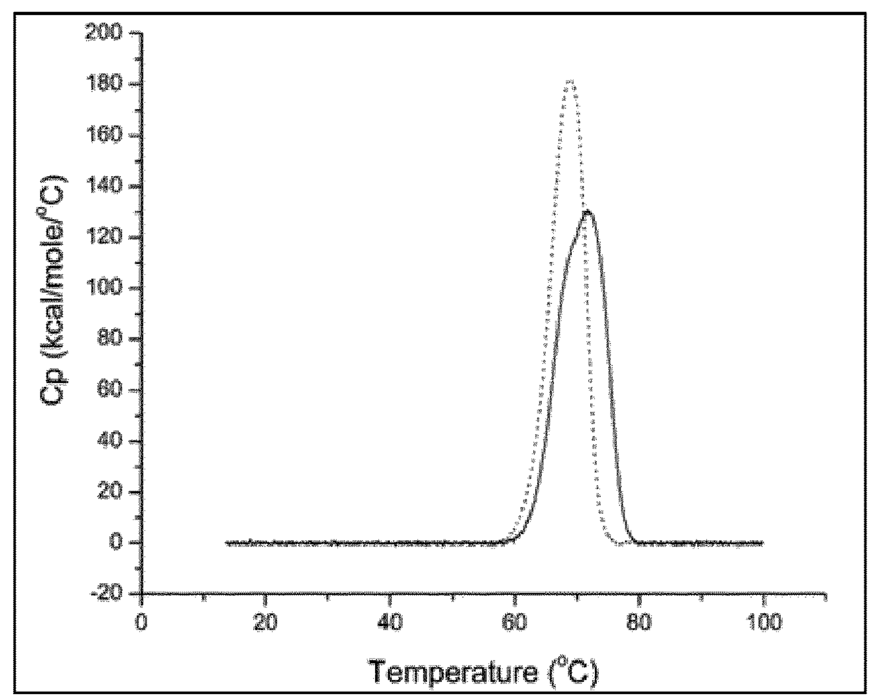
Figure 23:
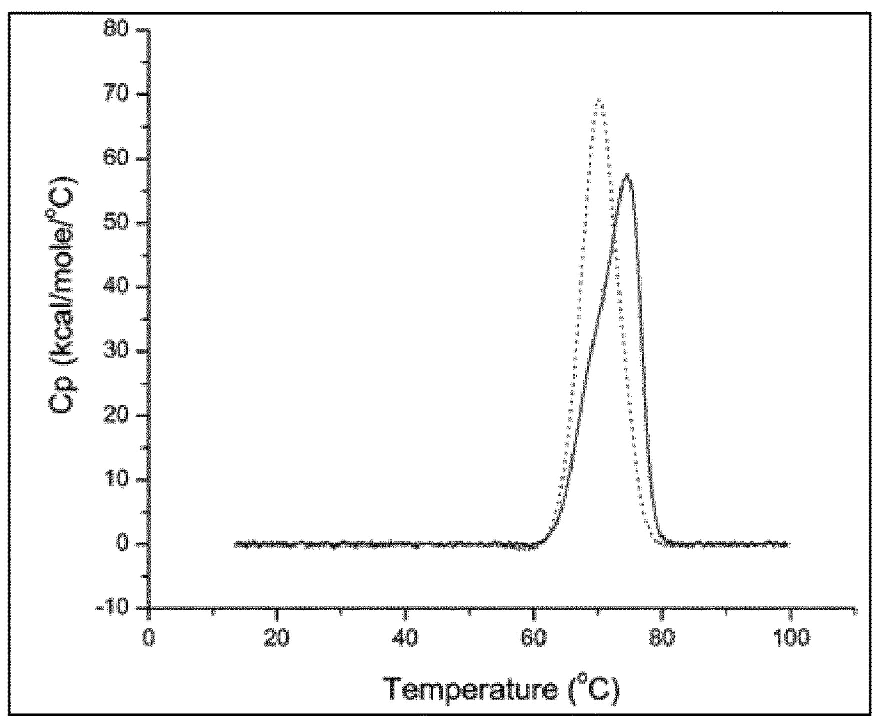

FIG. 23: DSC curves. (A) IgG4P anti-CD28 comprising a dsscFv anti-CD3 within the Fwk3 region (solid line); IgG4P anti-CD3 comprising a dsscFv anti-CD3 within the Fwk3 region (dotted line). (B) Fab anti-CD28 comprising a dsscFv anti-CD3 within the Fwk3 region (solid line); Fab anti-CD3 comprising a dsscFv anti-CD3 within the Fwk3 region (dotted line).

Figure 24:
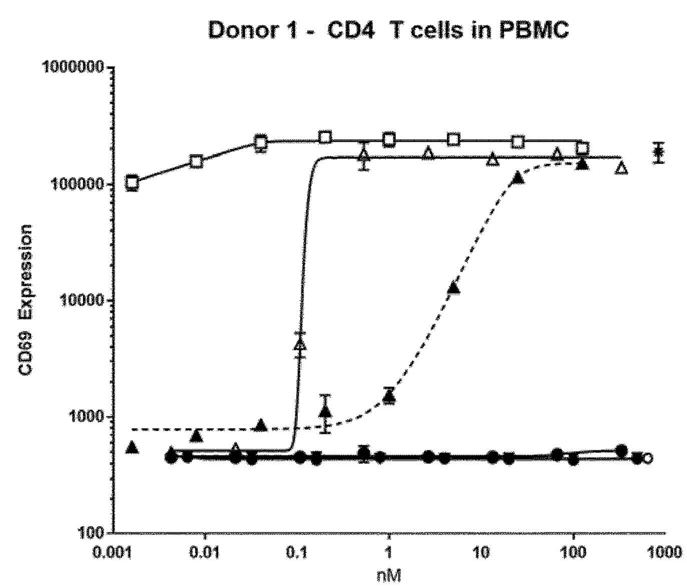
Figure 24:
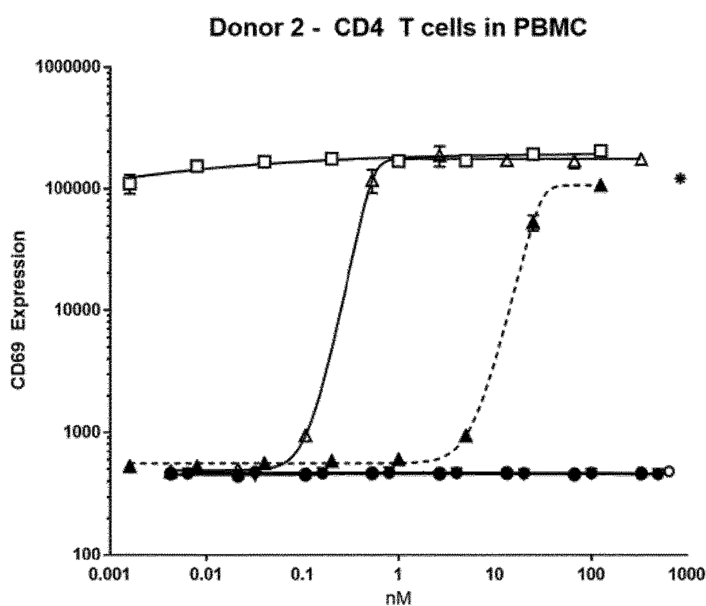
Figure 24:
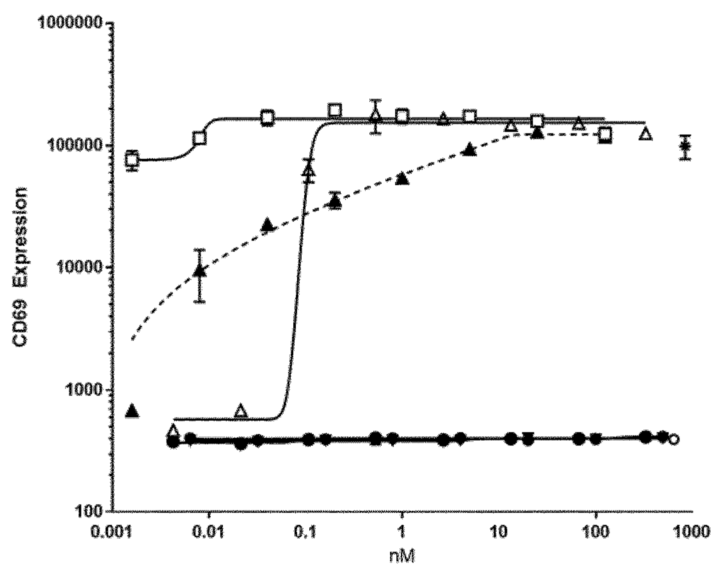
Figure 24:
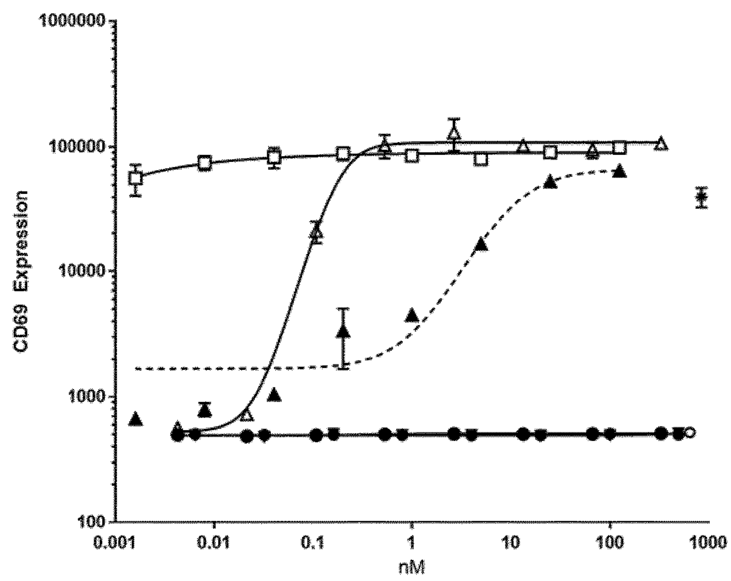

FIG. 24: T cell activation assay in PBMC. Open triangle: anti-CD28 Fab Fwk3-anti-CD3 dsscFv; solid circle: anti-CD3 Fab; solid inverted triangle: anti-CD28 Fab; solid circle: anti-CD3 Fab Fwk3-anti-CD3 dsscFv; open square: anti-CD28 IgG4P Fwk3-anti-CD3 dsscFv; solid triangle: anti-CD3 IgG4P-Fwk3 anti-CD3 dsscFv; * symbol: OKT3; open circle: Cells only control. (A) CD4 T cell activation (patient 1) (B) CD4 T cell activation (patient 2) (C) CD8 T cell activation (patient 1) (D) CD8 T cell activation (patient 2).

DETAILED DESCRIPTION

Antibody

The present invention provides an antibody comprising a variable (V) domain and an insert polypeptide, wherein the insert polypeptide is within the framework 3 (Fwk3) region of the V domain.

The antibody of the present invention is typically constructed by incorporating the insert polypeptide into the Fwk3 region of a V domain of an antibody. The V domain may for example be a VH domain or a VL domain. The antibody into which the insert polypeptide is incorporated may be considered a scaffold antibody and/or where the insert polypeptide is also an antibody, the antibody into which the insert polypeptide is incorporated may alternatively be termed the first antibody while the insert polypeptide is termed the second antibody. The terms "scaffold antibody" and "first antibody" can be used interchangeably in the context of the present disclosure to refer to the antibody into which the insert polypeptide is incorporated.

In some embodiments, the antibody of the invention is a full-length antibody or a binding fragment thereof. In some embodiments, the antibody is a full-length IgG or a binding fragment thereof. In some embodiments, the antibody is a full-length IgG1. In some embodiments, the antibody is a full-length IgG4. In some embodiments, the antibody is a full-length IgG4P, wherein the serine at position 241 (numbered according to the Kabat numbering system) has been changed to proline. In some embodiments, the antibody is a Fab, Fab', F(ab')$_2$, VHH, or scFv. In some embodiments, the antibody is a disulphide stabilised scFv or "dsscFv". "Disulphide-stabilised single chain variable fragment" or "dsscFv" as employed herein refer to a single chain variable fragment which is stabilised by a peptide linker between the VH and VL variable domain and also includes an inter-domain disulphide bond between VH and VL. (see for example, Weatherill et al., Protein Engineering, Design & Selection, 25 (321-329), 2012; WO2007109254. In some embodiments, the inter-domain disulphide bond between $V_H$ and $V_L$ is formed between positions $V_H$44 and $V_L$100 (numbering according to Kabat numbering system).

The term 'antibody' as used herein generally relates to full length (intact, whole) antibodies, i.e. comprising elements of two heavy chains and two light chains in the case of an IgG antibody.

The terms "antibody construct", "engineered antibody", "antibody fusion protein" can be used interchangeably in the context of the present invention to refer to an antibody of the invention.

Binding fragments of antibodies generally comprise at least one variable light (VL) or variable heavy (VH) domain and include: single chain antibodies (e.g. a full length heavy chain or light chain), Fab, modified Fab, Fab', modified Fab', F(ab')2, Fv, Fab-Fv, Fab-dsFv, single domain antibodies (sdAb, e.g. VH or VL or VHH), scFv, dsscFv, Bis-scFv, diabodies, tribodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody binding fragments are well known in the art (see for example Verma et al., 1998, Journal of Immunological Methods, 216, 165-181). For example, antibody binding fragments may be obtained from any whole antibody, especially a whole monoclonal antibody, using any suitable enzymatic cleavage and/or digestion techniques, e.g. treatment with pepsin. Alternatively, the antibody starting material may be prepared by the use of recombinant DNA techniques involving the manipulation and re-expression of DNA encoding antibody variable and/or constant regions. Standard molecular biology techniques may be used to modify, add or delete amino acids or domains as desired. Any alterations to the variable or constant regions are still encompassed by the terms 'variable' and 'constant' regions as used herein. The antibody fragment starting material may be obtained from any species including, for example, mouse, rat, rabbit, hamster, camel, llama, goat or human. Parts of the antibody fragment may be obtained from more than one species; for example, the antibody fragments may be chimeric. In one example, the constant regions are from one species and the variable regions from another. The antibody fragment starting material may also be modified. In another example, the variable region of the antibody fragment has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and, optionally, one or more framework amino acids from one antibody and the remainder of the variable region domain from a second antibody. The Fab-Fv format was first disclosed in WO2009/040562, and the disulphide stabilised version thereof, the Fab-dsFv, was first disclosed in WO2010/035012. Other antibody fragments include the Fab and Fab' fragments described in International patent applications WO2005/003169, WO2005/003170 and WO2005/003171. Multi-valent antibodies may comprise multiple specificities e.g. bispecific or may be monospecific (see for example WO 92/22583 and WO05/113605). One such example of the latter is a Tri-Fab (or TFM) as described in WO92/22583. Another multi-specific format is described in WO2015/197772.

A typical Fab' molecule comprises a heavy and a light chain pair in which the heavy chain comprises a variable region VH, a constant domain CH1 and a natural or modified hinge region and the light chain comprises a variable region VL and a constant domain CL.

A binding domain of an antibody typically comprises 6 CDRs, three from a heavy chain and three from a light chain. In such an antibody, the CDRs are in a framework and together form a variable region. Thus, in one embodiment the antibody comprises a binding domain specific for an antigen comprising a light chain variable region and a heavy chain variable region. In other embodiments, for example wherein the antibody is a single domain antibody, the binding domain may only comprise the 3 CDRs from a single V domain of either a heavy chain or a light chain. Thus, in one embodiment the antibody comprises a binding domain specific for an antigen comprising one of a light chain variable region (VL domain) or a heavy chain variable region (VH or VHH domain). It will be appreciated that the V domain which binds the antigen may do so alone, or co-operatively with another V domain, for example as a complementary VH/VL pair. Accordingly, the antibody comprising a V domain may bind its antigen co-operatively with a complementary V (VH or VL) domain. In one embodiment, the V domain is a VH domain, and the antibody of the invention further comprises a VL domain, wherein the VH domain binds its antigen co-operatively with the VL domain as a VH/VL pair, i-e the antibody of the invention comprises a VH domain and binds its antigen co-operatively with a complementary VL domain. In one embodiment, the V domain is a VL domain, and the antibody of the invention further comprises a VH domain, wherein the VL binds its antigen co-operatively with the VH domain as a VH/VL pair, i-e the antibody of the invention comprises a VL domain and binds its antigen co-operatively with a complementary VH domain. The binding domain of the antibody of the invention typically refers to the VH, VL, or pair of VH/VL which binds the antigen. Antibodies contain generally one or more binding domains. For example, an unmodified Fab fragment comprises one binding domain formed by a VH/VL pair, and a whole IgG comprises two binding domains, each one being formed by a VH/VL pair, wherein the two binding domains are identical (monospecific antibody) or different (bispecific or bivalent antibody). In one example, the antibody of the invention may be a Fab fragment comprising a VH domain and an insert polypeptide within the Fwk3 region of the VH domain, and further comprising a VL domain which forms a complementary pair with the VH domain. In one example, the VL domain may be unmodified (i-e the antibody of the invention is a Fab fragment comprising a single insert polypeptide within the Fwk3 region of the VH domain) or may comprise an insert polypeptide in its Fwk3 region (i-e the antibody of the invention is a Fab fragment comprising two insert polypeptides, identical, similar or different, one inserted within the Fwk3 region of the VH domain and the other one inserted within the Fwk3 region of the VL domain). In one example, the antibody of the invention may be a Fab fragment comprising a VL domain and an insert polypeptide within the Fwk3 region of the VL domain, and further comprising a VH domain which forms a complementary pair with the VL domain. In one example, the VH domain may be unmodified (i-e the antibody of the invention is a Fab fragment comprising a single insert polypeptide within the Fwk3 region of the VL domain) or may comprise an insert polypeptide in its Fwk3 region (i-e the antibody of the invention is a Fab fragment comprising two insert polypeptides, identical, similar or different, one inserted within the Fwk3 region of the VL domain and the other one inserted within the Fwk3 region of the VH domain). In another example, the antibody of the invention is a full IgG comprising a VH domain and an insert polypeptide within the Fwk3 region of the VH domain, and further comprising a VL domain which forms a complementary pair with the VH domain. In one example, the VL domain may be unmodified (i-e the antibody of the invention is an IgG comprising two insert polypeptides, each one being inserted into one of the two VH domains of the IgG) or may comprise an insert polypeptide in its Fwk3 region (i-e the antibody of the invention is an IgG comprising four insert polypeptides, identical, similar or different, each of them being inserted into the Fwk3 region of each one of its two VH and two VL domains). In another example, the antibody of the invention is a full IgG comprising a VL domain and an insert polypeptide within the Fwk3 region of the VL domain, and further comprising a VH domain which forms a complementary pair with the VL. The VH domain may be unmodified (i-e the antibody of the invention is an IgG comprising two insert polypeptides, each one being inserted into one of the two VL domains of the IgG) or may comprise an insert polypeptide in its Fwk3 region (i-e the antibody of the invention is an IgG comprising four insert polypeptides, identical, similar or different, each of them being inserted into the Fwk3 region of each one of its two VL and two VH domains).

The residues in antibody variable domains are conventionally numbered according to a system devised by Kabat et al. This system is set forth in Kabat et al., 1987, in Sequences of Proteins of Immunological Interest, US Department of Health and Human Services, NIH, USA. This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence by methods known in the art.

Figure 1:
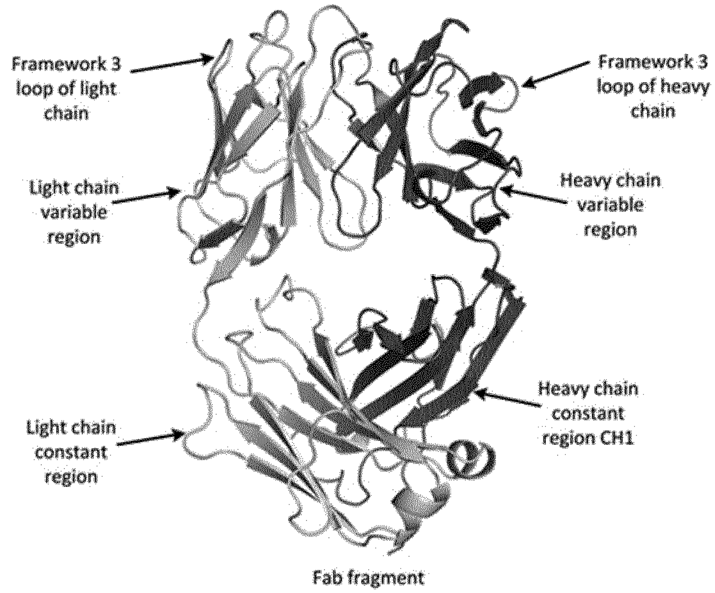
FIG. 1: (A) Typical Fab structure, highlighting framework 3 loop region; (B) highlighting certain residues in the heavy chain variable domain framework 3 region; (C) highlighting certain residues in the light chain variable domain framework 3 region.
Figure 1:
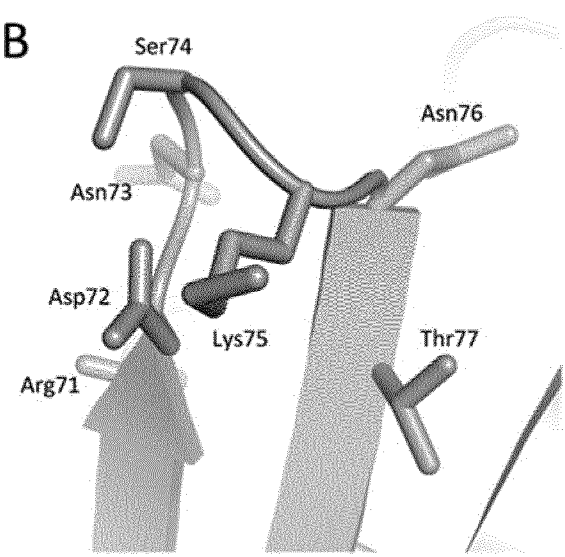
Figure 1:
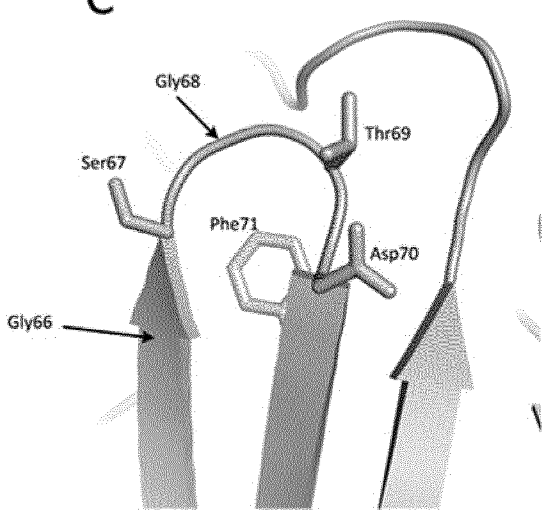

The CDRs of the heavy chain variable domain are located at residues 31-35 (CDR-H1), residues 50-65 (CDR-H2) and residues 95-102 (CDR-H3) according to the Kabat numbering system. The CDRs of the light chain variable domain are located at residues 24-34 (CDR-L1), residues 50-56 (CDR-L2) and residues 89-97 (CDR-L3) according to the Kabat numbering system. In addition to the CDR loops, a fourth loop exists between CDR-2 and CDR-3 which is formed by framework 3 (Fwk3). FIG. 1A provides a representation of the framework 3 loop in the context of a Fab having a light and a heavy chain. FIGS. 1B and 1C also shows representative residues from these loops. The Kabat numbering system defines framework 3 as positions 66-94 in a heavy chain and positions 57-88 in a light chain.

Thus, in one embodiment, an antibody of the present invention comprises a variable (V) domain and an insert polypeptide, wherein the insert polypeptide is within positions 66-94 when the V domain is a VH domain, or positions 57-88 when the V domain is a VL domain, in accordance with the Kabat numbering system.

In some embodiments, the insert polypeptide is between amino acid residues 73 and 76 of the VH domain, in accordance with the Kabat numbering system. Preferably, the insert polypeptide may be between amino acid residues 73 and 74, 74 and 75, or 75 and 76 of the VH domain, in accordance with the Kabat numbering system. In some embodiments, the insert polypeptide is between amino acid residues 76 and 77, or 77 and 78 of the VH domain, in accordance with the Kabat numbering system. In some embodiments, one or more amino acid residues of the VH domain are replaced by the insert polypeptide.

In some embodiments, the insert polypeptide is between amino acid residues 67 and 70 of the VL domain, in accordance with the Kabat numbering system. Preferably, the insert polypeptide may be between amino acid residues 67 and 68, 68 and 69, or 69 and 70 of the VL domain, in accordance with the Kabat numbering system. In some embodiments, one or more amino acid residues of the VL domain are replaced by the insert polypeptide.

The antibody of the present invention may further comprise constant region domains. The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when antibody effector functions are required. Alternatively, IgG2 and IgG4 isotypes may be used when antibody effector functions are not required. It will be appreciated that sequence variants of these constant region domains may also be used. For example, IgG4 molecules in which the serine at position 241 has been changed to proline as described in Angal et al. Molecular Immunology, 1993, 30 (1), 105-108 may be used. It will also be understood by one skilled in the art that antibodies may undergo a variety of post-translational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705:129-134, 1995).

Antibodies for use in the present invention may be fully human antibodies, humanised antibodies, or chimeric antibodies.

In one embodiment, the antibody of the present invention is not a murine antibody. The term “murine antibody” refers to an antibody having heavy and light chains derived exclusively from murine B cells. This antibody is thus constituted of murine amino acid sequences, whatever the origin of the cell which enables the production thereof.

In one embodiment, the antibody of the present invention is a chimeric antibody. The term “chimeric antibody” refers to an antibody or antigen-binding fragment thereof wherein each light chain and/or each heavy chain sequence of which it is constituted comprises or consists of a hybrid sequence derived from at least two different animals, notably mammals, in particular, an antibody that combines the rabbit, murine, rat, or cynomolgus variable region with the human constant region.

In one embodiment, the antibody of the present invention is a humanised antibody. Humanised antibodies are antibody molecules from non-human species having one or more complementarity determining regions (CDRs) from the non-human species and a framework region from a human immunoglobulin molecule (see, for example, U.S. Pat. No. 5,585,089). In particular, the term “humanised” refers to an antibody or antigen-binding fragment thereof wherein the heavy and/or light chain contains one or more CDRs from a non-human antibody (such as a rabbit, murine, rat, cynomolgus or llama monoclonal antibody) grafted into a heavy and/or light chain variable region framework of an acceptor antibody such as a human antibody. Rather than the entire CDR being transferred, only one or more of the specificity determining residues from any one of the CDRs described herein above can be transferred to the human antibody framework (see for example, Kashmiri et al., 2005, Methods, 36, 25-34). Selected framework residues of the humanised antibody can be substituted with corresponding residues (so-called donor residues) from a non-human antibody (e.g. the antibody from which the CDRs or the specificity determining residues are derived) e.g. to restore or improve the antibody specificity or affinity.

Fully human antibodies are those antibodies in which the variable region(s) and the constant region(s) (where present) of both the heavy and/or the light chains are all of human origin, or substantially identical to sequences of human origin, not necessarily from the same antibody. Examples of fully human antibodies may include antibodies produced for example by phage display methods and antibodies produced by mice in which the murine immunoglobulin variable and/or constant region genes have been replaced by their human counterparts, e.g. as described in general terms in EP0546073 B1, U.S. Pat. Nos. 5,545,806, 5,569,825, 5,625,126, 5,633,425, 5,661,016, 5,770,429, EP 0438474 B1 and EP0463151 B1.

The antibodies comprising a V domain and an insert polypeptide as disclosed herein may be further modified, for example chemically conjugated to further compounds which may affect e.g. its pharmacokinetic properties or antigen binding.

In one example the antibodies of the present invention are attached to poly(ethyleneglycol) (PEG) moieties. Antibodies linked to PEG may display further increased serum half-life, for example. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971, WO2008/038024). In one example, the antibody of the present invention is a modified Fab fragment wherein the modification is the addition to the C-terminal end of its heavy chain of one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules may be covalently linked through a thiol group of at least one cysteine residue located in the antibody fragment. Each polymer molecule attached to the modified antibody fragment may be covalently linked to the sulphur atom of a cysteine residue located in the antibody fragment. The covalent linkage will generally be a disulphide bond or, in particular, a sulphur-carbon bond. Where a thiol group is used as the point of attachment, appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

Preferably, the antibody of the present invention has a binding affinity (as measured by its dissociation constant $K_D$) for its cognate antigen of $10^{-5}$ M or less, $10^{-6}$ M or less, $10^{-7}$ M or less, $10^{-8}$ M or less, $10^{-9}$ M or less, $10^{-10}$ M or less, or $10^{-11}$ M or less. Affinity can be measured by known techniques such as surface plasmon resonance techniques including Biacore™. Affinity may be measured at room temperature, 25° C. or 37° C. Affinity may be measured at physiological pH, i.e. at about pH 7.4.

It will be appreciated that the affinity of antibodies provided by the present invention may be altered using any suitable method known in the art. The present invention therefore also relates to variants of the antibody molecules of the present invention, which have an improved affinity for albumin. Such variants can be obtained by a number of affinity maturation protocols including mutating the CDRs (Yang et al., J. Mol. Biol, 254. 392-403, 1995), chain shuffling (Marks et al., Bio/Technology, 10, 779-783, 1992), use of mutator strains of *E. coli* (Low et al., J. Mol. Biol., 260. 359-368, 1996), DNA shuffling (Patten et al., Curr. Opin. BiotechnoL, 8, 724-733, 1997), phage display (Thompson et al., J. Mol. Biol, 256. 77-88, 1996) and sexual PCR (Crameri et al. Nature, 391, 288-291, 1998).

Human Serum Albumin-Binding Antibody

In one embodiment, the antibody of the invention comprises a V domain which binds to human serum albumin (HSA). In such an embodiment, the antibody may be useful in extending the serum half-life of the insert polypeptide. It will be appreciated that the V domain which binds albumin may do so alone, or co-operatively with another V domain, for example as a complementary VH/VL pair. Accordingly, in some embodiments, the antibody comprising a V domain binds albumin co-operatively with a complementary VH or VL domain. In one embodiment, the V domain is a VH domain, and the antibody of the invention further comprises a VL domain, wherein the VH binds albumin co-operatively with the VL domain as a VH/VL pair, i-e the antibody of the invention comprises a VH domain and binds to albumin co-operatively with a complementary VL. In one embodiment, the V domain is a VL domain, and the antibody of the invention further comprises a VH domain, wherein the VL binds albumin co-operatively with the VH domain as a VH/VL pair, i-e the antibody of the invention comprises a VL domain and binds to albumin co-operatively with a complementary VH. Where the antibody of the invention binds albumin, the VH/VL is typically termed "albumin binding domain". As such, the albumin binding domain of the antibody of the invention refers to the VH, VL, or pair of VH/VL which binds to albumin.

In one embodiment, the antibody of the present invention binds cynomolgus serum albumin, murine serum albumin and/or rat serum albumin.

In one embodiment, the antibody of the present invention comprising a V domain which binds to human serum albumin is humanised. In one embodiment, the antibody of the present invention comprising an albumin binding domain is a humanised antibody wherein the heavy and/or light chain contains one or more CDRs from a rabbit, murine, or rat monoclonal antibody grafted into a heavy and/or light chain variable region framework of a human antibody. In one embodiment, the antibody of the present invention comprising an albumin binding domain is a humanised antibody wherein the heavy and/or light chain contains one or more CDRs from a rabbit antibody grafted into a heavy and/or light chain variable region framework of a human antibody, and wherein the heavy and/or light chain variable region framework comprises at least one amino acid substitution, such as an amino acid which is a donor residue.

In one embodiment, the antibody of the present invention, comprising a V domain which binds to human serum albumin, comprises a light and/or heavy chain sequence as shown below. (Variable domain underlined; CDRs in bold and italics.) In one embodiment, the antibody of the present invention, comprising a V domain which binds to human serum albumin, comprises a light and/or heavy chain sequence selected from below. In one embodiment, the antibody of the present invention, comprising a V domain which binds to human serum albumin, comprises a light and/or heavy chain variable domain sequence selected from below. In one embodiment, the antibody of the present invention, comprising a V domain which binds to human serum albumin, comprises at least one of CDR-L1, CDR-L2, and CDR-L3 sequence and/or at least one of CDR-H1, CDR-H2, and CDR-H3 sequence selected from below. In one embodiment, the antibody of the present invention, comprising a V domain which binds to human serum albumin, comprises a light and/or heavy chain sequence; and/or a light and/or heavy chain variable domain sequence; and/or at least one of CDR-L1, CDR-L2, and CDR-L3 sequence; and/or at least one of CDR-H1, CDR-H2, and CDR-H3 sequence selected from below.

CA645 Light Chain (gL5)

(SEQ ID NO: 1)

DIQMTQSPSSVSASVGDRVTITC*QSSPSVWSNFLS*WYQQKPGKAPKLLI

Y*EASKLTS*GVPSRFSGSGSGTDFTLTISSLQPEDFATYYC*GGGYSSISD*

*TT*FGGGTKVEIKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC

VL domain (gL5):

(SEQ ID NO: 2)

DIQMTQSPSSVSASVGDRVTITCQSSPSVWSNFLSWYQQKPGKAPKLLI

YEASKLTSGVPSRFSGSGSGTDFTLTISSLQPEDFATYYCGGGYSSISD

TTFGGGTKVEIK

CDR-L1:

(SEQ ID NO: 3)

QSSPSVWSNFLS

CDR-L2:

(SEQ ID NO: 4)

EASKLTS

CDR-L3:

(SEQ ID NO: 5)

GGGYSSISDTT

CA645 Heavy Chain (gH5)

(SEQ ID NO: 6)

EVQLLESGGGLVQPGGSLRLSCAVS*GIDLSNYAI*NWVRQAPGKGLEWIG

-continued

*IIWASGTTFYATWAKG*RFTISRDNSKNTVYLQMNSLRAEDTAVYYCAR*T*

*VPGYSTAPYFDL*WGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSC

VH domain (gH5):

(SEQ ID NO: 7)

EVQLLESGGGLVQPGGSLRLSCAVSGIDLSNYAINWVRQAPGKGLEWIG

IIWASGTTFYATWAKGRFTISRDNSKNTVYLQMNSLRAEDTAVYYCART

VPGYSTAPYFDLWGQGTLVTVSS

CDR-H1:

(SEQ ID NO: 8)

GIDLSNYAIN

CDR-H2:

(SEQ ID NO: 9)

IIWASGTTFYATWAKG

CDR-H3:

(SEQ ID NO: 10)

TVPGYSTAPYFDL

In some embodiments, the antibody of the present invention comprises variants of the VL and VH domains which bind human serum albumin as described above (SEQ ID NO: 2 and 7 respectively) that comprise an additional cysteine residue such that a disulphide bond may be formed between the VL and VH domains. The additional cysteine-containing variants may have the following sequences (wherein the additional cysteine residues are underlined):

CA645-Cys VL domain (gL5):

(SEQ ID NO: 102)

DIQMTQSPSSVSASVGDRVTITCQSSPSVWSNFLSWYQQKPGKAPKLLI

YEASKLTSGVPSRFSGSGSGTDFTLTISSLQPEDFATYYCGGGYSSISD

TTFGCGTKVEIK

CA645-Cys VH domain (gH5):

(SEQ ID NO: 103)

EVQLLESGGGLVQPGGSLRLSCAVSGIDLSNYAINWVRQAPGKCLEWIG

IIWASGTTFYATWAKGRFTISRDNSKNTVYLQMNSLRAEDTAVYYCART

VPGYSTAPYFDLWGQGTLVTVSS

Additional examples of VL and VH domains which bind human serum albumin, and which may be used in the antibody of the invention comprise SEQ ID NO: 105, 106, 107, 108 and 109 as described below (CDRs in *bold and italics*).

CA645 VH domain (gH1):

(SEQ ID NO: 105)

EVQLLESGGGLVQPGGSLRLSCAVS*GIDLSNYAIN*WVRQAPGKGLEWIG

*IIWASGTTFYATWAKG*RFTISRDSTTVYLQMNSLRAEDTAVYYCAR*TVP*

*GYSTAPYFDL*WGQGTLVTVSS

CA645 VH domain (gH37):

(SEQ ID NO: 106)

EVQLLESGGGLVQPGGSLRLSCAVS*GIDLSNYAI*NWVRQAPGKGLEWIG

*IIWASGTTAYATWAKG*RFTISRDNSKNTVYLQMNSLRAEDTAVYYCAR*T*

*VPGYSTAPYFDL*WGQGTLVTVSS

CA645 VH domain (gH47):

(SEQ ID NO: 107)

EVQLLESGGGLVQPGGSLRLSCAVS*GIDLSNYAI*NWVRQAPGKGLEWIG

*IIWASGTTFYATWAKG*RFTISRDNSKNTVYLQMNSLRAEDAVYYCAR*TV*

*PGYSAAPYFDL*WGQGTLVTVSS

CA645 VL domain (gL1):

(SEQ ID NO: 108)

DIVMTQSPSSVSASVGDRVTITC*QSSPSVWSNFLS*WYQQKPGKAPKLLI

Y*EASKLTS*GVPSRFKGSGSGTDFTLTISSLQPEDFATYYC*GGGYSSISD*

*TT*FGGGTKVEIK

CA645 VL domain (gL4):

(SEQ ID NO: 109)

DIQMTQSPSSVSASVGDRVTITC*QSSPSVWSNFLS*WYQQKPGKAPKLLI

Y*EASKLTS*GVPSRFSGSGSGTDFTLTISSLQPEDFATYYC *GGGYSSIS*

*D TT*FGGGTKVEIK

In some embodiments, the antibody of the present invention comprises variants of the VL and VH domains which bind human serum albumin as described above (SEQ ID NO: 105 to SEQ ID NO: 109) that comprise an additional cysteine residue such that a disulphide bond may be formed between the VL and VH domains. The additional cysteine-containing variants may have the following sequence (wherein the additional cysteine residue is underlined):

CA645-Cys VL (gL4):

(SEQ ID NO: 110)

DIQMTQSPSSVSASVGDRVTITC*QSSPSVWSNFLS*WYQQKPGKAPKLLI

Y*EASKLTS*GVPSRFSGSGSGTDFTLTISSLQPEDFATYYC*GGGYSSISD*

*TT*FGCGTKVEIKRT

In some embodiments, the VH framework of the albumin binding domain is human (for example VH3, such as VH3 1-3 3-23), and comprises for example 1, 2, 3, 4, 5 or 6 amino acid substitutions, such as amino acids which are donor residues. In such embodiments, the VH may have a sequence shown in SEQ ID NO: 7, SEQ ID NO: 103, SEQ ID NO: 105, SEQ ID NO: 106, SEQ ID NO: 107 or a variant of any one of the same with at least 95, 96, 97, 98 or 99% similarity of identity.

In some embodiments, the VL framework of the albumin binding domain is human (for example Vκ1, such as 2-1-(1) L5), and comprises for example 1, 2, 3, 4, 5 or 6 amino acid substitutions, such as amino acids which are donor residues. In such embodiments, the VL may have a sequence shown in SEQ ID NO: 2, SEQ ID NO: 102, SEQ ID NO: 108, SEQ ID NO: 109, SEQ ID NO: 110, or a variant of any one of the same with at least 95, 96, 97, 98 or 99% similarity of identity.

In some embodiments, the albumin binding domain comprises VH and VL sequences selected from the combinations SEQ ID NO: 7&2, 7&102, 7&108, 7&109, 7&110, 103&2, 103&102, 103&108, 103&109, 103&110, 105&2, 105&102, 105&108, 105&109, 105&110, 106&2, 106&102, 106&108, 106&109, 106&110, 107&2, 107&102, 107&108, 107&109, 107&110 or a variant or variants of any of the same with at least 95, 96, 97, 98 or 99% similarity or identity.

In some embodiments, the VL and VH sequences of the albumin binding domain are SEQ ID NO:102 and SEQ ID NO: 103, respectively. In some embodiments, the VL and VH sequences of the albumin binding domain are SEQ ID NO:2 and SEQ ID NO: 7, respectively.

In one embodiment, the antibody comprising a V domain which binds human serum albumin is a Fab or scFv. The VL and VH domains of SEQ ID NOs: 2 and 7 are preferred for the Fab format. In one embodiment, the antibody comprising a V domain which binds human serum albumin is a scFv which binds albumin cooperatively with a complementary V (VL or VH) domain. In such embodiment, the scFv may comprise any one of the VH domains and any one of the VL domains as described above, linked in the VH-VL or VL-VH orientation by a $(G4S)_4$ linker (SEQ ID NO:16). The VL and VH domains of SEQ ID NOs: 2 and 7 are preferred for the scFv format. The VL domain of SEQ ID NO: 2 may comprise the additional two amino acids RT at the C-terminus. In one embodiment, the antibody comprising a V domain which binds human serum albumin is a scFv which comprises the VL and VH domains of SEQ ID NOs: 2 and 7 separated by a $(G4S)_4$ linker. In one example, the scFv is VH-VL oriented. In another example, the scFv is VL-VH oriented. In one embodiment, the antibody comprising a V domain which binds human serum albumin is a scFv which comprises or has the SEQ ID NO: 143 as shown below. In one particular embodiment, the antibody comprising a V domain which binds human serum albumin is a dsscFv. In one embodiment, the antibody comprising a V domain which binds human serum albumin is a dsscFv which binds albumin cooperatively with a complementary V (VL or VH) domain. In such embodiment, the dsscFv may comprise any one of the VH domains and any one of the VL domains as described above, comprising, if not already present, an additional cysteine residue such that a disulphide bond may be formed between the VL and VH domains, wherein the VL and VH domains are linked in the VH-VL or VL-VH orientation by a $(G4S)_4$ linker. The VL and VH domains of SEQ ID NOs: 102 and 103 are preferred for the dsscFv format. The VL domain of SEQ ID NO: 102 may comprise the additional two amino acids RT at the C-terminus. In one embodiment, the antibody comprising a V domain which binds human serum albumin is a dsscFv which comprises the VL and VH domains of SEQ ID NOs: 102 and 103 separated by a $(G4S)_4$ linker (SEQ ID NO:16). In one example, the dsscFv is VH-VL oriented. In another example, the dsscFv is VL-VH oriented. In one embodiment, the antibody comprising a V domain which binds human serum albumin is a dsscFv which comprises or has the SEQ ID NO: 144 as shown below.

```
CA645 scFv (VH-VL):
                                   (SEQ ID NO: 143)
EVQLLESGGGLVQPGGSLRLSCAVSGIDLSNYAINWVRQAPGKGLEWIG

IIWASGTTFYATWAKGRFTISRDNSKNTVYLQMNSLRAEDTAVYYCART

VPGYSTAPYFDLWGQGTLVTVSSGGGGSGGGGSGGGGSGGGGSDIQMTQ

SPSSVSASVGDRVTITCQSSPSVWSNFLSWYQQKPGKAPKLLIYEASKL

TSGVPSRFSGSGSGTDFTLTISSLQPEDFATYYCGGGYSSISDTTFGQG

TKVEIK

CA645 dsscFv (VH-VL) wherein the additional
cysteine residues are underlined:
                                   (SEQ ID NO: 144)
EVQLLESGGGLVQPGGSLRLSCAVSGIDLSNYAINWVRQAPGKCLEWIG

IIWASGTTFYATWAKGRFTISRDNSKNTVYLQMNSLRAEDTAVYYCART
```

-continued

```
VPGYSTAPYFDLWGQGTLVTVSSGGGGSGGGGSGGGGSGGGGSDIQMTQ

SPSSVSASVGDRVTITCQSSPSVWSNFLSWYQQKPGKAPKLLIYEASKL

TSGVPSRFSGSGSGTDFTLTISSLQPEDFATYYCGGGYSSISDTTFGCG

TKVEIK
```

In another embodiment, the antibody comprising a V domain which binds human serum albumin is a full-length IgG. The VL and VH domains of SEQ ID NOs: 2 and 7 are preferred for the IgG format. In one embodiment, the antibody comprising a V domain which binds human serum albumin is an IgG1. In one embodiment, the antibody comprising a V domain which binds human serum albumin is an IgG4. In one embodiment, the antibody comprising a V domain which binds human serum albumin is an IgG4P.

It will be appreciated that one or more (for example 1, 2, 3 or 4) amino acid substitutions, additions and/or deletions may be made to the CDRs or other sequences (e.g. variable domains) provided by the present invention without significantly altering the ability of the antibody to bind to its cognate antigen (e.g. HSA). The effect of any amino acid substitutions, additions and/or deletions can be readily tested by one skilled in the art. For example, one or more (for example 1, 2, 3 or 4) amino acid substitutions, additions and/or deletions may be made to the framework region employed in the antibody or fragment provided by the present invention, wherein binding affinity to the cognate antigen is retained or increased. In some embodiments, the amino acid at position 72 of the framework 3 of the VH domain is wild type amino acid, naturally present at position 72 of said VH domain.

As such, the present invention also includes antibodies which comprise sequences which are at least 90%, 91%, 92%, 93%, 94%, 95%, 96%, 97%, 98% or 99% similar or identical to a sequence given herein. "Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

- phenylalanine, tyrosine and tryptophan (amino acids having aromatic side chains);
- lysine, arginine and histidine (amino acids having basic side chains);
- aspartate and glutamate (amino acids having acidic side chains);
- asparagine and glutamine (amino acids having amide side chains); and
- cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

The antibody of the present invention may bind to albumin with a binding affinity sufficient to extend the half-life of the insert polypeptide, such as a therapeutic protein or a second antibody, in vivo. In one embodiment, the insert polypeptide binds to HSA. In such embodiment, the insert polypeptide may bind to albumin with a binding affinity sufficient to extend the half-life of the scaffold antibody. It has been reported that a $K_D$ for albumin of less than or equal to 2.5 μM will extend half-life in vivo (Nguyen, A. et al (2006) Protein Engineering, Design & Selection, 19(7), 291-297). In one example the antibody of the present invention may bind to albumin with a high binding affinity which is nanomolar or micromolar, for example a $K_D$ equal to or less than 3 nM. Affinity may be measured using any suitable method known in the art, including surface plasmon resonance using natural or recombinant serum albumin.

In some embodiments, the insert polypeptide is an albumin binding peptide. Examples of albumin binding peptides are provided in WO2007/106120 and include:

| SEQ ID NO: | SEQUENCE |
|---|---|
| 111 | DLCLRDWGCLW |
| 112 | DICLPRWGCLW |
| 113 | MEDICLPRWGCLWGD |
| 114 | QRLMEDICLPRWGCLWEDDE |
| 115 | QGLIGDICLPRWGCLWGRSV |
| 116 | QGLIGDICLPRWGCLWGRSVK |
| 117 | EDICLPRWGCLWEDD |
| 118 | RLMEDICLPRWGCLWEDD |
| 119 | MEDICLPRWGCLWEDD |
| 120 | MEDICLPRWGCLWED |
| 121 | RLMEDICLARWGCLWEDD |
| 122 | EVRSFCTRWPAEKSCKPLRG |
| 123 | RAPESFVCYWETICFERSEQ |
| 124 | EMCYFPGICWM |

In one embodiment, the insert polypeptide is a second antibody which binds to HSA. In such embodiment, the insert polypeptide may have the features described above for the antibody comprising a V domain, i-e the scaffold antibody. In some embodiments, the insert polypeptide may comprise at least one of the CDRs, at least one of the VL or VH domains, or at least one of the light or heavy chains which bind albumin, as described above. In one embodiment, the insert polypeptide comprises at least one of the CDR-L1, CDR-L2 and CDR-L3 of sequence SEQ ID NO: 3, SEQ ID NO: 4 and SEQ ID NO: 5 respectively and/or one of the CDR-H1, CDR-H2 and CDR-H3 of sequence SEQ ID NO: 8, SEQ ID NO: 9 and SEQ ID NO: 10 respectively.

Insert Polypeptide

In accordance with the present invention, the present disclosure is directed to antibodies comprising an insert polypeptide within a framework 3 region in a V domain. The V domain may be a VL or a VH domain. In one example, the antibody of the invention may comprise an insert polypeptide within a framework 3 region of both VL and VH, i-e the antibody of the invention may comprise two insert polypeptides, wherein one insert polypeptide is inserted into the framework 3 region of a VL and one insert polypeptide is inserted into the framework 3 region of a VH, and wherein the insert polypeptides are identical, similar or different. In one embodiment, the insert polypeptide is heterologous to the antibody. As used herein, "heterologous" generally means derived from a genotypically distinct entity from the rest of the entity to which it is being compared. In this context, it means that the inserted polypeptide would not normally be present in the native antibody sequence. In one embodiment, the insert polypeptide is a full-length protein. In one embodiment, the insert polypeptide is a fragment of a full-length protein. In one embodiment, the insert polypeptide is a functional fragment of a full-length protein. In one embodiment, the insert polypeptide is functional when expressed on its own. In one embodiment, the insert polypeptide is functional and/or retains functionality when present in the framework 3 region in a V domain of the antibody of the invention. Thus, in one embodiment, the present invention provides an antibody comprising a variable (V) domain and an insert polypeptide, wherein the insert polypeptide is within the framework 3 (Fwk3) region of the V domain and wherein the insert polypeptide is functional and/or retains functionality when present in the framework 3 region in the V domain of the antibody of the invention.

In one embodiment, the insert polypeptide comprises at least 10, 15, 20, 25, 30, 35, 40, 45, 50, 55, 60, 65, 70, 75, 80, 85, 90, 95, 100, 150, or 200 amino acids. In one embodiment, the insert polypeptide comprises less than 250, 300 or 350 amino acids. In one embodiment, the insert polypeptide comprises less than 250 amino acids. In one embodiment, the insert polypeptide comprises at least 10, 15, 20, 25, 30, 35, 40, 45, 50, 55, 60, 65, 70, 75, 80, 85, 90, 95, 100, 150, or 200 amino acids and less than 250 amino acids. In one embodiment, the insert polypeptide comprises between 50 and 250, preferably 100 and 250, more preferably between 150 and 250 amino acids.

In one embodiment, the insert polypeptide may be a therapeutic or diagnostic polypeptide. Suitable therapeutic polypeptides may include, for example, receptor agonists or antagonists, enzyme inhibitors, metal chelators, anti-viral agents, anti-fungal agents, cardiovascular drugs and chemotherapeutic drugs. In some embodiments, the insert polypeptide is a cytokine. The cytokine may be selected from, for example, IL-10, IL-15, IL-2, G-CSF, GM-CSF, EPO. In other embodiments, the insert polypeptide is sclerostin. In some embodiments, the insert polypeptide comprises more than one polypeptide sequence such as two copies of the same polypeptide, optionally linked. Advantageously in such embodiment, the insert polypeptide may form a multimer, in particular a functional multimer. In some embodiments the insert polypeptide comprises two, three or four polypeptide sequences and is able to form a dimer, trimer or tetramer of the polypeptide. In some embodiments, the insert polypeptide forms a homodimer, a homotrimer or a homotetramer. In some embodiments, the insert polypeptide comprises at least two cytokines. In one embodiment, the insert polypeptide comprises two human IL-10 sequences, optionally separated by a peptide linker, e.g. (G4S)3 (SEQ ID NO: 15), i-e two human IL-10 sequences are inserted into the Fwk3 region of a V domain of the antibody of the invention.

In such embodiment, the two human IL-10 sequences form an homodimer of IL-10 incorporated into the antibody of the invention.

In some embodiments, the insert polypeptide is a chemokine. The chemokine may be selected from, for example, CCLs (C-C motif chemokine ligands), CXCLs (CXC motif chemokine ligands). In some embodiments, the insert polypeptide is a hormone. The hormone may be selected from, for example, insulin or leptin. In some embodiments, the insert polypeptide is a growth factor.

It has been surprisingly found by the present inventors that insertion of a polypeptide into an antibody in the framework 3 loop region of a V domain does not significantly hinder the functionality of either the antibody or the insert polypeptide. In particular, the examples herein show that specific and cognate binding to the respective binding partners of both the antibody and the insert polypeptide is seen for several tested fusion protein constructs.

In some embodiments, the antibody of the invention binds its cognate antigen by said V domain with a binding affinity which is at least 50%, 60%, 70%, 80% or 90% when compared to the antibody without the insert polypeptide present. It will be appreciated that the V domain which binds the antigen may do so alone, or co-operatively with another V domain depending on the antibody format, for example as a complementary VH/VL pair. Accordingly, the antibody comprising a V domain may bind its antigen co-operatively with a complementary V (VH or VL) domain. In some embodiments, the antibody of the invention binds its cognate antigen with a binding affinity which is at least 50%, 60%, 70%, 80% or 90% when compared to the antibody without the insert polypeptide present. In some embodiments, the antibody of the invention comprises a VH domain and binds its antigen co-operatively with a complementary VL with a binding affinity which is at least 50%, 60%, 70%, 80% or 90% when compared to the antibody without the insert polypeptide present. In some embodiments, the antibody of the invention comprises a VL domain and binds its antigen co-operatively with a complementary VH with a binding affinity which is at least 50%, 60%, 70%, 80% or 90% when compared to the antibody without the insert polypeptide present. In some embodiments, the insert polypeptide part of the antibody binds its cognate binding partner with a binding affinity which is at least 50%, 60%, 70%, 80% or 90% when compared to the free polypeptide when not linked to the antibody.

Therefore, in one embodiment, the antibody of the invention comprises a variable (V) domain and an insert polypeptide, wherein the insert polypeptide is within the framework 3 (Fwk3) region of the V domain and wherein both the antibody comprising a V domain and the insert polypeptide are functional and/or retain functionality when the insert polypeptide is present. In such embodiments, the antibody of the invention has functionality of both the scaffold antibody and the insert polypeptide. Advantageously, the antibody of the invention may exercise simultaneously the functionality of both the scaffold antibody and the insert polypeptide.

The antibody comprising a variable (V) domain is considered functional and/or retaining functionality when the insert polypeptide is present in the framework 3 region of the V domain, where the antibody of the invention exhibits at least 50%, 60%, 70%, 80% or 90% of at least one of the functions of the antibody comprising a variable (V) domain without the insert polypeptide present. The insert polypeptide is considered functional and/or retaining functionality when it is present in the framework 3 region of the V domain, where the insert polypeptide exhibits at least 50%, 60%, 70%, 80% or 90% of at least one of the functions of the insert polypeptide when expressed on its own, i-e when compared to the free polypeptide when not linked to the antibody.

Functional or functionality of the antibody and/or the insert polypeptide refers to at least one biological activity of said antibody and/or insert polypeptide including for example target binding (e.g. antigen binding), binding affinity, cross-reactivity, neutralisation, half-life in serum, activation of cell surface proteins, e.g. T cell surface receptors. Methods for measuring functionality, e.g. binding affinity, neutralisation and activation of target cells are well known in the art and include for example the methods described in the Examples provided herein. For example, standard assays such as Scatchard analysis, or surface plasmon resonance technique (e.g. using BIACORE®) may be used to determine target binding (e.g. antigen binding) and binding affinity.

Surprisingly, the V domain (VL or VH domain) of the antibody of the invention can still form a functional binding domain with its corresponding or complementary V domain (VH or VL), where present.

In some embodiments, the insert polypeptide may be a second antibody, or binding fragment thereof. In such embodiments, the insert polypeptide may have any of the features of antibodies as described above. In particular, in some embodiments, the insert polypeptide is a scFv, a dsscFv, a single domain antibody such as a VH or VL or VHH. In some embodiments, the insert polypeptide may be a fully human, humanised, or chimeric antibody. The insert polypeptide may be comprised of one or more CDRs or may consist of one or more CDRs. For example, the insert polypeptide may comprise or consist of at least one of CDR-H1, CDR-H2, CDR-H3 and/or CDR-L1, CDR-L2, CDR-L3, optionally linked.

It will be appreciated by those skilled in the art that this would function as a bivalent antibody, or bispecific antibody. Thus, in one aspect, the invention provides a novel bivalent or bispecific antibody format, capable of simultaneous binding two different epitopes. In some aspects, the epitopes are distinct epitopes present on the same antigen. In another aspect, the invention provides a novel bispecific antibody format capable of simultaneous binding two different antigens.

In one embodiment, an antigen of interest bound by the first or the second antibody or antibody fragment may be a cell-associated protein, for example a cell surface protein on cells such as bacterial cells, yeast cells, T-cells, endothelial cells or tumour cells, or it may be a soluble protein. Antigens of interest may also be any medically relevant protein such as those proteins upregulated during disease or infection, for example receptors and/or their corresponding ligands. Particular examples of cell surface proteins include adhesion molecules, for example integrins such as β1 integrins e.g. VLA-4, E-selectin, P selectin or L-selectin, CD2, CD3, CD4, CD5, CD7, CD8, CD11a, CD11b, GDIS, CD19, CD20, CD23, CD25, CD28, CD33, CD38, CD40, CD45, CDW52, CD69, CD 134 (OX40), ICOS, BCMP7, CD 137, CD27L, CDCP1, DPCR1, DPCR1, dudulin2, F1120584, F1140787, HEK2, KIAA0634, KIAA0659, KIAA1246, KIAA1455, FTBP2, FTK, MAF2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, and VEGF, and where appropriate, receptors thereof. Soluble antigens include interleukins such as IL-1, IL-2, IL-3, IL-4, IL-5, IL-6, IL-8, IL-12, IL-16 or IL-17, viral antigens for example respiratory syncytial virus or cytomegalovirus antigens, immunoglobulins, such as IgE, interferons such as interferon α, interferon β or interferon γ, tumour necrosis factor-α, tumour necrosis factor-β, colony stimulating factors such as G-CSF or GM-CSF, and platelet derived growth factors such as PDGF-α, and PDGF-β and where appropriate receptors thereof. Other antigens include bacterial cell surface antigens, bacterial toxins, viruses such as influenza, EBV, Hep A, B and C, bioterrorism agents, radionuclides and heavy metals, and snake and spider venoms and toxins.

In some embodiments, neither the scaffold antibody nor the insert polypeptide binds the hapten (4-hydroxy-3-nitrophenyl) acetyl (NP) or hapten (4-hydroxy-5-iodo-3-nitrophenyl) acetyl (NIP). In some embodiments, the antibody is different from BI-8 murine antibody.

In one embodiment, the second antibody binds to a different antigen to the V domain of the antibody.

In other embodiments, the second antibody binds to the same antigen as the V domain of the antibody. Preferably, the second antibody binds to a different epitope compared to the V domain of the antibody. In such embodiments, the antibody may bind its cognate antigen with a binding affinity which is greater than when compared to the antibody without the second antibody present.

In one embodiment, the insert polypeptide is a second antibody which binds IL-17, in particular IL-17A. In one embodiment, the insert polypeptide is a second antibody which binds IL-17AA, IL-17AF, and IL-17FF. In one embodiment, the second antibody which binds IL-17 is a scFv. In one embodiment, the second antibody which binds IL-17 is a dsscFv. In one embodiment, the antibody of the present invention is a Fab fragment that binds to both HSA and IL-17, in particular the antibody comprising a V domain binds to HSA and the insert polypeptide is a dsscFv which binds IL-17 i.e. the scaffold antibody is a Fab fragment which binds HSA and the second antibody inserted into the Fwk3 region of the V domain of the scaffold antibody is a dsscFv which binds IL-17. In another embodiment, the antibody of the invention is a whole IgG that binds to both HSA and IL-17, in particular the antibody comprising a V domain binds to HSA and the insert polypeptide is a dsscFv which binds IL-17 i.e. the scaffold antibody is a full IgG which binds HSA and the second antibody inserted into the Fwk3 region of the V domain of the scaffold antibody is a dsscFv which binds IL-17. In one embodiment, the antibody of the invention is a Fab fragment which comprises or has the heavy and light chains of SEQ ID NO: 129 (CA645 Fab heavy chain with CA497 dsscFv (vHvL) inserted into framework 3) and SEQ ID NO: 1 respectively, or a variant or variants of any of the same with at least 90, 91, 92, 93, 94, 95, 96, 97, 98 or 99% similarity or identity provided that it retains its functionality, e.g. binding to HSA and/or IL-17. In one embodiment, the antibody of the invention is a Fab fragment which comprises or has the heavy and light chains of SEQ ID NO: 130 (CA645 Fab heavy chain with CA497 dsscFv (vLvH) inserted into framework 3) and SEQ ID NO: 1 respectively or a variant or variants of any of the same with at least 90, 91, 92, 93, 94, 95, 96, 97, 98 or 99% similarity or identity provided that it retains its functionality e.g. binding to HSA and/or IL-17. In one embodiment, the antibody of the invention is a whole IgG which comprises or has the heavy and light chains of SEQ ID NO: 131 (CA645 IgG4P heavy chain with CA497 dsscFv (vHvL) inserted into framework 3) and SEQ ID NO: 1 respectively, or a variant or variants of any of the same with at least 90, 91, 92, 93, 94, 95, 96, 97, 98 or 99% similarity or identity provided that it retains its functionality, e.g. binding to HSA and/or IL-17. In one embodiment, the antibody of the invention is a whole IgG which comprises or has the heavy and light chains of SEQ ID NO: 132 (CA645 IgG4P heavy chain with CA497 dsscFv (vLvH) inserted into framework 3) and SEQ ID NO: 1 respectively, or a variant or variants of any of the same with at least 90, 91, 92, 93, 94, 95, 96, 97, 98 or 99% similarity or identity provided that it retains its functionality, e.g. binding to HSA and/or IL-17.

In one embodiment, the antibody of the invention binds to both CD3 and CD28. In one embodiment, the antibody of the invention is a Fab fragment that binds to both CD3 and CD28, in particular the antibody comprising a V domain binds to CD3 and the insert polypeptide is a dsscFv which binds CD28 i.e. the scaffold antibody is a Fab fragment which binds CD3 and the second antibody inserted into the Fwk3 region of the V domain of the scaffold antibody is a dsscFv which binds CD28. In one embodiment, the antibody of the invention is a Fab fragment that binds to both CD3 and CD28, in particular the antibody comprising a V domain binds to CD28 and the insert polypeptide is a dsscFv which binds CD3 i.e. the scaffold antibody is a Fab fragment which binds CD28 and the second antibody inserted into the Fwk3 region of the V domain of the scaffold antibody is a dsscFv which binds CD3. In another embodiment, the antibody of the invention is a whole IgG that binds to both CD3 and CD28, in particular the antibody comprising a V domain binds to CD3 and the insert polypeptide is a dsscFv which binds CD28 i.e. the scaffold antibody is a full IgG which binds CD3 and the second antibody inserted into the Fwk3 region of the V domain of the scaffold antibody is a dsscFv which binds CD28. In another embodiment, the antibody of the invention is a whole IgG that binds to both CD3 and CD28, in particular the antibody comprising a V domain binds to CD28 and the insert polypeptide is a dsscFv which binds CD3 i.e. the scaffold antibody is a full IgG which binds CD28 and the second antibody inserted into the Fwk3 region of the V domain of the scaffold antibody is a dsscFv which binds CD3. In one embodiment, the antibody of the invention is a Fab fragment which comprises or has the heavy and light chains of SEQ ID NO: 139 (anti-CD28 Fab heavy chain with anti-CD3 dsscFv inserted into framework 3) and SEQ ID NO: 136 respectively, or a variant or variants of any of the same with at least 90, 91, 92, 93, 94, 95, 96, 97, 98 or 99% similarity or identity provided that it retains its functionality, e.g. binding to CD3 and/or CD28. In another embodiment, the antibody of the invention is a whole IgG which comprises or has the heavy and light chains of SEQ ID NO: 141 (anti-CD28 IgG4P heavy chain with anti-CD3 dsscFv inserted into framework 3) and SEQ ID NO: 136 respectively or a variant or variants of any of the same with at least 90, 91, 92, 93, 94, 95, 96, 97, 98 or 99% similarity or identity provided that it retains its functionality e.g. binding to CD3 and/or CD28.

```
Example sequences for use in the present
invention include
SEQ ID NO: 53, SEQ ID NO: 54, SEQ ID NO: 55,

SEQ ID NO: 56, SEQ ID NO: 57, SEQ ID NO: 58,

SEQ ID NO: 59, SEQ ID NO: 60, SEQ ID NO: 61,

SEQ ID NO: 62, SEQ ID NO: 63, SEQ ID NO: 64,

SEQ ID NO: 65, SEQ ID NO: 66, SEQ ID NO: 67,
```

-continued

```
SEQ ID NO: 68, SEQ ID NO: 69, SEQ ID NO: 70,

SEQ ID NO: 71, SEQ ID NO: 72, SEQ ID NO: 73,

SEQ ID NO: 74, SEQ ID NO: 75, SEQ ID NO: 76,

SEQ ID NO: 83, SEQ ID NO: 84, SEQ ID NO: 85,

SEQ ID NO: 86, SEQ ID NO: 87, SEQ ID NO: 88,

SEQ ID NO: 89, SEQ ID NO: 90, SEQ ID NO: 91,

SEQ ID NO: 92, SEQ ID NO: 93, SEQ ID NO: 94,

SEQ ID NO: 95, SEQ ID NO: 96, SEQ ID NO: 97,

SEQ ID NO: 98, SEQ ID NO: 99, SEQ ID NO: 100,

SEQ ID NO: 101, SEQ ID NO: 102, SEQ ID NO: 103,

SEQ ID NO: 105, SEQ ID NO: 106, SEQ ID NO: 107,

SEQ ID NO: 108, SEQ ID NO: 109, SEQ ID NO: 110,

SEQ ID NO: 125, SEQ ID NO: 126, SEQ ID NO: 127,

SEQ ID NO: 128, SEQ ID NO: 129, SEQ ID NO: 130,

SEQ ID NO: 131, SEQ ID NO: 132, SEQ ID NO: 133,

SEQ ID NO: 134, SEQ ID NO: 135, SEQ ID NO: 136,

SEQ ID NO: 137, SEQ ID NO: 138, SEQ ID NO: 139,

SEQ ID NO: 140, SEQ ID NO: 141, SEQ ID NO: 142,

SEQ ID NO: 143 and SEQ ID NO: 144.

Example combinations of heavy and light chains
for use in the Fab fragments of the present
invention include
SEQ ID NO: 54 and SEQ ID NO: 1, SEQ ID NO: 56

and SEQ ID NO: 1, SEQ ID NO: 58 and SEQ ID NO: 1,

SEQ ID NO: 60 and SEQ ID NO: 1, SEQ ID NO: 61

and SEQ ID NO: 1, SEQ ID NO: 63 and SEQ ID NO: 1,

SEQ ID NO: 64 and SEQ ID NO: 1, SEQ ID NO: 66

and SEQ ID NO: 1, SEQ ID NO: 68 and SEQ ID NO: 1,

SEQ ID NO: 70 and SEQ ID NO: 1, SEQ ID NO: 73

and SEQ ID NO: 1, SEQ ID NO: 74 and SEQ ID NO: 1,

SEQ ID NO: 75 and SEQ ID NO: 1, SEQ ID NO: 76

and SEQ ID NO: 1, SEQ ID NO: 93 and SEQ ID NO: 1,

SEQ ID NO: 94 and SEQ ID NO: 1, SEQ ID NO: 95

and SEQ ID NO: 1, SEQ ID NO: 101 and SEQ ID NO: 1,

SEQ ID NO: 129 and SEQ ID NO: 1, SEQ ID NO: 130

and SEQ ID NO: 1, SEQ ID NO: 139 and SEQ ID NO:

136, SEQ ID NO: 140 and SEQ ID NO: 133.

Example combinations of heavy and light chains for
use in the whole IgG of the present invention
include
SEQ ID NO: 131 and SEQ ID NO: 1, SEQ ID NO: 132

and SEQ ID NO: 1, SEQ ID NO: 141 and SEQ ID NO:

136, SEQ ID NO: 142 and SEQ ID NO: 133.
```

Linker Sequence

In some embodiments, the insert polypeptide is linked directly to the framework 3 region of the antibody. Linked directly as employed herein is intended to refer to the fact that the N- and C-terminal amino acids of the heterologous insert polypeptide would be linked by a peptide bond to the framework 3 region of the V domain of the antibody of the present invention.

In some embodiments, the antibody of the invention further comprises a linker sequence. In such embodiments, the linker sequence is preferably heterologous to both the antibody and insert polypeptide, that is the linker sequence would not normally be present in the native antibody sequence or insert polypeptide at that position.

In some embodiments, the linker sequence comprises at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty or thirty-one amino acids joining the N- and/or C-terminal end of the insert polypeptide to the framework 3 region. In some embodiments, the linker sequence comprises between one and thirty-one, or between five and thirty-one, or between six and twenty-eight, or between ten and twenty-six, or between fifteen and twenty-six, or between ten and twenty-one or between five and ten amino acids joining the N- and/or C-terminal end of the insert polypeptide to the framework 3 region.

In some embodiments, the linker sequence comprises at most thirty amino acids joining the N- and/or C-terminal end of the insert polypeptide to the framework 3 region.

In some embodiments, the linker at the N-terminus of the insert polypeptide is different in composition and/or length to the linker at the C-terminal end of the insert polypeptide. In some embodiments, the linker at the N-terminus of the insert polypeptide is identical or similar in composition and/or length to the linker at the C-terminal end of the insert polypeptide. In some embodiments, the linker sequence is derived from a human sequence. In some embodiments, the linker is a human linker. In some embodiments, the linker sequence is derived from a non-human sequence. In some embodiments, the linker is derived from a bovine sequence. In some embodiments, the linker is a bovine linker.

Examples of suitable linker regions for linking the insert polypeptide to the framework 3 region of a V domain include, but are not limited to, flexible linker sequences and rigid linker sequences. Flexible linker sequences include those disclosed in Huston et al., 1988, PNAS 85:5879-5883; Wright & Deonarain, Mol. Immunol., 2007, 44(11):2860-2869; Alfthan et al., Prot. Eng., 1995, 8(7):725-731; Luo et al., J. Biochem., 1995, 118(4):825-831; Tang et al., 1996, J. Biol. Chem. 271(26):15682-15686; and Turner et al., 1997, JIMM 205, 42-54 (see Table 1 below for representative examples).

TABLE 1

Examples of Flexible Linker Sequences

| SEQ ID NO: | SEQUENCE |
|---|---|
| 11 | SGGGGSE |
| 12 | DKTHTS |
| 13 | (S)GGGGS |
| 14 | (S)GGGGSGGGGS |

TABLE 1-continued

Examples of Flexible Linker Sequences

| SEQ ID NO: | SEQUENCE |
|---|---|
| 15 | (S)GGGGSGGGGSGGGGS |
| 16 | (S)GGGGSGGGGSGGGGSGGGGS |
| 17 | (S)GGGGSGGGGSGGGGSGGGGSGGGGS |
| 18 | AAAGSG-GASAS |
| 19 | AAAGSG-XGGGS-GASAS |
| 20 | AAAGSG-XGGGSXGGGS-GASAS |
| 21 | AAAGSG-XGGGSXGGGSXGGGS-GASAS |
| 22 | AAAGSG-XGGGSXGGGSXGGGSXGGGS-GASAS |
| 23 | AAAGSG-XS-GASAS |
| 24 | PGGNRGTTTTRRPATTTGSSPGPTQSHY |
| 25 | ATTTGSSPGPT |
| 26 | ATTTGS |
| — | GS |
| 27 | EPSGPISTINSPPSKESHKSP |
| 28 | GTVAAPSVFIFPPSD |
| 29 | GGGGIAPSMVGGGGS |
| 30 | GGGGKVEGAGGGGGS |
| 31 | GGGGSMKSHDGGGGS |
| 32 | GGGGNLITIVGGGGS |
| 33 | GGGGVVPSLPGGGGS |
| 34 | GGEKSIPGGGGS |
| 35 | RPLSYRPPFPFGFPSVRP |
| 36 | YPRSIYIRRRHPSPSLTT |
| 37 | TPSHLSHILPSFGLPTEN |
| 38 | RPVSPFTFPRLSNSWLPA |
| 39 | SPAAHFPRSIPRPGPIRT |
| 40 | APGPSAPSHRSLPSRAFG |
| 41 | PRNSIHFLHPLLVAPLGA |
| 42 | MPSLSGVLQVRYLSPPDL |
| 43 | SPQYPSPLTLTLPPHPSL |
| 44 | NPSLNPPSYLHRAPSRIS |
| 45 | LPWRTSLLPSLPLRRRP |
| 46 | PPLFAKGPVGLLSRSFPP |
| 47 | VPPAPVVSLRSAHARPPY |
| 48 | LRPTPPRVRSYTCCPTP- |
| 49 | PNVAHVLPLLTVPWDNLR |
| 50 | CNPLLPLCARSPAVRTFP |
| 77 | KYQSGGSGMG |
| 78 | SGGSYTY |
| 79 | GGGSGGGG |
| 80 | GSSSSGS |
| — | GGG |
| 81 | SGGGG |
| — | S |

(S) is optional in sequences 13 to 17. X represents any residue.

In particular embodiments, the antibody comprises the linker sequences SEQ ID NOs: 106 and 107.

Examples of rigid linkers include the peptide sequences GAPAPAAPAPA (SEQ ID NO:51), PPPP (SEQ ID NO:52), PPP, IPFTV (SEQ ID NO: 82) and EYHGLQ (SEQ ID NO: 104). Further examples include sequences derived from the elongated stalk of CDRH3 of bovine antibodies (Wang et al., Cell, 2013, 153:1379-1393); preferable sequences include long linker sequences such as TSVHQETKKYQS (SEQ ID NO: 96) and SYTYNYEWHVDV (SEQ ID NO: 97) (comprising both solvent exposed and buried residues from a bovine CDH3 stalk); and short linker sequences such as ETKKYQS (SEQ ID NO: 98) and SYTYNYE (SEQ ID NO: 99) (comprising only the solvent exposed residues from a bovine CDH3 stalk).

In some embodiments, variants of any of the linker sequences disclosed herein may be used, for example, variants where in one, two, three, four or more amino acid residues have been substituted, inserted, or removed with respect to the original linker sequence. Variants of linker sequences may also include repeat variants, where the linker sequence is elongated by repeating the linker sequence. In one embodiment, a preferred linker sequence to be repeated is SEQ ID NO: 13, leading to the motif: $(G_mS)_n$, where m is 4 and n can be any integer (for example 1, 2 or 3). In other embodiments, m can be a different integer from 1 to 10.

Whether or not the insert polypeptide is linked directly or via a linker sequence, in some embodiments, one or more amino acids in the framework 3 region may be deleted as a result of linking the polypeptide insert. In some embodiments, the insert polypeptide is between amino acid residues 73 and 75 of the VH domain, in accordance with the Kabat numbering system and the amino acid in position 74 is deleted.

Pharmaceutical Compositions and Methods of Use

Antibodies of the invention and as described herein are useful in the treatment of diseases or disorders including inflammatory diseases and disorders, immune diseases and disorders, fibrotic disorders and cancers.

The term "inflammatory disease" or "disorder" and "immune disease or disorder" includes rheumatoid arthritis, psoriatic arthritis, still's disease, Muckle Wells disease, psoriasis, Crohn's disease, ulcerative colitis, SLE (Systemic Lupus Erythematosus), asthma, allergic rhinitis, atopic dermatitis, multiple sclerosis, vasculitis, Type I diabetes mellitus, transplantation and graft-versus-host disease.

The term "fibrotic disorder" includes idiopathic pulmonary fibrosis (IPF), systemic sclerosis (or scleroderma), kidney fibrosis, diabetic nephropathy, IgA nephropathy, hypertension, end-stage renal disease, peritoneal fibrosis (continuous ambulatory peritoneal dialysis), liver cirrhosis, age-related macular degeneration (ARMD), retinopathy, cardiac reactive fibrosis, scarring, keloids, burns, skin ulcers, angioplasty, coronary bypass surgery, arthroplasty and cataract surgery.

The term "cancer" includes a malignant new growth that arises from epithelium, found in skin or, more commonly, the lining of body organs, for example: breast, ovary, prostate, lung, kidney, pancreas, stomach, bladder or bowel. Cancers tend to infiltrate into adjacent tissue and spread (metastasise) to distant organs, for example: to bone, liver, lung or the brain.

Thus, according to a further aspect of the invention, there is provided a pharmaceutical composition which comprises an antibody of the invention in association with one or more pharmaceutically acceptable carriers, excipients or diluents.

Also provided is the use of an antibody of the invention for the manufacture of a medicament for the treatment of a disease or disorder. Most preferably, the disease or disorder is an inflammatory disease or disorder.

Pharmaceutical compositions according to the invention may, for example, take a form suitable for parenteral, subcutaneous, or ophthalmic administration. Where appropriate, for example if the antibody binds to albumin via its V domain, it may be desirable to pre-formulate the antibody of the invention with human or recombinant serum albumin, using any suitable method known in the art.

Where the pharmaceutical formulation is a liquid, for example a solution or suspension, then the formulation may further comprise albumin, for example human serum albumin, in particular recombinant albumin such as recombinant human serum albumin. Suitable amounts may be in the range of less than 2% w/w of the total formulation, in particular less than 1, 0.5, or 0.1% w/w. This may assist in stabilizing the antibody component in the formulation. The pharmaceutical composition may be lyophilized for reconstitution later, with an aqueous solvent. In one embodiment there is provided a unit dose container, such as a vial, comprising a lyophilized antibody according to the invention.

The antibodies of the invention may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

The compositions may, if desired, be presented in a pack or dispenser device which may contain one or more unit dosage forms containing the active ingredient. The pack or dispensing device may be accompanied by instructions for administration.

The antibody formats of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

The quantity of an antibody of the invention required for the prophylaxis or treatment of a particular condition will vary depending on the antibody and the condition to be treated. In general, however, daily dosages may range from around 10 ng/kg to 1000 mg/kg, from 100 ng/kg to 100 mg/kg, or from 0.1 mg/kg to 10 mg/kg body weight.

The present invention also provides for methods and compositions for the delivery of the antibodies as described herein by gene therapy, particularly by adeno-associated virus (AAV) vector.

Hence, the present invention provides for a pharmaceutical composition comprising a viral vector having a viral capsid and an artificial genome comprising an expression cassette flanked by inverted terminal repeats (ITRs) wherein the expression cassette comprises a transgene comprising a polynucleotide sequence encoding the antibody as described herein. The ITRs sequences may be used for packaging the artificial genome comprising the polynucleotide sequences encoding the antibody as described herein into the virion of the viral vector.

The transgene in the expression cassette is operably linked to expression control elements such as promoters that will control expression of the transgene in human cells.

The viral vector is preferably AAV based viral vectors. A variety of AAV capsids have been described in the art. Methods of generating AAV vectors have also been described extensively in the literature (e.g., WO 2003/042397; WO 2005/033321, WO 2006/110689; U.S. Pat. No. 7,588,772 B2). The source of AAV capsids may be selected from an AAV which targets a desired tissue. For example, suitable AAV may include, e.g., AAV9 (U.S. Pat. No. 7,906,111; US 2011-0236353-A1), rh10 (WO 2003/042397) and/or hu37 (U.S. Pat. No. 7,906,111B2; US20110236353). However, other AAV, including, e.g., AAV1, AAV2, AAV-TT, AAV3, AAV4, AAV5, AAV6, AAV7, AAV8 and AAV.PHP.B (or variants thereof) and others may also be selected.

Methods for generating and isolating AAV viral vectors suitable for delivery to a subject are known in the art (U.S. Pat. No. 7,790,449B2; U.S. Pat. No. 7,282,199B2; WO 2003/042397; WO 2005/033321, WO 2006/110689; and U.S. Pat. No. 7,588,772 B2).

The pharmaceutical composition comprising a viral vector having a viral capsid and an artificial genome according to the invention is designed to ensure that both the heavy and light chains are expressed. The polynucleotide sequences of the heavy and light chain of the antibodies according to the present invention may be engineered in a single construct and separated by, for example, a cleavable linker or internal ribosome entry site (IRES) element so that the heavy and light chains are separately expressed. In some embodiments, the cleavable linker is a self-cleaving furin/F2A linker (Fang et al., Nature Biotechnology 23: 584-590, 2005 and Fang et al. Mol Ther 15: 1153-9, 2007). For example, a furin/F2A linker may be incorporated into an expression cassette to separate the heavy and light chain polynucleotide coding sequences.

In some other embodiments, the polynucleotide sequence of the heavy and light chains of the antibodies according to the present invention are connected via a flexible, non-cleavable linker. In some embodiments such linker may be a flexible peptide linker such as those encoding scFv (composed of Gly and Ser) so that the heavy and light chain domains are free to move relative to one another.

The invention will now be described with reference to the following examples, which are merely illustrative and should not in any way be construed as limiting the scope of the present invention.

EXAMPLES

General Methodology

Framework 3 Insertion

In addition to three CDR loops, antibody light and heavy chains, both conventional and single-chain camelid VHH, have a fourth loop which is formed by framework 3 (FIG. 1A). The Kabat numbering system defines framework 3 as positions 66-94 in a heavy chain and positions 57-88 in a light chain.

Gene Design and Transient Cell Expression

Genes encoding light and heavy chain V-regions, including variants with a framework 3 insertion, were designed and constructed by an automated synthesis approach (ATUM).

The genes were cloned into expression vectors containing DNA encoding human Cκ region (Km3 allotype) and heavy chain γ1 CH1 region, respectively. Heavy and light chain expression vectors were then co-transfected into HEK293 cells and the recombinant antibody/Fab fusion protein molecules screened using an SPR binding assay.

The light V-region or light chain of the CA645 Fab fusion proteins described in the following Examples comprised or had SEQ ID NO: 2 (CA645 VL domain (gL5)) or SEQ ID NO: 1 (CA645 light chain gL5) respectively. Alternative light chains or light V-regions may be used, for example light V-regions comprising the VL domain of SEQ ID NO: 108 or SEQ ID NO: 109.

Determination of Antibody/Fab Fusion Protein Binding Potency by Surface Plasmon Resonance All surface plasmon resonance (SPR) experiments were carried out at 25° C. on a Biacore 3000 system using a pH 7.4 running buffer containing 10 mM HEPES, 150 mM NaCl, EDTA 2 mM and 0.005% (v/v) P20 (HBS-EP buffer).

Polyclonal goat $F(ab)_2$ fragment anti-human $F(ab)_2$, (Jackson Labs product code #109-006-097) was immobilized to the surface of CMS sensor chips (GE Healthcare) by amine coupling. Briefly, the carboxymethyl dextran surface was activated with a fresh 1:1 (v/v) mixture of 50 mM N-hydroxysuccimide and 200 mM 1-ethyl-3-(3-dimethylaminopropyl)-carbodiimide for 5 minutes at a flow rate of 10 μL/min. The anti-human $F(ab)_2$ in 10 mM acetate pH 5.0 buffer was covalently coupled to chips at 50 μg/mL in a 10 minute pulse at the same flow rate. Finally the surface was deactivated with a 10 minute pulse of 1 M ethanolamine·HCl pH 8.5. A reference flow cell was prepared on the chip by omitting the protein from the above procedure.

Supernatants containing Fab-loop insert constructs, wild type Fab or control supernatants were diluted 1 in 5 in HPS-EP buffer prior to testing for binding of their respective ligand or receptor.

Human serum albumin (HSA) was supplied by Jackson ImmunoResearch (catalog #009-000-051) and was diluted in HBS-EP buffer to 1000 nM. The following cytokines and receptors were obtained from R&D Systems Ltd.: IL-15, IL-15-Rα-hFc, IL-2, IL-2-sRβ, G-CSF, G-CSF-Ra, GM-CSF, GM-CSF-Ra, EPO, EPO-R, IL-6, LRP4(ecd)-hFc, LRP6(ecd)-hFc, Lysozyme, KLK5. These proteins were reconstituted at typically 100 μg/mL and stored at −20° C. For experimental purposes they were freshly diluted in HBS-EP buffer to typically 50, 100 or 200 nM.

A typical SPR cycle comprised a flow rate of 10 μL/min with HBS-EP as running buffer and diluted supernatant was injected for 1 min to capture the antibody/Fab fusion protein. This was followed by a 30 μl injection of the diluted cognate ligand or receptor or buffer control. The subsequent dissociation phase was monitored for at least 3 min. In some experiments an additional 30 μL injection of the relevant cognate antigen of the antibody portion was included, HSA in the case of fusion protein constructs using CA645 Fab as the antibody polypeptide portion. In some experiments a specificity control cycle was included where the cognate receptor/ligand (the insert portion of the antibody/Fab fusion protein) was pre-mixed with a 2-fold molar excess of its binding partner. Each cycle terminated with a regeneration step comprising two 10 μL injections of 40 mM HCl interspersed with a 5 μL injection of 5 mM NaOH.

Report points were collected 10 s before supernatant and ligand/receptor injections for measuring fusion protein construct capture and at 5 s before and 15 s after the end of the ligand/receptor injection for assessing binding of cognate ligand/receptor. Report point and sensorgram data collected represented the difference in resonance units (RU) between the polyclonal capture flow cell and the reference flow cell.

Report point and sensorgram data were processed by subtracting the respective control cycle from the ligand/receptor cycle to account for any slow dissociation of the fusion protein construct from the capture surface. In every experiment the respective wild type Fab supernatant was included to check for any non-specific binding of ligand/receptor. If significant this was subtracted from the above.

In examples where dissociation constants ($K_D$) were estimated, the above method was modified by increasing the flow rate to 30 μl/min. Following capture of the Fab construct, 90 μl of the cognate ligand or buffer control was injected followed by a dissociation phase of 180 sec. A ligand binding over a range of concentrations (0.1, 0.2, 0.5, 1, 2, 5, & 10 nM) was tested. Sensorgrams were corrected for drift by subtraction of a zero ligand sensorgram and for non-specific interaction by subtraction of the wild type Fab corrected sensorgram. Affinity constants were calculated from separate dissociation and association rate constants that were fitted to the corrected sensorgrams using the Langmuir model of the BIAevaluation software (version 4.1.1).

Example 1—CA645 Fab with IL-15 Insert Polypeptide

Interleukin 15 (IL-15), is a cytokine which plays a role in the immune response, and functions to promote the proliferation of T cells and natural killer (NK) cells. It is structurally similar to IL-2, and its receptor shares common chains with the IL-2 receptor.

A fusion protein was generated and expressed in accordance with the above methods to insert the human IL-15 sequence into the framework 3 region of the CA645 Fab construct, as shown below.

Human IL-15 Sequence:
NWVNVISDLKKIEDLIQSMHIDATLYTESDVHPSCKVTAMKCFLLELQVISLESGDAS IHDTVENLIILANNSLSSNGNVTESGCKECEELEEKNIKEFLQSFVHIVQMFIN (SEQ ID NO: 53)

```
CA645 Fab heavy chain with human IL-15 (bold and
italics) inserted into framework 3, linkers
underlined:
                                        (SEQ ID NO: 54)
EVQLLESGGGLVQPGGSLRLSCAVSGIDLSNYAINWVRQAPGKGLEWIGI

IWASGTTFYATWAKGRFTISRDNKYQSGGSGMGNWVNVISDLKKIEDLIQ

SMHIDATLYTESDVHPSCKVTAMKCFLLELQVISLESGDASIHDTVENLI

ILANNSLSSNGNVTESGCKECEELEEKNIKEFLQSFVHIVQMFINSGGSY

TYKNTVYLQMNSLRAEDTAVYYCARTVPGYSTAPYFDLWGQGTLVTVSSA

STKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPK

SC
```

Figure 2:
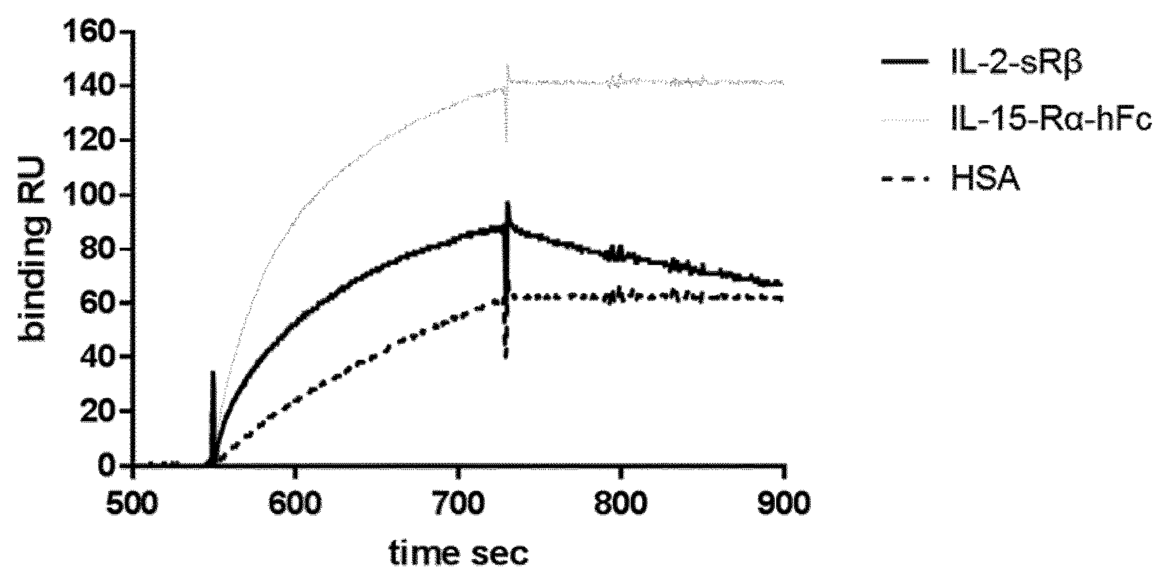
FIG. 2: (A) SPR sensorgram showing CA645/IL-$15_{Fwk3}$ binding to IL-15 receptor chains; (B) Modelled structure showing the IL-15 insert into framework 3 of the CA645 VH domain.
Figure 2:
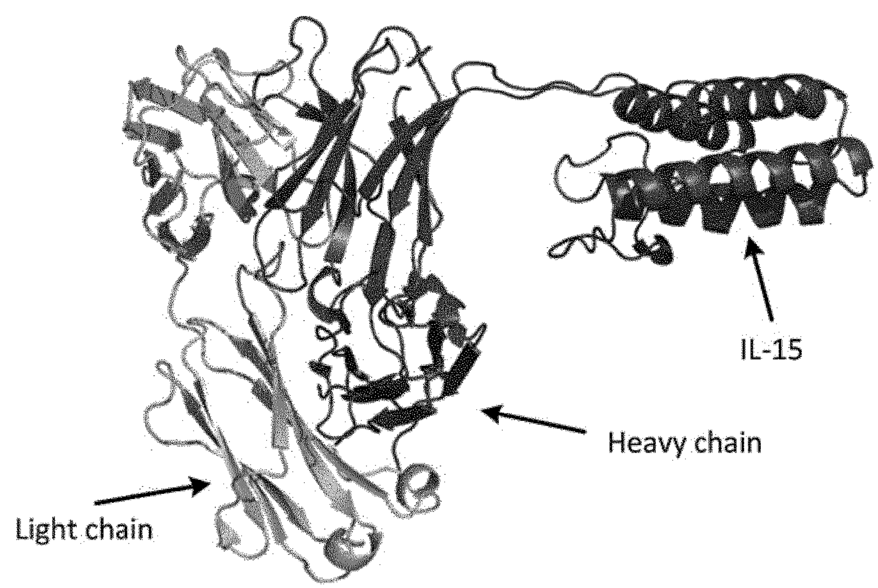

FIG. 2A shows the Biacore analysis of binding potency for this CA645/IL-15 antibody fusion protein when tested with 100 nM IL-2-Rβ, IL-15-Rα (both of which are binding partners for IL-15) and 1000 nM HSA (ligand for CA645). As is clearly seen in FIG. 2A, binding was seen to all three ligands showing that functionality is retained in both the CA645 Fab portion as well as the IL-15 graft in the framework 3 region. FIG. 2B shows a modelled representation of the CA645/IL-$15_{Fwk3}$ protein.

Example 2—CA645 Fab with IL-2 Insert Polypeptide

Interleukin 2 (IL-2) is a pluripotent cytokine produced primarily by activated CD4+ T cells, which plays a crucial role in generating a normal immune response. IL-2 promotes proliferation and expansion of activated T lymphocytes, potentiates B cell growth, and activates monocytes and natural killer cells.

A fusion protein was generated and expressed in accordance with the above methods to insert the human IL-2 sequence into the framework 3 region of the CA645 Fab construct, as shown below.

```
Human IL-2 sequence:
                                        (SEQ ID NO: 55)
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT

CA645 Fab heavy chain with human IL-2 (bold and
italics) inserted into framework 3, linkers
underlined:
                                        (SEQ ID NO: 56)
EVQLLESGGGLVQPGGSLRLSCAVSGIDLSNYAINWVRQAPGKGLEWIGI

IWASGTTFYATWAKGRFTISRDNSGGGSGGGGAPTSSSTKKTQLQLEHLL
```

-continued

```
LDLQMILNGINNYKNPKLTRMLTFKFYMPKKATELKHLQCLEEELKPLEE

VLNLAQSKNFHLRPRDLISNINVIVLELKGSETTFMCEYADETATIVEFL

NRWITFCQSIISTLTGGGKNTVYLQMNSLRAEDTAVYYCARTVPGYSTAP

YFDLWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSC
```

Figure 3:
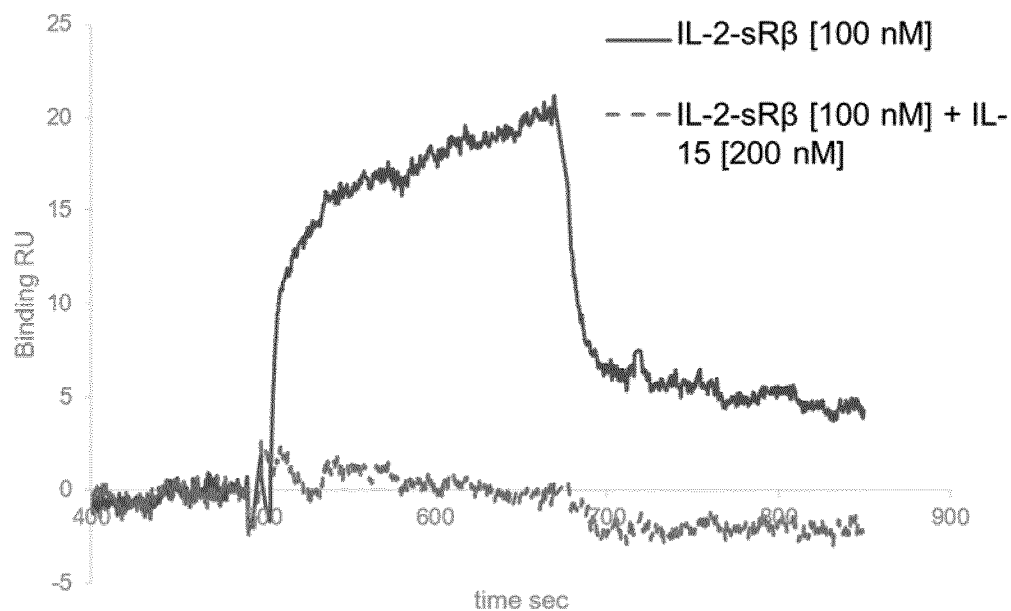
FIG. 3: (A) SPR sensorgram showing CA645/IL-$2_{Fwk3}$ binding to IL-2 receptor β chain with and without added IL-15; (B) Modelled structure showing the IL-2 insert into framework 3 of the CA645 VH domain.
Figure 3:
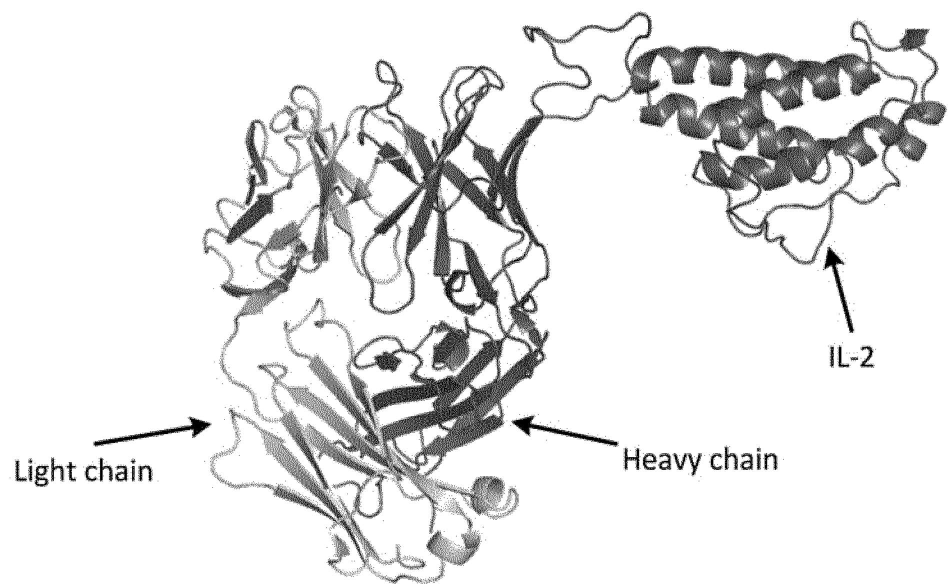

FIG. 3A shows the Biacore analysis of binding potency for this CA645/IL-2 antibody fusion protein when tested with 100 nM IL-2-Rβ (binding partner for IL-2), with and without prior incubation with 200 nM IL-15 (a competing ligand). As is shown in FIG. 3A, binding seen to IL-2-Rβ is abolished in the presence of the competing ligand in molar excess, showing that the binding seen to the IL-2 portion in framework 3 of the fusion protein is a genuine functional interaction and not non-specific. FIG. 3B shows a modelled representation of the CA645/IL-$2_{Fwk3}$ protein.

Example 3—CA645 Fab with G-CSF Insert Polypeptide

Granulocyte-colony stimulating factor (G-CSF) is a cytokine produced by a number of different cell types (e.g. endothelium, macrophages) which acts to simulate the production of mature granulocytes from bone marrow.

A fusion protein was generated and expressed in accordance with the above methods to insert the human G-CSF sequence into the framework 3 region of the CA645 Fab construct, as shown below.

```
Human G-CSF sequence:
                                        (SEQ ID NO: 57)
ATPLGPASSLPQSFLLKCLEQVRKIQGDGAALQEKLVSECATYKLCHPEE

LVLLGHSLGIPWAPLSSCPSQALQLAGCLSQLHSGLFLYQGLLQALEGIS

PELGPTLDTLQLDVADFATTIWQQMEELGMAPALQPTQGAMPAFASAFQR

RAGGVLVASHLQSFLEVSYRVLRHLAQP

CA645 Fab heavy chain with human G-CSF (bold and
italics) inserted into framework 3, Gly-Ser
linkers underlined:
                                        (SEQ ID NO: 58)
EVQLLESGGGLVQPGGSLRLSCAVSGIDLSNYAINWVRQAPGKGLEWIGI

IWASGTTFYATWAKGRFTISRDNSGGGGSATPLGPASSLPQSFLLKCLEQ

VRKIQGDGAALQEKLVSECATYKLCHPEELVLLGHSLGIPWAPLSSCPSQ

ALQLAGCLSQLHSGLFLYQGLLQALEGISPELGPTLDTLQLDVADFATTI

WQQMEELGMAPALQPTQGAMPAFASAFQRRAGGVLVASHLQSFLEVSYRV

LRHLAQPSGGGGKNTVYLQMNSLRAEDTAVYYCARTVPGYSTAPYFDLWG

QGTLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPSN

TKVDKKVEPKSC
```

Figure 4:
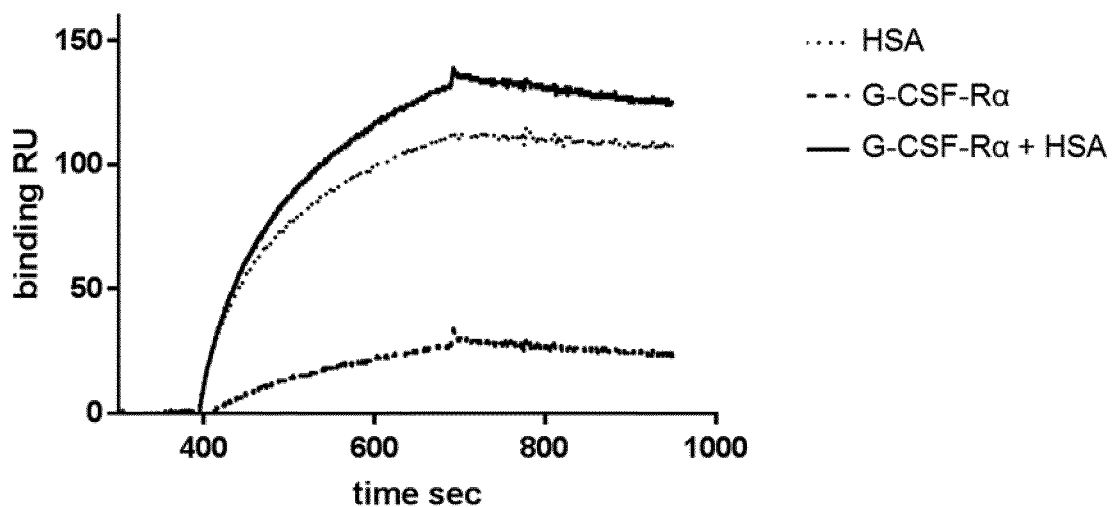
FIG. 4: (A) SPR sensorgram showing CA645/G-$CSF_{Fwk3}$ binding to HSA and/or G-CSF receptor; (B) Modelled structure showing the G-CSF insert into framework 3 of the CA645 VH domain.
Figure 4:
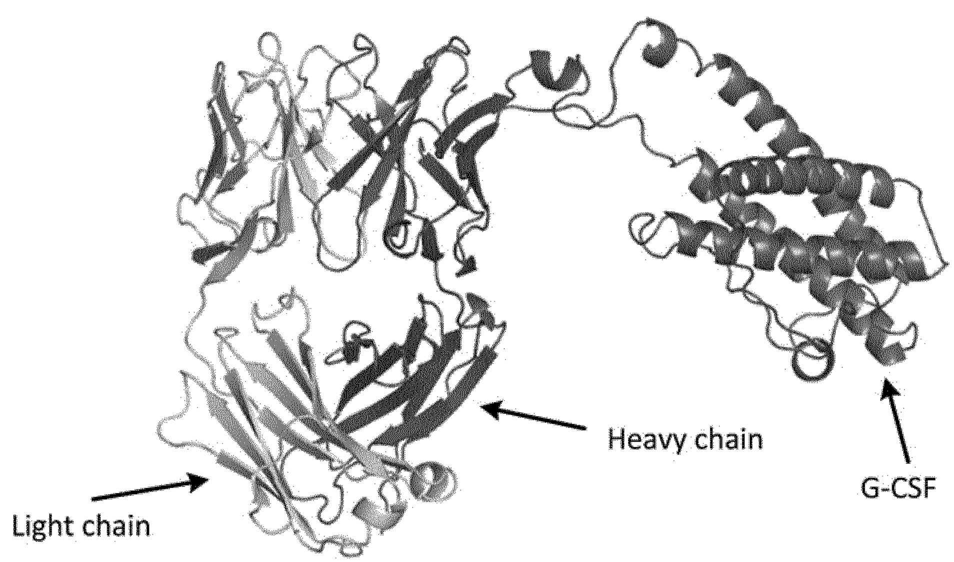

FIG. 4A shows the Biacore analysis of binding potency for this CA645/G-CSF antibody fusion protein when tested with 100 nM G-CSF-Rα (binding partner for G-CSF), 1000 nM HSA (ligand for CA645), and both G-CSF-Rα and HSA. FIG. 4A shows in line with the other Examples, both the G-CSF and Fab portions of the fusion protein are functionally active and are able to bind their respective binding partners. FIG. 4A further shows that in the presence of both binding partners, the signal seen from the SPR trace is additive from the single-binder traces, showing that binding to both functional portions can occur simultaneously. FIG. 4B shows a modelled representation of the CA645/G-$CSF_{Fwk3}$ protein.

Example 4—CA645 Fab with GM-CSF Insert Polypeptide

GM-CSF is a cytokine which stimulates stem cells to produce granulocytes (neutrophils, eosinophils, and basophils) and monocytes.

A fusion protein was generated and expressed in accordance with the above methods to insert the human and the murine GM-CSF sequences into the framework 3 region of the CA645 Fab construct, as shown below.

Human GM-CSF (hGM-CSF) sequence:

(SEQ ID NO: 59)

APARSPSPSTQPWEHVNAIQEARRLLNLSRDTAAEMNETVEVISEMFDLQ

REPTCLQTLELYKQGLRGSLTKLKGPLTMMASHYKQHCPPTPETSCATQI

ITFESFKENLKDFLLVIPFDCWEPVQE

CA645 Fab heavy chain with human GM-CSF (bold and italics) inserted into framework 3, Gly-Ser linkers underlined:

(SEQ ID NO: 60)

EVQLLESGGGLVQPGGSLRLSCAVSGIDLSNYAINWVRQAPGKGLEWIGI

IWASGTTFYATWAKGRFTISRDNSGGGSGGGG*APARSPSPSTQPWEHVNA*

*IQEARRLLNLSRDTAAEMNETVEVISEMFDLQEPTCLQTRLELYKQGLRG*

*SLTKLKGPLTMMASHYKQHCPPTPETSCATQIITFESFKENLKDFLLVIP*

*FDCWEPVQE*GGGKNTVYLQMNSLRAEDTAVYYCARTVPGYSTAPYFDLWG

QGTLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPSN

TKVDKKVEPKSC

CA645 Fab heavy chain with human GM-CSF (bold and italics) at C-terminus of CH1, Gly-Ser linker underlined (for comparison purposes):

(SEQ ID NO: 61)

EVQLLESGGGLVQPGGSLRLSCAVSGIDLSNYAINWVRQAPGKGLEWIGI

IWASGTTFYATWAKGRFTISRDNSKNTVYLQMNSLRAEDTAVYYCARTVP

GYSTAPYFDLWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCGGGSGGGG*APARSPSPSTQPWEHVNA*

*IQEARRLLNLSRDTAAEMNETVEVISEMFDLQEPTCLQTRLELYKQGLRG*

*SLTKLKGPLTMMASHYKQHCPPTPETSCATQIITFESFKENLKDFLLVIP*

*FDCWEPVQE*

Murine GM-CSF (mGM-CSF) sequence:

(SEQ ID NO: 62)

APTRSPITVTRPWKHVEAIKEALNLLDDMPVTLNEEVEVVSNEFSFKKLT

CVQTRLKIFEQGLRGNFTKLKGALNMTASYYQTYCPPTPETDCETQVTTY

ADFIDSLKTFLTDIPFECKKPGQK

CA645 Fab heavy chain with murine GM-CSF (bold and

-continued italics) inserted into framework 3, Gly-Ser linkers underlined:

(SEQ ID NO: 63)

EVQLLESGGGLVQPGGSLRLSCAVSGIDLSNYAINWVRQAPGKGLEWIGI

IWASGTTFYATWAKGRFTISRDNSGGGSGGGG*APTRSPITVTRPWKHVEA*

*IKEALNLLDDMPVTLNEEVEVVSNEFSFKKLTCVQTRLKIFEQGLRGNFT*

*KLKGALNMTASYYQTYCPPTPETDCETQVTTYADFIDSLKTFLTDIPFEC*

*KKPGQK*GGGKNTVYLQMNSLRAEDTAVYYCARTVPGYSTAPYFDLWGQGT

LVTVSSASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKV

DKKVEPKSC

CA645 Fab heavy chain with murine GM-CSF (bold and italics) at C-terminus of CH1, Gly-Ser linkers underlined (for comparison purposes):

(SEQ ID NO: 64)

EVQLLESGGGLVQPGGSLRLSCAVSGIDLSNYAINWVRQAPGKGLEWIGI

IWASGTTFYATWAKGRFTISRDNSKNTVYLQMNSLRAEDTAVYYCARTVP

GYSTAPYFDLWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCGGGSGGGG*APTRSPITVTRPWKHVEA*

*IKEALNLLDDMPVTLNEEVEVVSNEFSFKKLTCVQTRLKIFEQGLRGNFT*

*KLKGALNMTASYYQTYCPPTPETDCETQVTTYADFIDSLKTFLTDIPFEC*

*KKPGQK*

Figure 5:
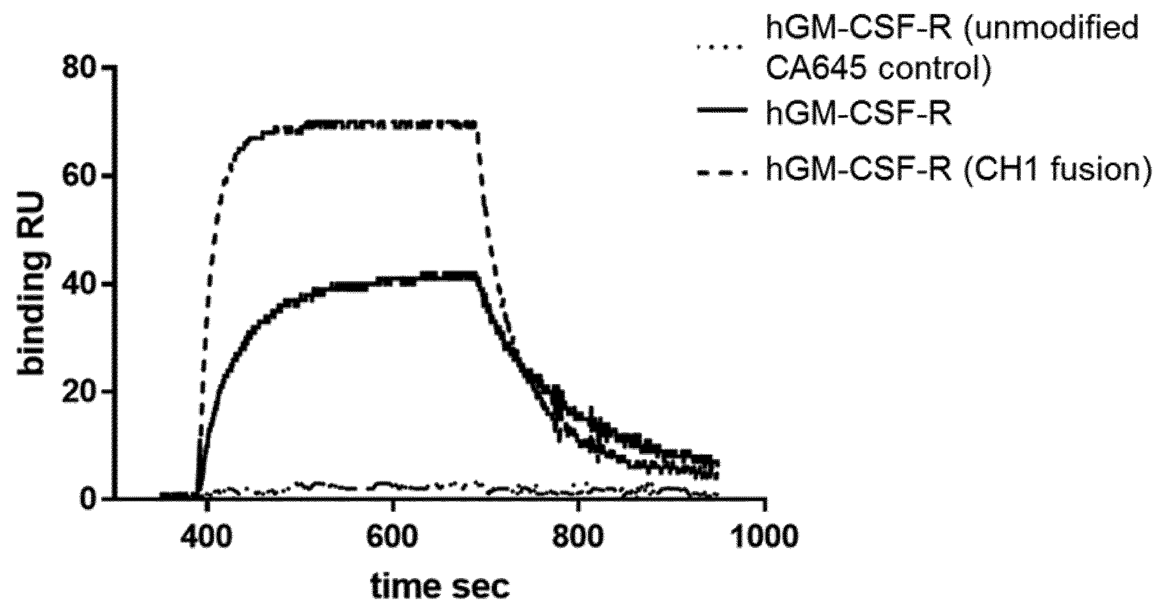
FIG. 5: (A) SPR sensorgram showing CA645/GM-$CSF_{Fwk3}$ (human) binding to GM-CSF receptor, with comparison to a CA645/GM-$CSF_{CH1}$ (human) construct; (B) Modelled structure showing the GM-CSF insert into framework 3 of the CA645 VH domain.
Figure 5:
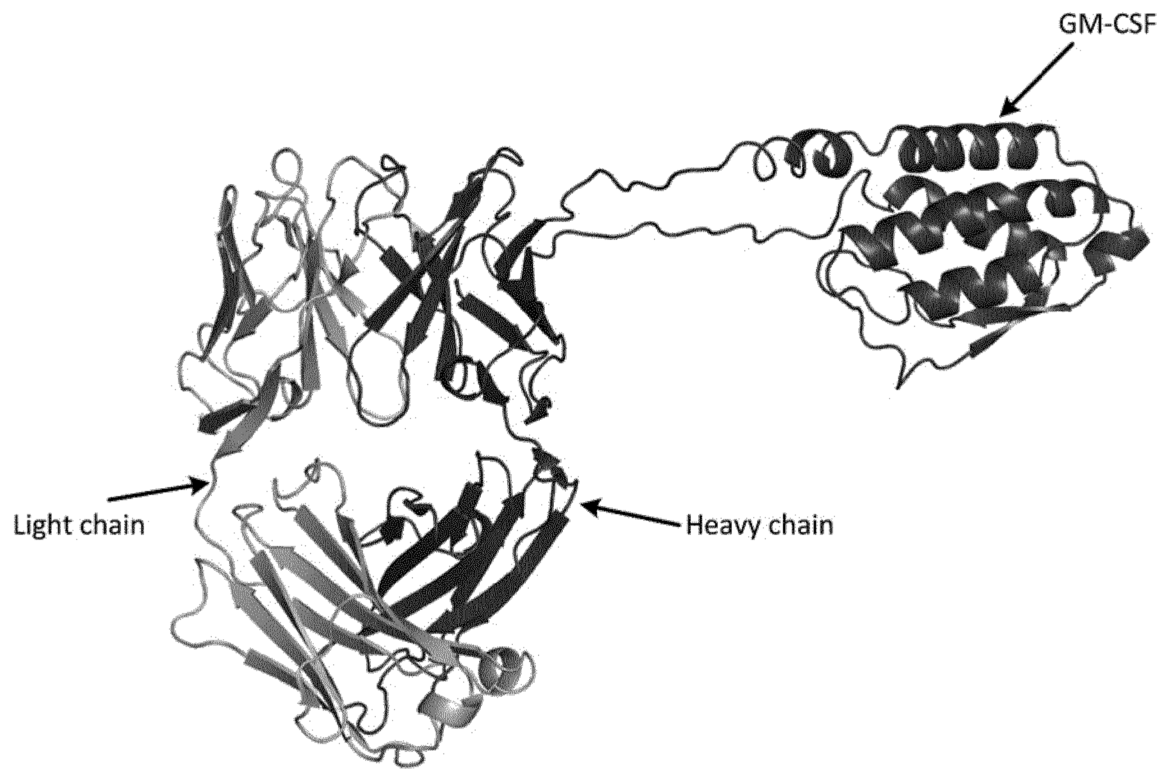
Figure 6:
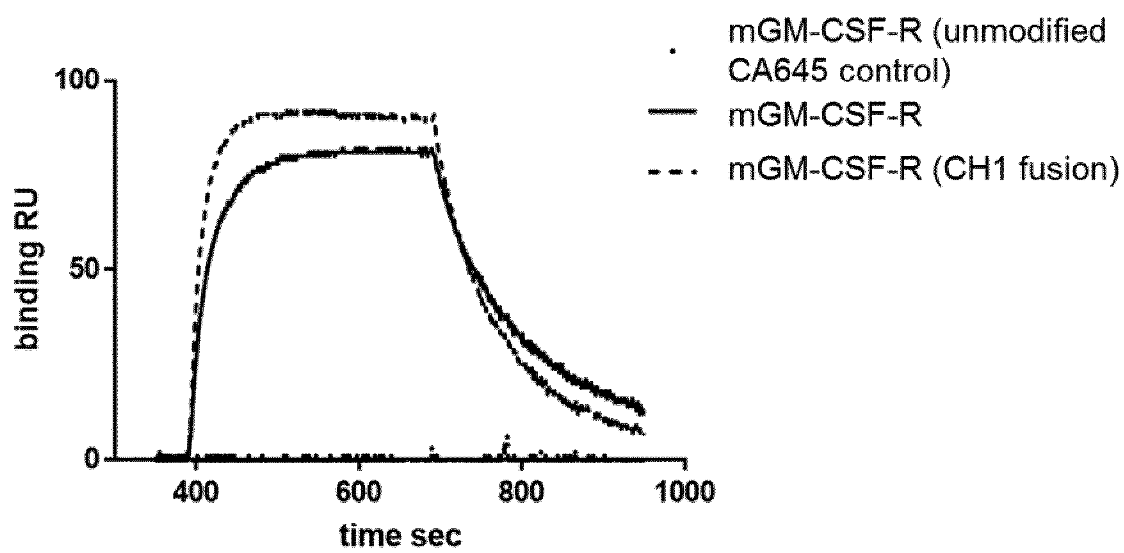
FIG. 6: SPR sensorgram showing CA645/GM-$CSF_{Fwk3}$ (murine) binding to GM-CSF receptor, with comparison to a CA645/GM-$CSF_{CH1}$ (murine) construct.

FIGS. 5A and 6 shows the Biacore analysis of binding potency for the CA645/hGM-CSF and CA645/mGM-CSF antibody fusion proteins (respectively) when tested with the cognate GM-CSF receptor (at 100 nM). The results demonstrate that the binding to the GM-CSF receptor is specific and dependent upon the presence of the insert polypeptide. The Figures also show a separate trace for a constant domain (CH1) fusion of the GM-CSF peptide, showing that the framework 3 insert functions in a comparable manner. FIG. 5B shows a modelled representation of the CA645/GM-$CSF_{Fwk3}$ protein.

Example 5—CA645 Fab with EPO Insert Polypeptide

Erythropoietin (EPO) is a cytokine released by the kidney in response to cellular hypoxia which stimulates red blood cell production in the bone marrow.

A fusion protein was generated and expressed in accordance with the above methods to insert the human EPO sequence into the framework 3 region of the CA645 Fab construct, as shown below.

Human EPO sequence:

(SEQ ID NO: 65)

APPRLICDSRVLERYLLEAKEAENITTGCAEHCSLNENITVPDTKVNFYA

WKRMEVGQQAVEVWQGLALLSEAVLRGQALLVNSSQPWEPLQLHVDKAVS

GLRSLTTLLRALGAQKEAISPPDAASAAPLRTITADTFRKLFRVYSNFLR

GKLKLYTGEACRTGDR

CA645 Fab heavy chain with human EPO (bold and italics) inserted into framework 3, Gly-Ser -continued linkers underlined:

(SEQ ID NO: 66)

EVQLLESGGGLVQPGGSLRLSCAVSGIDLSNYAINWVRQAPGKGLEWIGI

IWASGTTFYATWAKGRFTISRDNSGGGSGGGG*APPRLICDSRVLERYLLE*

*AKEAENITTGCAEHCSLNENITVPDTKVNFYAWKRMEVGQQAVEVWQGLA*

*LLSEAVLRGQALLVNSSQPWEPLQLHVDKAVSGLRSLTTLLRALGAQKEA*

*ISPPDAASAAPLRTITADTFRKLFRVYSNFLRGKLKLYTGEACRTGDR*GG

GKNTVYLQMNSLRAEDTAVYYCARTVPGYSTAPYFDLWGQGTLVTVSSAS

TKGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKKVEPKS

C

Figure 7:
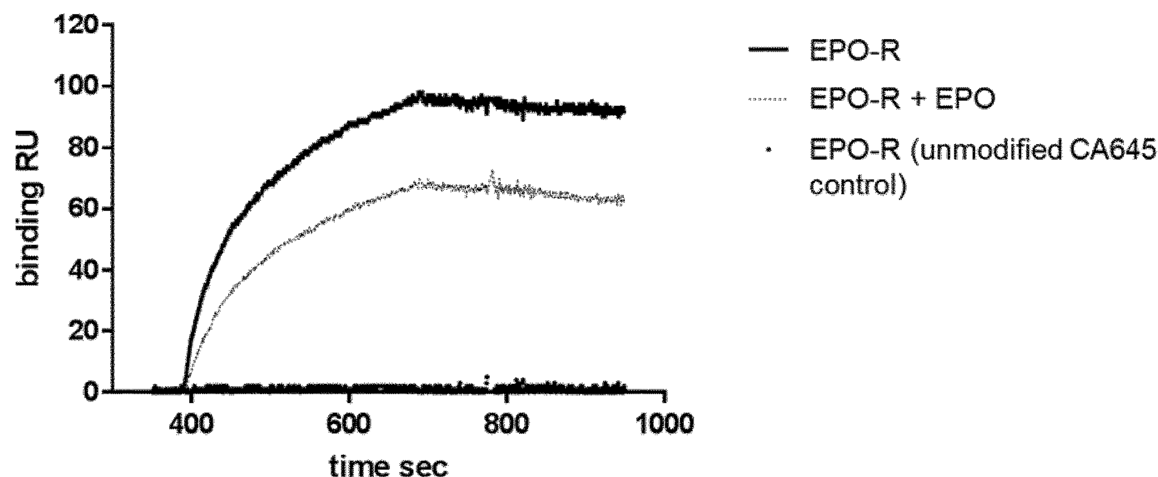
FIG. 7: (A) SPR sensorgram showing CA645/$EPO_{Fwk3}$ binding to EPO receptor with and without added EPO; (B) Modelled structure showing the EPO insert into framework 3 of the CA645 VH domain.
Figure 7:
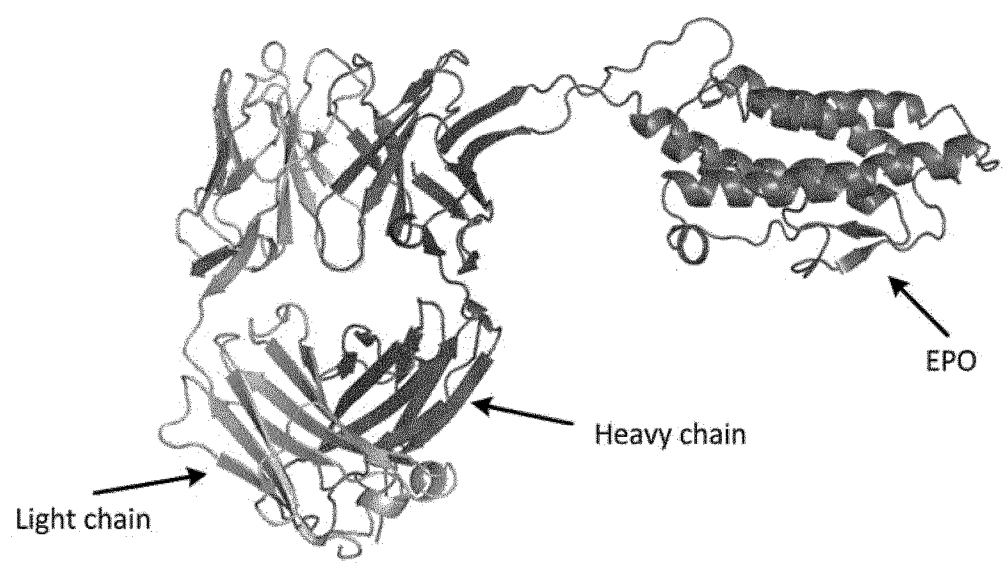

FIG. 7A shows the Biacore analysis of binding potency for this CA645/EPO antibody fusion protein when tested with 50 nM EPO-R (binding partner for EPO), with and without prior incubation with 500 nM soluble EPO at (competing ligand). FIG. 7A shows in line with the other Examples, the EPO portion of the fusion protein is functionally active and is able to bind its cognate receptor. Furthermore, the decrease in signal seen with the prior incubation of EPO shows the specificity of the interaction, while the unmodified CA645 Fab acts as a further control to demonstrate that the binding seen is derived from the EPO graft. FIG. 7B shows a modelled representation of the CA645/$EPO_{Fwk3}$ protein.

Example 6—Antibody/Fab Fusion Protein with CA645 Fab with VHH6 Insert

VHH6 is an engineered single-domain heavy-chain camelid antibody which binds a junctional epitope in that it is able to bind the IL-6:gp80 complex, but not the individual components alone.

A fusion protein was generated and expressed in accordance with the above methods to insert the VHH6 sequence into the framework 3 region of the CA645 Fab construct, as shown below.

Camelid VHH6 sequence:

(SEQ ID NO: 67)

DVQFVESGGGSVHAGGSLRLNCATSGYIYSTYCMGWFRQAPGKEREGVAH

IYTNSGRTYYADSVKGRFTISQDNAKNTVYLQMNSLKPEDTAIYYCAARP

SIRCASFSATEYKDWGQGTQVTVSS

CA645 Fab heavy chain with VHH6 (bold and italics) inserted into framework 3, Gly-Ser linkers underlined:

(SEQ ID NO: 68)

EVQLLESGGGLVQPGGSLRLSCAVSGIDLSNYAINWVRQAPGKGLEWIGI

IWASGTTFYATWAKGRFTISRDNSGGGGSGGGGS*DVQFVESGGGSVHAGG*

*SLRLNCATSGYIYSTYCMGWFRQAPGKEREGVAHIYTNSGRTYYADSVKG*

*RFTISQDNAKNTVYLQMNSLKPEDTAIYYCAARPSIRCASFSATEYKDWG*

*QGTQVTVSS*GGGGSGGGGSKNTVYLQMNSLRAEDTAVYYCARTVPGYSTA

PYFDLWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSC

Figure 8:
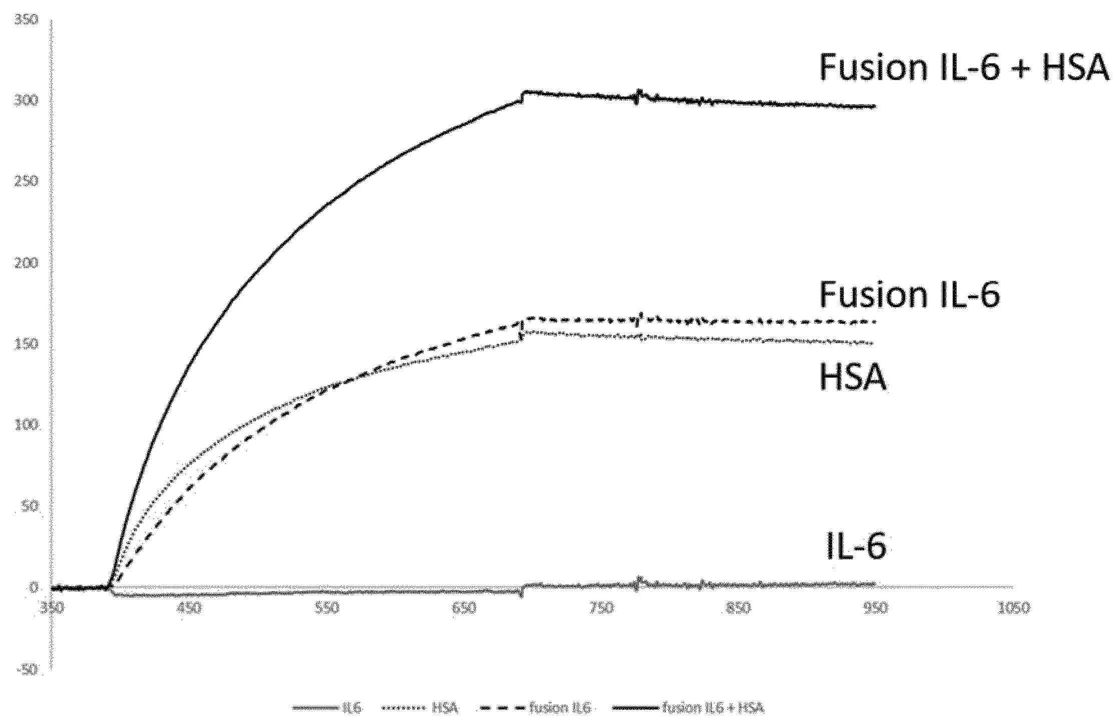
FIG. 8: (A) SPR sensorgram showing CA645/$VHH6_{Fwk3}$ binding to IL-6, HSA, IL-6:gp80 with or without HSA; (B) Modelled structure showing the VHH6 insert into framework 3 of the CA645 VH domain.
Figure 8:
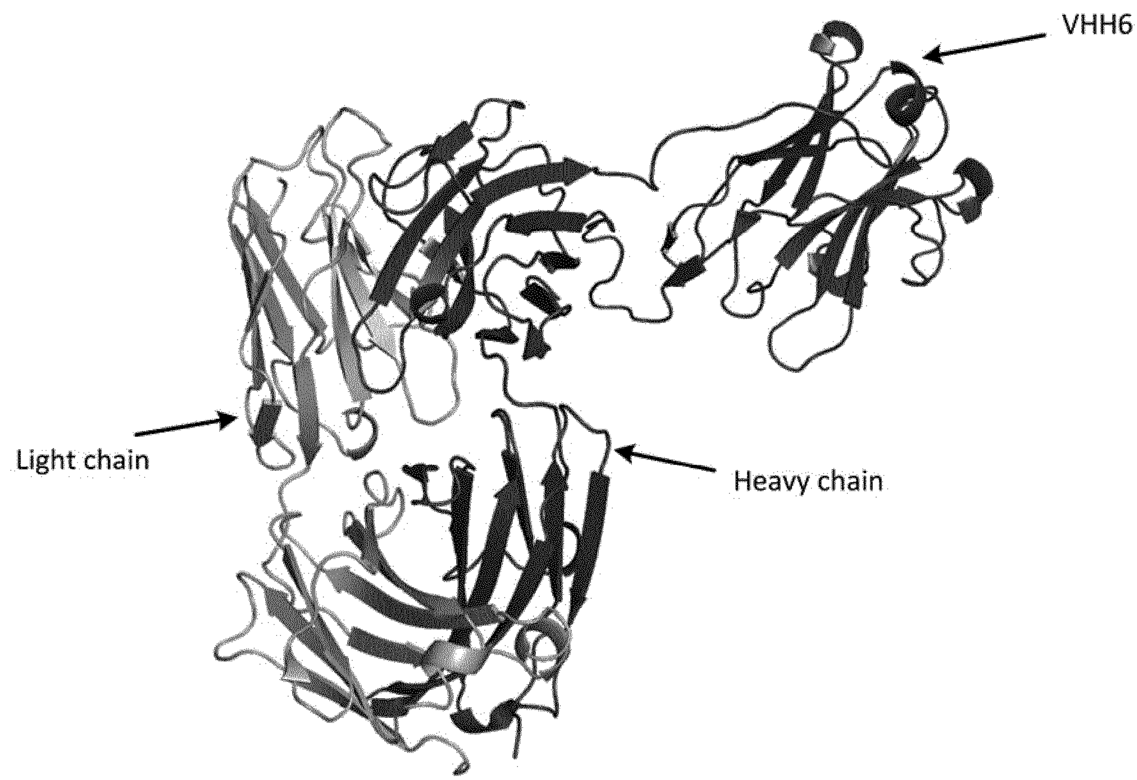

FIG. 8A shows the Biacore analysis of binding potency for this CA645/VHH6 antibody fusion protein when tested with 100 nM IL-6 (negative control for VHH6 as VHH6 solely binds the complex), 100 nM IL-6/gp80 fusion (binding partner for VHH6), 1000 nM HSA (binding partner for CA645) and both the IL-6 fusion and HSA together. FIG. 8A shows in line with the other Examples, both the VHH6 and CA645 parts of the antibody fusion protein are functionally active as binding fragments and are able to bind their respective binding partners. FIG. 8A further shows that in the presence of both binding partners, the signal seen from the SPR trace is additive from the single-binder traces, showing that binding to both functional portions can occur simultaneously. FIG. 8B shows a modelled representation of the CA645/$VHH6_{Fwk3}$ protein.

Example 7—Antibody/Fab Fusion Protein with CA645 Fab with VHH15 Insert

VHH15 is an engineered single domain heavy-chain camelid antibody which recognises and binds to IL-6.

A fusion protein was generated and expressed in accordance with the above methods to insert the VHH15 sequence into the framework 3 region of the CA645 Fab construct, as shown below.

Camelid VHH15 sequence:

(SEQ ID NO: 69)

QVQLVESGGGSVQAGGSLRLSCVAASGYTGCTYDMRWYRQAPGKEREFVS

GIDSDGRATYADSVKGRFTISQSNAKIAVYLQMDSLKLEDTAMYYCNLQC

LRYPGEYYWGQGTQVTVSS

CA645 Fab heavy chain with VHH15, an anti-IL-6 camelid domain antibody (bold and italics), inserted into framework 3, Gly-Ser linkers underlined:

(SEQ ID NO: 70)

EVQLLESGGGLVQPGGSLRLSCAVSGIDLSNYAINWVRQAPGKGLEWIGI

IWASGTTFYATWAKGRFTISRDNSGGGGSGGGGS*QVQLVESGGGSVQAGG*

*SLRLSCVAASGYTGCTYDMRWYRQAPGKEREFVSGIDSDGRATYADSVKG*

*RFTISQSNAKIAVYLQMDSLKLEDTAMYYCNLQCLRYPGEYYWGQGTQVT*

*VSS*GGGGSGGGGSKNTVYLQMNSLRAEDTAVYYCARTVPGYSTAPYFDLW

GQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPS

NTKVDKKVEPKSC

Figure 9:
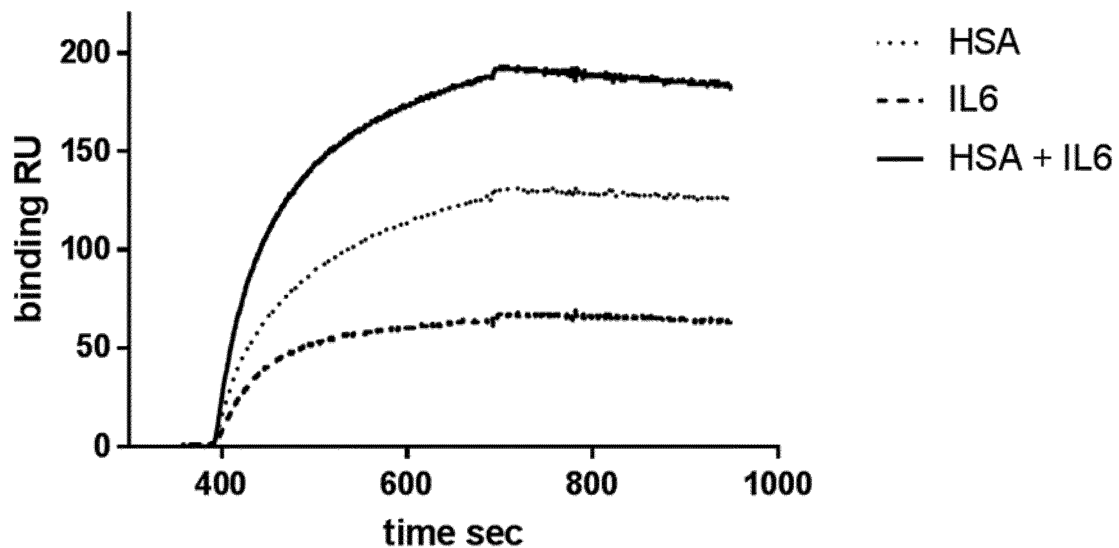
FIG. 9: (A) SPR sensorgram showing CA645/$VHH15_{Fwk3}$ binding to HSA and/or IL-6; (B) Modelled structure showing the VHH15 insert into framework 3 of the CA645 VH domain.
Figure 9:
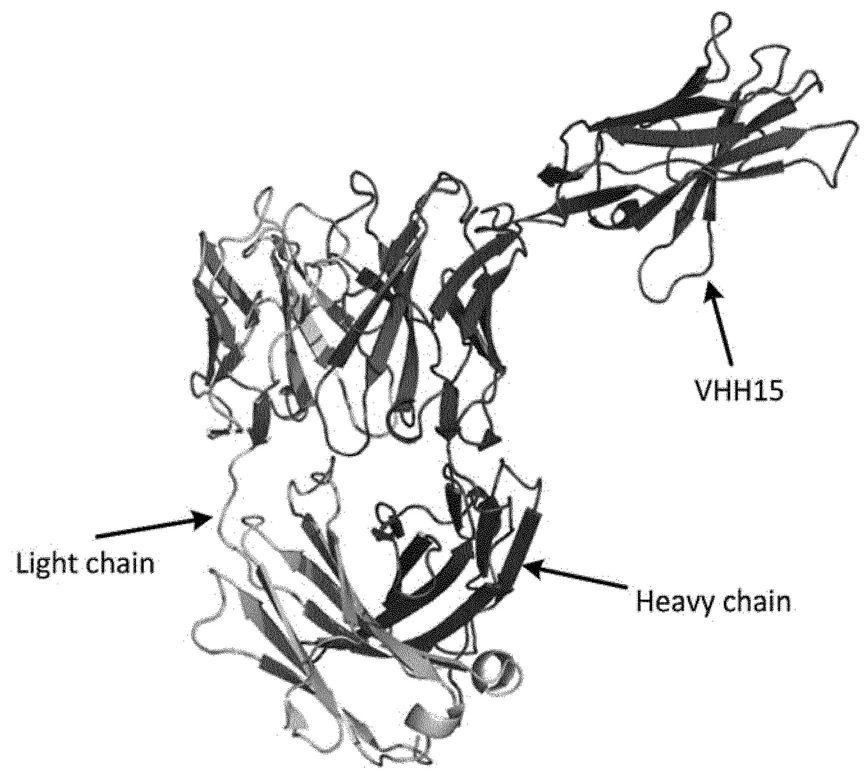

FIG. 9A shows the Biacore analysis of binding potency for this CA645/VHH15 antibody fusion protein when tested with 100 nM IL-6 (ligand for VHH15), 1000 nM HSA (ligand for CA645), and both IL-6 and HSA. FIG. 9A shows in line with the other Examples, both the VHH15 and Fab portions of the antibody fusion protein are functionally active as binding fragments and are able to bind their respective binding partners. FIG. 9A further shows that in the presence of both binding partners, the signal seen from the SPR trace is additive from the single-binder traces, showing that binding to both functional portions can occur simultaneously. FIG. 9B shows a modelled representation of the CA645/$VHH15_{Fwk3}$ protein.

Example 8—CA645 Fab with Sclerostin Insert Polypeptide

Sclerostin is the product of the SOST gene in humans and is involved in the process of bone formation, being largely expressed in osteocytes. Sclerostin functions as a regulatory protein in the Wnt signalling pathway through binding to the LRP-type co-receptors.

Fusion proteins were generated and expressed in accordance with the above methods to insert the core or the whole Sclerostin sequence into the framework 3 region of the CA645 Fab construct, as shown below.

Human mature full-length sclerostin sequence:
(SEQ ID NO: 71)

QGWQAFKNDATEIIPELGEYPEPPPELENNKTMNRAENGGRPPHHPFETK

DVSEYSCRELHFTRYVTDGPCRSAKPVTELVCSGQCGPARLLPNAIGRGK

WWRPSGPDFRCIPDRYRAQRVQLLCPGGEAPRARKVRLVASCKCKRLTRF

HNQSELKDFGTEAARPQKGRKPRPRARSAKANQAELENAY

Sequence of core domain of human sclerostin:
(SEQ ID NO: 72)

CRELHFTRYVTDGPCRSAKPVTELVCSGQCGPARLLPNAIGRGKWWRPSG

PDFRCIPDRYRAQRVQLLCPGGEAPRARKVRLVASCKC

CA645 Fab heavy chain with human sclerostin core domain (bold and italics) inserted into framework 3, single S linkers underlined:
(SEQ ID NO: 73)

EVQLLESGGGLVQPGGSLRLSCAVSGIDLSNYAINWVRQAPGKGLEWIGI

IWASGTTFYATWAKGRFTISRDNSS*CRELHFTRYVTDGPCRSAKPVTELV*

*CSGQCGPARLLPNAIGRGKWWRPSGPDFRCIPDRYRAQRVQLLCPGGEAP*

*RARKVRLVASCKC*SKNTVYLQMNSLRAEDTAVYYCARTVPGYSTAPYFDL

WGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDKKVEPKSC

CA645 Fab heavy chain with human sclerostin core domain (bold and italics) inserted into framework 3, Gly-Ser (2X $G_4S$) linkers underlined:
(SEQ ID NO: 74)

EVQLLESGGGLVQPGGSLRLSCAVSGIDLSNYAINWVRQAPGKGLEWIGI

IWASGTTFYATWAKGRFTISRDNSGGGGSGGGGS*CRELHFTRYVTDGPCR*

*SAKPVTELVCSGQCGPARLLPNAIGRGKWWRPSGPDFRCIPDRYRAQRVQ*

*LLCPGGEAPRARKVRLVASCKC*SGGGGSGGGGSKNTVYLQMNSLRAEDTA

VYYCARTVPGYSTAPYFDLWGQGTLVTVSSASTKGPSVFPLAPSSKSTSG

GTAALGCLVKDYFPEPVTVSWNSGALTSGVHTFPAVLQSSGLYSLSSVVT

VPSSSLGTQTYICNVNHKPSNTKVDKKVEPKSC

CA645 Fab heavy chain with human sclerostin core domain (bold and italics) inserted into framework 3, rigid linkers underlined:
(SEQ ID NO: 75)

EVQLLESGGGLVQPGGSLRLSCAVSGIDLSNYAINWVRQAPGKGLEWIGI

IWASGTTFYATWAKGRFTISRDNSIPFTV*CRELHFTRYVTDGPCRSAKPV*

*TELVCSGQCGPARLLPNAIGRGKWWRPSGPDFRCIPDRYRAQRVQLLCPG*

*GEAPRARKVRLVASCKC*EYHGLQKNTVYLQMNSLRAEDTAVYYCARTVPG

YSTAPYFDLWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSC

CA645 Fab heavy chain with human mature full-length sclerostin (bold and italics) inserted into framework 3, Gly-Ser (1X $G_4S$) linkers underlined:

-continued (SEQ ID NO: 76)

EVQLLESGGGLVQPGGSLRLSCAVSGIDLSNYAINWVRQAPGKGLEWIGI

IWASGTTFYATWAKGRFTISRDNSGGGGS*QGWQAFKNDATEIIPELGEYP*

*EPPPELENNKTMNRAENGGRPPHHPFETKDVSEYSCRELHFTRYVTDGPC*

*RSAKPVTELVCSGQCGPARLLPNAIGRGKWWRPSGPDFRCIPDRYRAQRV*

*QLLCPGGEAPRARKVRLVASCKCKRLTRFHNQSELKDFGTEAARPQKGRK*

*PRPRARSAKANQAELENAY*SGGGGSKNTVYLQMNSLRAEDTAVYYCARTV

PGYSTAPYFDLWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSC

Figure 10:
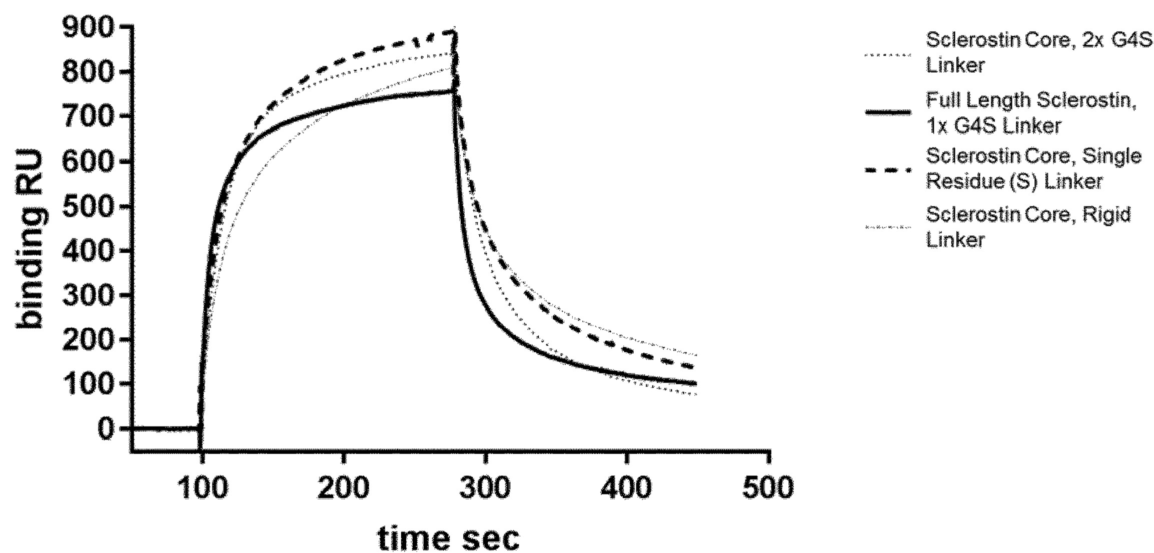
FIG. 10: (A) SPR sensorgram showing CA645/$Sclerostin_{Fwk3}$ (core or full-length) binding to LRP6 extracellular domain with various linker constructs; (B) Modelled structure showing the sclerostin core insert into framework 3 of the CA645 VH domain.
Figure 10:
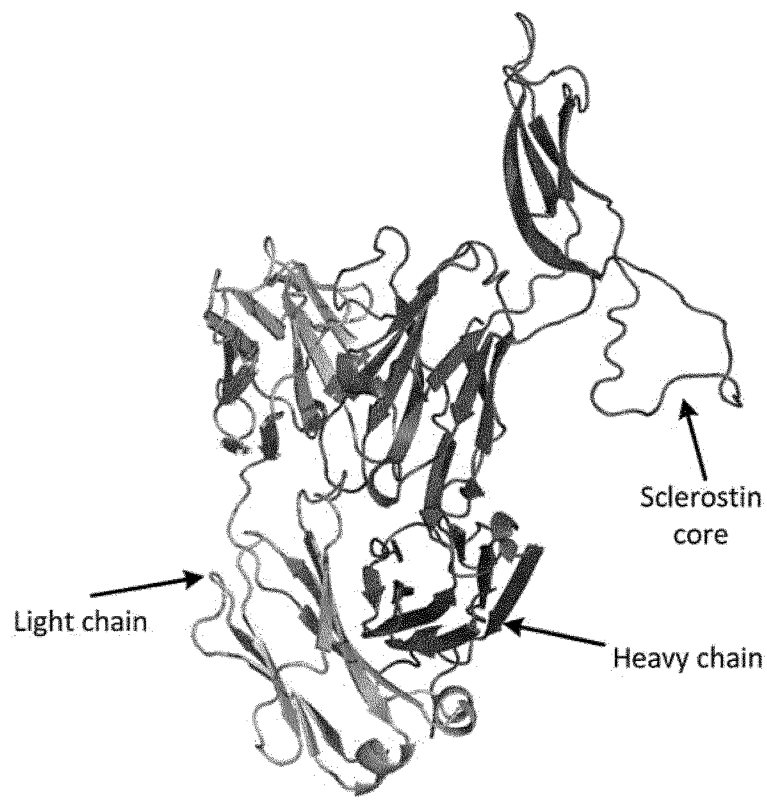
Figure 11:
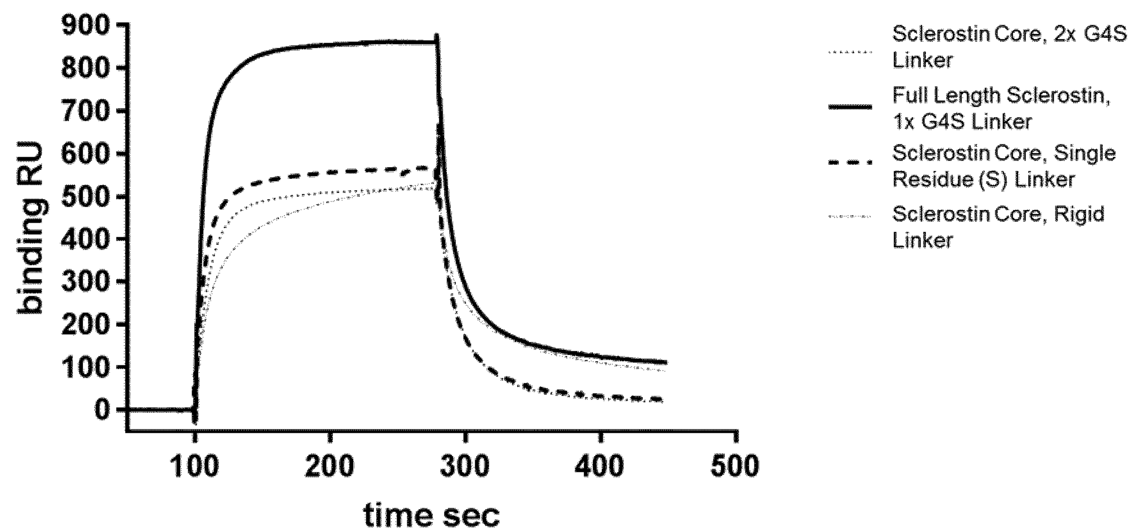
FIG. 11: SPR sensorgram showing CA645/$Sclerostin_{Fwk3}$ (core or full-length) binding to LRP4 extracellular domain with various linker constructs.

FIGS. 10A and 11 show the Biacore analysis of potency for this CA645/sclerostin antibody fusion protein when tested as 1 in 5 diluted supernatant for binding to immobilized extracellular domains of LRP6 and LRP4 respectively (binding partners for Sclerostin). This experiment also investigated the effects of different linker region constructs. It was noted that all of the tested constructs showed binding to LRP6 and LRP4. FIG. 10B shows a modelled representation of the CA645/Sclerostin$_{core\text{-}Fwk3}$ protein.

Example 9—CA645 Fab with IL-10 Insert Polypeptide (IL-10 Dimer)

Interleukin 10 (IL-10), also known as human cytokine synthesis inhibitory factor (CSIF), is an anti-inflammatory cytokine. It functions generally as a homodimer.

A fusion protein was generated and expressed in accordance with the above methods to insert two human IL-10 sequences into the framework 3 region of the CA645 Fab construct, as shown below.

Human IL-10 Monomer Sequence:

NCWLRQAKNGRCQVLYKTELSKEECCSTGRLSTSWTEEDVNDNTLFKWMIFNGGA PNCIPCKEPRCVCAPDCSNITWKGPVCGLDGKTYRNECALLKARCKEQPELEVQYQ GRCKKTCRDVFCPGSSTCVVDQTNNAYCVTCNRICPEPASSEQYLCGNDGVTYSSAC HLRKATCLLGRSIGLAGEYK (SEQ ID NO: 100)

CA645 Fab heavy chain with two human IL-10 (bold and italics) monomers inserted into framework 3, linkers underlined:
(SEQ ID NO: 101)

EVQLLESGGGLVQPGGSLRLSCAVSGIDLSNYAINWVRQAPGKGLEWIGI

IWASGTTFYATWAKGRFTISRDNSGGGGSGS*NCWLRQAKNGRCQVLYKTE*

*LSKEECCSTGRLSTSWTEEDVNDNTLFKWMIFNGGAPNCIPCKEPRCVCA*

*PDCSNITWKGPVCGLDGKTYRNECALLKARCKEQPELEVQYQGRCKKTCR*

*DVFCPGSSTCVVDQTNNAYCVTCNRICPEPASSEQYLCGNDGVTYSSACH*

*LRKATCLLGRSIGLAGEYK*GGGGSGGGGSGGGGS*NCWLRQAKNGRCQVLY*

*KTELSKEECCSTGRLSTSWTEEDVNDNTLFKWMIFNGGAPNCIPCKEPRC*

*VCAPDCSNITWKGPVCGLDGKTYRNECALLKARCKEQPELEVQYQGRCKK*

*TCRDVFCPGSSTCVVDQTNNAYCVTCNRICPEPASSEQYLCGNDGVTYSS*

*ACHLRKATCLLGRSIGLAYE*GGGGSGSKNTVYLQMNSLRAEDTAVYYCAR

-continued

TVPGYSTAPYFDLWGQGTLVTVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSC

Figure 12:
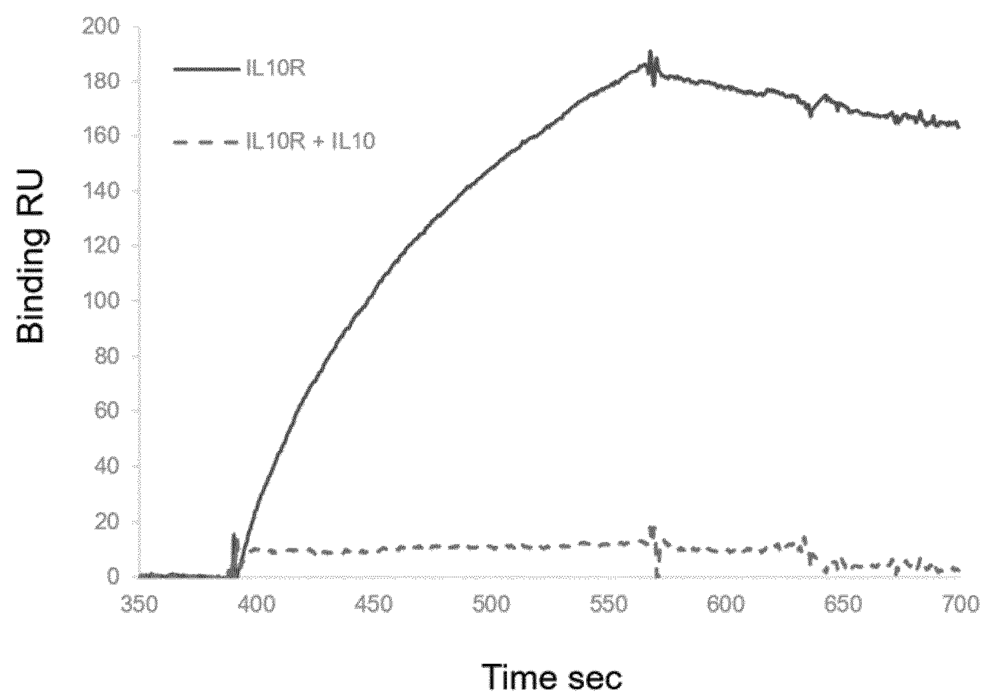
FIG. 12: (A) SPR sensorgram showing CA645/(IL-$10_{Fwk3})_2$ having different linker sequences binding to IL-10 receptor; (B) Modelled structure showing the IL-10 dimer insert into framework 3 of the CA645 VH domain.
Figure 12:
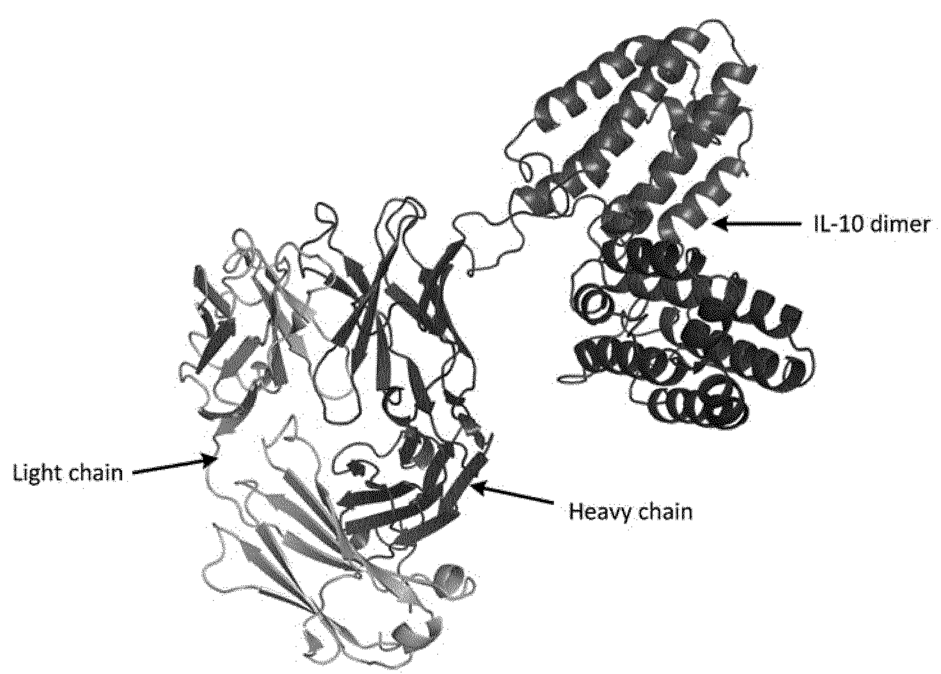

FIG. 12A shows the Biacore analysis of binding potency for this CA645/IL-10 antibody fusion protein when tested with 100 nM IL-10 receptor (binding partner for IL-10), with and without prior incubation with 200 nM IL-10 (competing ligand). As is shown in FIG. 12A, binding seen to IL-10 receptor is abolished in the presence of the competing ligand in molar excess, showing that the binding seen to the IL-10 portion in framework 3 of the fusion protein is a genuine functional interaction and not non-specific. This result also suggests that the inserted IL-10 monomers are also able to form a functional dimer within the framework 3 construct. FIG. 12B shows a modelled representation of the CA645/IL-$10_{Fwk3}$ protein.

Example 10—Antibody-Framework 3 Insertion Constructs with Other Fabs

Fusion proteins were generated and expressed in accordance with the above methods to insert the human IL-15 sequence into the framework 3 region of the CA497 and CA240 Fab constructs, as shown below.

Anti-IL-17A CA497 Fab heavy chain sequence (Fab, CH1 from IgG1; Variable domain underlined; CDRs in bold and italics.)

(SEQ ID NO: 125)

EVQLVESGGGLVKPGGSLRLSCAAS*GVIFSDYYMA*WVRQAPGKGLEWVA

*SINFNADISYYRESVKG*RFTISRDDSKNTLYLQMNSLKTEDTAVYYCTT

*DANRQNYDWFAY*WGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSC

Anti-IL-17A CA497 Fab heavy chain with human IL-15 (bold and italics) inserted into framework 3, Gly-Ser linkers underlined:

(SEQ ID NO: 83)

EVQLVESGGGLVKPGGSLRLSCAASGVIFSDYYMAWVRQAPGKGLEWVA

SINFNADISYYRESVKGRFTISRDDSGGGSGGGG*NWVNVISDLKKIEDL*

*IQSMHIDATLYTESDVHPSCKVTAMKCFLLELQVISLESGDASIHDTVE*

*NLIILANNSLSSNGNVTESGCKECEELEEKNIKEFLQSFVHIVQMFIN*G

GGKNTLYLQMNSLKTEDTAVYYCTTDANRQNYDWFAYWGQGTLVTVSSA

STKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVE

PKSC

Anti-IL-17A CA497 Fab light chain sequence:

(SEQ ID NO: 84)

AIQLTQSPSSLSASVGDRVTITCKASESVSSSMYSYMHWYQQKPGKAPK

LLIYRASNLESGVPSRFSGSGSGTDFTLTISSLQPEDFATYYCQQSWTA

PRTFGQGTKVEIKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC

-continued

Anti-IL-6 CA240 Fab heavy chain sequence (Fab, CH1 from IgG1; Variable domain underlined; CDRs in bold and italics):

(SEQ ID NO: 126)

EVQLVESGGGLVQPGGSLRLSCAAS*GFNFNDYFMN*WVRQAPGKGLEWVA

*QMRNKNYQYGTYYAESLEG*RFTISRDDSKNSLYLQMNSLKTEDTAVYYC

AR*ESYYGFTSYWG*QGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSC

Anti-IL-6 CA240 Fab heavy chain with human IL-15 (bold and italics) inserted into framework 3, Gly-Ser linkers underlined:

(SEQ ID NO: 85)

EVQLVESGGGLVQPGGSLRLSCAASGFNFNDYFMNWVRQAPGKGLEWVA

QMRNKNYQYGTYYAESLEGRFTISRDDSGGGSGGGG*NWVNVISDLKKIE*

*DLIQSMHIDATLYTESDVHPSCKVTAMKCFLLELQVISLESGDASIHDT*

*VENLIILANNSLSSNGNVTESGCKECEELEEKNIKEFLQSFVHIVQMFI*

*N*GGGKNSLYLQMNSLKTEDTAVYYCARESYYGFTSYWGQGTLVTVSSAS

TKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEP

KSC

Anti-IL-6 CA240 Fab light chain sequence:

(SEQ ID NO: 86)

DIQMTQSPSSLSASVGDRVTITCQASQDIGISLSWYQQKPGKAPKLLIY

NANNLADGVPSRFSGSGSGTDFTLTISSLQPEDFATYYCLQHNSAPYTF

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Figure 13:
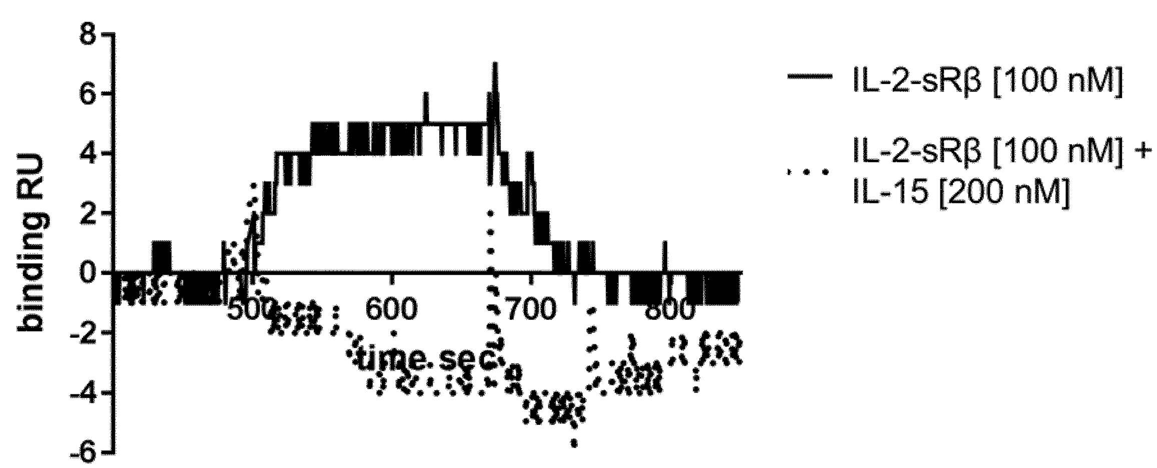
FIG. 13: SPR sensorgram showing CA497/IL-$15_{Fwk3}$ binding to IL-2 receptor β chain with and without added IL-15.
Figure 14:
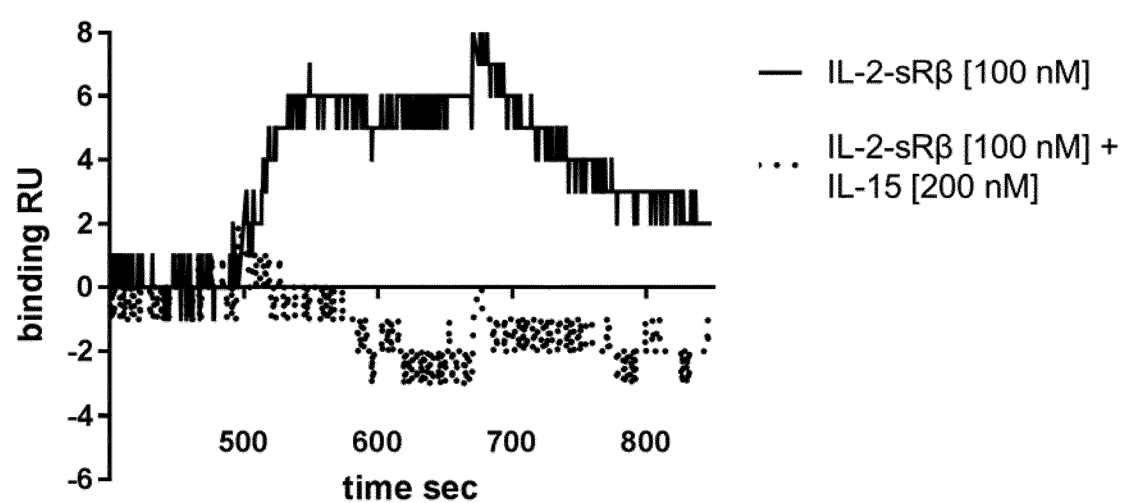
FIG. 14: SPR sensorgram showing CA240/IL-$15_{Fwk3}$ binding to IL-2 receptor β chain with and without added IL-15.

FIGS. 13 and 14 show the Biacore analysis of binding potency for the CA497/IL-15 and CA240/IL-15 (respectively) antibody fusion proteins when tested with 100 nM IL-2-Rβ (binding partner for IL-15), with and without prior incubation with IL-15 (a competing ligand). As is shown in both experiments, binding seen to IL-2-Rβ is abolished in the presence of the competing ligand in molar excess, showing that the binding seen to the IL-15 portion in framework 3 of the fusion proteins is a genuine functional interaction and not non-specific.

Example 11—Fab Constructs with a VHH Inserted into Framework 3

HyHEL5 is an anti-lysozyme Fab with the following sequences:

HyHEL5 heavy chain:

(SEQ ID NO: 87)

EVQLQQSGAELMKPGASVKISCKASGYTFSDYWIEWVKQRPGHGLEWIG

EILPGSGSTNYHERFKGKATFTADTSSSTAYMQLNSLTSEDSGVYYCLH

GNYDFDGWGQGTTLTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSC

-continued

```
HyHEL5 light chain:
                                              (SEQ ID NO: 88)
DIVLTQSPAIMSASPGEKVTMTCSASSSVNYMYWYQQKSGTSPKRWIYD

TSKLASGVPVRFSGSGSGTSYSLTISSMETEDAATYYCQQWGRNPTFGG

GTKLEIKRTVAAPSVFIFPPSDEQLKSGTASVVCLLNNFYPREAKVQWK

VDNALQSGNSQESVTEQDSKDSTYSLSSTLTLSKADYEKHKVYACEVTH

QGLSSPVTKSFNRGEC
```

D3LL5 is an anti-lysozyme VHH with the following sequence:

```
D3L11:
                                              (SEQ ID NO: 89)
DVQLVESGGGSVQAGGSLRLSCAASGSTDSIEYMTWFRQAPGKAREGVA

ALYTHTGNTYYTDSVKGRFTISQDKAKNMAYLRMDSVKSEDTAIYTCGA

TRKYVPVRFALDQSSYDYWGQGTQVTVSS
```

The following fusion constructs were generated to test whether inserting a second antibody molecule into the framework 3 region of a first antibody where the antibodies bound the same target antigen would result in a greater affinity for the antigen than either of the individual antibodies.

Anti-lysozyme HyHEL5 light chain with anti-lysozyme VHH D3L11 (bold) inserted into framework 3, Gly-Ser linkers underlined:

(SEQ ID NO: 90)

DIVLTQSPAIMSASPGEKVTMTCSASSSVNYMYWYQQKSGTSPKRWIYD

TSKLASGVPVRFSGSGSGS<u>GGGGS</u>DVQLVESGGGSVQAGGSLRLSCAAS

GSTDSIEYMTWFRQAPGKAREGVAALYTHTGNTYYTDSVKGRFTISQDK

AKNMAYLRMDSVKSEDTAIYTCGATRKYVPVRFALDQSSYDYWGQGTQV

TVSS<u>GGGGSGGGGSGGGGS</u>TSYSLTISSMETEDAATYYCQQWGRNPTFG

GGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC

Anti-lysozyme HyHEL5 light chain with anti-IL-6 VHH15 (bold) inserted into framework 3, Gly-Ser linkers underlined:

(SEQ ID NO: 91)

DIVLTQSPAIMSASPGEKVTMTCSASSSVNYMYWYQQKSGTSPKRWIYD

TSKLASGVPVRFSGSGSG<u>SGGGGS</u>QVQLVESGGGSVQAGGSLRLSCVAA

SGYTGCTYDMRWYRQAPGKEREFVSGIDSDGRATYADSVKGRFTISQSN

AKIAVYLQMDSLKLEDTAMYYCNLQCLRYPGEYYWGQGTQVTVSS<u>GGGG</u>

<u>SGGGGSGGGGS</u>TSYSLTISSMETEDAATYYCQQWGRNPTFGGGTKLEIK

RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC

CA645 light chain with anti-lysozyme VHH D3L11 (bold) inserted into framework 3, Gly-Ser linkers underlined:

(SEQ ID NO: 92)

DIQMTQSPSSVSASVGDRVTITCQSSPSVWSNFLSWYQQKPGKAPKLLI

YEASKLTSGVPSRFSGSGSG<u>SGGGGS</u>DVQLVESGGGSVQAGGSLRLSCA

ASGSTDSIEYMTWFRQAPGKAREGVAALYTHTGNTYYTDSVKGRFTISQ

DKAKNMAYLRMDSVKSEDTAIYTCGATRKYVPVRFALDQSSYDYWGQGT

QVTVSS<u>GGGGSGGGGSGGGGS</u>TDFTLTISSLQPEDFATYYCGGGYSSIS

DTTFGGGTKVEIKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC

Figure 15:
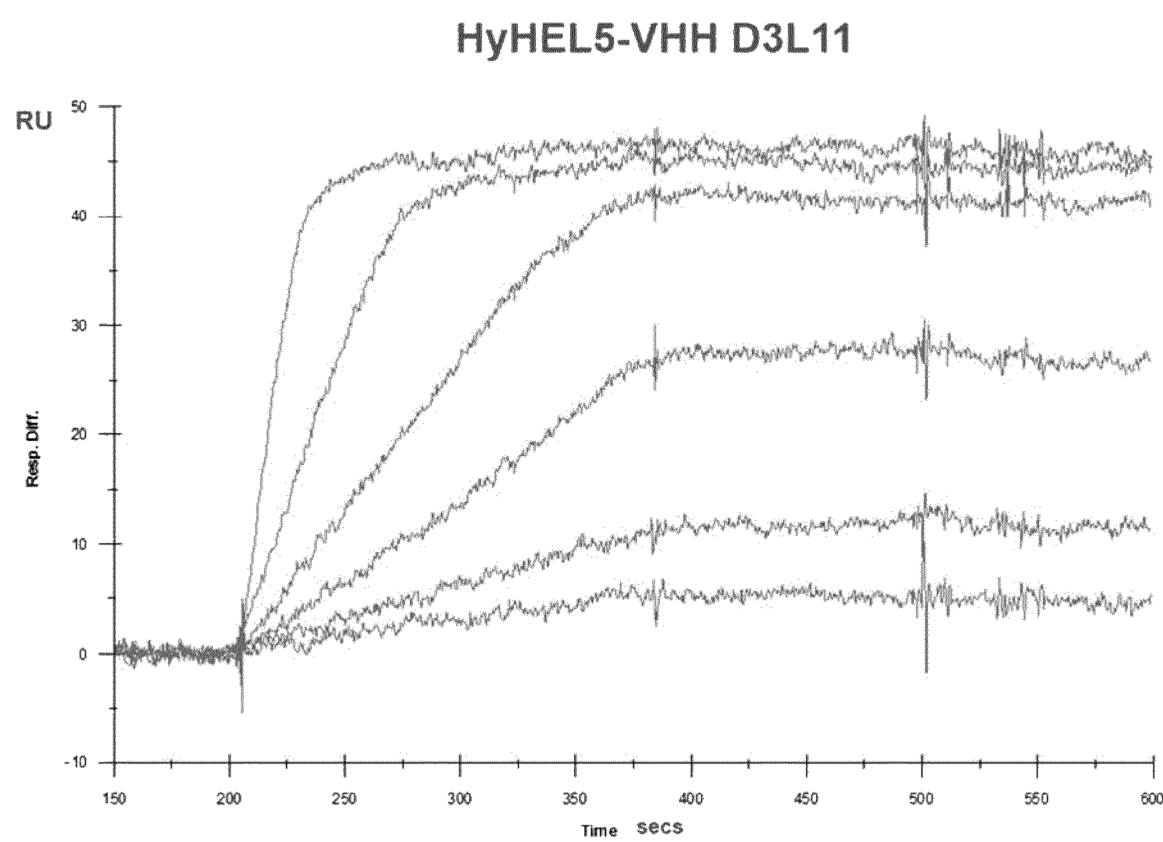
FIG. 15: SPR sensorgram showing dilution series for HyHEL5/VHH $D3L11_{Fwk3}$ binding to lysozyme.
Figure 16:
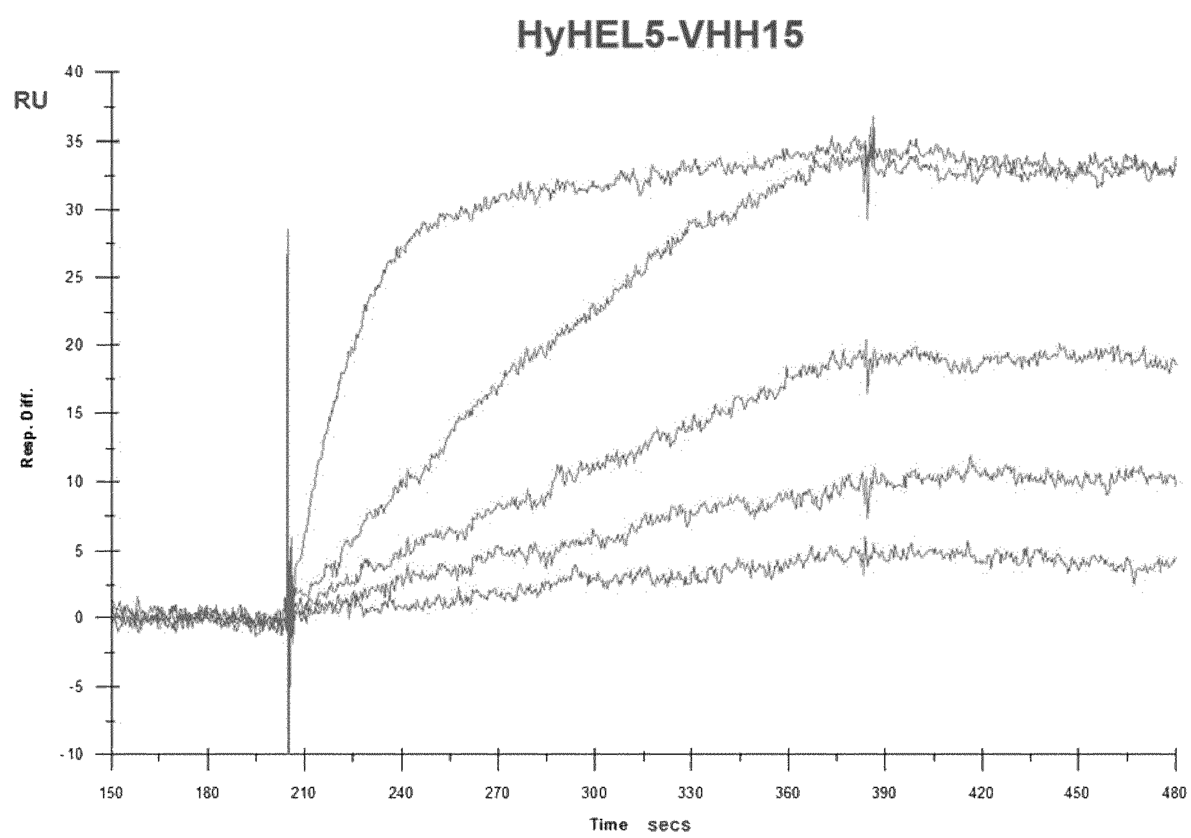
FIG. 16: SPR sensorgram showing dilution series for HyHEL5/$VHH15_{Fwk3}$ binding to lysozyme.
Figure 17:
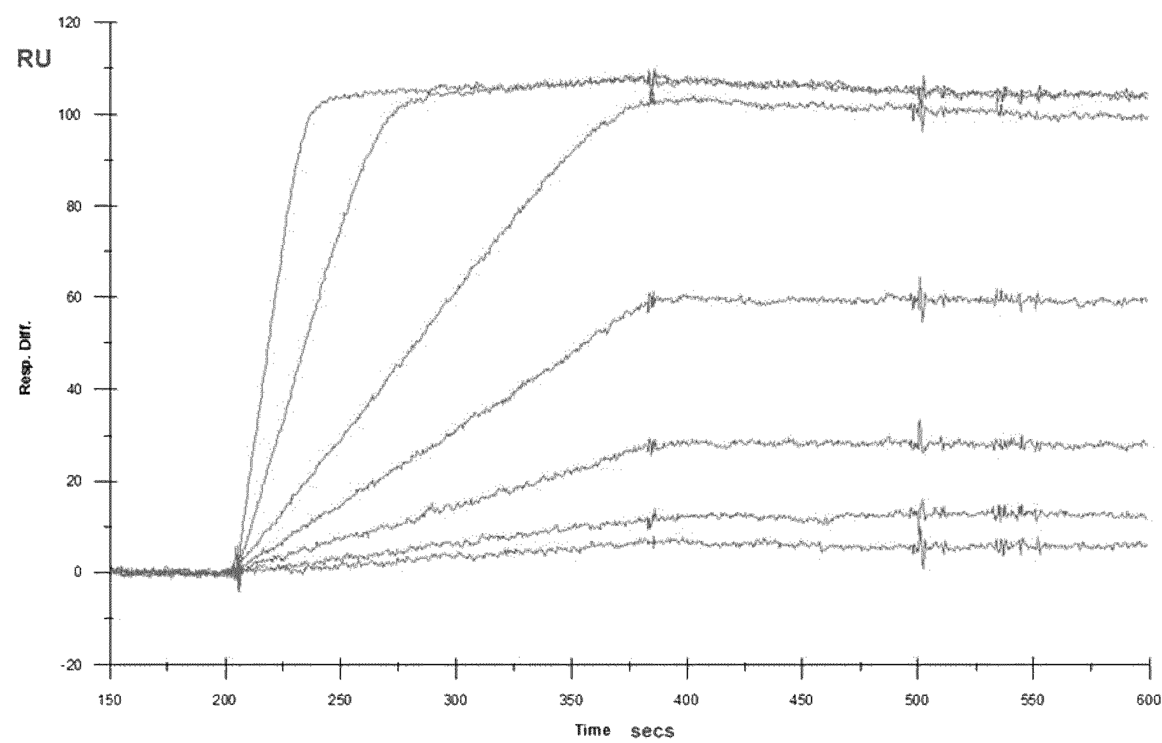
FIG. 17: SPR sensorgram showing dilution series for CA645/VHH $D3L11_{Fwk3}$ binding to lysozyme.

The SPR traces from the dilution series conducted for each of the constructs when tested for binding to lysozyme is shown in FIGS. 15 to 17. From the subsequent analysis, using the methods described above, the following table reveals the binding affinity for lysozyme calculated for each construct:

TABLE 2

Binding affinities for antibody constructs

| construct | Fab specificity | VHH specificity | Binding Affinity for lysozyme ($K_D$) |
|---|---|---|---|
| Antibody: HyHEL5 Fab Framework 3 Insert: VHH D3L11 | lysozyme | lysozyme | $2.6 \times 10^{-11}$M |
| Antibody: HyHEL5 Fab Framework 3 Insert: VHH15 | lysozyme | IL-6 | $3.1 \times 10^{-10}$M |
| Antibody: CA645 Fab Framework 3 Insert: VHH D3L11 | Human serum albumin | lysozyme | $4.8 \times 10^{-10}$M |

Figure 18:
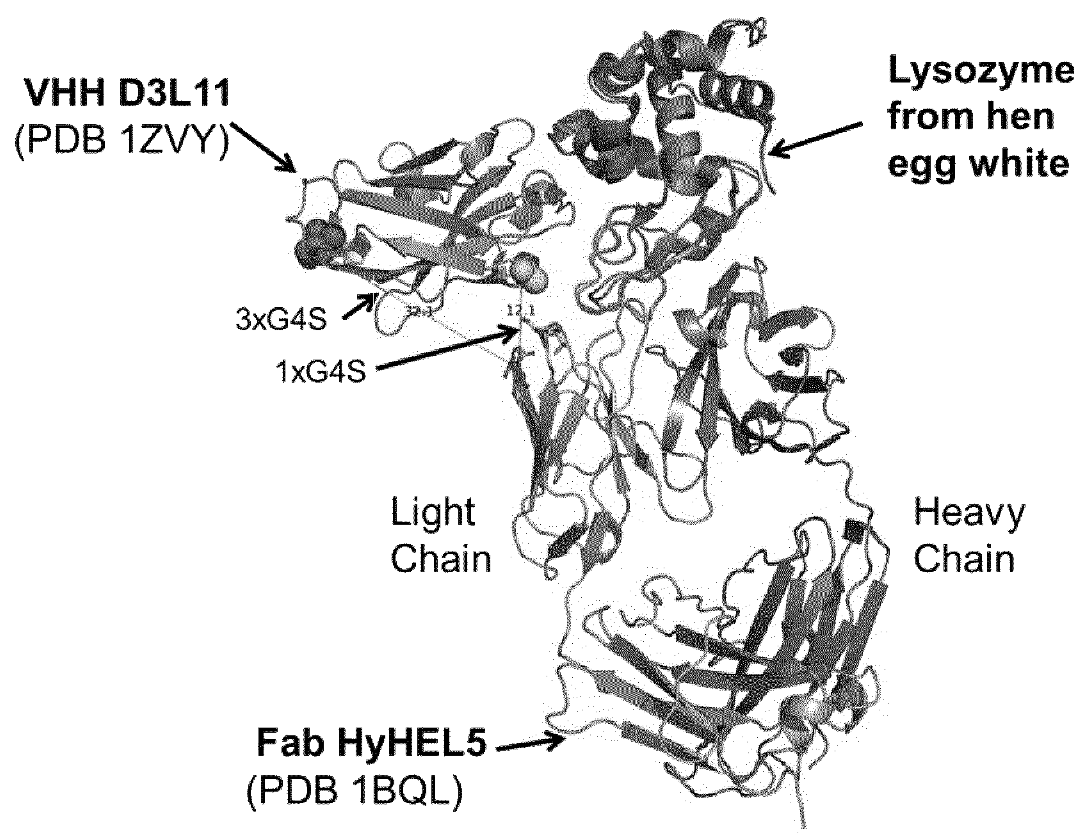
FIG. 18: Representation of potential binding schematic of HyHEL5/VHH $D3L11_{Fwk3}$ to lysozyme.

As is clearly seen from the above results, the binding affinity for lysozyme increases (i.e. a decrease is seen in the $K_D$) for the construct where the Fab and the VHH insert both bound to lysozyme. FIG. 18 illustrates how this may happen at a molecular level. This also hypothesises that the linker length may be important to enable multivalent interactions on the same target molecule in such antibodies.

Example 12—CA645 Fab with IL-15 Insert Polypeptide Using Bovine Linkers

Variants were generated on the CA645/IL-$15_{Fwk3}$ protein described in Example 1, where the linkers were changed to other types of linkers including bovine linkers, and their effects on binding tested. As well as the original heavy chain construct (SEQ ID NO: 54), further constructs were generated as shown below:

CA645 Fab heavy chain with human IL-15 (bold and italics) inserted into framework 3 with bovine long linker (underlined)

(SEQ ID NO: 93)

EVQLLESGGGLVQPGGSLRLSCAVSGIDLSNYAINWVRQAPGKGLEWIGI

IWASGTTFYATWAKGRFTISRDNS<u>TSVHQETKKYQS</u>*NWVNVISDLKKIED*

*LIQSMHIDATLYTESDVHPSCKVTAMKCFLLELQVISLESGDASIHDTVE*

*NLIILANNSLSSNGNVTESGCKECEELEEKNIKEFLQSFVHIVQMFIN*<u>SY</u>

<u>TYNYEWHVDV</u>KNTVYLQMNSLRAEDTAVYYCARTVPGYSTAPYFDLWGQG

-continued

TLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTK
VDKKVEPKSC

CA645 Fab heavy chain with human IL-15 (bold and italics) inserted into framework 3 with bovine short linker (underlined)

(SEQ ID NO: 94)

EVQLLESGGGLVQPGGSLRLSCAVSGIDLSNYAINWVRQAPGKGLEWIGI
IWASGTTFYATWAKGRFTISRDNSETKKYQS*NWVNVISDLKKIEDLIQSM*
*HIDATLYTESDVHPSCKVTAMKCFLLELQVISLESGDASIHDTVENLIIL*
*ANNSLSSNGNVTESGCKECEELEEKNIKEFLQSFVHIVQMFIN*SYTYNYE
KNTVYLQMNSLRAEDTAVYYCARTVPGYSTAPYFDLWGQGTLVTVSSAST
KGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSC

CA645 Fab heavy chain with human IL-15 (bold and italics) inserted into framework 3 with $2xG_4S$ linker (underlined)

(SEQ ID NO: 95)

EVQLLESGGGLVQPGGSLRLSCAVSGIDLSNYAINWVRQAPGKGLEWIGI
IWASGTTFYATWAKGRFTISRDNSGGGGSGGGGS*NWVNVISDLKKIEDLI*
*QSMHIDATLYTESDVHPSCKVTAMKCFLLELQVISLESGDASIHDTVENL*
*IILANNSLSSNGNVTESGCKECEELEEKNIKEFLQSFVHIVQMFIN*GGGG
SGGGGSKNTVYLQMNSLRAEDTAVYYCARTVPGYSTAPYFDLWGQGTLVT
VSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKK
VEPKSC

Figure 19:
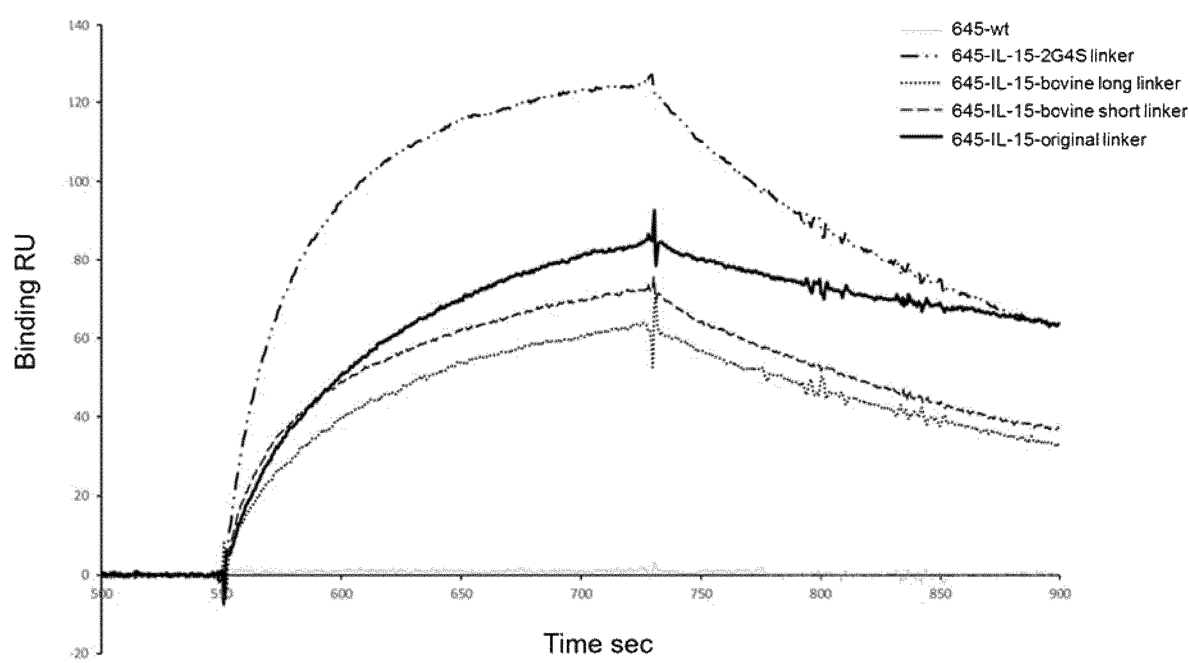
FIG. 19: SPR sensorgram showing CA645/IL-$15_{Fwk3}$ having different linker sequences binding to IL-15 receptor chain.

FIG. 19 shows the Biacore binding analysis of the above CA645/IL-$15_{Fwk3}$ constructs when tested with 100 nM IL-2-Rβ, and compared against the construct in Example 1 (original linker) and the wild type CA645 Fab, which has no IL-15 insert. It was noted that all of the tested constructs showed successful binding.

Example 13—CA645 Fab Fragment with a dsscFv Inserted into Framework 3

Gene Design

Two antibodies of the invention were generated and expressed in accordance with the above methods to insert an anti-IL17A CA497 dsscFv (vHvL, or vLvH) into the framework 3 region of the CA645 Fab fragment (scaffold antibody), as shown below. The resulting antibodies may be termed CA645 Fab-Fwk3 CA497 dsscFv (vHvL) or CA645 Fab-Fwk3 CA497 dsscFv (vLvH) respectively. The CA497 dsscFv and the CA645 Fab were generated as controls. Genes encoding light and heavy chain V-regions, including variants with a framework 3 insertion, were designed and constructed by an automated synthesis approach (ATUM). Light chain V-region genes (e.g, coding for the CA645 VL domain of SEQ ID NO: 2) were cloned into expression vectors containing DNA encoding human Cκ region (Km3 allotype). Heavy chain V-region genes were cloned into expression vectors containing DNA encoding IgG1 CH1 region.

CA497 dsscFv (vHvL)

(SEQ ID NO: 127)

EVQLVESGGGLVKPGGSLRLSCAASGVIFSDYYMAWVRQAPGKCLEWVAS
INFNADISYYRESVKGRFTISRDDSKNTLYLQMNSLKTEDTAVYYCTTDA
NRQNYDWFAYWGQGTLVTVSSGGGGSGGGGSGGGGSAIQLTQSPSSLSAS
VGDRVTITCKASESVSSSMYSYMHWYQQKPGKAPKLLIYRASNLESGVPS
RFSGSGSGTDFTLTISSLQPEDFATYYCQQSWTAPRTFGCGTKVEIK

CA497 dsscFv (vLvH)

(SEQ ID NO: 128)

AIQLTQSPSSLSASVGDRVTITCKASESVSSSMYSYMHWYQQKPGKAPKL
LIYRASNLESGVPSRFSGSGSGTDFTLTISSLQPEDFATYYCQQSWTAPR
TFGCGTKVEIKGGGGSGGGGSGGGGSEVQLVESGGGLVKPGGSLRLSCAA
SGVIFSDYYMAWVRQAPGKCLEWVASINFNADISYYRESVKGRFTISRDD
SKNTLYLQMNSLKTEDTAVYYCTTDANRQNYDWFAYWGQGTLVTVSS

CA645 Fab heavy chain with CA497 dsscFv (vHvL) (bold and italics) inserted into framework 3, linkers underlined (SEQ ID NO: 129)

EVQLLESGGGLVQPGGSLRLSCAVSGIDLSNYAINWVRQAPGKGLEWIGI
IWASGTTFYATWAKGRFTISRDNSGGGGSGGGGS*EVQLVESGGGLVKPGG*
*SLRLSCAASGVIFSDYYMAWVRQAPGKCLEWVASINFNADISYYRESVKG*
*RFTISRDDSKNTLYLQMNSLKTEDTAVYYCTTDANRQNYDWFAYWGQGTL*
VTVSSGGGGSGGGGSGGGGSAIQLT*QSPSSLSASVGDRVTITCKASESVS*
*SSMYSYMHWYQQKPGKAPKLLIYRASNLESGVPSRFSGSGSGTDFTLTIS*
*SLQPEDFATYYCQQSWTAPRTFGCGTKVEIK*GGGGSGGGGSKNTVYLQMN
SLRAEDTAVYYCARTVPGYSTAPYFDLWGQGTLVTVSSASTKGPSVFPLA
PSSKSTSGGTAALGCLVKDYFPEPVTVSWNSGALTSGVHTFPAVLQSSGL
YSLSSVVTVPSSSLGTQTYICNVNHKPSNTKVDKKVEPKSC

CA645 Fab heavy chain with CA497 dsscFv (vLvH) (bold and italics) inserted into framework 3, linkers underlined:

(SEQ ID NO: 130)

EVQLLESGGGLVQPGGSLRLSCAVSGIDLSNYAINWVRQAPGKGLEWIGI
IWASGTTFYATWAKGRFTISRDNSGGGGSGGGGS*AIQLTQSPSSLSASVG*
*DRVTITCKASESVSSSMYSYMHWYQQKPGKAPKLLIYRASNLESGVPSRF*
*SGSGSGTDFTLTISSLQPEDFATYYCQQSWTAPRTFGCGTKVEIKGGGGS*
*GGGGSGGGGSEVQLVESGGGLVKPGGSLRLSCAASGVIFSDYYMAWVRQA*
*PGKCLEWVASINFNADISYYRESVKGRFTISRDDSKNTLYLQMNSLKTED*
*TAVYYCTTDANRQNYDWFAYWGQGTLVTVSS*GGGGSGGGGSKNTVYLQMN
SLRAEDTAVYYCARTVPGYSTAPYFDLWGQGTLVTVSSASTKGPSVFPLA
PSSKSTSGGTAALGCLVKDYFPEPVTVSWNSGALTSGVHTFPAVLQSSGL
YSLSSVVTVPSSSLGTQTYICNVNHKPSNTKVDKKVEPKSC

Transient Cell Expression

Engineered Fab fragments were transiently expressed in either HEK-293 cells using ExpiFectamine 293 transfection kit (Life Technologies, according to the manufacturer's instructions) or CHO-S XE cells, a CHO-K1 derived cell line (Cain K et al, A CHO cell line engineered to express XBP1 and ERO1-Lα has increased levels of transient protein expression. Biotechnology Progress 2013; 29: 697-

706), using ExpiFectamine CHO transfection kit (Life Technologies, according to the manufacturer's instructions). HEK-293 cells were used for small scale expression (2 ml) to prepare antibody constructs for direct SPR analysis. CHO-S XE cells were used for large scale expression (200 ml) to prepare antibody constructs for purification prior to further characterization.

Purification

Affinity chromatography was used to purify Fab fragments from culture supernatants. Supernatants containing the antibodies were passed over a HiTrap Protein G column (GE Healthcare). Following a washing step with phosphate buffered saline (PBS) pH 7.4, the bound material was eluted with a gradient of PBS pH 7.4 versus an increasing percentage by volume of 0.1M phosphate citrate buffer pH 2.6. The eluate was neutralized with 2 M Tris-HCl (pH 8). Fractions were pooled, quantified by absorbance at 280 nm, and concentrated using Amicon Ultra centrifugal filters (Merck Millipore). To isolate the monomeric fractions of the constructs, size exclusion chromatography over a HiLoad 16/60, Superdex 200 column (GE Healthcare) equilibrated with PBS pH 7.4, was used. Fractions containing monomeric Fab were pooled, quantified, concentrated and stored at 4° C.

UPLC (Ultra-High-Performance Liquid Chromatography):

2 µg of sample was injected onto a SEC BEH200 column, pre-equilibrated in PBS, pH7.4 and run for 10 mins. Fluorescence intensity was recorded against elution time and peak areas picked manually in EMpower software.

The UPLC elution profiles were obtained and analysed. Peaks appeared>98% monomeric (99.42% for CA645 Fab-Fwk3 CA497 dsscFv (vLvH), 99.51% for CA645 Fab-Fwk3 CA497 dsscFv (vHvL)). The controls CA497 dsscFv and CA645 Fab showed respectively 99.99% and 98.43% of multimeric forms (data not shown). Accordingly, the purified proteins were homogenous and lacked multimeric forms or aggregates.

Molecular Stability

The molecular stability was measured by melting temperature (Tm) (measure of unfolding) analysis by Differential Scanning calorimetry (DSC) method. Thermograms were acquired on an automated MicroCal VP DSC (Malvern Panalytical) from 0-100° C., using a step rate of 1° C./min, with a pre-incubation scan time of 15 min, a filtering period of 5s and feedback set to passive. The data was buffer subtracted before a manual baseline subtraction and concentration correction. The thermograms were fitted to a non-2-state model in Origin7.0.

Figure 20:
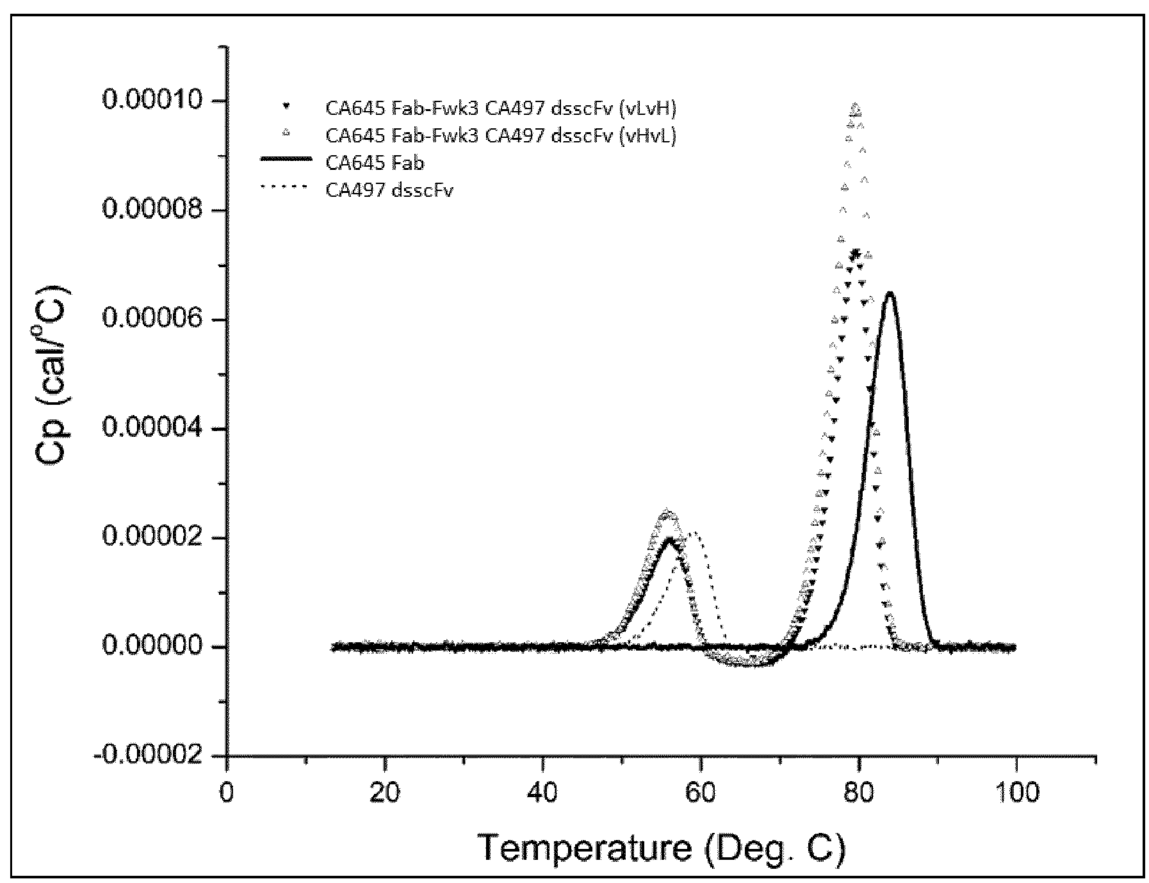
FIG. 20: DSC curves (solid line: CA645 Fab; dotted line: CA497 dsscFv; inverted triangle: CA645 Fab-Fwk3 CA497 dsscFv (vLvH); triangle: CA645 Fab-Fwk3 CA497 dsscFv (vHvL)).

The results are shown in FIG. 20 (DSC curves; vertical axis: (Cp) specific heat; horizontal axis: temperature in Degrees C. (° C.)) and in the table 3 below. CA497 dsscFv and CA645 Fab showed single transitions of 58.40° C. and 83.57° C. respectively. When combined in the Fab-Fwk3 inserted dsscFv format, the CA497 dsscFv Tm is almost identical (difference of 2-3° C.) and the CA645 Fab has a variation of Tm of about 4-5° C. Accordingly, the pairing of CA497 dsscFv and CA645 Fab in this antibody format according to the invention does not impact significantly the conformational stability of either domain.

TABLE 3

Unfolding transition temperatures

| Sample | Tm1 (° C.) | Tm2 (° C.) |
|---|---|---|
| CA645 Fab | 83.57 | |
| CA497 dsscFv | 58.40 | |
| CA645 Fab heavy chain with CA497 dsscFv (vLvH) inserted into Fwk3 | 55.59 | 78.64 |
| CA645 Fab heavy chain with CA497 dsscFv (vHvL) inserted into Fwk3 | 55.41 | 78.73 |

Neutralisation Assay

The potency of antibody CA497 IgG4, CA645 Fab-Fwk3 CA497 dsscFv (vHvL) and CA645 Fab-Fwk3 CA497 dsscFv (vLvH) against human recombinant IL-17A in Hela cells was tested, in presence or in absence of HSA. Hela cells were obtained from the cell bank at ATCC (ATCC CCL-2). Cells were grown in Dulbecco's modified Eagle's medium (DMEM) supplemented with 10% foetal calf serum, penicillin, gentamycin and glutamine. $1\times10^4$ cells were plated out into 96 well flat bottomed tissue culture plates. Cells were incubated overnight and washed once in assay buffer. Human IL-17A (25 ng $ml^{-1}$) was incubated in the presence of a fixed concentration of human TNF-α, and this mixture was preincubated with the tested antibody. The cytokines and antibody were then added to the Hela cells to stimulate the cells which were incubated overnight. In the Hela cell line, IL-17A synergises with TNF-alpha to induce the production of IL-6 which can be quantified, e.g. by ELISA. The production of IL-6 in the cell culture supernatant is proportionate to the amount of IL-17A added to the cells. Human IL-6 levels were measured by ELISA and quantified by comparison with known standard concentrations of human IL-6. In this assay, the inhibition of the secretion of IL-6 is correlated with the inhibition of IL-17A.

Figure 21:
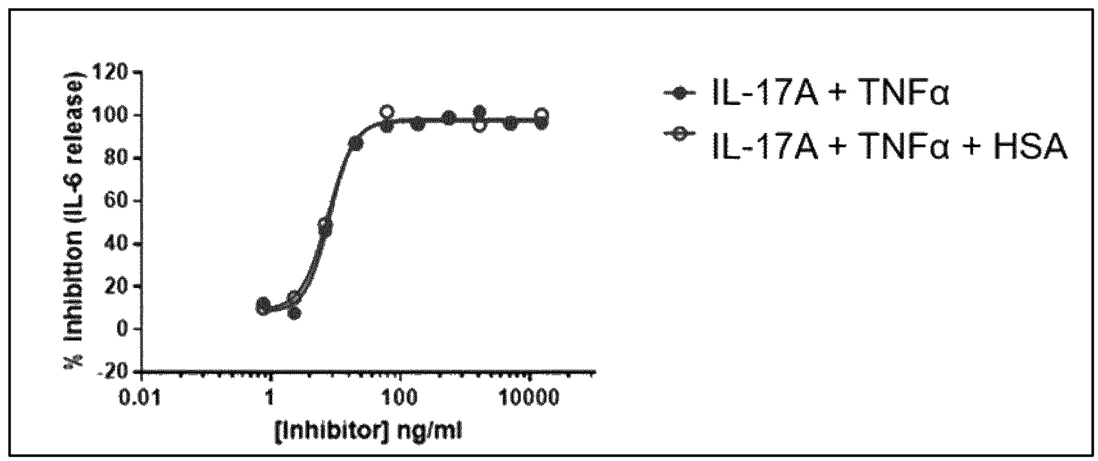
FIG. 21: Inhibition curves of IL-17A in absence (solid circle) or in presence (open circle) of HSA; (A) CA497
Figure 21:
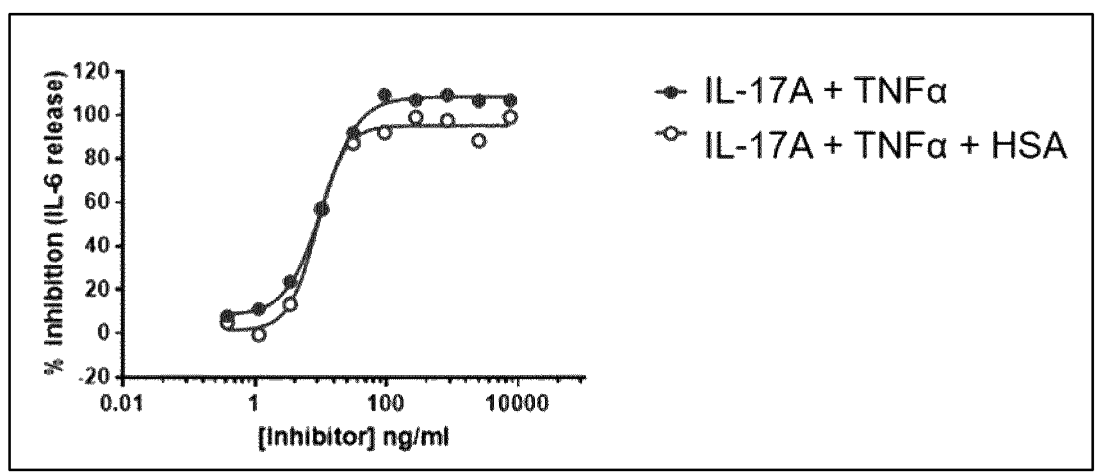
Figure 21:
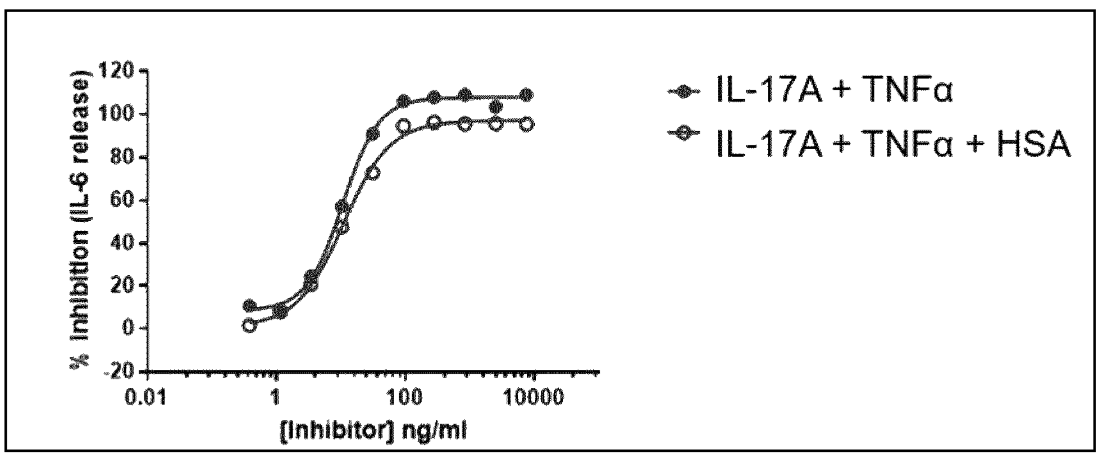

The inhibition curves are shown in FIG. 21 (horizontal axis: antibody (inhibitor) concentration in ng/ml, vertical axis: inhibition of the secretion of IL-6(%)) and indicate that the parent antibody CA497 IgG4 and both antibody fusion constructs potently neutralised human recombinant IL-17A. In addition, the results indicate that the dsscFv anti-IL-17 retained functionality when inserted into the Fwk3 region of the Fab anti-HSA. The EC50 values calculated from these experiments (table 4 below) indicated that antibody CA645 Fab-Fwk3 CA497 dsscFv (vLvH) and CA645 Fab-Fwk3 CA497 dsscFv (vHvL) gave an $EC_{50}$ of 10.5 ng/ml and 10.6 ng/ml respectively against human recombinant IL-17A (25 ng·$ml^{-1}$) and that the neutralisation potency was not affected by the presence of HSA ($EC_{50}$ of 10.8 and 8.7 ng/ml respectively, in presence of HSA). Also, the CA645 Fab-Fwk3 CA497 dsscFv constructs had a neutralisation potency comparable to the one of the parent CA497 IgG4 antibody.

TABLE 4

EC50 values for the neutralisation of IL-17A in presence or absence of HSA

| | HSA (2.5%) | IL-17A EC50 (ng/ml) |
|---|---|---|
| CA497 IgG4 | − | 8.1 |
| CA497 IgG4 | + | 7.6 |
| CA645 Fab-Fwk3 CA497 dsscFv (vLvH) | − | 10.5 |
| CA645 Fab-Fwk3 CA497 dsscFv (vLvH) | + | 10.8 |
| CA645 Fab-Fwk3 CA497 dsscFv (vHvL) | − | 10.6 |

TABLE 4-continued

| EC50 values for the neutralisation of IL-17A in presence or absence of HSA | | |
|---|---|---|
| | HSA (2.5%) | IL-17A EC50 (ng/ml) |
| CA645 Fab-Fwk3 CA497 dsscFv (vHvL) | + | 8.7 |

Example 14—Full CA645 IgG with a dsscFv Inserted into Framework 3

A fusion protein was generated and expressed in accordance with the above methods to insert CA497 dsscFv (vH-vL) or CA497 dsscFv (vL-vH) into the framework 3 region of the CA645 IgG4P construct, as shown below. The resulting antibody fusion proteins may be termed CA645 IgG4P Fwk3-CA497 dsscFv (vHvL) and CA645 IgG4P Fwk3-CA497 dsscFv (vLvH).

Gene Design

Genes encoding light and heavy chain V-regions, including variants with a framework 3 insertion, were designed and constructed by an automated synthesis approach (ATUM). Light chain V-region genes (e.g. coding for the CA645 VL domain of SEQ ID NO: 2) were cloned into expression vectors containing DNA encoding human Cκ region (Km3 allotype). Heavy chain V-region genes were cloned into expression vectors containing DNA encoding IgG4P constant regions for full-length antibody.

CA645 IgG4P heavy chain with CA497 dsscFv (vHvL) (bold and italics) inserted into framework 3, linkers underlined:

(SEQ ID NO: 131)

EVQLLESGGGLVQPGGSLRLSCAVSGIDLSNYAINWVRQAPGKGLEWIGI

IWASGTTFYATWAKGRFTISRDNSGGGGSGGGGS*EVQLVESGGGLVKPGG*

*SLRLSCAASGVIFSDYYMAWVRQAPGKCLEWVASINFNADISYYRESVKG*

*RFTISRDDSKNTLYLQMNSLKTEDTAVYYCTTDANRQNYDWFAYWGQGTL*

*VTVSSGGGGSGGGGSGGGGSAIQLTQSPSSLSASVGDRVTITCKASESVS*

*SSMYSYMHWYQQKPGKAPKLLIYRASNLESGVPSRFSGSGSGTDFTLTIS*

*SLQPEDFATYYCQQSWTAPRTFGCGTKVEIK*GGGGSGGGGSKNTVYLQMN

SLRAEDTAVYYCARTVPGYSTAPYFDLWGQGTLVTVSSASTKGPSVFPLA

PSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMH

EALHNHYTQKSLSLSPGK

CA645 IgG4P heavy chain with CA497 dsscFv (vLvH) (bold and italics) inserted intoframework 3, linkers underlined:

(SEQ ID NO: 132)

EVQLLESGGGLVQPGGSLRLSCAVSGIDLSNYAINWVRQAPGKGLEWIGI

IWASGTTFYATWAKGRFTISRDNSGGGGSGGGGS*AIQLTQSPSSLSASVG*

-continued

*DRVTITCKASESVSSSMYSYMHWYQQKPGKAPKLLIYRASNLESGVPSRF*

*SGSGSGTDFTLTISSLQPEDFATYYCQQSWTAPRTFGCGTKVEIKGGGGS*

*GGGGSGGGGSEVQLVESGGGLVKPGGSLRLSCAASGVIFSDYYMAWVRQA*

*PGKCLEWVASINFNADISYYRESVKGRFTISRDDSKNTLYLQMNSLKTED*

*TAVYYCTTDANRQNYDWFAYWGQGTLVTVSS*GGGGSGGGGSKNTVYLQMN

SLRAEDTAVYYCARTVPGYSTAPYFDLWGQGTLVTVSSASTKGPSVFPLA

PSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMH

EALHNHYTQKSLSLSPGK

Transient Cell Expression

Engineered antibodies were transiently expressed in either HEK-293 cells using ExpiFectamine 293 transfection kit (Life Technologies, according to the manufacturer's instructions) or CHO-S XE cells, a CHO-K1 derived cell line, using ExpiFectamine CHO transfection kit (Life Technologies, according to the manufacturer's instructions). HEK-293 cells were used for small scale expression (2 ml) to prepare antibody constructs for direct SPR analysis. CHO-S XE cells were used for large scale expression (200 ml) to prepare antibody constructs for purification prior to further characterization.

Purification

Affinity chromatography was used to purify IgG from culture supernatants. Supernatants containing IgG were passed over a MabSelect SuRe column (GE Healthcare). Following a washing step with phosphate buffered saline (PBS) pH 7.4, the bound material was eluted with a gradient of PBS pH 7.4 versus an increasing percentage by volume of 0.1M phosphate citrate buffer pH 2.6. The eluate was neutralized with 2 M Tris-HCl (pH 8). Fractions were pooled, quantified by absorbance at 280 nm, and concentrated using Amicon Ultra centrifugal filters (Merck Millipore). To isolate the monomeric fractions of IgG-based constructs, size exclusion chromatography over a HiLoad 16/60, Superdex 200 column (GE Healthcare) equilibrated with PBS pH 7.4, was used. Fractions containing monomeric IgG constructs were pooled, quantified, concentrated and stored at 4° C.

Simultaneous Binding to IL-17 and HSA

In order to test simultaneous binding of IL-17A and HSA to CA645 IgG4P Fwk3-CA497 dsscFv (vHvL), the latter was immobilised on a Biacore chip in place of polyclonal goat $F(ab)_2$ in the same procedure as previously. Three concentrations of both IL-17A and HSA were selected to give low, medium and high levels of binding to the immobilized antibody, specifically these corresponded to stoichiometric ratios of ligand to antibody in the ranges 0.15 to 0.3, 0.4 to 0.6 and 0.65 to 0.75 respectively. In the case of IL-17A concentrations were 4, 20 and 100 nM and for HSA concentrations were 40, 200 and 1000 nM respectively. The above low, medium and high concentrations, were tested by SPR as previously described in individual cycles either as separate ligands or as IL17A/HSA mixtures and report points corrected by subtraction of buffer control cycles. The results are shown in FIG. 22 and show that the CA645 IgG4P Fwk3-CA497 dsscFv (vHvL) bind both IL-17A and HSA, in a concentration dependent manner. FIG. 22 further shows that in the presence of both binding partners, the signal is additive, showing that binding to both IL-17A and HSA can occur simultaneously.

Example 15—Antibodies of the Invention which Bind to Both CD3 and CD28

Gene Design

The antibodies were generated and expressed in accordance with the methods described above to insert anti-CD3 dsscFv (vH-vL) into the framework 3 region of the anti-CD3 or anti-CD28 scaffold antibody (IgG4P or Fab fragment) as shown below in Table 5. The resulting antibody constructs according to the invention may be termed anti-CD28 Fab Fwk3-anti-CD3 dsscFv (LC of SEQ ID NO: 136, HC of SEQ ID NO: 139), anti-CD3 Fab Fwk3-anti-CD3 dsscFv (LC of SEQ ID NO: 133, HC of SEQ ID NO: 140), anti-CD28 IgG4P Fwk3-anti-CD3 dsscFv (LC of SEQ ID NO: 136, HC of SEQ ID NO: 141), anti-CD3 IgG4P Fwk3-anti-CD3 dsscFv (LC of SEQ ID NO: 133, HC of SEQ ID NO: 142).

TABLE 5

Antibody Constructs

| Scaffold antibody | Antigen specificity (V-domain of the scaffold) | Antigen specificity (dsscFv inserted into Fwk3) | Sequence |
|---|---|---|---|
| Fab | CD3 | none | Light chain of SEQ ID NO: 133<br>Heavy chain of SEQ ID NO: 134 |
| Fab | CD28 | none | Light chain of SEQ ID NO: 136<br>Heavy chain of SEQ ID NO: 137 |
| Fab | CD28 | CD3 | Light chain of SEQ ID NO: 136<br>Heavy chain of SEQ ID NO: 139 |
| Fab | CD3 | CD3 | Light chain of SEQ ID NO: 133<br>Heavy chain of SEQ ID NO: 140 |
| IgG4P | CD3 | none | Light chain of SEQ ID NO: 133<br>Heavy chain of SEQ ID NO: 135 |
| IgG4P | CD28 | none | Light chain of SEQ ID NO: 136<br>Heavy chain of SEQ ID NO: 138 |
| IgG4P | CD28 | CD3 | Light chain of SEQ ID NO: 136<br>Heavy chain of SEQ ID NO: 141 |
| IgG4P | CD3 | CD3 | Light chain of SEQ ID NO: 133<br>Heavy chain of SEQ ID NO: 142 |

Anti-CD3 Light chain, muromonab (humanised OKT3) (Variable domain underlined; CDRs in bold and italics):

(SEQ ID NO: 133)

```
DIQMTQSPSSLSASVGDRVTITCSASSSVSYMNWYQQTPGKAPKLLIYD
TSKLASGVPSRFSGSGSGTDYTFTISSLQPEDIATYYCQQWSSNPFTFG
QGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVT
HQGLSSPVTKSFNRGEC
```

Anti-CD3 Heavy chain Fab, CH1 from IgG1, muromonab (humanised OKT3) (Variable domain underlined; CDRs in bold and italics):

(SEQ ID NO: 134)

```
QVQLVQSGGGVVQPGRSLRLSCKASGYTFTRYTMHWVRQAPGKGLEWIG
```

-continued

```
YINPSRGYTNYNQKFKDRFTISRDNSKNTAFLQMDSLRPEDTGVYFCAR
YYDDHYCLDYWGQGTPVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSC
```

Anti-CD3 Heavy chain IgG4P, muromonab (humanised OKT3) (Variable domain underlined; CDRs in bold and italics):

(SEQ ID NO: 135)

```
QVQLVQSGGGVVQPGRSLRLSCKASGYTFTRYTMHWVRQAPGKGLEWIG
YINPSRGYTNYNQKFKDRFTISRDNSKNTAFLQMDSLRPEDTGVYFCAR
YYDDHYCLDYWGQGTPVTVSSASTKGPSVFPLAPCSRSTSESTAALGCL
VKDYFPEPVTVSWNSGALTSGVHTFPAVLQSSGLYSLSSVVTVPSSSLG
TKTYTCNVDHKPSNTKVDKRVESKYGPPCPPCPAPEFLGGPSVFLFPPK
PKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPR
EPQVYTLPPSQEEMTKNQVSLTCLVKGFYPSDIAVEWESNGQPENNYKT
TPPVLDSDGSFFLYSRLTVDKSRWQEGNVFSCSVMHEALHNHYTQKSLS
LSLGK
```

Anti-CD28 Light chain, theralizumab (Variable domain underlined; CDRs in bold and italics):

(SEQ ID NO: 136)

```
DIQMTQSPSSLSASVGDRVTITCHASQNIYVWLNWYQQKPGKAPKLLIY
KASNLHTGVPSRFSGSGSGTDFTLTISSLQPEDFATYYCQQGQTYPYTF
GGGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC
```

Anti-CD28 Heavy chain Fab, CH1 from IgG1, theralizumab (Variable domain underlined; CDRs in bold and italics):

(SEQ ID NO: 137)

```
QVQLVQSGAEVKKPGASVKVSCKASGYTFTSYYIHWVRQAPGQGLEWIG
CIYPGNVNTNYNEKFKDRATLTVDTSISTAYMELSRLRSDDTAVYFCTR
SHYGLDWNFDVWGQGTTVTVSSASTKGPSVFPLAPSSKSTSGGTAALGC
LVKDYFPEPVTVSWNSGALTSGVHTFPAVLQSSGLYSLSSVVTVPSSSL
GTQTYICNVNHKPSNTKVDKKVEPKSC
```

Anti-CD28 Heavy chain IgG4P, theralizumab (Variable domain underlined; CDRs in bold and italics):

(SEQ ID NO: 138)

```
QVQLVQSGAEVKKPGASVKVSCKASGYTFTSYYIHWVRQAPGQGLEWIG
CIYPGNVNTNYNEKFKDRATLTVDTSISTAYMELSRLRSDDTAVYFCTR
SHYGLDWNFDVWGQGTTVTVSSASTKGPSVFPLAPCSRSTSESTAALGC
LVKDYFPEPVTVSWNSGALTSGVHTFPAVLQSSGLYSLSSVVTVPSSSL
GTKTYTCNVDHKPSNTKVDKRVESKYGPPCPPCPAPEFLGGPSVFLFPP
KPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQP
REPQVYTLPPSQEEMTKNQVSLTCLVKGFYPSDIAVEWESNGQPENNYK
```

-continued

TTPPVLDSDGSFFLYSRLTVDKSRWQEGNVFSCSVMHEALHNHYTQKSL

SLSLGK

Anti-CD28 Fab heavy chain with anti-CD3 dsscFv (vHvL) (bold and italics) inserted into framework 3, linkers underlined:

(SEQ ID NO: 139)

QVQLVQSGAEVKKPGASVKVSCKASGYTFTSYYIHWVRQAPGQGLEWIG

CIYPGNVNTNYNEKFKDRATLTVDTSGGGGSGGGGS*QVQLVQSGGGVVQ*

*PGRSLRLSCKASGYTFTRYTMHWVRQAPGKCLEWIGYINPSRGYTNYNQ*

*KFKDRFTISRDNSKNTAFLQMDSLRPEDTGVYFCARYYDDHYCLDYWGQ*

*GTPVTVSSGGGGSGGGGSGGGGSGGGGSDIQMTQSPSSLSASVGDRVTI*

*TCSASSSVSYMNWYQQTPGKAPKLLIYDTSKLASGVPSRFSGSGSGTDY*

*TFTISSLQPEDIATYYCQQWSSNPFTFGCGTKLEIK*GGGGSGGGGSIST

AYMELSRLRSDDTAVYFCTRSHYGLDWNFDVWGQGTTVTVSSASTKGPS

VFPLAPSSKSTSGGTAALGCLVKDYFPEPVTVSWNSGALTSGVHTFPAV

LQSSGLYSLSSVVTVPSSSLGTQTYICNVNHKPSNTKVDKKVEPKSC

Anti-CD3 Fab heavy chain with anti-CD3 dsscFv (vHvL) (bold and italics) inserted into framework 3, linkers underlined:

(SEQ ID NO: 140)

QVQLVQSGGGVVQPGRSLRLSCKASGYTFTRYTMHWVRQAPGKGLEWIG

YINPSRGYTNYNQKFKDRFTISRDNSGGGGSGGGGS*QVQLVQSGGGVVQ*

*PGRSLRLSCKASGYTFTRYTMHWVRQAPGKCLEWIGYINPSRGYTNYNQ*

*KFKDRFTISRDNSKNTAFLQMDSLRPEDTGVYFCARYYDDHYCLDYWGQ*

*GTPVTVSSGGGGSGGGGSGGGGSGGGGSDIQMTQSPSSLSASVGDRVTI*

*TCSASSSVSYMNWYQQTPGKAPKLLIYDTSKLASGVPSRESGSGSGTDY*

*TFTISSLQPEDIATYYCQQWSSNPFTFGCGTKLEIK*GGGGSGGGGSKNT

AFLQMDSLRPEDTGVYFCARYYDDHYCLDYWGQGTPVTVSSASTKGPSV

FPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSC

Anti-CD28 IgG4P heavy chain with anti-CD3 dsscFv (vHvL) (bold and italics) inserted into framework 3, linkers underlined:

(SEQ ID NO: 141)

QVQLVQSGAEVKKPGASVKVSCKASGYTFTSYYIHWVRQAPGQGLEWIG

CIYPGNVNTNYNEKFKDRATLTVDTSGGGGSGGGGS*QVQLVQSGGGVVQ*

*PGRSLRLSCKASGYTFTRYTMHWVRQAPGKCLEWIGYINPSRGYTNYNQ*

*KFKDRFTISRDNSKNTAFLQMDSLRPEDTGVYFCARYYDDHYCLDYWGQ*

*GTPVTVSSGGGGSGGGGSGGGGSGGGGSDIQMTQSPSSLSASVGDRVTI*

*TCSASSSVSYMNWYQQTPGKAPKLLIYDTSKLASGVPSRFSGSGSGTDY*

*TFTISSLQPEDIATYYCQQWSSNPFTFGCGTKLEIK*GGGGGGGGSISTA

YMELSRLRSDDTAVYFCTRSHYGLDWNFDVWGQGTTVTVSSASTKGPSV

FPLAPCSRSTSESTAALGCLVKDYFPEPVTVSWNSGALTSGVHTFPAVL

QSSGLYSLSSVVTVPSSSLGTKTYTCNVDHKPSNTKVDKRVESKYGPPC

PPCPAPEFLGGPSVFLFPPKPKDTLMISRTPEVTCVVVDVSQEDPEVQF

NWYVDGVEVHNAKTKPREEQFNSTYRVVSVLTVLHQDWLNGKEYKCKVS

-continued

NKGLPSSIEKTISKAKGQPREPQVYTLPPSQEEMTKNQVSLTCLVKGFY

PSDIAVEWESNGQPENNYKTTPPVLDSDGSFFLYSRLTVDKSRWQEGNV

FSCSVMHEALHNHYTQKSLSLSLGK

Anti-CD3 IgG4P heavy chain with anti-CD3 dsscFv (vHvL) (bold and italics) inserted into framework 3, linkers underlined:

(SEQ ID NO: 142)

QVQLVQSGGGVVQPGRSLRLSCKASGYTFTRYTMHWVRQAPGKGLEWIG

YINPSRGYTNYNQKFKDRFTISRDNSGGGGSGGGGS*QVQLVQSGGGVVQ*

*PGRSLRLSCKASGYTFTRYTMHWVRQAPGKCLEWIGYINPSRGYTNYNQ*

*KFKDRFTISRDNSKNTAFLQMDSLRPEDTGVYFCARYYDDHYCLDYWGQ*

*GTPVTVSSGGGGSGGGGSGGGGSGGGGSDIQMTQSPSSLSASVGDRVTI*

*TCSASSSVSYMNWYQQTPGKAPKLLIYDTSKLASGVPSRFSGSGSGTDY*

*TFTISSLQPEDIATYYCQQWSSNPFTFGCGTKLEIK*GGGGSGGGGSKNT

AFLQMDSLRPEDTGVYFCARYYDDHYCLDYWGQGTPVTVSSASTKGPSV

FPLAPCSRSTSESTAALGCLVKDYFPEPVTVSWNSGALTSGVHTFPAVL

QSSGLYSLSSVVTVPSSSLGTKTYTCNVDHKPSNTKVDKRVESKYGPPC

PPCPAPEFLGGPSVFLFPPKPKDTLMISRTPEVTCVVVDVSQEDPEVQF

NWYVDGVEVHNAKTKPREEQFNSTYRVVSVLTVLHQDWLNGKEYKCKVS

NKGLPSSIEKTISKAKGQPREPQVYTLPPSQEEMTKNQVSLTCLVKGFY

PSDIAVEWESNGQPENNYKTTPPVLDSDGSFFLYSRLTVDKSRWQEGNV

FSCSVMHEALHNHYTQKSLSLSLGK

UPLC (Ultra-High-Performance Liquid Chromatography):

2 μg of sample was injected onto a SEC BEH200 column, pre-equilibrated in PBS, pH7.4 and run for 10 mins. Fluorescence intensity was recorded against elution time and peak areas picked manually in EMpower software.

The UPLC elution profiles were obtained and analysed. Peaks appeared>98% monomeric (anti-CD3 IgG4P Fwk3-anti-CD3 dsscFv: 99.02%, anti-CD3 Fab Fwk3-anti-CD3 dsscFv: 99.79%, anti-CD28 Fab Fwk3-anti-CD3 dsscFv: 99.48%) with the exception of a lower molecular weight shoulder of 12.12% in anti-CD28 IgG4P Fwk3-anti-CD3 dsscFv. There was no evidence of multimerization of any format.

Molecular Stability

The molecular stability was measured by melting temperature (Tm) (measure of unfolding) analysis by Differential Scanning calorimetry (DSC) method as described above. The DSC curves are shown in FIGS. 23 (A) and (B), and the Tm values presented in Table 6 and 7 below.

TABLE 6

| Fab-Fwk3-dsscFv | | |
|---|---|---|
| Antibody of the invention | Tm1 (° C.) | Tm2 (° C.) |
| Anti-CD28 Fab Fwk3-anti CD3 dsscFv | 70.16 | 74.73 |
| Anti-CD3 Fab Fwk3-anti-CD3 dsscFv | 70.04 | |

The DSC curves for anti-CD3 Fab Fwk3-anti-CD3 dsscFv showed a single unfolding transition at 70.04° C. In contrast, the unfolding of the construct containing anti-CD28 cannot be accurately described by a single transition but fit better to a non-2-state, two transition model; the lowest of which can be attributed to the dsscFv component. The results notably show that inserting the Fab in the framework 3 position resulted in stable constructs, as the values 65° C.-75° C. are in line with that of a typical IgG.

TABLE 7

| IgG4P-Fwk3-dsscFv | | |
|---|---|---|
| Antibody of the invention | Tm1 (° C.) | Tm2 (° C.) |
| Anti-CD28 IgG4P Fwk3-anti-CD3 dsscFv | 68.97 | 73.28 |
| Anti-CD3 IgG4P Fwk3-anti-CD3 dsscFv | 68.55 | |

The DSC curves for anti-CD3 IgG4P Fwk3-anti-CD3 dsscFv showed a single unfolding transition at 68.55° C. In contrast, the unfolding of constructs containing anti-CD28 cannot be accurately described by a single transition but fit better to a non-2-state, two transition model; the lowest of which can be attributed to the dsscFv component. The results notably show that inserting the IgG in the framework 3 position resulted in stable constructs, as the Tm values of 65° C.-75° C. are typical of IgG-like molecules.

Evaluation of Fab and IgG4P Constructs with Framework 3 Inserts in a Human Functional PBMC Assay Constructs were tested for their ability to stimulate T cell activation in a culture of peripheral blood mononuclear cells (PBMC) according to the method described below.

Reagents

Antibodies used to detect CD4 and CD8 T cells, distinguish live and dead cells and measure the activation marker CD69 were obtained from BD Biosciences (Anti-CD4 antibody, anti-CD8, anti-CD69 antibody and the antibody distinguishing Live/dead cells were coupled respectively to the fluorophores FITC, PE, BV421 and Near Infrared. All cell culture was performed in RPMI1640 (Thermo) plus 5% heat-inactivated human AB serum (Sigma) and 2 mM glutamine (Thermo). All flow cytometry staining was performed using a standard flow cytometry buffer comprising Dulbecco's PBS (Thermo) plus 1% bovine serum albumin (Sigma), 2 mM EDTA (Sigma) and 0.1% sodium azide (Sigma). Human OKT3 (Ebioscience) and T cell Transact (Miltenyi) a colloidal suspension of anti-CD3 and CD28. All flow cytometry data was acquired using an iQUEplus (Sartorius). T cells were identified using Forecyt software (Sartorius) and data metrics imported into GraphPad Prism 7 (GraphPad) for data transformations and graphical representation.

Method

Antibody constructs in table 5 were diluted down from 25 μg/ml in eight 1 in 5 dilution steps. In the post analysis step all these values were converted into nM concentrations to allow equal comparisons of all constructs. Into 96 well 'U' bottomed tissue culture plates $1.5\times10^5$ PBMC (from two different donors anonymised as donor 1 and 2) were mixed with the diluted antibodies. OKT3 (5 μg/ml), Transact (CD3/CD28 diluted 1 in 100) and media alone were reference controls for the experiment. After mixing, plates were incubated at 37 degrees Celsius for 24 hours. After this time, plates were cooled on ice and spun (all subsequent spins were at 500 g for 5 mins at 4 degrees Celsius) and supernatant removed from each well. Plates were washed again, supernatant aspirated and 20 μl of an antibody cocktail added to each well (all antibodies were diluted 1:20 in flow cytometry buffer and 1 μl of live/dead stain added per 1ml of cocktail). Plates were left on ice in the dark for 1 hour. After this time plates were washed a further two times and supernatant removed from all wells. Plates were finally resuspended in 20 μl of flow cytometry buffer and at least 10,000 cells per well acquired.

Results

The results are shown in FIG. 24 (A-D; the vertical axis represents the level of expression of CD69 (MFI) and the horizontal axis represents the concentration of antibody construct in nM). The experiment was deemed successful since the positive control (OKT3) induced the early activation marker, CD69, on both CD4 and CD8 T cells. The minimum (cells only) level of activation was determined by the cells only control. As can be seen from FIGS. 24(A) and (B), the induction of CD69 on CD4 T cells for the tested constructs was consistent between donors.

The antibodies of the invention containing CD3 and CD28 (either in the Fab or IgG4P format) were the most potent activators of CD4 T cells. As expected in this assay constructs containing an Fc can also bring in added activity via Fc receptors on other (non) T cells, in particular monocytes, which give enhanced costimulatory signals. In this respect the anti-CD3 IgG4P Fwk3-anti-CD3dsscFv also showed activity in this assay (as does the OKT3 control which is a whole IgG anti-CD3 antibody). This data demonstrates that antibodies of the invention which bind to both CD3 and CD28 are functional activators of human CD4 T cells in a mixed PBMC assay, and as such are capable of exercising the function of a bispecific antibody.

In addition, activation of CD8 T cells was also measured in the same assay. As described previously all positive and negative controls performed as expected. As can be seen from FIGS. 24 (C) and (D), the induction of CD69 on CD8 T cells for the tested constructs was consistent between donors. The antibodies of the invention containing CD3 and CD28 (either in the Fab or IgG4P format) were the most potent activators of CD8 T cells. The anti-CD3 IgG4P Fwk3 anti-CD3dsscFv also showed activity in this assay (as does the OKT3 control which is a whole IgG anti-CD3 antibody). This data demonstrates that antibodies of the invention which bind to both CD3 and CD28 are functional activators of human CD8 T cells in a mixed PBMC assay, and as such are capable of exercising the function of a bispecific antibody.

The results show that antibodies according to the invention have the functionality of both the scaffold antibody (e.g. anti-CD28 Fab or IgG4P), and the insert polypeptide, i-e the second antibody (e.g. anti-CD3 dsscFv) when the insert polypeptide is present in the Fwk3 region of the scaffold antibody.

Comprising in the context of the present specification is intended to mean including.

Where technically appropriate, embodiments of the invention may be combined. Embodiments are described herein as comprising certain features/elements. The disclosure also extends to separate embodiments consisting or consisting essentially of said features/elements.

It will of course be understood that, although the present invention has been described by way of example, the examples are in no way meant to be limiting, and modifications can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication was specifically and individually indicated to be incorporated by reference herein.

The invention claimed is:

1. An antibody comprising a variable (V) domain and an insert polypeptide, wherein (a) the insert polypeptide is within framework 3 region of the VH domain between amino acid residues 73 and 74, between amino acid residues 74 and 75, or between amino acid residues 75 and 76, or (b) wherein the insert polypeptide is within framework 3 region of the VL domain between amino acid residues 67 and 68, between amino acid residues 68 and 69, or between amino acid residues 69 and 70.

2. The antibody according to claim 1, wherein the insert polypeptide is in the VH domain: (i) between amino acid residues 73 and 74; (ii) between amino acid residues 74 and 75; or (iii) between amino acid residues 75 and 76.

3. The antibody according to claim 1, wherein one or more amino acid residues between 73 and 76 of the VH domain are replaced by the insert polypeptide.

4. The antibody according to claim 1, wherein the insert polypeptide is in the VL domain: (i) between amino acid residues 67 and 68; (ii) between amino acid residues 68 and 69; or (iii) between amino acid residues 69 and 70.

5. The antibody according to claim 1, wherein one or more amino acid residues between 67 and 70 of the VL domain are replaced by the insert polypeptide.

6. The antibody according to claim 1, which is a full-length antibody.

7. The antibody according to claim 1, which is a full-length IgG.

8. The antibody according to claim 1, which is a Fab, Fab', $F(ab')_2$, VHH, or scFv.

9. The antibody according to claim 1, which is humanised.

10. The antibody according to claim 1, wherein said V domain binds to human serum albumin.

11. The antibody according to claim 10, which comprises a VL domain comprising CDR-L1 having the sequence set forth in SEQ ID NO: 3; CDR-L2 having the sequence set forth in SEQ ID NO: 4; and CDR-L3 having the sequence set forth in SEQ ID NO: 5.

12. The antibody according to claim 11, which comprises a VL domain comprising the sequence set forth in SEQ ID NO: 2 or SEQ ID NO: 102.

13. The antibody according to claim 12, which comprises a L chain comprising the sequence set forth in SEQ ID NO: 1.

14. The antibody according to claim 10, which comprises a VH domain comprising CDR-H1 having the sequence set forth in SEQ ID NO: 8; CDR-H2 having the sequence set forth in SEQ ID NO: 9; and CDR-H3 having the sequence set forth in SEQ ID NO: 10.

15. The antibody according to claim 14, which comprises a VH domain comprising the sequence set forth in SEQ ID NO: 7 or SEQ ID NO: 103.

16. The antibody according to claim 15, which comprises a H chain comprising the sequence set forth in SEQ ID NO: 6.

17. The antibody according to claim 1, wherein the insert polypeptide is a cytokine.

18. The antibody according to claim 17, wherein the cytokine is selected from IL-10, IL-15, IL-2, G-CSF, GM-CSF and EPO.

19. The antibody according to claim 1, wherein the insert polypeptide is a second antibody.

20. The antibody according to claim 19, wherein the second antibody is an scFv or a domain antibody.

21. The antibody according to claim 20, wherein the the domain antibody is a VHH comprising a sequence selected from SEQ ID NOs: 67, 69 and 89.

22. The antibody according to claim 20, wherein the second antibody binds to the same antigen as the V domain.

23. The antibody according to claim 22, wherein the second antibody binds to a different epitope compared to the V domain.

24. The antibody according to claim 20, wherein the second antibody binds to a different antigen to the antibody comprising a V domain.

25. The antibody according to claim 20, wherein the second antibody binds to IL-17 and the antibody comprising a V domain binds to human serum albumin (HSA).

26. The antibody according to claim 20, wherein the second antibody binds to CD3 and the antibody comprising a V domain binds to CD28.

27. The antibody according to claim 20, wherein the second antibody binds to CD28 and the antibody comprising a V domain binds to CD3.

28. An isolated DNA molecule or a pair of DNA molecules encoding the antibody according to claim 1.

29. A cloning or expression vector or a pair of cloning or expression vectors encoding the antibody according to claim 1.

30. A host cell comprising a cloning or expression vector or a pair of cloning of expression vectors according to claim 29.

31. A process for the production of an antibody as defined in claim 1, comprising culturing the host cell of claim 30 and isolating the antibody.

32. A pharmaceutical composition comprising an antibody as defined in claim 1 in combination with one or more of a pharmaceutically acceptable excipient, diluent or carrier.

* * * * *